United States Patent
Argyros et al.

(10) Patent No.: US 10,604,772 B2
(45) Date of Patent: Mar. 31, 2020

(54) METHODS FOR REGULATING NITROGEN METABOLISM DURING THE PRODUCTION OF ETHANOL FROM CORN BY METABOLICALLY ENGINEERED YEAST STRAINS

(71) Applicant: Lallemand Hungary Liquidity Management LLC, Budapest (HU)

(72) Inventors: Aaron Argyros, White River Junction, VT (US); Trisha Barrett, Bradford, VT (US)

(73) Assignee: Lallemand Hungary Liquidity Management LLC, Budapest (HU)

( * ) Notice: Subject to any disclaimer, the term of this patent is extended or adjusted under 35 U.S.C. 154(b) by 66 days.

(21) Appl. No.: 14/771,831

(22) PCT Filed: Mar. 13, 2014

(86) PCT No.: PCT/US2014/025460
§ 371 (c)(1),
(2) Date: Sep. 1, 2015

(87) PCT Pub. No.: WO2014/151318
PCT Pub. Date: Sep. 25, 2014

(65) Prior Publication Data
US 2016/0017377 A1    Jan. 21, 2016

Related U.S. Application Data

(60) Provisional application No. 61/800,323, filed on Mar. 15, 2013.

(51) Int. Cl.
| | |
|---|---|
| C12P 7/06 | (2006.01) |
| C12N 9/06 | (2006.01) |
| C12N 9/00 | (2006.01) |
| C12N 15/52 | (2006.01) |
| C12N 9/02 | (2006.01) |
| C12N 9/04 | (2006.01) |
| C12N 9/10 | (2006.01) |
| C12N 9/34 | (2006.01) |
| C12N 9/50 | (2006.01) |
| C12P 7/10 | (2006.01) |

(52) U.S. Cl.
CPC .............. *C12P 7/06* (2013.01); *C12N 9/0004* (2013.01); *C12N 9/0006* (2013.01); *C12N 9/0008* (2013.01); *C12N 9/0016* (2013.01); *C12N 9/1029* (2013.01); *C12N 9/2428* (2013.01); *C12N 9/50* (2013.01); *C12N 9/93* (2013.01); *C12N 15/52* (2013.01); *C12Y 104/01002* (2013.01); *C12Y 104/01004* (2013.01); *C12Y 104/01014* (2013.01); *C12Y 603/01002* (2013.01); *C12Y 603/04006* (2013.01); *C12P 7/10* (2013.01); *C12Y 101/01001* (2013.01); *C12Y 101/01002* (2013.01); *C12Y 102/0101* (2013.01); *C12Y 197/01004* (2013.01); *C12Y 203/01054* (2013.01); *C12Y 302/01003* (2013.01); *C12Y 304/23041* (2013.01); *Y02E 50/17* (2013.01)

(58) Field of Classification Search
None
See application file for complete search history.

(56) References Cited

U.S. PATENT DOCUMENTS

| | | |
|---|---|---|
| 7,018,829 B1 | 3/2006 | Nielsen et al. |
| 7,935,514 B2 | 5/2011 | Piatkowski et al. |
| 8,956,851 B2 | 2/2015 | Argyros et al. |
| 2011/0129566 A1 | 6/2011 | Van Vuuren et al. |
| 2011/0171709 A1 | 7/2011 | Bardsley |

FOREIGN PATENT DOCUMENTS

| | | |
|---|---|---|
| EP | 2 277 989 A1 | 1/2011 |
| WO | 2005/093041 A1 | 10/2005 |
| WO | 2011/140386 A2 | 11/2011 |
| WO | 2012/138942 A1 | 10/2012 |
| WO | 2014/081803 A1 | 5/2014 |

OTHER PUBLICATIONS

Bro, C., et al., "In silico aided metabolic engineering of *Saccharomyces cerevisiae* for improved bioethanol production," Metabolic Engineering 8:102-111, Elsevier Inc., United States (2006).
Coulon, J., et al., Metabolic Engineering of *Saccharomyces cerevisiae* to; Minimize the Production of Ethyl Carbamate in Wine. Am J Enol Vitic. 2006;57(2):113-124;.
Dahabieh, M.S., et al., Functional Expression of the DUR3 Gene in a Wine Yeast Strain to Minimize Ethyl Carbamate in Chardonnay Wine. Am J Enol Vitic. 2009;60(4):537-541.
Guo, Z.P., et al., Expression of aspartic protease from Neurospora crassa in industrial ethanol-producing yeast and its application in ethanol production. Enzyme Microb Technol. Feb. 8, 2011;48(2):148-54. doi: 10.1016/j. enzmictec.2010.10.008. Epub Oct. 30, 2010.
Guo, Z.P., et al., Minimization of glycerol synthesis in industrial ethanol yeast without influencing its fermentation performance. Metabolic Engineering, Jan. 2011;13(1):49-59, Elsevier, Inc., United States.
Hahn-Hägerdal, B., et al., "Metabolic Engineering of *Saccharomyces cerevisiae* for Xylose Utilization," Adv. in Biochem. Eng. Biotechnol. 73:53-84, Springer-Verlag, Germany (2001).

(Continued)

*Primary Examiner* — Anand U Desai
(74) *Attorney, Agent, or Firm* — Nutter McClennen & Fish LLP

(57) ABSTRACT

The present invention provides for a mechanism to reduce glycerol production and increase nitrogen utilization and ethanol production of recombinant microorganisms. One aspect of this invention relates to strains of *S. cerevisiae* with reduced glycerol productivity that get a kinetic benefit from higher nitrogen concentration without sacrificing ethanol yield. A second aspect of the invention relates to metabolic modifications resulting in altered transport and/or intracellular metabolism of nitrogen sources present in corn mash.

21 Claims, 74 Drawing Sheets

Specification includes a Sequence Listing.

(56) References Cited

OTHER PUBLICATIONS

Higgins, D.G., et al., Fast and sensitive multiple sequence alignments on a microcomputer, CABIOS, 5:151-153, Oxford University Press, UK (1989).

International Search Report and Written Opinion for Application No. PCT/US2014/025460, dated Sep. 24, 2014 (13 pages).

Kong, Q.X., et al., Overexpressing GLT1 in gpd1Delta mutant to improve the production of ethanol of *Saccharomyces cerevisiae*. Appl Microbiol Biotechnol. Jan. 2007;73(6):1382-6. Epub Oct. 5, 2006.

Ljungdahl, P.O., et al., Regulation of amino acid, nucleotide, and phosphate metabolism in *Saccharomyces cerevisiae*. Genetics. Mar. 2012;190(3):885-929. doi: 10.1534/genetics.111.133306.

Medina, V.G., et al.,Elimination of Glycerol Production in Anaerobic Cultures of a *Saccharomyces cerevisiae* Strain Engineered to Use Acetic Acid as an Electron Acceptor. Applied and Environmental Microbiology, Jan. 2010;76 (1):190-195, American Societyfor Microbiology., United States.

Nissen, T.L., et al., Optimization of ethanol production in *Saccharomyces cerevisiae* by metabolic engineering of the ammonium assimilation. Metab Eng. Jan. 2000;2(1):69-77.

Roca, C., et al., Metabolic engineering of ammonium assimilation in xylose-fermenting *Saccharomyces cerevisiae* improves ethanol production. Appl Environ Microbiol. Aug. 2003;69(8):4732-6.

Salmon, J.M., et al., Improvement of nitrogen assimilation and fermentation kinetics under enological conditions by derepression of alternative nitrogen-assimilatory pathways in an industrial *Saccharomyces cerevisiae* strain. Appl Environ Microbiol. Oct. 1998;64(10):3831-7.

Sharp, P.M., et al., The codon adaptation indexa measure of directional synonymous codon usage bias, and its potential applications. Nucleic Acids Res, 1987;15(3):1281-1295, IRL Press Limited, Oxford, England.

Van Maris, et al., Alcoholic fermentation of carbon sources in biomass hydrolysates by *Saccharomyces cerevisiae*: current status. Antonie Van Leeuwenhoek. Nov. 2006;90(4):391-418. Epub Oct. 11, 2006.

Welch, M., et al., Designing genes for successful protein expression. Methods Enzymol. 2011;498:43-66. doi: 10.1016/B978-0-12-385120-8.00003-6.

Chinese Office Action for Application No. CN 201480028538.1, dated Jul. 25, 2017 (23 pages).

Guo, Z.P., et al., "Improving ethanol productivity by modification of glycolytic redox factor generation in glycerol-3-phosphate dehydrogenase mutants of an industrial ethanol yeast," J. Ind. Microbiol. Biotechnol. 38:935-43, Springer, Germany (2011).

Zhang, J., "Influence of Different Level of Assimilable Nitrogen on Alcoholic Fermentation by Yeasts," China Master's Thesis; China Excellent Master's Theses Full-Text Datatbase, Dec. 15, 2011 (7 pgs; abstract).

MA0631

Marked Deletion of GDH1 (just kan showed here – nat construct the same)

MA0631

| Fragment | Primers | Template | Expected Size |
|---|---|---|---|
| GDH1 5' Flank | X14961/X21291 | gDNA | 2065bp |
| AGTEF pro-kan/nat/tdk-HXT2 pro | X21289/X21290 | pMU2873/pMU2879 | 3820bp and 3583bp |
| GDH1 3' Flank | X21292/X14966 | gDNA | 2056bp |

MA0631 GDH1::knt 11808 bp

MA0425

<u>4 copy *S. cerevisiae* GDH2 integrated at GDH1 locus</u>
MA0425

| Fragment | Primers | Template | Expected Size |
|---|---|---|---|
| GDH1 5' Flank | X14961/X19722 | gDNA | 2065bp |
| PGKpro-GDH2-ENO1ter | X19721/X15464 | pMU2908 | 5283bp |
| ADH1pro-GDH2-PDC1ter | X15465/X19727 | pMU2909 | 4546bp |
| GDH1 3' Flank | X19726/X14966 | gDNA | 2056bp |

MA0425
17884bp

MA0426

2 copy *S. cerevisiae* GLT1/GLN1 integrated at GDH1 locus

MA0426

| Fragment | Primers | Template | Expected Size |
|---|---|---|---|
| GDH1 5' Flank | X14961/X19722 | M2390 gDNA | 2065bp |
| PGKpro-GLT1-ENOter | X19721/X15464 | pMU2913 | 8442bp |
| ADH1pro-GLN1-PDC1ter | X15465/X19727 | pMU2911 | 2363bp |
| GDH1 3' Flank | X19726/X14966 | M2390 gDNA | 2056bp |

MA0426
18860 bp

MA0888

Clean deletion of GDH1

| MA0888 | | | |
|---|---|---|---|
| Fragment | Primers | Template | Expected Size |
| 5' Flank | X14961/X19949 | M2390 gDNA | 2065bp |
| 3' Flank | X19948/X14966 | M2390 gDNA | 2056bp |

MA0888 GDH1::deletion
8055bp

MA0837

<u>2 copy *N. crassa* GDH2 integrated at GDH1 locus</u>

MA0837

| Fragment | Primers | Template | Expected Size |
|---|---|---|---|
| GDH1 5' Flank | X14961/X23320 | gDNA | 2065bp |
| ADH1pro-GDH2-PDC1 ter | X23319/X23322 | pMU3597 | 4403bp |
| GDH1 3' Flank | X23321/X14966 | gDNA | 2056bp |

MA0837
12458 bp

MA0616

GDH2 marked deletion
MA0616

| Fragment | Primers | Template | Expected Size |
|---|---|---|---|
| GDH2 5' Flank | X21123/X21124 | M2390 gDNA | 2024bp |
| AGTEFpro-kan/nat/tdk-HXT2pro | X21127/X21128 | pMU2873/pMU2879 | 3820bp and 3583bp |
| GDH2 3' Flank | X21125/X21126 | M2390 gDNA | 1990bp |

MA0616
11754 bp

MA0616.1

GDH2 clean deletion

MA0616.1

| Fragment | Primers | Template | Expected Size |
|---|---|---|---|
| GDH2 5' Flank | X21123/X21507 | M2390 gDNA | 2024bp |
| GDH2 3' Flank | X21133/X21126 | M2390 gDNA | 1990bp |

MA0616.1
8000 bp

MA0615

GDH3 marked deletion
MA0615

| Fragment | Primers | Template | Expected Size |
| --- | --- | --- | --- |
| GDH3 5' Flank | X21135/X21136 | M2390 gDNA | 1976bp |
| AGTEFpro-kan/nat/tdk-HXT2pro | X21139/X21140 | pMU2873/pMU2879 | 3820bp and 3583bp |
| GDH3 3' Flank | X21137/X21138 | M2390 gDNA | 2015bp |

MA0615
11730 bp

MA0615.1

GDH3 clean deletion
MA0615.1

| Fragment | Primers | Template | Expected Size |
|---|---|---|---|
| GDH3 5' Flank | X21135/X21148 | M2390 gDNA | 1976bp |
| GDH3 3' Flank | X21147/X21138 | M2390 gDNA | 2015bp |

MA0615.1
7976 bp

MA0622

URE2 marked deletion
MA0622

| Fragment | Primers | Template | Expected Size |
|---|---|---|---|
| URE2 5' Flank | X20022/X20023 | M2390 gDNA | 1968bp |
| AGTEF pro-kan/nat/tdk-HXT2 pro | X20028/X20029 | pMU2873, pMU2879 | 3820bp and 3583bp |
| URE2 3' Flank | X20024/X20025 | M2390 gDNA | 1885bp |

MA0622
11517 bp

MA0622.1

<u>URE2 clean deletion</u>

MA0622.1

| Fragment | Primers | Template | Expected Size |
|---|---|---|---|
| URE2 5' Flank | X20022/X20027 | M2390 gDNA | 1968bp |
| URE2 3' Flank | X20026/X20025 | M2390 gDNA | 1885bp |

MA0622.1
8000 bp

MA0580

DUR1,2,3 over expression at URE2 locus

MA0580

| Fragment | Primers | Template | Exp size |
|---|---|---|---|
| URE2 5' Flank | X20022/X21180 | M2390 gDNA | 1968bp |
| TEF2pro-DUR3-ADH3ter | X21179/X19513 | pMU3464 | 3208bp |
| ADH1pro-DUR1,2-PDC1ter | X19514/X21181 | pMU3411 | 6758bp |
| URE2 3' Flank | X21182/X20025 | M2390 gDNA | 1885bp |

MA0580
17966 bp

MA0581

MEP1 over expression at URE2 locus
MA0581

| Fragment | Primers | Template | Exp size |
|---|---|---|---|
| URE2 5' Flank | X20022/X21180 | M2390 gDNA | 1968bp |
| TEF2pro-MEP1-ADH3ter | X21179/X19513 | pMU3465 | 2479bp |
| ADH1pro-MEP1-PDC1ter | X19514/X21181 | pMU3460 | 2729bp |
| URE2 3' Flank | X21182/X20025 | M2390 gDNA | 1885bp |

MA0581
13208 bp

MA0582

MEP2 over expression at URE2 locus
MA0582

| Fragment | Primers | Template | Exp size |
|---|---|---|---|
| URE2 5' Flank | X20022/X21180 | M2390 gDNA | 1968bp |
| TEF2pro-MEP2-ADH3ter | X21179/X19513 | pMU3465 | 2479bp |
| ADH1pro-MEP2-PDC1ter | X19514/X21181 | pMU3461 | 2750bp |
| URE2 3' Flank | X21182/X20025 | M2390 gDNA | 1885bp |

MA0582
13250 bp

MA0583

GAP1 over expression at URE2 locus

MA0583

| Fragment | Primers | Template | Exp size |
|---|---|---|---|
| URE2 5' Flank | X20022/X21180 | M2390 gDNA | 1968bp |
| TEF2pro-GAP1-ADH3ter | X21179/X19513 | pMU3468 | 2809bp |
| ADH1pro-GAP1-PDC1ter | X19514/X21181 | pMU3463 | 3059bp |
| URE2 3' Flank | X21182/X20025 | M2390 gDNA | 1885bp |

MA0583
13868 bp

MA0584

<u>S. cerevisiae GDH2 over expression at URE2 locus</u>
MA0584

| Fragment | Primers | Template | Exp size |
|---|---|---|---|
| URE2 5' Flank | X20022/X21320 | M2390 gDNA | 1968bp |
| ADH1pro-GDH2-PDC1ter | X21319/X15465 | pMU2909 | 4546bp |
| PGKpro-GDH2-ENO1ter | X15464/X21322 | pMU2908 | 5283bp |
| URE2 3' Flank | X21321/X20025 | M2390 gDNA | 1885bp |

MA0584
17829 bp

MA0585

GLT1/GLN1 over expression at the URE2 locus
MA0585

| Fragment | Primers | Template | Exp size |
|---|---|---|---|
| URE2 5' Flank | X20022/X21320 | M2390 gDNA | 1968bp |
| ADH1pro-GLTI-PDC1ter | X21319/X15465 | pMU2911 | 2363bp |
| PGKpro-GLN1-ENO1ter | X15464/X21322 | pMU2913 | 8442bp |
| URE2 3' Flank | X21321/X20025 | M2390 gDNA | 1885bp |

MA0585
18794 bp

MA0617

AUA1 marked deletion
MA0617

| Fragment | Primers | Template | Expected Size |
|---|---|---|---|
| AUA1 5' Flank | X20620/X20621 | M2390 gDNA | 1947bp |
| AGTEFpro-kan/nat/tdk-HXT2pro | X20630/X20631 | pMU2873,pMU2879 | 3820bp and 3583bp |
| AUA1 3' Flank | X20622/X20623 | M2390 gDNA | 2015bp |

MA0617
11754 bp

MA0617.1

AUA1 clean deletion

| MA0617.1 | | | |
|---|---|---|---|
| Fragment | Primers | Template | Expected Size |
| AUA1 5' Flank | X20620/X20633 | M2390 gDNA | 1947bp |
| AUA1 3' Flank | X20632/X20623 | M2390 gDNA | 2015bp |

MA0617.1
8000 bp

MA0434

DUR3 over expression at FCY1 locus

| MA0434 | DUR3 | | |
|---|---|---|---|
| Fragment | Primers | Template | Exp Size |
| FCY 5' Flank | X21754/X18859 | gDNA | 2049bp |
| TP1pro-DUR3-FBA1ter | X18858/X18861 | pMU3471 | 3157bp |
| FCY 3' Flank | X18860/X18869 | gDNA | 2166bp |

MA0434 with DUR3
11157 bp

MA0434.2

MEP1 over expression at FCY1 locus

| MA0434.2 | MEP1 | | |
|---|---|---|---|
| Fragment | Primers | Template | Exp Size |
| FCY 5' Flank | X21754/X18859 | gDNA | 2049bp |
| TP1pro-MEP1-FBA1ter | X18858/X18861 | pMU3472 | 2428bp |
| FCY 3' Flank | X18860/X18869 | gDNA | 2166bp |

MA0434.2 with MEP1
10428 bp

MA0434.3

MEP2 over expression at FCY1 locus

| MA0434.3 | MEP2 | | |
|---|---|---|---|
| Fragment | Primers | Template | Exp Size |
| FCY 5' Flank | X21754/X18859 | gDNA | 2049bp |
| TP1pro-MEP2-FBA1ter | X18858/X18861 | pMU3473 | 2449bp |
| FCY 3' Flank | X18860/X18869 | gDNA | 2166bp |

MA0434.3 with MEP2
10449 bp

MA0434.4

GAP1 over expression at FCY1 locus

| MA0434.4 | GAP1 | | |
|---|---|---|---|
| Fragment | Primers | Template | Exp Size |
| FCY 5' Flank | X21754/X18859 | gDNA | 2049bp |
| TP1pro-GAP1-FBA1ter | X18858/X18861 | pMU3475 | 2758bp |
| FCY 3' Flank | X18860/X18869 | gDNA | 2166bp |

MA0434.4 with GAP1
10758 bp

MA0434.5

MEP3 over expression at FCY1 locus

| MA0434.5 | MEP3 | | |
|---|---|---|---|
| Fragment | Primers | Template | Exp Size |
| FCY 5' Flank | X21754/X18859 | gDNA | 2049bp |
| TP1pro-MEP3-FBA1ter | X18858/X18861 | pMU3607 | 2420bp |
| FCY 3' Flank | X18860/X18869 | gDNA | 2166bp |

MA0434.5 with MEP3
10419 bp

MA0454.14

DUR1,2 over expression at FCY1 locus
MA0454.14

| Fragment | Primers | Template | Exp Size |
|---|---|---|---|
| FCY 5' Flank | X21754/X19552 | gDNA | 2018bp |
| pTEF2/ADH3t | X19551/X19968 | pMU3409 | 6508bp |
| pHXT7/PMA1trc | X19967/X19969 | pMU3410 | 6458bp |
| FCY3' Flank | X19970/X18869 | gDNA | 2159bp |

MA0454.14 with DUR1,2
24889 bp

MA0464

DUR3 over expression at FCY1 locus

| MA0464 | DUR3 | | |
|---|---|---|---|
| Fragment | Primers | Template | Exp Size |
| FCY 5' Flank | X21754/X19552 | M2390 gDNA | 2018bp |
| TEF2pro-DUR3-ADH3ter | X19551/X20043 | pMU3464 | 3208bp |
| FCY 3' Flank | X20044/X18869 | M2390 gDNA | 2133bp |

MA0464 with DUR3
11208 bp

MA0464.1

DUR1,2 over expression at FCY1 locus

| MA0464.1 | DUR1,2 | | |
|---|---|---|---|
| Fragment | Primers | Template | Exp Size |
| FCY 5' Flank | X21754/X19552 | M2390 gDNA | 2049bp |
| TEF2pro-DUR1,2-ADH3ter | X19551/X20043 | pMU3409 | 6508bp |
| FCY 3' Flank | X20044/X18869 | M2390 gDNA | 2166bp |

MA0464.1 with DUR1,2
14508 bp

MA0464.2

MEP1 over expression at FCY1 locus

| MA0464.2 | MEP1 | | |
|---|---|---|---|
| Fragment | Primers | Template | Exp Size |
| FCY 5' Flank | X21754/X19552 | M2390 gDNA | 2049bp |
| TEF2pro-MEP1-ADH3ter | X19551/X20043 | pMU3465 | 2479bp |
| FCY 3' Flank | X20044/X18869 | M2390 gDNA | 2166bp |

MA0464.2 with MEP1
10479 bp

MA0464.3

MEP2 over expression at FCY1 locus

| MA0464.3 | MEP2 | | |
|---|---|---|---|
| Fragment | Primers | Template | Exp Size |
| FCY 5' Flank | X21754/X19552 | M2390 gDNA | 2049bp |
| TEF2pro-MEP2-ADH3ter | X19551/X20043 | pMU3466 | 2500bp |
| FCY 3' Flank | X20044/X18869 | M2390 gDNA | 2166bp |

MA0464.3 with MEP2
10500 bp

MA0464.4

GAP1 over expression at FCY1 locus

| MA0464.4 | GAP1 | | |
|---|---|---|---|
| Fragment | Primers | Template | Exp Size |
| FCY 5' Flank | X21754/X19552 | M2390 gDNA | 2049bp |
| TEF2pro-GAP1-ADH3ter | X19551/X20043 | pMU3468 | 2809bp |
| FCY 3' Flank | X20044/X18869 | M2390 gDNA | 2166bp |

MA0464.4 with GAP1
10809 bp

MA0464.5

MEP3 over expression at FCY1 locus

| MA0464.5 | MEP3 | | |
|---|---|---|---|
| Fragment | Primers | Template | Exp Size |
| FCY 5' Flank | X21754/X19552 | M2390 gDNA | 2049bp |
| TEF2pro-DUR1,2-ADH3ter | X19551/X20043 | pMU3606 | 6508bp |
| FCY 3' Flank | X20044/X18869 | M2390 gDNA | 2166bp |

MA0464.5 with MEP3
10470 bp

MA0465.1

DUR1,2 over expression at FCY1

| MA0465.1 | DUR1,2 | | |
|---|---|---|---|
| Fragment | Primers | Template | Exp Size |
| FCY 5' Flank | X21754/X20283 | M2390 gDNA | 2049bp |
| HXT7pro-DUR1,2-PMA1ter | X20282/X20285 | pMU3410 | 6458bp |
| FCY 3' Flank | X20284/X18869 | M2390 gDNA | 2166bp |

MA0465 with DUR1,2
14458 bp

MA0467

DUR3 over expression at FCY1 locus

| MA0467 | DUR3 | | |
|---|---|---|---|
| Fragment | Primers | Template | Exp Size |
| FCY 5' Flank | X21754/X21736 | M2390 gDNA | 2049bp |
| ADH1pro-DUR3-PDC1ter | X21735/X18847 | pMU3459 | 3458bp |
| FCY 3' Flank | X18846/X18869 | M2390 gDNA | 2166bp |

MA0467 with DUR3
11458 bp

MA0467.1

DUR1,2 over expression at FCY1 locus

| MA0467.1 | DUR1,2 | | |
|---|---|---|---|
| Fragment | Primers | Template | Exp Size |
| FCY 5' Flank | X21754/X21736 | M2390 gDNA | 2049bp |
| ADH1pro-DUR1,2-PDC1ter | X21735/X18847 | pMU3411 | 6758bp |
| FCY 3' Flank | X18846/X18869 | M2390 gDNA | 2166bp |

MA0467.1 with DUR1,2
14758 bp

MA0467.2

<u>MEP1 over expression at FCY1 locus</u>

| MA0467.2 | MEP1 | | |
|---|---|---|---|
| Fragment | Primers | Template | Exp Size |
| FCY 5' Flank | X21754/X21736 | M2390 gDNA | 2049bp |
| ADH1pro-MEP1-PDC1ter | X21735/X18847 | pMU3460 | 2729bp |
| FCY 3' Flank | X18846/X18869 | M2390 gDNA | 2166bp |

MA0467.2 with MEP1
10729 bp

MA0467.3

MEP2 over expression at FCY1 locus

| MA0467.3 | MEP2 | | |
|---|---|---|---|
| Fragment | Primers | Template | Exp Size |
| FCY 5' Flank | X21754/X21736 | M2390 gDNA | 2049bp |
| ADH1pro-MEP2-PDC1ter | X21735/X18847 | pMU3461 | 2750bp |
| FCY 3' Flank | X18846/X18869 | M2390 gDNA | 2166bp |

MA0467.3 with MEP2
10750 bp

MA0467.4

GAP1 over expression at FCY1 locus

| MA0467.4 | GAP1 | | |
|---|---|---|---|
| Fragment | Primers | Template | Exp Size |
| FCY 5' Flank | X21754/X21736 | M2390 gDNA | 2049bp |
| ADH1pro-GAP1-PDC1ter | X21735/X18847 | pMU3463 | 3059bp |
| FCY 3' Flank | X18846/X18869 | M2390 gDNA | 2166bp |

MA0467.4 with GAP1
11059 bp

MA0881

S. cerevisiae GDH2 over expression at FCY1 locus

MA0881

| Fragment | Primers | Template | Expected Size |
|---|---|---|---|
| 5' Flank | X21754/X23408 | M2390 gDNA | 2049bp |
| pPGK-GDH2-ENO1t | X23409/X15464 | pMU2908 | 5283bp |
| pADH-GDH2-PDC1trc | X15465/X18955 | pMU2909 | 4546bp |
| 3' Flank | X19950/X18869 | M2390 gDNA | 2166bp |

MA0881
21752 bp

MA0881.1

GLT1/GLN1 over expression at FCY1 locus

MA0881.1

| Fragment | Primers | Template | Expected Size |
|---|---|---|---|
| 5' Flank | X21754/X23408 | M2390 gDNA | 2049bp |
| pPGK-GLT1-ENO1t | X23409/X15464 | pMU2913 | 8442bp |
| pADH-GLN1-PDC1trc | X15465/X18955 | pMU2911 | 2363bp |
| 3' Flank | X19950/X18869 | M2390 gDNA | 2166bp |

MA0881.1
22745 bp

```
SEQUENCE LISTING

<160> NUMBER OF SEQ ID NOS: 163

<210> SEQ ID NO 1
<211> LENGTH: 1131
<212> TYPE: DNA
<213> ORGANISM: Saccharomyces cerevisiae

<400> SEQUENCE: 1
atgtcgaagg gaaaggtttt gctggttctt tacgaaggtg gtaagcatgc tgaagagcag      60
gaaaagttat tggggtgtat tgaaaatgaa cttggtatca gaaatttcat tgaagaacag     120
ggatacgagt tggttactac cattgacaag gaccctgagc caacctcaac ggtagacagg     180
gagttgaaag acgctgaaat tgtcattact acgcccttt tccccgccta catctcgaga      240
aacaggattg cagaagctcc taacctgaag ctctgtgtaa ccgctggcgt cggttcagac     300
catgtcgatt tagaagctgc aaatgaacgg aaaatcacgg tcaccgaagt tactggttct     360
aacgtcgttt ctgtcgcaga gcacgttatg gccacaattt tggttttgat aagaaactat     420
aatggtggtc atcaacaagc aattaatggt gagtgggata ttgccggcgt ggctaaaaat     480
gagtatgatc tggaagacaa ataatttca acggtaggtg ccggtagaat tggatatagg      540
gttctggaaa gattggtcgc atttaatccg aagaagttac tgtactacga ctaccaggaa     600
ctacctgcgg aagcaatcaa tagattgaac gaggccagca agcttttcaa tggcagaggt     660
gatattgttc agagagtaga gaaattggag gatatggttg ctcagtcaga tgttgttacc     720
atcaactgtc cattgcacaa ggactcaagg ggtttattca ataaaaagct tatttcccac     780
atgaaagatg gtgcatactt ggtgaatacc gctagaggtg ctatttgtgt cgcagaagat     840
gttgccgagg cagtcaagtc tggtaaattg gctggctatg gtggtgatgt ctgggataag     900
caaccagcac caaaagacca tccctggagg actatggaca ataaggacca cgtgggaaac     960
gcaatgactg ttcatatcag tggcacatct ctggatgctc aaaagaggta cgctcaggga    1020
gtaaagaaca tcctaaatag ttacttttcc aaaaagtttg attaccgtcc acaggatatt    1080
attgtgcaga atggttctta tgccaccaga gcttatggac agaagaaata a             1131

<210> SEQ ID NO 2
<211> LENGTH: 376
<212> TYPE: PRT
<213> ORGANISM: Saccharomyces cerevisiae
```

<400> SEQUENCE: 2

```
Met Ser Lys Gly Lys Val Leu Leu Val Leu Tyr Glu Gly Gly Lys His
1               5                   10                  15

Ala Glu Glu Gln Glu Lys Leu Leu Gly Cys Ile Glu Asn Glu Leu Gly
                20                  25                  30

Ile Arg Asn Phe Ile Glu Glu Gln Gly Tyr Glu Leu Val Thr Thr Ile
            35                  40                  45

Asp Lys Asp Pro Glu Pro Thr Ser Thr Val Asp Arg Glu Leu Lys Asp
        50                  55                  60

Ala Glu Ile Val Ile Thr Thr Pro Phe Phe Pro Ala Tyr Ile Ser Arg
65                  70                  75                  80

Asn Arg Ile Ala Glu Ala Pro Asn Leu Lys Leu Cys Val Thr Ala Gly
                85                  90                  95

Val Gly Ser Asp His Val Asp Leu Glu Ala Ala Asn Glu Arg Lys Ile
            100                 105                 110

Thr Val Thr Glu Val Thr Gly Ser Asn Val Val Ser Val Ala Glu His
        115                 120                 125

Val Met Ala Thr Ile Leu Val Leu Ile Arg Asn Tyr Asn Gly Gly His
130                 135                 140

Gln Gln Ala Ile Asn Gly Glu Trp Asp Ile Ala Gly Val Ala Lys Asn
145                 150                 155                 160

Glu Tyr Asp Leu Glu Asp Lys Ile Ile Ser Thr Val Gly Ala Gly Arg
                165                 170                 175

Ile Gly Tyr Arg Val Leu Glu Arg Leu Val Ala Phe Asn Pro Lys Lys
            180                 185                 190

Leu Leu Tyr Tyr Asp Tyr Gln Glu Leu Pro Ala Glu Ala Ile Asn Arg
        195                 200                 205

Leu Asn Glu Ala Ser Lys Leu Phe Asn Gly Arg Gly Asp Ile Val Gln
    210                 215                 220

Arg Val Glu Lys Leu Glu Asp Met Val Ala Gln Ser Asp Val Val Thr
225                 230                 235                 240

Ile Asn Cys Pro Leu His Lys Asp Ser Arg Gly Leu Phe Asn Lys Lys
                245                 250                 255

Leu Ile Ser His Met Lys Asp Gly Ala Tyr Leu Val Asn Thr Ala Arg
            260                 265                 270

Gly Ala Ile Cys Val Ala Glu Asp Val Ala Glu Ala Val Lys Ser Gly
        275                 280                 285

Lys Leu Ala Gly Tyr Gly Gly Asp Val Trp Asp Lys Gln Pro Ala Pro
    290                 295                 300

Lys Asp His Pro Trp Arg Thr Met Asp Asn Lys Asp His Val Gly Asn
305                 310                 315                 320

Ala Met Thr Val His Ile Ser Gly Thr Ser Leu Asp Ala Gln Lys Arg
                325                 330                 335

Tyr Ala Gln Gly Val Lys Asn Ile Leu Asn Ser Tyr Phe Ser Lys Lys
            340                 345                 350

Phe Asp Tyr Arg Pro Gln Asp Ile Ile Val Gln Asn Gly Ser Tyr Ala
        355                 360                 365

Thr Arg Ala Tyr Gly Gln Lys Lys
    370                 375
```

<210> SEQ ID NO 3
<211> LENGTH: 1129
<212> TYPE: DNA
<213> ORGANISM: Saccharomyces cerevisiae

<400> SEQUENCE: 3

```
atgtcgaagg gaaaggtttt gctggttctt tatgaaggtg gtaagcatgc tgaagagcag      60
gaaaagttat tggggtgtat tgaaaatgaa cttggtatca gaaatttcat tgaagaacag     120
ggatacgagt tggttactac cattgacaag gaccctgagc aacctcaac ggtagacagg      180
gagttgaaag acgctgaaat tgtcattact acgcccttt tccccgccta catctcgaga      240
aacaggattg cagaagctcc taacctgaag ctctgtgtaa ccgctggcgt cggttcagac     300
catgtcgatt tagaagctgc aaatgaacgg aaaatcacgg tcaccgaagt tactggttct     360
aacgtcgttt ctgtcgcaga gcacgttatg gccacaattt tggttttgat aagaaactat     420
aatggtggtc atcaataagc aattaatggt gagtgggata ttgccggcgt ggctaaaaaa     480
tgagtatgat ctggaagaca aaataatttc aacggtaggt gccggtagaa ttggatatag     540
ggttctggaa agattggtcg catttaatcc gaagaagtta ctgtactacg actaccagga    600
actacctgcg gaagcaatca atagattgaa cgaggccagc aagcttttca atggcagagg     660
tgatattgtt cagagagtag agaaattgga ggatatggtg gctcagtcag atgttgttac     720
catcaactgt ccattgcaca aggactcaag gggtttattc aataaaaagc ttatttccca     780
catgaaagat ggtgcatact tggtgaatac cgctagaggt gctatttgtg tcgcagaaga    840
tgttgccgag gcagtcaagt ctggtaaatt ggctggctat ggtggtgatg tctgggataa     900
gcaaccagca ccaaaagacc atccctggag gactatggca ataaggacc acgtgggaaa     960
cgcaatgact gttcatatca gtggcacatc tctgcatgct caaaagaggt acgctcaggg    1020
agtaaagaac atcctaaata gttactttc caaaaagttt gattaccgtc acaggatat      1080
tattgtgcag aatggttctt atgccaccag agcttatgga cagaagaaa                 1129
```

<210> SEQ ID NO 4
<211> LENGTH: 1176
<212> TYPE: DNA
<213> ORGANISM: Saccharomyces cerevisiae

<400> SEQUENCE: 4

```
atgtctgctg ctgctgatag attaaactta acttccggcc acttgaatgc tggtagaaag      60
agaagttcct cttctgtttc tttgaaggct gccgaaaagc ctttcaaggt tactgtgatt     120
ggatctggta actggggtac tactattgcc aaggtggttg ccgaaaattg taagggatac    180
ccagaagttt cgctccaat agtacaaatg tgggtgttcg aagaagagat caatggtgaa     240
aaattgactg aaatcataaa tactagacat caaaacgtga atacttgcc tggcatcact    300
ctaccgaca atttggttgc taatccagac ttgattgatt cagtcaagga tgtcgacatc     360
atcgttttca acattccaca tcaattttg ccccgtatct gtagccaatt gaaaggtcat    420
gttgattcac acgtcagagc tatctcctgt ctaaagggtt tgaagttgg tgctaaaggt     480
gtccaattgc tatcctctta catcactgag gaactaggta ttcaatgtgg tgctctatct     540
ggtgctaaca ttgccaccga agtcgctcaa gaacactggt ctgaaacaac agttgcttac    600
cacattccaa aggatttcag aggcgagggc aaggacgtcg accataaggt tctaaaggcc    660
ttgttccaca gaccttactt ccacgttagt gtcatcgaag atgttgctgg tatctccatc     720
tgtggtgctt tgaagaacgt tgttgcctta ggttgtggtt tcgtcgaagg tctaggctgg     780
ggtaacaacg cttctgctgc catccaaaga gtcggtttgg gtgagatcat cagattcggt     840
caaatgtttt tccagaaatc tagagaagaa acatactacc aagagtctgc tggtgttgct     900
gatttgatca ccacctgcgc tggtggtaga aacgtcaagg ttgctaggct aatggctact    960
```

```
tctggtaagg acgcctggga atgtgaaaag gagttgttga atggccaatc cgctcaaggt    1020
ttaattacct gcaaagaagt tcacgaatgg ttggaaacat gtggctctgt cgaagacttc    1080
ccattatttg aagccgtata ccaaatcgtt tacaacaact acccaatgaa gaacctgccg    1140
gacatgattg aagaattaga tctacatgaa gattag                              1176
```

<210> SEQ ID NO 5
<211> LENGTH: 391
<212> TYPE: PRT
<213> ORGANISM: Saccharomyces cerevisiae

<400> SEQUENCE: 5

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Glu
            20                  25                  30

Lys Pro Phe Lys Val Thr Val Ile Gly Ser Gly Asn Trp Gly Thr Thr
            35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
            115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
            195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
            275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335
```

Ser Ala Gln Gly Leu Ile Thr Cys Lys Glu Val His Glu Trp Leu Glu
        340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 6
<211> LENGTH: 1320
<212> TYPE: DNA
<213> ORGANISM: Saccharomyces cerevisiae

<400> SEQUENCE: 6

```
atgcttgctg tcagaagatt aacaagatac acattcctta agcgaacgca tccggtgtta      60
tatactcgtc gtgcatataa aattttgcct tcaagatcta ctttcctaag aagatcatta     120
ttacaaacac aactgcactc aaagatgact gctcatacta atatcaaaca gcacaaacac     180
tgtcatgagg accatcctat cagaagatcg gactctgccg tgtcaattgt acatttgaaa     240
cgtgcgccct tcaaggttac agtgattggt tctggtaact gggggaccac catcgccaaa     300
gtcattgcgg aaaacacaga attgcattcc catatcttcg agccagaggt gagaatgtgg     360
gttttttgatg aaaagatcgg cgacgaaaat ctgacggata tcataaatac aagacaccag     420
aacgttaaat atctacccaa tattgacctg ccccataatc tagtggccga tcctgatctt     480
ttacactcca tcaagggtgc tgacatcctt gttttcaaca tccctcatca attttttacca     540
aacatagtca acaattgca aggccacgtg gcccctcatg taagggccat ctcgtgtcta     600
aaagggttcg agttgggctc caagggtgtg caattgctat cctcctatgt tactgatgag     660
ttaggaatcc aatgtggcgc actatctggt gcaaacttgg caccggaagt ggccaaggag     720
cattggtccg aaaccaccgt ggcttaccaa ctaccaaagg attatcaagg tgatggcaag     780
gatgtagatc ataagatttt gaaattgctg ttccacagac cttacttcca cgtcaatgtc     840
atcgatgatg ttgctggtat atccattgcc ggtgccttga gaacgtcgt ggcacttgca     900
tgtggtttcg tagaaggtat gggatggggt aacaatgcct ccgcagccat tcaaaggctg     960
ggtttaggtg aaattatcaa gttcggtaga atgttttcc cagaatccaa agtcgagacc    1020
tactatcaag aatccgctgg tgttgcagat ctgatcacca cctgctcagg cggtagaaac    1080
gtcaaggttg ccacatacat ggccaagacc ggtaagtcag ccttggaagc agaaaaggaa    1140
ttgcttaacg tcaatccgc caagggata atcacatgca gagaagttca cgagtggcta    1200
caaacatgtg agttgaccca agaattccca ttattcgagg cagtctacca gatagtctac    1260
aacaacgtcc gcatggaaga cctaccggag atgattgaag agctagacat cgatgacgaa    1320
```

<210> SEQ ID NO 7
<211> LENGTH: 440
<212> TYPE: PRT
<213> ORGANISM: Saccharomyces cerevisiae

<400> SEQUENCE: 7

Met Leu Ala Val Arg Arg Leu Thr Arg Tyr Thr Phe Leu Lys Arg Thr
1               5                   10                  15

His Pro Val Leu Tyr Thr Arg Arg Ala Tyr Lys Ile Leu Pro Ser Arg
            20                  25                  30

```
Ser Thr Phe Leu Arg Arg Ser Leu Leu Gln Thr Gln Leu His Ser Lys
         35                  40                  45

Met Thr Ala His Thr Asn Ile Lys Gln His Lys His Cys His Glu Asp
 50                  55                  60

His Pro Ile Arg Arg Ser Asp Ser Ala Val Ser Ile Val His Leu Lys
 65                  70                  75                  80

Arg Ala Pro Phe Lys Val Thr Val Ile Gly Ser Gly Asn Trp Gly Thr
                 85                  90                  95

Thr Ile Ala Lys Val Ile Ala Glu Asn Thr Glu Leu His Ser His Ile
             100                 105                 110

Phe Glu Pro Glu Val Arg Met Trp Val Phe Asp Glu Lys Ile Gly Asp
             115                 120                 125

Glu Asn Leu Thr Asp Ile Ile Asn Thr Arg His Gln Asn Val Lys Tyr
130                 135                 140

Leu Pro Asn Ile Asp Leu Pro His Asn Leu Val Ala Asp Pro Asp Leu
145                 150                 155                 160

Leu His Ser Ile Lys Gly Ala Asp Ile Leu Val Phe Asn Ile Pro His
                165                 170                 175

Gln Phe Leu Pro Asn Ile Val Lys Gln Leu Gln Gly His Val Ala Pro
             180                 185                 190

His Val Arg Ala Ile Ser Cys Leu Lys Gly Phe Glu Leu Gly Ser Lys
             195                 200                 205

Gly Val Gln Leu Leu Ser Ser Tyr Val Thr Asp Glu Leu Gly Ile Gln
210                 215                 220

Cys Gly Ala Leu Ser Gly Ala Asn Leu Ala Pro Glu Val Ala Lys Glu
225                 230                 235                 240

His Trp Ser Glu Thr Thr Val Ala Tyr Gln Leu Pro Lys Asp Tyr Gln
                245                 250                 255

Gly Asp Gly Lys Asp Val Asp His Lys Ile Leu Lys Leu Leu Phe His
             260                 265                 270

Arg Pro Tyr Phe His Val Asn Val Ile Asp Asp Val Ala Gly Ile Ser
             275                 280                 285

Ile Ala Gly Ala Leu Lys Asn Val Val Ala Leu Ala Cys Gly Phe Val
290                 295                 300

Glu Gly Met Gly Trp Gly Asn Asn Ala Ser Ala Ala Ile Gln Arg Leu
305                 310                 315                 320

Gly Leu Gly Glu Ile Ile Lys Phe Gly Arg Met Phe Phe Pro Glu Ser
                325                 330                 335

Lys Val Glu Thr Tyr Tyr Gln Glu Ser Ala Gly Val Ala Asp Leu Ile
             340                 345                 350

Thr Thr Cys Ser Gly Gly Arg Asn Val Lys Val Ala Thr Tyr Met Ala
             355                 360                 365

Lys Thr Gly Lys Ser Ala Leu Glu Ala Glu Lys Glu Leu Leu Asn Gly
370                 375                 380

Gln Ser Ala Gln Gly Ile Ile Thr Cys Arg Glu Val His Glu Trp Leu
385                 390                 395                 400

Gln Thr Cys Glu Leu Thr Gln Glu Phe Pro Leu Phe Glu Ala Val Tyr
                405                 410                 415

Gln Ile Val Tyr Asn Asn Val Arg Met Glu Asp Leu Pro Glu Met Ile
             420                 425                 430

Glu Glu Leu Asp Ile Asp Asp Glu
             435                 440
```

```
<210> SEQ ID NO 8
<211> LENGTH: 2376
<212> TYPE: DNA
<213> ORGANISM: Bifidobacterium adolescentis

<400> SEQUENCE: 8
atggcagcag ttgatgcaac ggcggtctcc caggaggaac ttgaggctaa ggcttgggaa      60
ggcttcaccg agggcaactg gcagaaggac attgatgtcc gcgacttcat ccagaagaac     120
tacacgccat atgagggcga cgagtccttc ctggctgacg ccaccgacaa gaccaagcac     180
ctgtggaagt atctggacga caactatctg tccgtggagc gcaagcagcg cgtctacgac     240
gtggacaccc acaccccggc gggcatcgac gccttcccgg ccggctacat cgattccccg     300
gaagtcgaca atgtgattgt cggtctgcag accgatgtgc cgtgcaagcg cgccatgatg     360
ccgaacggcg gctggcgtat ggtcgagcag gccatcaagg aagccggcaa ggagcccgat     420
ccggagatca agaagatctt caccaagtac cgcaagaccc acaacgacgg cgtcttcggc     480
gtctacacca gcagatcaa ggtagctcgc acaacaagaa tcctcaccgg cctgccggat     540
gcctacggcc gtggccgcat catcggcgat taccgtcgtg tggccctgta cggcgtgaac     600
gcgctgatca agttcaagca gcgcgacaag gactccatcc cgtaccgcaa cgacttcacc     660
gagccggaga tcgagcactg gatccgcttc cgtgaggagc atgacgagca gatcaaggcc     720
ctgaagcagc tgatcaacct cggcaacgag tacggcctcg acctgtcccg cccggcacag     780
accgcacagg aagccgtgca gtggacctac atgggctacc tcgcctccgt caagagccag     840
gacggcgccg ccatgtcctt cggccgtgtc tccaccttct tcgacgtcta cttcgagcgc     900
gacctgaagg ccggcaagat caccgagacc gacgcacagg agatcatcga taacctggtc     960
atgaagctgc gcatcgtgcg cttcctgcgc accaaggatt acgacgcgat cttctccggc    1020
gatccgtact gggcgacttg gtccgacgcc ggcttcggcg acgacggccg taccatggtc    1080
accaagacct cgttccgtct gctcaacacc ctgaccctcg agcacctcgg acctggcccg    1140
gagccgaaca tcaccatctt ctgggatccg aagctgccgg aagcctacaa gcgcttctgc    1200
gcccgaatct ccatcgacac ctcggccatc cagtacgagt ccgataagga aatccgctcc    1260
cactggggcg acgacgccgc catcgcatgc tgcgtctccc cgatgcgcgt gggcaagcag    1320
atgcagttct tcgccgcccg tgtgaactcc gccaaggccc tgctgtacgc catcaacggc    1380
ggacgcgacg agatgaccgg catgcaggtc atcgacaagg gcgtcatcga cccgatcaag    1440
ccggaagccg atggcacgct ggattacgag aaggtcaagg ccaactacga aaggccctc    1500 gaatggctgt ccgagaccta tgtgatggct ctgaacatca tccattacat gcatgataag    1560
tacgcttacg agtccatcga gatggctctg cacgacaagg aagtgtaccg caccctcggc    1620
tgcggcatgt ccggcctgtc gatcgcggcc gactccctgt ccgcatgcaa gtacgccaag    1680
gtctacccga tctacaacaa ggacgccaag accacgccgg ccacgagaa cgagtacgtc    1740 gaaggcgccg atgacgatct gatcgtcggc taccgcaccg aaggcgactt cccgctgtac    1800
ggcaacgatg atgaccgtgc cgacgacatc gccaagtggg tcgtctccac cgtcatgggc    1860
caggtcaagc gtctgccggt gtaccgcgac ccgtcccga ccagtccat cctgaccatc    1920 acctccaatg tggaatacgg caaggccacc ggcgccttcc cgtccggcca aagaagggc    1980 accccgtacg ctccgggcgc caacccggag aacggcatgg actcccacgg catgctgccg    2040
tccatgttct ccgtcggcaa gatcgactac aacgacgctc ttgacggcat ctcgctgacc    2100
aacaccatca cccctgatgg tctgggccgc gacgaggaag agcgtatcgg caacctcgtt    2160
```

```
ggcatcctgg acgccggcaa cggccacggc ctgtaccacg ccaacatcaa cgtgctgcgc    2220
aaggagcagc tcgaggatgc cgtcgagcat ccggagaagt acccgcacct gaccgtgcgc    2280
gtctccggct acgcggtgaa cttcgtcaag ctcaccaagg aacagcagct cgacgtgatc    2340
tcccgtacgt tccaccaggg cgctgtcgtc gactga                             2376
```

<210> SEQ ID NO 9
<211> LENGTH: 791
<212> TYPE: PRT
<213> ORGANISM: Bifidobacterium adolescentis

<400> SEQUENCE: 9

```
Met Ala Val Asp Ala Thr Ala Val Ser Gln Glu Glu Leu Glu Ala
1               5                   10                  15

Lys Ala Trp Glu Gly Phe Thr Glu Gly Asn Trp Gln Lys Asp Ile Asp
            20                  25                  30

Val Arg Asp Phe Ile Gln Lys Asn Tyr Thr Pro Tyr Glu Gly Asp Glu
        35                  40                  45

Ser Phe Leu Ala Asp Ala Thr Asp Lys Thr Lys His Leu Trp Lys Tyr
    50                  55                  60

Leu Asp Asp Asn Tyr Leu Ser Val Glu Arg Lys Gln Arg Val Tyr Asp
65                  70                  75                  80

Val Asp Thr His Thr Pro Ala Gly Ile Asp Ala Phe Pro Ala Gly Tyr
                85                  90                  95

Ile Asp Ser Pro Glu Val Asp Asn Val Ile Val Gly Leu Gln Thr Asp
            100                 105                 110

Val Pro Cys Lys Arg Ala Met Met Pro Asn Gly Gly Trp Arg Met Val
        115                 120                 125

Glu Gln Ala Ile Lys Glu Ala Gly Lys Glu Pro Asp Pro Glu Ile Lys
    130                 135                 140

Lys Ile Phe Thr Lys Tyr Arg Lys Thr His Asn Asp Gly Val Phe Gly
145                 150                 155                 160

Val Tyr Thr Lys Gln Ile Lys Val Ala Arg His Asn Lys Ile Leu Thr
                165                 170                 175

Gly Leu Pro Asp Ala Tyr Gly Arg Gly Arg Ile Ile Gly Asp Tyr Arg
            180                 185                 190

Arg Val Ala Leu Tyr Gly Val Asn Ala Leu Ile Lys Phe Lys Gln Arg
        195                 200                 205

Asp Lys Asp Ser Ile Pro Tyr Arg Asn Asp Phe Thr Glu Pro Glu Ile
    210                 215                 220

Glu His Trp Ile Arg Phe Arg Glu Glu His Asp Glu Gln Ile Lys Ala
225                 230                 235                 240

Leu Lys Gln Leu Ile Asn Leu Gly Asn Glu Tyr Gly Leu Asp Leu Ser
                245                 250                 255

Arg Pro Ala Gln Thr Ala Gln Glu Ala Val Gln Trp Thr Tyr Met Gly
            260                 265                 270

Tyr Leu Ala Ser Val Lys Ser Gln Asp Gly Ala Ala Met Ser Phe Gly
        275                 280                 285

Arg Val Ser Thr Phe Phe Asp Val Tyr Phe Glu Arg Asp Leu Lys Ala
        290                 295                 300

Gly Lys Ile Thr Glu Thr Asp Ala Gln Glu Ile Ile Asp Asn Leu Val
305                 310                 315                 320

Met Lys Leu Arg Ile Val Arg Phe Leu Arg Thr Lys Tyr Asp Ala
                325                 330                 335
```

```
Ile Phe Ser Gly Asp Pro Tyr Trp Ala Thr Trp Ser Asp Ala Gly Phe
            340                 345                 350

Gly Asp Asp Gly Arg Thr Met Val Thr Lys Thr Ser Phe Arg Leu Leu
        355                 360                 365

Asn Thr Leu Thr Leu Glu His Leu Gly Pro Gly Pro Glu Pro Asn Ile
    370                 375                 380

Thr Ile Phe Trp Asp Pro Lys Leu Pro Glu Ala Tyr Lys Arg Phe Cys
385                 390                 395                 400

Ala Arg Ile Ser Ile Asp Thr Ser Ala Ile Gln Tyr Glu Ser Asp Lys
                405                 410                 415

Glu Ile Arg Ser His Trp Gly Asp Asp Ala Ala Ile Ala Cys Cys Val
            420                 425                 430

Ser Pro Met Arg Val Gly Lys Gln Met Gln Phe Phe Ala Ala Arg Val
        435                 440                 445

Asn Ser Ala Lys Ala Leu Leu Tyr Ala Ile Asn Gly Gly Arg Asp Glu
    450                 455                 460

Met Thr Gly Met Gln Val Ile Asp Lys Gly Val Ile Asp Pro Ile Lys
465                 470                 475                 480

Pro Glu Ala Asp Gly Thr Leu Asp Tyr Glu Lys Val Lys Ala Asn Tyr
                485                 490                 495

Glu Lys Ala Leu Glu Trp Leu Ser Glu Thr Tyr Val Met Ala Leu Asn
            500                 505                 510

Ile Ile His Tyr Met His Asp Lys Tyr Ala Tyr Glu Ser Ile Glu Met
            515                 520                 525

Ala Leu His Asp Lys Glu Val Tyr Arg Thr Leu Gly Cys Gly Met Ser
        530                 535                 540

Gly Leu Ser Ile Ala Ala Asp Ser Leu Ser Ala Cys Lys Tyr Ala Lys
545                 550                 555                 560

Val Tyr Pro Ile Tyr Asn Lys Asp Ala Lys Thr Thr Pro Gly His Glu
                565                 570                 575

Asn Glu Tyr Val Glu Gly Ala Asp Asp Leu Ile Val Gly Tyr Arg
            580                 585                 590

Thr Glu Gly Asp Phe Pro Leu Tyr Gly Asn Asp Asp Arg Ala Asp
        595                 600                 605

Asp Ile Ala Lys Trp Val Val Ser Thr Val Met Gly Gln Val Lys Arg
610                 615                 620

Leu Pro Val Tyr Arg Asp Ala Val Pro Thr Gln Ser Ile Leu Thr Ile
625                 630                 635                 640

Thr Ser Asn Val Glu Tyr Gly Lys Ala Thr Gly Ala Phe Pro Ser Gly
                645                 650                 655

His Lys Lys Gly Thr Pro Tyr Ala Pro Gly Ala Asn Pro Glu Asn Gly
            660                 665                 670

Met Asp Ser His Gly Met Leu Pro Ser Met Phe Ser Val Gly Lys Ile
        675                 680                 685

Asp Tyr Asn Asp Ala Leu Asp Gly Ile Ser Leu Thr Asn Thr Ile Thr
690                 695                 700

Pro Asp Gly Leu Gly Arg Asp Glu Glu Arg Ile Gly Asn Leu Val
705                 710                 715                 720

Gly Ile Leu Asp Ala Gly Asn Gly His Gly Leu Tyr His Ala Asn Ile
                725                 730                 735

Asn Val Leu Arg Lys Glu Gln Leu Glu Asp Ala Val Glu His Pro Glu
            740                 745                 750
```

Lys Tyr Pro His Leu Thr Val Arg Val Ser Gly Tyr Ala Val Asn Phe
                755                 760                 765

Val Lys Leu Thr Lys Glu Gln Gln Leu Asp Val Ile Ser Arg Thr Phe
        770                 775                 780

His Gln Gly Ala Val Val Asp
785                 790

<210> SEQ ID NO 10
<211> LENGTH: 879
<212> TYPE: DNA
<213> ORGANISM: Bifidobacterium adolescentis

<400> SEQUENCE: 10

```
atgtctgaac atattttccg ttccacgacc agacacatgc tgagggattc caaggactac      60
gtcaatcaga cgctgatggg aggcctgtcc ggattcgaat cgccaatcgg cttggaccgt     120
ctcgaccgca tcaaggcgtt gaaaagcggc gatatcggtt tcgtgcactc gtgggacatc     180
aacacttccg tggatggtcc tggcaccaga atgaccgtgt tcatgagcgg atgccctctg     240
cgctgccagt actgccagaa tccggatact tggaagatgc gcgacggcaa gcccgtctac     300
tacgaagcca tggtcaagaa aatcgagcgg tatgccgatt tattcaaggc caccggcggc     360
ggcatcactt tctccggcgg cgaatccatg atgcagccgg ctttcgtgtc acgcgtgttc     420
catgccgcca gcagatgggg agtgcatacc tgcctcgaca cgtccggatt cctcggggcg     480
agctacaccg atgacatggt ggatgacatc gacctgtgcc tgcttgacgt caaatccggc     540
gatgaggaga cctaccataa ggtgaccggc ggcatcctgc agccgaccat cgacttcgga     600
cagcgtctgg ccaaggcagg caagaagatc tgggtgcgtt tcgtgctcgt gccgggcctc     660
acatcctccg aagaaaacgt cgagaacgtg gcgaagatct gcgagacctt cggcgacgcg     720
ttggaacata tcgacgtatt gcccttccac cagcttggcc gtccgaagtg gcacatgctg     780
aacatcccat acccgttgga ggaccagaaa ggcccgtccg cggcaatgaa caacgtgtg      840
gtcgagcagt tccagtcgca cggcttcacc gtgtactaa                            879
```

<210> SEQ ID NO 11
<211> LENGTH: 292
<212> TYPE: PRT
<213> ORGANISM: Bifidobacterium adolescentis

<400> SEQUENCE: 11

Met Ser Glu His Ile Phe Arg Ser Thr Thr Arg His Met Leu Arg Asp
1               5                   10                  15

Ser Lys Asp Tyr Val Asn Gln Thr Leu Met Gly Gly Leu Ser Gly Phe
            20                  25                  30

Glu Ser Pro Ile Gly Leu Asp Arg Leu Asp Arg Ile Lys Ala Leu Lys
        35                  40                  45

Ser Gly Asp Ile Gly Phe Val His Ser Trp Asp Ile Asn Thr Ser Val
    50                  55                  60

Asp Gly Pro Gly Thr Arg Met Thr Val Phe Met Ser Gly Cys Pro Leu
65                  70                  75                  80

Arg Cys Gln Tyr Cys Gln Asn Pro Asp Thr Trp Lys Met Arg Asp Gly
                85                  90                  95

Lys Pro Val Tyr Tyr Glu Ala Met Val Lys Lys Ile Glu Arg Tyr Ala
            100                 105                 110

Asp Leu Phe Lys Ala Thr Gly Gly Gly Ile Thr Phe Ser Gly Gly Glu
        115                 120                 125

```
Ser Met Met Gln Pro Ala Phe Val Ser Arg Val Phe His Ala Ala Lys
    130                 135                 140
Gln Met Gly Val His Thr Cys Leu Asp Thr Ser Gly Phe Leu Gly Ala
145                 150                 155                 160
Ser Tyr Thr Asp Asp Met Val Asp Asp Ile Asp Leu Cys Leu Leu Asp
                165                 170                 175
Val Lys Ser Gly Asp Glu Glu Thr Tyr His Lys Val Thr Gly Gly Ile
            180                 185                 190
Leu Gln Pro Thr Ile Asp Phe Gly Gln Arg Leu Ala Lys Ala Gly Lys
        195                 200                 205
Lys Ile Trp Val Arg Phe Val Leu Val Pro Gly Leu Thr Ser Ser Glu
210                 215                 220
Glu Asn Val Glu Asn Val Ala Lys Ile Cys Glu Thr Phe Gly Asp Ala
225                 230                 235                 240
Leu Glu His Ile Asp Val Leu Pro Phe His Gln Leu Gly Arg Pro Lys
                245                 250                 255
Trp His Met Leu Asn Ile Pro Tyr Pro Leu Glu Asp Gln Lys Gly Pro
            260                 265                 270
Ser Ala Ala Met Lys Gln Arg Val Val Glu Gln Phe Gln Ser His Gly
        275                 280                 285
Phe Thr Val Tyr
    290

<210> SEQ ID NO 12
<211> LENGTH: 2733
<212> TYPE: DNA
<213> ORGANISM: Bifidobacterium adolescentis

<400> SEQUENCE: 12
atggcagacg caaagaagaa ggaagagccg accaagccga ctccggaaga gaagctcgcc      60
gcagccgagg ctgaggtcga cgctctggtc aagaagggcc tgaaggctct tgatgaattc     120
gagaagctcg atcagaagca ggttgaccac atcgtggcca aggcttccgt cgcagccctg     180
aacaagcact tggtgctcgc caagatgggc gtcgaggaga cccaccgtgg tctggtcgaa     240
gacaaggcca ccaagaacat cttcgcctgc gagcatgtca ccaactacct ggctggtcag     300
aagaccgtcg gcatcatccg cgaggacgac gtgctgggca tcgacgaaat cgccgagccg     360
gttggcgtcg tcgctggcgt gaccccggtc accaacccga cctccaccgc catcttcaag     420
tcgctgatcg cactgaagac ccgctgcccg atcatcttcg gcttccaccc gggcgcacag     480
aactgctccg tcgcggccgc caagatcgtt cgcgatgccg ctatcgcagc aggcgctcct     540
gagaactgta ttcagtggat cgagcatccg tccatcgagg ccactggcgc cctgatgaag     600
catgatggtg tcgccaccat cctcgccacc ggtggtccgg gcatggtcaa ggccgcatac     660
tcctccggca gccggcccct gggcgtcggc gcgggcaatg ctccggcata cgttgacaag     720
aacgtcgacg tcgtcgtgc agccaacgat ctgattcttt ccaagcactt cgattacggc     780
atgatctgcg ctaccgagca ggccatcatc gccgacaagg acatctacgc tccgctcgtt     840
aaggaactca gcgtcgcaa ggcctatttc gtgaacgctg acgagaaggc caagctcgag     900
cagtacatgt tcggctgcac cgcttactcc ggacagaccc cgaagctcaa ctccgtggtg     960
ccgggcaagt ccccgcagta catcgccaag gccgccggct tcgagattcc ggaagacgcc    1020
accatccttg ccgctgagtg caaggaagtc ggcgagaacg agccgctgac catggagaag    1080
cttgctccgg tccaggccgt gctgaagtcc gacaacaagg aacaggcctt cgagatgtgc    1140
```

-continued

```
gaagccatgc tgaagcatgg cgccggccac accgccgcca tccacaccaa cgaccgtgac    1200
ctggtccgcg agtacggcca gcgcatgcac gcctgccgta tcatctggaa ctccccgagc    1260
tccctcggcg gcgtgggcga catctacaac gccatcgctc cgtccctgac cctgggctgc    1320
ggctcctacg gcggcaactc cgtgtccggc aacgtccagg cagtcaacct catcaacatc    1380
aagcgcatcg ctcggaggaa caacaacatg cagtggttca agattccggc caagacctac    1440
ttcgagccga cgccatcaa gtacctgcgc gacatgtacg gcatcgaaaa ggccgtcatc    1500
gtgtgcgata aggtcatgga gcagctcggc atcgttgaca agatcatcga tcagctgcgt    1560
gcacgttcca accgcgtgac cttccgtatc atcgattatg tcgagccgga gccgagcgtg    1620
gagaccgtcg aacgtggcgc cgccatgatg cgcgaggagt cgagccgga taccatcatc    1680 gccgtcggcg gtggttcccc gatggatgcg tccaagatta tgtggctgct gtacgagcac    1740
ccggaaatct ccttctccga tgtgcgtgag aagttcttcg atatccgtaa gcgcgcgttc    1800
aagattccgc cgctgggcaa gaaggccaag ctggtctgca ttccgacttc ttccggcacc    1860
ggttccgaag tcacgccgtt cgctgtgatt accgaccaca agaccggcta taagtacccg    1920
atcaccgatt acgcgctgac cccgtccgtc gctatcgtcg atccggtgct ggcacgtact    1980
cagccgcgca gctggcttc cgatgctggt ttcgatgctc tgacccacgc ttttgaggct    2040
tatgtgtccg tgtatgccaa cgacttcacc gatggtatgg cattgcacgc tgccaagctg    2100
gtttgggaca acctcgctga gtccgtcaat ggcgagccgg tgaggagaa acccgtgcc    2160 caggagaaga tgcataatgc cgccaccatg gccggcatgg ctttcggctc cgccttcctc    2220
ggcatgtgcc acggcatggc ccacaccatt ggtgcactgt gccacgttgc ccacggtcgt    2280
accaactcca tcctcctgcc gtacgtgatc cgttacaacg gttccgtccc ggaggagccg    2340
accagctggc cgaagtacaa caagtacatc gctccggaac gctaccagga gatcgccaag    2400
aaccttggcg tgaacccggg caagactccg gaagagggcg tcgagaacct ggccaaggct    2460
gttgaggatt accgtgacaa caagctcggt atgaacaaga gcttccagga gtgcggtgtg    2520
gatgaggact actattggtc catcatcgac cagatcggca tgcgcgccta cgaagaccag    2580
tgcgcaccgg cgaacccgcg tatcccgcag atcgaggata tgaaggatat cgccattgcc    2640
gcctactacg gcgtcagcca ggcggaaggc cacaagctgc gcgtccagcg tcagggcgaa    2700
gccgctacgg aggaagcttc cgagcgcgcc tga                                 2733
```

<210> SEQ ID NO 13
<211> LENGTH: 910
<212> TYPE: PRT
<213> ORGANISM: Bifidobacterium adolescentis

<400> SEQUENCE: 13

```
Met Ala Asp Ala Lys Lys Lys Glu Glu Pro Thr Lys Pro Thr Pro Glu
1               5                   10                  15

Glu Lys Leu Ala Ala Ala Glu Ala Glu Val Asp Ala Leu Val Lys Lys
            20                  25                  30

Gly Leu Lys Ala Leu Asp Glu Phe Glu Lys Leu Asp Gln Lys Gln Val
        35                  40                  45

Asp His Ile Val Ala Lys Ser Val Ala Ala Leu Asn Lys His Leu
    50                  55                  60

Val Leu Ala Lys Met Ala Val Glu Glu Thr His Arg Gly Leu Val Glu
65                  70                  75                  80

Asp Lys Ala Thr Lys Asn Ile Phe Ala Cys Glu His Val Thr Asn Tyr
            85                  90                  95
```

```
Leu Ala Gly Gln Lys Thr Val Gly Ile Ile Arg Glu Asp Val Leu
            100                 105                 110
Gly Ile Asp Glu Ile Ala Glu Pro Val Gly Val Ala Gly Val Thr
        115                 120                 125
Pro Val Thr Asn Pro Thr Ser Thr Ala Ile Phe Lys Ser Leu Ile Ala
130                 135                 140
Leu Lys Thr Arg Cys Pro Ile Ile Phe Gly Phe His Pro Gly Ala Gln
145                 150                 155                 160
Asn Cys Ser Val Ala Ala Ala Lys Ile Val Arg Asp Ala Ala Ile Ala
                165                 170                 175
Ala Gly Ala Pro Glu Asn Cys Ile Gln Trp Ile Glu His Pro Ser Ile
            180                 185                 190
Glu Ala Thr Gly Ala Leu Met Lys His Asp Gly Val Ala Thr Ile Leu
        195                 200                 205
Ala Thr Gly Gly Pro Gly Met Val Lys Ala Ala Tyr Ser Ser Gly Lys
        210                 215                 220
Pro Ala Leu Gly Val Gly Ala Gly Asn Ala Pro Ala Tyr Val Asp Lys
225                 230                 235                 240
Asn Val Asp Val Arg Ala Ala Asn Asp Leu Ile Leu Ser Lys His
                245                 250                 255
Phe Asp Tyr Gly Met Ile Cys Ala Thr Glu Gln Ala Ile Ile Ala Asp
                260                 265                 270
Lys Asp Ile Tyr Ala Pro Leu Val Lys Glu Leu Lys Arg Arg Lys Ala
                275                 280                 285
Tyr Phe Val Asn Ala Asp Glu Lys Ala Lys Leu Glu Gln Tyr Met Phe
            290                 295                 300
Gly Cys Thr Ala Tyr Ser Gly Gln Thr Pro Lys Leu Asn Ser Val Val
305                 310                 315                 320
Pro Gly Lys Ser Pro Gln Tyr Ile Ala Lys Ala Ala Gly Phe Glu Ile
                325                 330                 335
Pro Glu Asp Ala Thr Ile Leu Ala Ala Glu Cys Lys Glu Val Gly Glu
            340                 345                 350
Asn Glu Pro Leu Thr Met Glu Lys Leu Ala Pro Val Gln Ala Val Leu
        355                 360                 365
Lys Ser Asp Asn Lys Glu Gln Ala Phe Glu Met Cys Glu Ala Met Leu
370                 375                 380
Lys His Gly Ala Gly His Thr Ala Ala Ile His Thr Asn Asp Arg Asp
385                 390                 395                 400
Leu Val Arg Glu Tyr Gly Gln Arg Met His Ala Cys Arg Ile Ile Trp
                405                 410                 415
Asn Ser Pro Ser Ser Leu Gly Gly Val Gly Asp Ile Tyr Asn Ala Ile
                420                 425                 430
Ala Pro Ser Leu Thr Leu Gly Cys Gly Ser Tyr Gly Gly Asn Ser Val
            435                 440                 445
Ser Gly Asn Val Gln Ala Val Asn Leu Ile Asn Ile Lys Arg Ile Ala
        450                 455                 460
Arg Arg Asn Asn Asn Met Gln Trp Phe Lys Ile Pro Ala Lys Thr Tyr
465                 470                 475                 480
Phe Glu Pro Asn Ala Ile Lys Tyr Leu Arg Asp Met Tyr Gly Ile Glu
                485                 490                 495
Lys Ala Val Ile Val Cys Asp Lys Val Met Glu Gln Leu Gly Ile Val
            500                 505                 510
```

-continued

```
Asp Lys Ile Ile Asp Gln Leu Arg Ala Arg Ser Asn Arg Val Thr Phe
        515                 520                 525

Arg Ile Ile Asp Tyr Val Glu Pro Glu Pro Ser Val Glu Thr Val Glu
    530                 535                 540

Arg Gly Ala Ala Met Met Arg Glu Glu Phe Glu Pro Asp Thr Ile Ile
545                 550                 555                 560

Ala Val Gly Gly Gly Ser Pro Met Asp Ala Ser Lys Ile Met Trp Leu
                565                 570                 575

Leu Tyr Glu His Pro Glu Ile Ser Phe Ser Asp Val Arg Glu Lys Phe
            580                 585                 590

Phe Asp Ile Arg Lys Arg Ala Phe Lys Ile Pro Pro Leu Gly Lys Lys
        595                 600                 605

Ala Lys Leu Val Cys Ile Pro Thr Ser Ser Gly Thr Gly Ser Glu Val
    610                 615                 620

Thr Pro Phe Ala Val Ile Thr Asp His Lys Thr Gly Tyr Lys Tyr Pro
625                 630                 635                 640

Ile Thr Asp Tyr Ala Leu Thr Pro Ser Val Ala Ile Val Asp Pro Val
                645                 650                 655

Leu Ala Arg Thr Gln Pro Arg Lys Leu Ala Ser Asp Ala Gly Phe Asp
            660                 665                 670

Ala Leu Thr His Ala Phe Glu Ala Tyr Val Ser Val Tyr Ala Asn Asp
        675                 680                 685

Phe Thr Asp Gly Met Ala Leu His Ala Ala Lys Leu Val Trp Asp Asn
    690                 695                 700

Leu Ala Glu Ser Val Asn Gly Glu Pro Gly Glu Lys Thr Arg Ala
705                 710                 715                 720

Gln Glu Lys Met His Asn Ala Ala Thr Met Ala Gly Met Ala Phe Gly
                725                 730                 735

Ser Ala Phe Leu Gly Met Cys His Gly Met Ala His Thr Ile Gly Ala
            740                 745                 750

Leu Cys His Val Ala His Gly Arg Thr Asn Ser Ile Leu Leu Pro Tyr
        755                 760                 765

Val Ile Arg Tyr Asn Gly Ser Val Pro Glu Glu Pro Thr Ser Trp Pro
    770                 775                 780

Lys Tyr Asn Lys Tyr Ile Ala Pro Glu Arg Tyr Gln Glu Ile Ala Lys
785                 790                 795                 800

Asn Leu Gly Val Asn Pro Gly Lys Thr Pro Glu Glu Gly Val Glu Asn
                805                 810                 815

Leu Ala Lys Ala Val Glu Asp Tyr Arg Asp Asn Lys Leu Gly Met Asn
            820                 825                 830

Lys Ser Phe Gln Glu Cys Gly Val Asp Glu Asp Tyr Tyr Trp Ser Ile
        835                 840                 845

Ile Asp Gln Ile Gly Met Arg Ala Tyr Glu Asp Gln Cys Ala Pro Ala
    850                 855                 860

Asn Pro Arg Ile Pro Gln Ile Glu Asp Met Lys Asp Ile Ala Ile Ala
865                 870                 875                 880

Ala Tyr Tyr Gly Val Ser Gln Ala Glu Gly His Lys Leu Arg Val Gln
                885                 890                 895

Arg Gln Gly Glu Ala Ala Thr Glu Glu Ala Ser Glu Arg Ala
            900                 905                 910
```

<210> SEQ ID NO 14
<211> LENGTH: 2703
<212> TYPE: DNA
<213> ORGANISM: Leuconostoc mesenteroides

<400> SEQUENCE: 14

| | | | | | | |
|---|---|---|---|---|---|---|
| atggcagaag | caattgcaaa | gaaacccgca | aaaagggttt | tgacccctga | agaaaaagcg | 60 |
| gaattacaaa | cacaagctga | gaagatgact | gaggtattga | ttgaaaaatc | acaaaaggca | 120 |
| ttgtctgaat | tttcaacatt | ttcgcaagaa | caagttgata | aaattgttgc | agctatggcc | 180 |
| ttggcaggtt | ctgagaattc | acttctgtta | gcccatgctg | ctcacgacga | gactggacgt | 240 |
| ggggttgtgg | aagataagga | tacgaaaaat | cgtttcgcct | cagaatcagt | ttataacgct | 300 |
| attaagtttg | ataagactgt | gggtgttatt | agtgaagaca | agattcaagg | taaggtagaa | 360 |
| ttagcagccc | cacttggtat | tttggctgga | atcgtcccaa | cgacaaatcc | aacgtcgaca | 420 |
| actattttca | aatcaatgtt | gacagcaaag | acacgtaaca | caattatctt | tgcttttccat | 480 |
| ccccaggctc | aaaaagcatc | ggttcttgct | gcaaaaattg | tttatgatgc | tgctgttaaa | 540 |
| gcaggcgcac | cggaaaactt | tatccaatgg | attgaaaagc | cttcacttta | tgcaacaagt | 600 |
| gcgctgatac | aaaatcctca | cattgcttca | attctagcta | ctggtgggcc | atcaatggtt | 660 |
| aatgcagctt | tgaagtcagg | aaatccatcc | atgggtgtcg | gtgctggaaa | cggtgcagtt | 720 |
| tatattgatg | caactgttga | cacagatcgt | gccgtgtccg | atttgttgtt | atcaaagcgt | 780 |
| ttcgataatg | gcatgatttg | tgccacagaa | aactcagccg | ttattcaagc | accaatctat | 840 |
| gacgaaattt | taactaagtt | acaagaacaa | ggtgcatacc | ttgttcctaa | gaaagactac | 900 |
| aaaaaaattg | ctgattatgt | atttaagcct | aacgcagagg | gatttggtat | tgctggtcct | 960 |
| gttgctggta | tgtcaggacg | ttggattgct | gagcaagcag | gcgtaaagat | tcctgatggt | 1020 |
| aaagatgtac | ttttgttcga | attagatcag | aagaacatag | gtgaagcgtt | atcttctgaa | 1080 |
| aagttatcgc | cattactttc | aatttataaa | gttgagaagc | gtgaagaagc | tattgagact | 1140 |
| gttcaatcct | tgttaaacta | tcaaggcgcg | ggcacaacg | cagcaattca | aattggttca | 1200 |
| caagatgatc | cattcattaa | agagtatgct | gacgctattg | gtgcatcacg | tattttggtt | 1260 |
| aaccaacctg | actcaatcgg | tggtgttgga | gatatttaca | cagatgctat | gcgtccatcg | 1320 |
| ttgacacttg | gtaccggatc | atgggggaag | aattcattgt | ctcataactt | atcaacatac | 1380 |
| gacttactta | atattaagac | cgtggctcgc | cgccgtaatc | gtcctcaatg | ggttcgttta | 1440 |
| cctaaggaag | tttactacga | agccaatgcc | attacttact | tacaagactt | gcctactata | 1500 |
| aaccgtgcat | ttattgtcgc | tgatcctggt | atggttcagt | tcggatttgt | tggcagagta | 1560 |
| ctaggtcaac | ttgagttacg | tcaagaacag | gttgaaacaa | atatctatgg | ttcagttaag | 1620 |
| cctgacccaa | ctttgtcaca | agctgttgaa | attgctcgcc | aaatggcaga | cttcaaacca | 1680 |
| gatacagtta | ttttacttgg | cggtggttcg | gcacttgacg | ctggtaaaat | tggtcggttc | 1740 |
| ttgtacgaat | actcgacacg | ccatgaagga | attttagaag | atgacgaggc | gattaaagat | 1800 |
| ctattcttag | aactacaaca | aaagtttatg | gatattcgta | agcgaatcgt | taagttttac | 1860 |
| cacgcacgtt | tgacacaaat | ggttgcgatt | ccaacaactt | caggtactgg | atcagaagtc | 1920 |
| acaccatttg | ccgttattac | agatgatgaa | acacatgtaa | agtatccact | agccgattat | 1980 |
| gaattgacac | cggaagttgc | tattgttgat | ccagaatttg | ttatgaccgt | accacaacac | 2040 |
| acggtatctt | ggtcaggatt | agatgctttg | tcacatgctt | tggaatcgta | tgtctcagtg | 2100 |
| atggcttctg | aattcacacg | tccttgggca | ttacaagcta | ttaagttgat | ttttgataac | 2160 |

-continued

```
ttaacaaatt catacaatta tgatcctaaa cacccaacta aggaaggtca gaatgcacgc    2220
acaaagatgc actatgcgtc aacattggct ggtatgtcat ttgcgaatgc cttcttggga    2280
cttaaccact cactagcaca caaaactggt ggagaattcg gactacctca cggtatggca    2340
atcgctattg caatgccaca tgtgattaag tttaatgcgg taacaggaaa tgtaaagcgc    2400
acaccatacc cacgttacga aacctataca gcacaaaaag attatgctga tattgcacgt    2460
tacttaggtt tgaaaggtga aacagatgct gaattggtcg atgtattgat tgcagaaatc    2520
aagaagttgg ctgcatcagt gggtgtcaat caaacactat ctggcaacgg tgtttcaaag    2580
catgactttg atacaaagtt agaaaagatg attgacttag tttacaatga ccaatgcacg    2640
ccgggaaacc ctcgccaacc aagcttggca gaaattcgtc aattgttgaa agatcagttt    2700
taa                                                                  2703
```

<210> SEQ ID NO 15
<211> LENGTH: 900
<212> TYPE: PRT
<213> ORGANISM: Leuconostoc mesenteroides

<400> SEQUENCE: 15

```
Met Ala Glu Ala Ile Ala Lys Lys Pro Ala Lys Arg Val Leu Thr Pro
  1               5                  10                  15

Glu Glu Lys Ala Glu Leu Gln Thr Gln Ala Glu Lys Met Thr Glu Val
             20                  25                  30

Leu Ile Glu Lys Ser Gln Lys Ala Leu Ser Glu Phe Ser Thr Phe Ser
         35                  40                  45

Gln Glu Gln Val Asp Lys Ile Val Ala Ala Met Ala Leu Ala Gly Ser
     50                  55                  60

Glu Asn Ser Leu Leu Leu Ala His Ala Ala His Asp Glu Thr Gly Arg
 65                  70                  75                  80

Gly Val Val Glu Asp Lys Asp Thr Lys Asn Arg Phe Ala Ser Glu Ser
                 85                  90                  95

Val Tyr Asn Ala Ile Lys Phe Asp Lys Thr Val Gly Val Ile Ser Glu
            100                 105                 110

Asp Lys Ile Gln Gly Lys Val Glu Leu Ala Ala Pro Leu Gly Ile Leu
        115                 120                 125

Ala Gly Ile Val Pro Thr Thr Asn Pro Thr Ser Thr Thr Ile Phe Lys
    130                 135                 140

Ser Met Leu Thr Ala Lys Thr Arg Asn Thr Ile Ile Phe Ala Phe His
145                 150                 155                 160

Pro Gln Ala Gln Lys Ala Ser Val Leu Ala Ala Lys Ile Val Tyr Asp
                165                 170                 175

Ala Ala Val Lys Ala Gly Ala Pro Glu Asn Phe Ile Gln Trp Ile Glu
            180                 185                 190

Lys Pro Ser Leu Tyr Ala Thr Ser Ala Leu Ile Gln Asn Pro His Ile
        195                 200                 205

Ala Ser Ile Leu Ala Thr Gly Gly Pro Ser Met Val Asn Ala Ala Leu
    210                 215                 220

Lys Ser Gly Asn Pro Ser Met Gly Val Gly Ala Gly Asn Gly Ala Val
225                 230                 235                 240

Tyr Ile Asp Ala Thr Val Asp Thr Asp Arg Ala Val Ser Asp Leu Leu
                245                 250                 255

Leu Ser Lys Arg Phe Asp Asn Gly Met Ile Cys Ala Thr Glu Asn Ser
            260                 265                 270
```

```
Ala Val Ile Gln Ala Pro Ile Tyr Asp Glu Ile Leu Thr Lys Leu Gln
            275                 280                 285

Glu Gln Gly Ala Tyr Leu Val Pro Lys Lys Asp Tyr Lys Lys Ile Ala
    290                 295                 300

Asp Tyr Val Phe Lys Pro Asn Ala Glu Gly Phe Gly Ile Ala Gly Pro
305                 310                 315                 320

Val Ala Gly Met Ser Gly Arg Trp Ile Ala Glu Gln Ala Gly Val Lys
                325                 330                 335

Ile Pro Asp Gly Lys Asp Val Leu Leu Phe Glu Leu Asp Gln Lys Asn
            340                 345                 350

Ile Gly Glu Ala Leu Ser Ser Glu Lys Leu Ser Pro Leu Leu Ser Ile
        355                 360                 365

Tyr Lys Val Glu Lys Arg Glu Glu Ala Ile Glu Thr Val Gln Ser Leu
    370                 375                 380

Leu Asn Tyr Gln Gly Ala Gly His Asn Ala Ala Ile Gln Ile Gly Ser
385                 390                 395                 400

Gln Asp Asp Pro Phe Ile Lys Glu Tyr Ala Asp Ala Ile Gly Ala Ser
                405                 410                 415

Arg Ile Leu Val Asn Gln Pro Asp Ser Ile Gly Gly Val Gly Asp Ile
            420                 425                 430

Tyr Thr Asp Ala Met Arg Pro Ser Leu Thr Leu Gly Thr Gly Ser Trp
        435                 440                 445

Gly Lys Asn Ser Leu Ser His Asn Leu Ser Thr Tyr Asp Leu Leu Asn
    450                 455                 460

Ile Lys Thr Val Ala Arg Arg Asn Arg Pro Gln Trp Val Arg Leu
465                 470                 475                 480

Pro Lys Glu Val Tyr Tyr Glu Ala Asn Ala Ile Thr Tyr Leu Gln Asp
                485                 490                 495

Leu Pro Thr Ile Asn Arg Ala Phe Ile Val Ala Asp Pro Gly Met Val
            500                 505                 510

Gln Phe Gly Phe Val Gly Arg Val Leu Gly Gln Leu Glu Leu Arg Gln
        515                 520                 525

Glu Gln Val Glu Thr Asn Ile Tyr Gly Ser Val Lys Pro Asp Pro Thr
    530                 535                 540

Leu Ser Gln Ala Val Glu Ile Ala Arg Gln Met Ala Asp Phe Lys Pro
545                 550                 555                 560

Asp Thr Val Ile Leu Leu Gly Gly Gly Ser Ala Leu Asp Ala Gly Lys
                565                 570                 575

Ile Gly Arg Phe Leu Tyr Glu Tyr Ser Thr Arg His Glu Gly Ile Leu
            580                 585                 590

Glu Asp Asp Glu Ala Ile Lys Asp Leu Phe Leu Glu Leu Gln Gln Lys
        595                 600                 605

Phe Met Asp Ile Arg Lys Arg Ile Val Lys Phe Tyr His Ala Arg Leu
    610                 615                 620

Thr Gln Met Val Ala Ile Pro Thr Thr Ser Gly Thr Gly Ser Glu Val
625                 630                 635                 640

Thr Pro Phe Ala Val Ile Thr Asp Asp Glu Thr His Val Lys Tyr Pro
                645                 650                 655

Leu Ala Asp Tyr Glu Leu Thr Pro Glu Val Ala Ile Val Asp Pro Glu
            660                 665                 670

Phe Val Met Thr Val Pro Gln His Thr Val Ser Trp Ser Gly Leu Asp
        675                 680                 685
```

Ala Leu Ser His Ala Leu Glu Ser Tyr Val Ser Val Met Ala Ser Glu
690                 695                 700

Phe Thr Arg Pro Trp Ala Leu Gln Ala Ile Lys Leu Ile Phe Asp Asn
705                 710                 715                 720

Leu Thr Asn Ser Tyr Asn Tyr Asp Pro Lys His Pro Thr Lys Glu Gly
            725                 730                 735

Gln Asn Ala Arg Thr Lys Met His Tyr Ala Ser Thr Leu Ala Gly Met
        740                 745                 750

Ser Phe Ala Asn Ala Phe Leu Gly Leu Asn His Ser Leu Ala His Lys
    755                 760                 765

Thr Gly Gly Glu Phe Gly Leu Pro His Gly Met Ala Ile Ala Ile Ala
770                 775                 780

Met Pro His Val Ile Lys Phe Asn Ala Val Thr Gly Asn Val Lys Arg
785                 790                 795                 800

Thr Pro Tyr Pro Arg Tyr Glu Thr Tyr Thr Ala Gln Lys Asp Tyr Ala
            805                 810                 815

Asp Ile Ala Arg Tyr Leu Gly Leu Lys Gly Glu Thr Asp Ala Glu Leu
        820                 825                 830

Val Asp Val Leu Ile Ala Glu Ile Lys Lys Leu Ala Ala Ser Val Gly
    835                 840                 845

Val Asn Gln Thr Leu Ser Gly Asn Gly Val Ser Lys His Asp Phe Asp
850                 855                 860

Thr Lys Leu Glu Lys Met Ile Asp Leu Val Tyr Asn Asp Gln Cys Thr
865                 870                 875                 880

Pro Gly Asn Pro Arg Gln Pro Ser Leu Ala Glu Ile Arg Gln Leu Leu
            885                 890                 895

Lys Asp Gln Phe
            900

<210> SEQ ID NO 16
<211> LENGTH: 2697
<212> TYPE: DNA
<213> ORGANISM: Oenococcus oenii

<400> SEQUENCE: 16
atggcagttg aaacgaagaa gattactaaa aagatactga cttccgacga acttaaagac    60
aaaaaggaga cagcaaaaaa atacattgga gaattagtcg ataaatcaag acaggcatta   120
ttagaattct ctcaatatag tcaatcacaa gttgacaaaa ttgttgccgc aatggcttta   180
gccggttccg aacattcttt ggaattagca cactttgctc gaaatgaaac tggaagagga   240
gttgttgaag acaaagatac gaaaaatcgt tttgcctcgg aatctgtata taacacgatt   300
aaaaatgaca aaacagttgg cgtaattgat gaagacccaa tcactggcaa agttcagtta   360
gctgcaccac ttgggatttt agccggaatt gttccaacga caaatccaac gtctaccacg   420
atttttaaat cattgttaac cgctaagaca cgtaatacga tcattttgc ttttcacccg    480 caagcacaaa atcgtctgt agcggctgcg aaaattgttt accaggcggc tagaaaagct   540
ggagcaccga agatttcat tcagtggatc gaaacgcctt ccttggaaaa tacgactgct   600
ttgatgcaaa atcctgaaat agcttcaatt ttggctactg gaggcccttc tatggttcat   660
gccgcattaa catcgggaaa cccttcaatg ggtgttgggg caggaaatgg agctgttttc   720
attgaccata cggctcgtgt tcgtcgagcg gcagaagact tgttgctatc aaaacgtttt   780
gataatggaa tgtttgcgc tacagagaat tccgcagtta tcgaagcttc ggtttatgac   840
gaatttatga aattaatgca ggaaaagggt acttatctcg ttccgaagga tgattacaaa   900

```
aagatcgctg attttgtttt cagcgataaa catgcagtta atggtccggt tgccgggatg    960
agtggccgtt ggattgctga acatgccggt gttactttgc cgaagggcaa agatgttttg   1020
ttgtttgagt tggatcaaga cgacattggc gaaaaacttt cctcggaaaa acttagcccc   1080
ttgctttcgg tctataaagc tgctgatcgt aagaagcga taaaagttgt tcaaagactt    1140
ttgaactatc aaggagctgg tcataatgcg gcaatccaga ttggcgctca agacgatccc   1200
tttgttaaag aatatgccga tgcagtttct gcatctagaa ttttggttaa ccagcccgat   1260
tcaataggtg gagtcggcga tatttataca gatgcattgc gtccaagtat gacgcttggt   1320
actggttcat gggggaagaa ttcattgtca cataatttat caacttacga tttgttgaat   1380
gtcaaaacgg ttgcccgcag acgtaatcgt cctcaatggg ttcgtcttcc aaaagatatc   1440
tactatgaga aaaatgccat acctatctg caggaattac cgaacgtcaa tcgggctttc    1500
gttattaccg atcattcgtt ggtcaaatat ggattcgtcg atcggattct tgagcaattc   1560
gaattgcgtc ccgaccaggt taaaacaagt atttacagtt ctgttcaacc ggatccttat   1620
ttgagtcagg ctgttgaaat tgcaaaacaa atgcaggagt cgaaccgga tacagtaatt    1680
gctcttggag gaggttcctc tttggatgtt gccaagattt cccgttttct ttatgaatat   1740
tctcaagaac cggaccacat tggttttttg gaaaacattg acgatattaa agaattgttt   1800
aaaggattgc agcaaaagtt tatggatatt cggaacgga ttgttaaatt cgaacatcag    1860
aatttgactc aactggttgc tattccaaca acttcgggta ccggttcgga agtaacaccg   1920
ttttcggtta tcaccgatga tgaaactcac gttaaatacc ctttggccga ttatgaatta   1980
actccgcaag ttgcaatcgt tgatcctgaa ttggttatga ctgtaccaaa acggaccctg   2040
gcttggtctg gactggacgc cttatctcac tcgcttgaat cctacgtgtc ggttatgagt   2100
tctgaattta cacggccgtg ggctttacag gcaatcaaac tgattttga aaacatcgtt    2160
gattcctata attacgatcc aaagcaccca actaatcggg gcgccgaggc acgtgaaaaa   2220
atgcattatg ctgcaacttt ggccggcatg tctttcggaa acgccttctt gggtataaac   2280
cattcactgg cccataaaac cggtggagag ttcggtcttc ctcatggttt ggcaatcagc   2340
atcgcgatgc cacatgtaat tcgatttaat gcggttaccg aaacgtcaa acggactcct    2400
tttcctcgtt atgaggttta tacagcccaa aaagattatg ccgatattgc gcgccatatt   2460
ggcctcagcg gtaagaacga tgccgaattg gttgaaaaac ttatcgccaa aatcaaggaa   2520
ttaaccgatg cctttggatgt caatattact ttgagcggca atggagtcga taaaaagagc   2580
tttgaacatt ctttggatca actggttgat cttgtttacg atgaccagtg cacgccagga   2640
aatccgcgac aaccgaattt agctgaaatt aggcagttat tgatcgacca atttttaa     2697
```

<210> SEQ ID NO 17
<211> LENGTH: 898
<212> TYPE: PRT
<213> ORGANISM: Oenococcus oenii

<400> SEQUENCE: 17

```
Met Ala Val Glu Thr Lys Lys Ile Thr Lys Lys Ile Leu Thr Ser Asp
1               5                   10                  15

Glu Leu Lys Asp Lys Lys Glu Thr Ala Lys Lys Tyr Ile Gly Glu Leu
            20                  25                  30

Val Asp Lys Ser Arg Gln Ala Leu Leu Glu Phe Ser Gln Tyr Ser Gln
        35                  40                  45

Ser Gln Val Asp Lys Ile Val Ala Ala Met Ala Leu Ala Gly Ser Glu
    50                  55                  60
```

-continued

```
His Ser Leu Glu Leu Ala His Phe Ala Arg Asn Glu Thr Gly Arg Gly
 65                  70                  75                  80

Val Val Glu Asp Lys Asp Thr Lys Asn Arg Phe Ala Ser Glu Ser Val
                 85                  90                  95

Tyr Asn Thr Ile Lys Asn Asp Lys Thr Val Gly Val Ile Asp Glu Asp
            100                 105                 110

Pro Ile Thr Gly Lys Val Gln Leu Ala Ala Pro Leu Gly Ile Leu Ala
        115                 120                 125

Gly Ile Val Pro Thr Thr Asn Pro Thr Ser Thr Ile Phe Lys Ser
130                 135                 140

Leu Leu Thr Ala Lys Thr Arg Asn Thr Ile Ile Phe Ala Phe His Pro
145                 150                 155                 160

Gln Ala Gln Lys Ser Ser Val Ala Ala Ala Lys Ile Val Tyr Gln Ala
                165                 170                 175

Ala Arg Lys Ala Gly Ala Pro Lys Asp Phe Ile Gln Trp Ile Glu Thr
            180                 185                 190

Pro Ser Leu Glu Asn Thr Thr Ala Leu Met Gln Asn Pro Glu Ile Ala
        195                 200                 205

Ser Ile Leu Ala Thr Gly Gly Pro Ser Met Val His Ala Ala Leu Thr
210                 215                 220

Ser Gly Asn Pro Ser Met Gly Val Gly Ala Gly Asn Gly Ala Val Phe
225                 230                 235                 240

Ile Asp His Thr Ala Arg Val Arg Ala Ala Glu Asp Leu Leu Leu
                245                 250                 255

Ser Lys Arg Phe Asp Asn Gly Met Ile Cys Ala Thr Glu Asn Ser Ala
            260                 265                 270

Val Ile Glu Ala Ser Val Tyr Asp Glu Phe Met Lys Leu Met Gln Glu
        275                 280                 285

Lys Gly Thr Tyr Leu Val Pro Lys Asp Tyr Lys Lys Ile Ala Asp
290                 295                 300

Phe Val Phe Ser Asp Lys His Ala Val Asn Gly Pro Val Ala Gly Met
305                 310                 315                 320

Ser Gly Arg Trp Ile Ala Glu His Ala Gly Val Thr Leu Pro Lys Gly
                325                 330                 335

Lys Asp Val Leu Leu Phe Glu Leu Asp Gln Asp Ile Gly Glu Lys
            340                 345                 350

Leu Ser Ser Glu Lys Leu Ser Pro Leu Leu Ser Val Tyr Lys Ala Ala
        355                 360                 365

Asp Arg Lys Glu Ala Ile Lys Val Val Gln Arg Leu Leu Asn Tyr Gln
370                 375                 380

Gly Ala Gly His Asn Ala Ala Ile Gln Ile Gly Ala Gln Asp Asp Pro
385                 390                 395                 400

Phe Val Lys Glu Tyr Ala Asp Ala Val Ser Ala Ser Arg Ile Leu Val
                405                 410                 415

Asn Gln Pro Asp Ser Ile Gly Gly Val Gly Asp Ile Tyr Thr Asp Ala
            420                 425                 430

Leu Arg Pro Ser Met Thr Leu Gly Thr Gly Ser Trp Gly Lys Asn Ser
        435                 440                 445

Leu Ser His Asn Leu Ser Thr Tyr Asp Leu Leu Asn Val Lys Thr Val
450                 455                 460

Ala Arg Arg Arg Asn Arg Pro Gln Trp Val Arg Leu Pro Lys Asp Ile
465                 470                 475                 480
```

-continued

Tyr Tyr Glu Lys Asn Ala Ile Thr Tyr Leu Gln Glu Leu Pro Asn Val
            485                 490                 495

Asn Arg Ala Phe Val Ile Thr Asp His Ser Leu Val Lys Tyr Gly Phe
        500                 505                 510

Val Asp Arg Ile Leu Glu Gln Phe Glu Leu Arg Pro Asp Gln Val Lys
        515                 520                 525

Thr Ser Ile Tyr Ser Ser Val Gln Pro Asp Pro Tyr Leu Ser Gln Ala
        530                 535                 540

Val Glu Ile Ala Lys Gln Met Gln Glu Phe Glu Pro Asp Thr Val Ile
545                 550                 555                 560

Ala Leu Gly Gly Gly Ser Ser Leu Asp Val Ala Lys Ile Ser Arg Phe
            565                 570                 575

Leu Tyr Glu Tyr Ser Gln Glu Pro Asp His Ile Gly Phe Leu Glu Asn
            580                 585                 590

Ile Asp Asp Ile Lys Glu Leu Phe Lys Gly Leu Gln Gln Lys Phe Met
        595                 600                 605

Asp Ile Arg Lys Arg Ile Val Lys Phe Glu His Gln Asn Leu Thr Gln
        610                 615                 620

Leu Val Ala Ile Pro Thr Thr Ser Gly Thr Gly Ser Glu Val Thr Pro
625                 630                 635                 640

Phe Ser Val Ile Thr Asp Asp Glu Thr His Val Lys Tyr Pro Leu Ala
            645                 650                 655

Asp Tyr Glu Leu Thr Pro Gln Val Ala Ile Val Asp Pro Glu Leu Val
            660                 665                 670

Met Thr Val Pro Lys Arg Thr Leu Ala Trp Ser Gly Leu Asp Ala Leu
        675                 680                 685

Ser His Ser Leu Glu Ser Tyr Val Ser Val Met Ser Ser Glu Phe Thr
        690                 695                 700

Arg Pro Trp Ala Leu Gln Ala Ile Lys Leu Ile Phe Glu Asn Ile Val
705                 710                 715                 720

Asp Ser Tyr Asn Tyr Asp Pro Lys His Pro Thr Asn Arg Gly Ala Glu
            725                 730                 735

Ala Arg Glu Lys Met His Tyr Ala Ala Thr Leu Ala Gly Met Ser Phe
            740                 745                 750

Gly Asn Ala Phe Leu Gly Ile Asn His Ser Leu Ala His Lys Thr Gly
        755                 760                 765

Gly Glu Phe Gly Leu Pro His Gly Leu Ala Ile Ser Ile Ala Met Pro
        770                 775                 780

His Val Ile Arg Phe Asn Ala Val Thr Gly Asn Val Lys Arg Thr Pro
785                 790                 795                 800

Phe Pro Arg Tyr Glu Val Tyr Thr Ala Gln Lys Asp Tyr Ala Asp Ile
            805                 810                 815

Ala Arg His Ile Gly Leu Ser Gly Lys Asn Asp Ala Glu Leu Val Glu
            820                 825                 830

Lys Leu Ile Ala Lys Ile Lys Glu Leu Thr Asp Ala Leu Asp Val Asn
        835                 840                 845

Ile Thr Leu Ser Gly Asn Gly Val Asp Lys Lys Ser Phe Glu His Ser
        850                 855                 860

Leu Asp Gln Leu Val Asp Leu Val Tyr Asp Asp Gln Cys Thr Pro Gly
865                 870                 875                 880

Asn Pro Arg Gln Pro Asn Leu Ala Glu Ile Arg Gln Leu Leu Ile Asp
            885                 890                 895

Gln Phe

<210> SEQ ID NO 18
<211> LENGTH: 1476
<212> TYPE: DNA
<213> ORGANISM: Saccharomyces cerevisiae

<400> SEQUENCE: 18

```
atggagagtc gaactacagg gcctttaacg actgaaacct acgatggccc cactgtggcc      60
ttcatgatat taggtgccgc cctagtattt tttatggtgc ccggattggg attcttgtac     120
tccggattgg caagaaggaa gtctgcacta gcactaatct gggttgtatt aatggcgact     180
ttggtcggta tactgcaatg gtatttctgg ggttactctc tagcttttc aaagtccgct      240
ccgaataata aattcattgg gaatctagat tcgtttggct ttagaaacgt gtacggaaaa     300
aaattcgatg aagatgccta ccctgagctc gcgtatgcaa ccttccaaat gatgttttcg     360
tgcgtcaact taagtattat cgctggcgcc actgccgaaa gaggcaggct gctaccgcac     420
atggttttc tctttattct agctaccatt ggatattgtc cagtgacgta ttggatttgg     480
tcaccaggtg gttgggcata ccaatgggga gtcctcgatt gggcaggcgg cggcaacatt     540
gaaatattaa gcgctgtttc cgggtttgtt tactcttggt ttttgggcaa agaaatgaa      600
aagttactga taaatttcag gcctcataat gtttcattgg tcactctagg cacatccata     660
ctgtggtttg gctggctgct atttaattct gcatcctcat tatccccaaa tttgaggtca     720
gtttatgcat tcatgaatac atgtctcagt gccattactg gtgggatgac gtggtgtctt     780
ctggattaca gatcggagaa gaaatggtcg acagttggtc tgtgctccgg tatcatttct     840
gggctggtgg ctgcaacgcc aagctcaggc tgtataaccc tttacggttc acttattcaa     900
ggcattgtgg cgggggtagt gtgtaacttt gcgacgaagt tgaaatacta cgctaaagta     960
gatgatgcca tggacattct agctgagcac ggggttgcag gcgtaatagg actaattttc    1020
aatgcccttt ttggagcaga ctgggtcatt ggtatggatg cactacaga gcacgagggc    1080
ggctgggtaa ctcacaatta caagcaaatg tataagcaga tcgcttacat tgccgcatcc    1140
attgggtaca ctgctgctgt aactgcaata atctgctttg tgctcggcta catacccggt    1200
atgaggctaa gaatatcaga agaggcagag gaggcgggta tggacgaaga tcaaattggc    1260
gaatttgcgt acgattatgt ggaagtgaga agagattact atctatgggg tgtagacgaa    1320
gattcacaac gctctgatgt aaatcaccgg gtgaacaacg ctcatttggc cgctgaacgt    1380
agcagtagcg gtactaatag ttcctcggat gggaatggaa aaatgattca atccgaaaag    1440
atcctaccaa ttcatcaaga agatcctgcc aatagg                              1476
```

<210> SEQ ID NO 19
<211> LENGTH: 492
<212> TYPE: PRT
<213> ORGANISM: Saccharomyces cerevisiae

<400> SEQUENCE: 19

Met Glu Ser Arg Thr Thr Gly Pro Leu Thr Thr Glu Thr Tyr Asp Gly
1               5                   10                  15

Pro Thr Val Ala Phe Met Ile Leu Gly Ala Ala Leu Val Phe Phe Met
                20                  25                  30

Val Pro Gly Leu Gly Phe Leu Tyr Ser Gly Leu Ala Arg Arg Lys Ser
            35                  40                  45

Ala Leu Ala Leu Ile Trp Val Val Leu Met Ala Thr Leu Val Gly Ile
        50                  55                  60

Leu Gln Trp Tyr Phe Trp Gly Tyr Ser Leu Ala Phe Ser Lys Ser Ala
65                  70                  75                  80

```
Pro Asn Asn Lys Phe Ile Gly Asn Leu Asp Ser Phe Gly Phe Arg Asn
                85                  90                  95
Val Tyr Gly Lys Lys Phe Asp Glu Asp Ala Tyr Pro Glu Leu Ala Tyr
            100                 105                 110
Ala Thr Phe Gln Met Met Phe Ser Cys Val Asn Leu Ser Ile Ile Ala
            115                 120                 125
Gly Ala Thr Ala Glu Arg Gly Arg Leu Leu Pro His Met Val Phe Leu
            130                 135                 140
Phe Ile Leu Ala Thr Ile Gly Tyr Cys Pro Val Thr Tyr Trp Ile Trp
145                 150                 155                 160
Ser Pro Gly Gly Trp Ala Tyr Gln Trp Gly Val Leu Asp Trp Ala Gly
                165                 170                 175
Gly Gly Asn Ile Glu Ile Leu Ser Ala Val Ser Gly Phe Val Tyr Ser
            180                 185                 190
Trp Phe Leu Gly Lys Arg Asn Glu Lys Leu Leu Ile Asn Phe Arg Pro
            195                 200                 205
His Asn Val Ser Leu Val Thr Leu Gly Thr Ser Ile Leu Trp Phe Gly
    210                 215                 220
Trp Leu Leu Phe Asn Ser Ala Ser Ser Leu Ser Pro Asn Leu Arg Ser
225                 230                 235                 240
Val Tyr Ala Phe Met Asn Thr Cys Leu Ser Ala Ile Thr Gly Gly Met
                245                 250                 255
Thr Trp Cys Leu Leu Asp Tyr Arg Ser Glu Lys Lys Trp Ser Thr Val
            260                 265                 270
Gly Leu Cys Ser Gly Ile Ile Ser Gly Leu Val Ala Ala Thr Pro Ser
            275                 280                 285
Ser Gly Cys Ile Thr Leu Tyr Gly Ser Leu Ile Gln Gly Ile Val Ala
    290                 295                 300
Gly Val Val Cys Asn Phe Ala Thr Lys Leu Lys Tyr Tyr Ala Lys Val
305                 310                 315                 320
Asp Asp Ala Met Asp Ile Leu Ala Glu His Gly Val Ala Gly Val Ile
                325                 330                 335
Gly Leu Ile Phe Asn Ala Leu Phe Gly Ala Asp Trp Val Ile Gly Met
            340                 345                 350
Asp Gly Thr Thr Glu His Glu Gly Gly Trp Val Thr His Asn Tyr Lys
            355                 360                 365
Gln Met Tyr Lys Gln Ile Ala Tyr Ile Ala Ala Ser Ile Gly Tyr Thr
    370                 375                 380
Ala Ala Val Thr Ala Ile Ile Cys Phe Val Leu Gly Tyr Ile Pro Gly
385                 390                 395                 400
Met Arg Leu Arg Ile Ser Glu Glu Ala Glu Ala Gly Met Asp Glu
                405                 410                 415
Asp Gln Ile Gly Glu Phe Ala Tyr Asp Tyr Val Glu Val Arg Arg Asp
            420                 425                 430
Tyr Tyr Leu Trp Gly Val Asp Glu Asp Ser Gln Arg Ser Asp Val Asn
            435                 440                 445
His Arg Val Asn Asn Ala His Leu Ala Ala Glu Arg Ser Ser Ser Gly
    450                 455                 460
Thr Asn Ser Ser Ser Asp Gly Asn Gly Glu Met Ile Gln Ser Glu Lys
465                 470                 475                 480
Ile Leu Pro Ile His Gln Glu Asp Pro Ala Asn Arg
                485                 490
```

<210> SEQ ID NO 20
<211> LENGTH: 1497
<212> TYPE: DNA
<213> ORGANISM: Saccharomyces cerevisiae

<400> SEQUENCE: 20

```
atgtcttaca attttacagg tacgcctaca ggcgaaggaa cgggtggtaa ctcgttgaca        60
acagatttga atacacaatt tgacttggcc aacatgggat ggatcggtgt ggcttcagca       120
ggtgtgtgga ttatggtccc aggtatcggt ttattatatt ctggtttatc caggaaaaag       180
catgctttat ccttgctttg ggcctcgatg atggcttccg ccgtgtgtat tttccaatgg       240
ttttctggg gatactcatt agcttttctca cacaacacta gaggtaacgg ttttattggt       300
accttggaat tctttgggtt tcgtaacgtt ttaggagccc catctagtgt cagttctctt       360
cccgatatac tgtttgccgt ttaccaaggt atgtttgccg cagtcaccgg tgccctaatg       420
ctaggtggtg cctgcgagag ggcaaggttg tttcctatga tggtgttctt gttttttatgg      480
atgactattg tttattgtcc tattgcatgc tgggtctgga atgccgaggg ttggttggtc       540
aaattgggta gcttggacta tgcaggtggt ttatgtgtcc atttaacatc tggacatggt       600
ggtctagttt acgctttgat actgggtaag cgtaatgacc ctgttacacg taaagggatg       660
cccaagtaca aaccacattc cgtcacctcg gtggttttag gcacagtgtt cttatggttt       720
ggttggatgt tctttaacgg aggctctgca ggtaatgcaa ctatacgagc atggtactct       780
attatgtcca caaacttagc tgctgcttgc ggtggcttga catggatggt tatcgattat       840
ttcagatgcg gaagaaagtg gactacagtt ggtttgtgtt caggtatcat cgctggccta       900
gtgggtatca ccccagccgc cgggttcgtg ccaatctggt cagccgttgt cattggtgtg       960
gttactggtg caggatgtaa ccttgctgtt gacttaaaga gtctattgcg catcgatgat      1020
ggtctagatt gttactctat ccatggtgtg ggtggttgta ttggttctgt attaactggt      1080
atctttgctg cagactatgt aaatgccact gcaggctctt acattagtcc aattgatggt      1140
ggctggatca atcatcacta taaacaagtt ggttatcaat tagcaggtat atgcgctgca      1200
ctagcctgga ctgttactgt cacatctatc ttgcttctaa ctatgaatgc cattccattt      1260
ttaaaactaa gattaagtgc tgatgaggaa gaattaggta ccgacgctgc tcaaattggt      1320
gaatttacat acgaggaatc cactgcttac atcccagaac caatcagatc taaaacatcg      1380
gcacaaatgc cacctcctca tgaaaacatt gatgataaga ttgtgggtaa cacagacgca      1440
gaaaagaatt ctacgccttc cgacgcttct tctactaaga acactgacca tatagta         1497
```

<210> SEQ ID NO 21
<211> LENGTH: 499
<212> TYPE: PRT
<213> ORGANISM: Saccharomyces cerevisiae

<400> SEQUENCE: 21

```
Met Ser Tyr Asn Phe Thr Gly Thr Pro Thr Gly Glu Gly Thr Gly Gly
1               5                   10                  15

Asn Ser Leu Thr Thr Asp Leu Asn Thr Gln Phe Asp Leu Ala Asn Met
            20                  25                  30

Gly Trp Ile Gly Val Ala Ser Ala Gly Val Trp Ile Met Val Pro Gly
        35                  40                  45

Ile Gly Leu Leu Tyr Ser Gly Leu Ser Arg Lys Lys His Ala Leu Ser
    50                  55                  60

Leu Leu Trp Ala Ser Met Met Ala Ser Ala Val Cys Ile Phe Gln Trp
65                  70                  75                  80
```

```
Phe Phe Trp Gly Tyr Ser Leu Ala Phe Ser His Asn Thr Arg Gly Asn
                85                  90                  95

Gly Phe Ile Gly Thr Leu Glu Phe Gly Phe Arg Asn Val Leu Gly
            100                 105                 110

Ala Pro Ser Ser Val Ser Leu Pro Asp Ile Leu Phe Ala Val Tyr
            115                 120                 125

Gln Gly Met Phe Ala Ala Val Thr Gly Ala Leu Met Leu Gly Gly Ala
130                 135                 140

Cys Glu Arg Ala Arg Leu Phe Pro Met Met Val Phe Leu Phe Leu Trp
145                 150                 155                 160

Met Thr Ile Val Tyr Cys Pro Ile Ala Cys Trp Val Trp Asn Ala Glu
                165                 170                 175

Gly Trp Leu Val Lys Leu Gly Ser Leu Asp Tyr Ala Gly Gly Leu Cys
                180                 185                 190

Val His Leu Thr Ser Gly His Gly Gly Leu Val Tyr Ala Leu Ile Leu
                195                 200                 205

Gly Lys Arg Asn Asp Pro Val Thr Arg Lys Gly Met Pro Lys Tyr Lys
210                 215                 220

Pro His Ser Val Thr Ser Val Leu Gly Thr Val Phe Leu Trp Phe
225                 230                 235                 240

Gly Trp Met Phe Phe Asn Gly Gly Ser Ala Gly Asn Ala Thr Ile Arg
                245                 250                 255

Ala Trp Tyr Ser Ile Met Ser Thr Asn Leu Ala Ala Ala Cys Gly Gly
                260                 265                 270

Leu Thr Trp Met Val Ile Asp Tyr Phe Arg Cys Gly Arg Lys Trp Thr
                275                 280                 285

Thr Val Gly Leu Cys Ser Gly Ile Ile Ala Gly Leu Val Gly Ile Thr
                290                 295                 300

Pro Ala Ala Gly Phe Val Pro Ile Trp Ser Ala Val Val Ile Gly Val
305                 310                 315                 320

Val Thr Gly Ala Gly Cys Asn Leu Ala Val Asp Leu Lys Ser Leu Leu
                325                 330                 335

Arg Ile Asp Asp Gly Leu Asp Cys Tyr Ser Ile His Gly Val Gly Gly
                340                 345                 350

Cys Ile Gly Ser Val Leu Thr Gly Ile Phe Ala Ala Asp Tyr Val Asn
                355                 360                 365

Ala Thr Ala Gly Ser Tyr Ile Ser Pro Ile Asp Gly Gly Trp Ile Asn
370                 375                 380

His His Tyr Lys Gln Val Gly Tyr Gln Leu Ala Gly Ile Cys Ala Ala
385                 390                 395                 400

Leu Ala Trp Thr Val Thr Val Thr Ser Ile Leu Leu Thr Met Asn
                405                 410                 415

Ala Ile Pro Phe Leu Lys Leu Arg Leu Ser Ala Asp Glu Glu Leu
                420                 425                 430

Gly Thr Asp Ala Ala Gln Ile Gly Glu Phe Thr Tyr Glu Glu Ser Thr
                435                 440                 445

Ala Tyr Ile Pro Glu Pro Ile Arg Ser Lys Thr Ser Ala Gln Met Pro
450                 455                 460

Pro Pro His Glu Asn Ile Asp Asp Lys Ile Val Gly Asn Thr Asp Ala
465                 470                 475                 480
```

Glu Lys Asn Ser Thr Pro Ser Asp Ala Ser Ser Thr Lys Asn Thr Asp
            485                 490                 495

His Ile Val

<210> SEQ ID NO 22
<211> LENGTH: 1467
<212> TYPE: DNA
<213> ORGANISM: Saccharomyces cerevisiae

<400> SEQUENCE: 22
atggctcggg gtgacggaca tctatggaca gagacatatg atagttccac agtcgctttt      60
atgattttag gtgccgccct ggttttcttc atggtaccag ggctgggctt tcttttttcc     120
ggtttagcaa gaagaaaatc tgctctggct ttgatttggg tagtgataat ggctacctta     180
gtaggtatac tgcaatggta ttttggggc tattctttag cattctctaa gactgcgacg      240
aacaacaaat ttatcggcaa cttggattca tttgggttta gaaacgtcta tggcaaaatt     300
tcggatgatt ccacgtatcc tgaactgatt tatgccattt ccaaatgat gttcatgtgt      360
gtcgcattga gtattatagc tggtgccact gcggaaagag gtaagctttt tccacatatg     420
gttttttcttt ttgttttttgc gactttggtt tactgtccca tcacttattg gatttgggcc     480
ccaggtggct gggcctacca atgggggggta ttagactggg ctggcggtgg aatattgaa     540
atcctaagtg ctgtggctgg tttcgtttat tcttatttc taggaagaag aaaagaaaac     600
ctcctgatca actttagacc acataatgtt tccatggtga ctttaggtac ttctatactt     660
tggtttggtt ggttgctttt caatgctgca agctcactgt caccaaatat gaggtccgta     720
tatgcgttca tgaacacttg tctcagcgcc accacgggtg gaatgacgtg gtgttttatta     780
gattatcgat ctgaaaaaaa atggtccact gttgggttat gctccggcat tatctgtggt     840
ttagttgctg ccacgcctag ctcgggttgt attactctat atggctcttt gatccaaggt     900
ataatagcgg gtgttgtttg taattttgca acaaaaataa agtattattt aaaagtggat     960
gattccttag atctattagc tgaacacggt atcgccggtg tggtgggatt gattttttaac    1020
gctctatttg cagctgattg ggttattgga atggacggca caacaaagca taagggtggt    1080
tggttgacgc ataactggaa acaaatgtat attcaaattg cctatatcgg tgcctctgcc    1140
ggctattgtg ctgtggtcac ggccatcatt tgcttcgtat taggtaaaat tccgggtgtc    1200
catctaagag tcactgagga agccgaagca ttggggttgg atgaagatca aataggcgaa    1260
ttcgcttacg attacgtgga ggttaggaga gattattacc agtggggtgt agatacagat    1320
gcacttcata ctacatgcaa tggcgctaat tctgcgtctg agacaaatcc tactgaggac    1380
agccaaaact cctcattgtc atcagctaca gtaagcggcc aaaacgaaaa agtaataat    1440
cctaaattgc atcacgcaaa agaagca                                        1467

<210> SEQ ID NO 23
<211> LENGTH: 489
<212> TYPE: PRT
<213> ORGANISM: Saccharomyces cerevisiae

<400> SEQUENCE: 23

Met Ala Arg Gly Asp Gly His Leu Trp Thr Glu Thr Tyr Asp Ser Ser
1               5                   10                  15

Thr Val Ala Phe Met Ile Leu Gly Ala Ala Leu Val Phe Phe Met Val
                20                  25                  30

Pro Gly Leu Gly Phe Leu Tyr Ser Gly Leu Ala Arg Arg Lys Ser Ala
            35                  40                  45

```
Leu Ala Leu Ile Trp Val Val Ile Met Ala Thr Leu Val Gly Ile Leu
 50                  55                  60

Gln Trp Tyr Phe Trp Gly Tyr Ser Leu Ala Phe Ser Lys Thr Ala Thr
 65                  70                  75                  80

Asn Asn Lys Phe Ile Gly Asn Leu Asp Ser Phe Gly Phe Arg Asn Val
                 85                  90                  95

Tyr Gly Lys Ile Ser Asp Asp Ser Thr Tyr Pro Glu Leu Ile Tyr Ala
                100                 105                 110

Ile Phe Gln Met Met Phe Met Cys Val Ala Leu Ser Ile Ile Ala Gly
                115                 120                 125

Ala Thr Ala Glu Arg Gly Lys Leu Phe Pro His Met Val Phe Leu Phe
130                 135                 140

Val Phe Ala Thr Leu Val Tyr Cys Pro Ile Thr Tyr Trp Ile Trp Ala
145                 150                 155                 160

Pro Gly Gly Trp Ala Tyr Gln Trp Gly Val Leu Asp Trp Ala Gly Gly
                165                 170                 175

Gly Asn Ile Glu Ile Leu Ser Ala Val Ala Gly Phe Val Tyr Ser Tyr
                180                 185                 190

Phe Leu Gly Arg Arg Lys Glu Asn Leu Leu Ile Asn Phe Arg Pro His
                195                 200                 205

Asn Val Ser Met Val Thr Leu Gly Thr Ser Ile Leu Trp Phe Gly Trp
                210                 215                 220

Leu Leu Phe Asn Ala Ala Ser Ser Leu Ser Pro Asn Met Arg Ser Val
225                 230                 235                 240

Tyr Ala Phe Met Asn Thr Cys Leu Ser Ala Thr Thr Gly Gly Met Thr
                245                 250                 255

Trp Cys Leu Leu Asp Tyr Arg Ser Glu Lys Lys Trp Ser Thr Val Gly
                260                 265                 270

Leu Cys Ser Gly Ile Ile Cys Gly Leu Val Ala Ala Thr Pro Ser Ser
                275                 280                 285

Gly Cys Ile Thr Leu Tyr Gly Ser Leu Ile Gln Gly Ile Ile Ala Gly
                290                 295                 300

Val Val Cys Asn Phe Ala Thr Lys Ile Lys Tyr Tyr Leu Lys Val Asp
305                 310                 315                 320

Asp Ser Leu Asp Leu Leu Ala Glu His Gly Ile Ala Gly Val Val Gly
                325                 330                 335

Leu Ile Phe Asn Ala Leu Phe Ala Ala Asp Trp Val Ile Gly Met Asp
                340                 345                 350

Gly Thr Thr Lys His Lys Gly Gly Trp Leu Thr His Asn Trp Lys Gln
                355                 360                 365

Met Tyr Ile Gln Ile Ala Tyr Ile Gly Ala Ser Ala Gly Tyr Cys Ala
                370                 375                 380

Val Val Thr Ala Ile Ile Cys Phe Val Leu Gly Lys Ile Pro Gly Val
385                 390                 395                 400

His Leu Arg Val Thr Glu Glu Ala Glu Ala Leu Gly Leu Asp Glu Asp
                405                 410                 415

Gln Ile Gly Glu Phe Ala Tyr Asp Tyr Val Glu Val Arg Arg Asp Tyr
                420                 425                 430

Tyr Gln Trp Gly Val Asp Thr Asp Ala Leu His Thr Thr Cys Asn Gly
                435                 440                 445

Ala Asn Ser Ala Ser Glu Thr Asn Pro Thr Glu Asp Ser Gln Asn Ser
450                 455                 460
```

Ser Leu Ser Ser Ala Thr Val Ser Gly Gln Asn Glu Lys Ser Asn Asn
465                 470                 475                 480

Pro Lys Leu His His Ala Lys Glu Ala
            485

<210> SEQ ID NO 24
<211> LENGTH: 1362
<212> TYPE: DNA
<213> ORGANISM: Saccharomyces cerevisiae

<400> SEQUENCE: 24

| | |
|---|---:|
| atgtcagagc cagaatttca acaagcttac gaagaagttg tctcctcttt ggaagactct | 60 |
| actcttttcg aacaacaccc agaatacaga aaggttttgc aattgtttc tgttccagaa | 120 |
| agaatcatac aattcagagt cacctgggaa atgacaagg gtgaacaaga agttgctcaa | 180 |
| ggttacagag tgcaatataa ctccgccaag ggtccataca agggtggtct acgtttccat | 240 |
| ccttccgtga acttgtctat cttgaaattc ttgggtttcg aacaaatctt caagaactcc | 300 |
| ttgaccggcc tagacatggg tggtggtaaa ggtggtctat gtgtggactt gaagggaaga | 360 |
| tctaataacg aaatcagaag aatctgttac gctttcatga gagaattgag cagacacatt | 420 |
| ggtcaagaca ctgacgtgcc agctggtgat atcggtgttg gtggtcgtga aattggttac | 480 |
| ctgttcggtg cttacagatc atacaagaac tcctgggaag tgtcttaac cggtaagggt | 540 |
| ttgaactggg gtggttcttt gatcagacca gaagccactg gttacggttt agtttactat | 600 |
| acccaagcta tgatcgacta tgccacaaac ggtaaggaat cttcgaagg taagcgcgtc | 660 |
| accatctctg gtagtggtaa cgttgctcaa tacgctgcct tgaaggttat tgagctaggt | 720 |
| ggtactgtcg tttccctatc tgactccaag ggttgtatca tctctgaaac tggtatcacc | 780 |
| tccgaacaag tcgctgatat ttccagtgct aaggtcaact tcaagtcctt ggaacaaatc | 840 |
| gtcaacgaat actctacttt ctccgaaaac aaagtgcaat acattgctgg tgctcgtcca | 900 |
| tggacccacg tccaaaaggt cgacattgct ttgccatgtg ccacccaaaa tgaagtcagc | 960 |
| ggtgaagaag ccaaggcctt ggttgctcaa ggtgtcaagt ttattgccga aggttccaac | 1020 |
| atgggttcca ctccagaagc tattgccgtc tttgaaactg ctcgttccac cgccactgga | 1080 |
| ccaagcgaag ctgtttggta cggtccacca aaggctgcta acttgggtgg tgttgctgtt | 1140 |
| tctggtttag aaatggcaca aaactctcaa gaatcacat ggactagcga aagagttgac | 1200 |
| caagagttga agagaattat gatcaactgt ttcaatgaat gtatcgacta tgccaagaag | 1260 |
| tacactaagg acggtaaggt cttgccatct ttggtcaaag gtgctaatat cgcaagtttc | 1320 |
| atcaaggtct ctgatgctat gtttgaccaa ggtgatgtat tt | 1362 |

<210> SEQ ID NO 25
<211> LENGTH: 454
<212> TYPE: PRT
<213> ORGANISM: Saccharomyces cerevisiae

<400> SEQUENCE: 25

Met Ser Glu Pro Glu Phe Gln Gln Ala Tyr Glu Glu Val Val Ser Ser
1               5                   10                  15

Leu Glu Asp Ser Thr Leu Phe Glu Gln His Pro Glu Tyr Arg Lys Val
            20                  25                  30

Leu Pro Ile Val Ser Val Pro Glu Arg Ile Ile Gln Phe Arg Val Thr
        35                  40                  45

```
Trp Glu Asn Asp Lys Gly Glu Gln Glu Val Ala Gln Gly Tyr Arg Val
     50                  55                  60
Gln Tyr Asn Ser Ala Lys Gly Pro Tyr Lys Gly Gly Leu Arg Phe His
 65                  70                  75                  80
Pro Ser Val Asn Leu Ser Ile Leu Lys Phe Leu Gly Phe Glu Gln Ile
                 85                  90                  95
Phe Lys Asn Ser Leu Thr Gly Leu Asp Met Gly Gly Lys Gly Gly
             100                 105                 110
Leu Cys Val Asp Leu Lys Gly Arg Ser Asn Asn Glu Ile Arg Arg Ile
             115                 120                 125
Cys Tyr Ala Phe Met Arg Glu Leu Ser Arg His Ile Gly Gln Asp Thr
 130                 135                 140
Asp Val Pro Ala Gly Asp Ile Gly Val Gly Gly Arg Glu Ile Gly Tyr
 145             150                 155                 160
Leu Phe Gly Ala Tyr Arg Ser Tyr Lys Asn Ser Trp Glu Gly Val Leu
                 165                 170                 175
Thr Gly Lys Gly Leu Asn Trp Gly Gly Ser Leu Ile Arg Pro Glu Ala
             180                 185                 190
Thr Gly Tyr Gly Leu Val Tyr Tyr Thr Gln Ala Met Ile Asp Tyr Ala
             195                 200                 205
Thr Asn Gly Lys Glu Ser Phe Glu Gly Lys Arg Val Thr Ile Ser Gly
 210                 215                 220
Ser Gly Asn Val Ala Gln Tyr Ala Ala Leu Lys Val Ile Glu Leu Gly
 225                 230                 235                 240
Gly Thr Val Val Ser Leu Ser Asp Ser Lys Gly Cys Ile Ile Ser Glu
                 245                 250                 255
Thr Gly Ile Thr Ser Glu Gln Val Ala Asp Ile Ser Ser Ala Lys Val
             260                 265                 270
Asn Phe Lys Ser Leu Glu Gln Ile Val Asn Glu Tyr Ser Thr Phe Ser
             275                 280                 285
Glu Asn Lys Val Gln Tyr Ile Ala Gly Ala Arg Pro Trp Thr His Val
 290                 295                 300
Gln Lys Val Asp Ile Ala Leu Pro Cys Ala Thr Gln Asn Glu Val Ser
 305                 310                 315                 320
Gly Glu Glu Ala Lys Ala Leu Val Ala Gln Gly Val Lys Phe Ile Ala
             325                 330                 335
Glu Gly Ser Asn Met Gly Ser Thr Pro Glu Ala Ile Ala Val Phe Glu
             340                 345                 350
Thr Ala Arg Ser Thr Ala Thr Gly Pro Ser Glu Ala Val Trp Tyr Gly
 355                 360                 365
Pro Pro Lys Ala Ala Asn Leu Gly Gly Val Ala Val Ser Gly Leu Glu
 370                 375                 380
Met Ala Gln Asn Ser Gln Arg Ile Thr Trp Thr Ser Glu Arg Val Asp
 385                 390                 395                 400
Gln Glu Leu Lys Arg Ile Met Ile Asn Cys Phe Asn Glu Cys Ile Asp
                 405                 410                 415
Tyr Ala Lys Lys Tyr Thr Lys Asp Gly Lys Val Leu Pro Ser Leu Val
             420                 425                 430
Lys Gly Ala Asn Ile Ala Ser Phe Ile Lys Val Ser Asp Ala Met Phe
             435                 440                 445
Asp Gln Gly Asp Val Phe
         450
```

<210> SEQ ID NO 26
<211> LENGTH: 3276
<212> TYPE: DNA
<213> ORGANISM: Saccharomyces cerevisiae

<400> SEQUENCE: 26

| | | | | | |
|---|---|---|---|---|---|
| atgcttttg | ataacaaaaa | tcgcggtgct | ttaaactcac | tgaacacacc | agatattgct | 60 |
| tctttatcaa | tatcatccat | gtcggactat | cacgtgtttg | attttcccgg | taaggacctg | 120 |
| cagagagagg | aagtgataga | tttgctagat | cagcaagggt | ttattcccga | cgatttgatc | 180 |
| gaacaagaag | tagattggtt | ttataactca | ttgggtattg | acgatttgtt | cttctcgaga | 240 |
| gaatctcccc | aattaatctc | gaatatcata | cattctttgt | atgcttcaaa | gctagatttc | 300 |
| tttgcgaagt | ccaaattcaa | cggaattcag | ccaaggctat | tcagcattaa | aaacaaaatt | 360 |
| ataactaatg | ataatcatgc | catctttatg | gaatctaata | ctggtgtcag | cataagcgat | 420 |
| tctcagcaaa | aaactttaa | atttgctagt | gacgccgtcg | gaaacgatac | tttggagcat | 480 |
| ggtaaggata | ccatcaaaaa | aaataggatt | gaaatggatg | attcttgtcc | accttatgaa | 540 |
| ttagattccg | aaattgatga | ccttttcctg | gataacaagt | ctcaaaaaaa | ctgcagatta | 600 |
| gtttcttttt | gggctccaga | aagcgaatta | aagctaactt | tgtttatga | gagtgtttac | 660 |
| cctaatgatg | atccagccgg | cgtagatatt | tcctctcagg | atttgctgaa | aggtgatatt | 720 |
| gaatcgatta | gtgataagac | catgtacaaa | gtttcgtcga | acgaaaataa | aaactatac | 780 |
| ggtctcttac | ttaagttggt | taaagaaaga | gaaggtcctg | tcattaagac | tactcgctcc | 840 |
| gtagaaaata | aggatgaaat | taggttatta | gtcgcttaca | agcgattcac | cactaagcgt | 900 |
| tattactctg | ctttgaactc | tttgttccac | tattacaagt | tgaaaccttc | taagttctat | 960 |
| ttagagtcgt | ttaatgttaa | ggatgatgac | atcattatct | tttccgttta | tttgaacgag | 1020 |
| aaccagcaat | tggaagatgt | tctacttcac | gatgtggagg | cagcattgaa | acaggttgaa | 1080 |
| agagaagctt | cattgctata | cgctatccca | aacaattctt | tccatgaggt | ttaccagaga | 1140 |
| cgtcaattct | cgcccaaaga | agctatatat | gctcatattg | gtgctatatt | cattaaccat | 1200 |
| tttgttaatc | gtttaggctc | tgattatcaa | aaccttttat | ctcaaatcac | cattaagcgt | 1260 |
| aatgatacta | ctcttttgga | gattgtagaa | aacctaaaaa | gaaagttaag | aaatgaaacc | 1320 |
| ttaactcagc | aaactattat | caacatcatg | tcgaagcatt | acactataat | ttccaagttg | 1380 |
| tataaaaatt | ttgctcaaat | tcactattat | cataatagta | ctaaagatat | ggagaagaca | 1440 |
| ttatcttttc | aaagactgga | aaaagtggag | cctttaaga | atgaccaaga | gttcgaagct | 1500 |
| tacttgaata | aattcattcc | aaatgattca | cctgatttgt | tgatcctgaa | aacactgaac | 1560 |
| atcttcaaca | gtctattttt | gaagacaaat | ttctttatta | caagaaaagt | agcaatatca | 1620 |
| ttcagattag | atccttccct | ggtgatgaca | aaattcgaat | atccagagac | accctatggt | 1680 |
| atattttttg | tcgttggtaa | tactttcaaa | gggttccata | tcaggttcag | agatatcgca | 1740 |
| aggggcggta | ttcgtatagt | ctgttccagg | aatcaggata | tttatgattt | gaattccaag | 1800 |
| aacgttattg | atgagaacta | tcaattggcc | tctactcagc | aacgtaaaaa | taaggatatt | 1860 |
| ccagagggtg | gctctaaagg | tgtcatctta | ttgaacccag | gattggtaga | acatgaccag | 1920 |
| acatttgtcg | ccttttccca | atatgtggat | gcaatgattg | acattctaat | caacgatcca | 1980 |
| ttaaaggaaa | actatgtcaa | ccttttacca | aaggaggaaa | tattattttt | tggcccagat | 2040 |
| gaaggaactg | ctggtttcgt | ggattgggca | actaaccatg | ctcgtgtgag | gaactgccca | 2100 |
| tggtggaaat | cattttttgac | tggaaaatcc | ccatctttgg | gtggtattcc | ccatgacgaa | 2160 |

```
tatggtatga cttctctggg tgttcgtgct tatgttaata aaatttacga aactttaaac    2220
ttgacaaatt ctactgttta caaattccaa actggtggtc cggatggtga tttgggatcc    2280
aatgaaattc ttttatcttc gccaaacgaa tgttatttgg caattctgga cggttcaggt    2340
gtcctgtgtg atcctaaagg tttagataaa gatgaattat gccgcttggc acatgaaagg    2400
aaaatgattt ccgatttcga cacttccaaa ttatcaaaca acggattttt tgtttctgtg    2460
gatgcaatgg atatcatgct accaaatggt acaattgtag ctaacggcac aaccttcaga    2520
aacacctttc atactcaaat tttcaaattt gtggatcatg tcgacatttt tgttccatgc    2580
ggtggtagac caaactcaat tactctaaat aatctacatt attttgttga cgaaaagact    2640
gggaaatgta aaattccata tattgtggag ggtgccaatc tatttataac gcaacctgct    2700
aaaaatgctt tggaggaaca tggctgtatt ctgttcaaag atgcttctgc aaacaaaggt    2760
ggtgtcacat cttcatcaat ggaagtgttg gcctcactag cgcttaacga taacgacttc    2820
gtgcacaaat ttattggaga tgttagtggt gagaggtctg cgttgtacaa gtcgtacgtt    2880
gtagaagtgc agtcaagaat tcagaaaaat gctgaattag agtttggtca gttatggaat    2940
ttgaatcaac taaatggaac ccacatttca gaaatttcaa accaattgtc cttcactata    3000
aacaaattga cgacgatct agttgcttct caagagttgt ggctcaatga tctaaaatta    3060
agaaactacc tattgttgga taaaataatt ccaaaaattc tgattgatgt tgctgggcct    3120
cagtccgtat tggaaaacat tccagagagc tatttgaaag ttcttctgtc gagttactta    3180
tcaagcactt ttgtttacca gaacggtatc gatgttaaca ttggaaaatt cttggaattt    3240
attggtgggt aaaaagaga agcggaggca agtgct                              3276
```

<210> SEQ ID NO 27
<211> LENGTH: 1092
<212> TYPE: PRT
<213> ORGANISM: Saccharomyces cerevisiae

<400> SEQUENCE: 27

```
Met Leu Phe Asp Asn Lys Asn Arg Gly Ala Leu Asn Ser Leu Asn Thr
1               5                   10                  15

Pro Asp Ile Ala Ser Leu Ser Ile Ser Ser Met Ser Asp Tyr His Val
            20                  25                  30

Phe Asp Phe Pro Gly Lys Asp Leu Gln Arg Glu Glu Val Ile Asp Leu
        35                  40                  45

Leu Asp Gln Gln Gly Phe Ile Pro Asp Leu Ile Glu Gln Glu Val
    50                  55                  60

Asp Trp Phe Tyr Asn Ser Leu Gly Ile Asp Leu Phe Phe Ser Arg
65                  70                  75                  80

Glu Ser Pro Gln Leu Ile Ser Asn Ile Ile His Ser Leu Tyr Ala Ser
            85                  90                  95

Lys Leu Asp Phe Phe Ala Lys Ser Lys Phe Asn Gly Ile Gln Pro Arg
        100                 105                 110

Leu Phe Ser Ile Lys Asn Lys Ile Ile Thr Asn Asp Asn His Ala Ile
    115                 120                 125

Phe Met Glu Ser Asn Thr Gly Val Ser Ile Ser Asp Ser Gln Gln Lys
130                 135                 140

Asn Phe Lys Phe Ala Ser Asp Ala Val Gly Asn Asp Thr Leu Glu His
145                 150                 155                 160

Gly Lys Asp Thr Ile Lys Lys Asn Arg Ile Glu Met Asp Asp Ser Cys
            165                 170                 175
```

```
Pro Pro Tyr Glu Leu Asp Ser Glu Ile Asp Asp Leu Phe Leu Asp Asn
            180                 185                 190

Lys Ser Gln Lys Asn Cys Arg Leu Val Ser Phe Trp Ala Pro Glu Ser
        195                 200                 205

Glu Leu Lys Leu Thr Phe Val Tyr Glu Ser Val Tyr Pro Asn Asp Asp
    210                 215                 220

Pro Ala Gly Val Asp Ile Ser Ser Gln Asp Leu Leu Lys Gly Asp Ile
225                 230                 235                 240

Glu Ser Ile Ser Asp Lys Thr Met Tyr Lys Val Ser Ser Asn Glu Asn
                245                 250                 255

Lys Lys Leu Tyr Gly Leu Leu Leu Lys Leu Val Lys Glu Arg Glu Gly
            260                 265                 270

Pro Val Ile Lys Thr Thr Arg Ser Val Glu Asn Lys Asp Glu Ile Arg
        275                 280                 285

Leu Leu Val Ala Tyr Lys Arg Phe Thr Thr Lys Arg Tyr Tyr Ser Ala
    290                 295                 300

Leu Asn Ser Leu Phe His Tyr Lys Leu Lys Pro Ser Lys Phe Tyr
305                 310                 315                 320

Leu Glu Ser Phe Asn Val Lys Asp Asp Ile Ile Ile Phe Ser Val
                325                 330                 335

Tyr Leu Asn Glu Asn Gln Gln Leu Glu Asp Val Leu Leu His Asp Val
            340                 345                 350

Glu Ala Ala Leu Lys Gln Val Glu Arg Glu Ala Ser Leu Leu Tyr Ala
        355                 360                 365

Ile Pro Asn Asn Ser Phe His Glu Val Tyr Gln Arg Arg Gln Phe Ser
    370                 375                 380

Pro Lys Glu Ala Ile Tyr Ala His Ile Gly Ala Ile Phe Ile Asn His
385                 390                 395                 400

Phe Val Asn Arg Leu Gly Ser Asp Tyr Gln Asn Leu Leu Ser Gln Ile
                405                 410                 415

Thr Ile Lys Arg Asn Asp Thr Thr Leu Leu Glu Ile Val Glu Asn Leu
            420                 425                 430

Lys Arg Lys Leu Arg Asn Glu Thr Leu Thr Gln Gln Thr Ile Ile Asn
        435                 440                 445

Ile Met Ser Lys His Tyr Thr Ile Ile Ser Lys Leu Tyr Lys Asn Phe
    450                 455                 460

Ala Gln Ile His Tyr Tyr His Asn Ser Thr Lys Asp Met Glu Lys Thr
465                 470                 475                 480

Leu Ser Phe Gln Arg Leu Glu Lys Val Glu Pro Phe Lys Asn Asp Gln
                485                 490                 495

Glu Phe Glu Ala Tyr Leu Asn Lys Phe Ile Pro Asn Asp Ser Pro Asp
            500                 505                 510

Leu Leu Ile Leu Lys Thr Leu Asn Ile Phe Asn Lys Ser Ile Leu Lys
        515                 520                 525

Thr Asn Phe Phe Ile Thr Arg Lys Val Ala Ile Ser Phe Arg Leu Asp
    530                 535                 540

Pro Ser Leu Val Met Thr Lys Phe Glu Tyr Pro Glu Thr Pro Tyr Gly
545                 550                 555                 560

Ile Phe Phe Val Val Gly Asn Thr Phe Lys Gly Phe His Ile Arg Phe
                565                 570                 575

Arg Asp Ile Ala Arg Gly Gly Ile Arg Ile Val Cys Ser Arg Asn Gln
            580                 585                 590

Asp Ile Tyr Asp Leu Asn Ser Lys Asn Val Ile Asp Glu Asn Tyr Gln
```

-continued

```
              595                 600                 605
Leu Ala Ser Thr Gln Gln Arg Lys Asn Lys Asp Ile Pro Glu Gly Gly
            610                 615                 620

Ser Lys Gly Val Ile Leu Leu Asn Pro Gly Leu Val Glu His Asp Gln
625                 630                 635                 640

Thr Phe Val Ala Phe Ser Gln Tyr Val Asp Ala Met Ile Asp Ile Leu
                645                 650                 655

Ile Asn Asp Pro Leu Lys Glu Asn Tyr Val Asn Leu Leu Pro Lys Glu
                660                 665                 670

Glu Ile Leu Phe Phe Gly Pro Asp Glu Gly Thr Ala Gly Phe Val Asp
            675                 680                 685

Trp Ala Thr Asn His Ala Arg Val Arg Asn Cys Pro Trp Trp Lys Ser
            690                 695                 700

Phe Leu Thr Gly Lys Ser Pro Ser Leu Gly Gly Ile Pro His Asp Glu
705                 710                 715                 720

Tyr Gly Met Thr Ser Leu Gly Val Arg Ala Tyr Val Asn Lys Ile Tyr
                725                 730                 735

Glu Thr Leu Asn Leu Thr Asn Ser Thr Val Tyr Lys Phe Gln Thr Gly
                740                 745                 750

Gly Pro Asp Gly Asp Leu Gly Ser Asn Glu Ile Leu Leu Ser Ser Pro
            755                 760                 765

Asn Glu Cys Tyr Leu Ala Ile Leu Asp Gly Ser Gly Val Leu Cys Asp
770                 775                 780

Pro Lys Gly Leu Asp Lys Asp Glu Leu Cys Arg Leu Ala His Glu Arg
785                 790                 795                 800

Lys Met Ile Ser Asp Phe Asp Thr Ser Lys Leu Ser Asn Asn Gly Phe
                805                 810                 815

Phe Val Ser Val Asp Ala Met Asp Ile Met Leu Pro Asn Gly Thr Ile
                820                 825                 830

Val Ala Asn Gly Thr Thr Phe Arg Asn Thr Phe His Thr Gln Ile Phe
            835                 840                 845

Lys Phe Val Asp His Val Asp Ile Phe Val Pro Cys Gly Gly Arg Pro
850                 855                 860

Asn Ser Ile Thr Leu Asn Asn Leu His Tyr Phe Val Asp Glu Lys Thr
865                 870                 875                 880

Gly Lys Cys Lys Ile Pro Tyr Ile Val Glu Gly Ala Asn Leu Phe Ile
                885                 890                 895

Thr Gln Pro Ala Lys Asn Ala Leu Glu Glu His Gly Cys Ile Leu Phe
            900                 905                 910

Lys Asp Ala Ser Ala Asn Lys Gly Gly Val Thr Ser Ser Ser Met Glu
            915                 920                 925

Val Leu Ala Ser Leu Ala Leu Asn Asp Asn Asp Phe Val His Lys Phe
            930                 935                 940

Ile Gly Asp Val Ser Gly Glu Arg Ser Ala Leu Tyr Lys Ser Tyr Val
945                 950                 955                 960

Val Glu Val Gln Ser Arg Ile Gln Lys Asn Ala Glu Leu Glu Phe Gly
                965                 970                 975

Gln Leu Trp Asn Leu Asn Gln Leu Asn Gly Thr His Ile Ser Glu Ile
            980                 985                 990

Ser Asn Gln Leu Ser Phe Thr Ile  Asn Lys Leu Asn Asp  Asp Leu Val
            995                 1000                1005

Ala Ser  Gln Glu Leu Trp Leu  Asn Asp Leu Lys Leu  Arg Asn Tyr
        1010                1015                1020
```

Leu Leu Leu Asp Lys Ile Ile Pro Lys Ile Leu Ile Asp Val Ala
    1025                1030                1035

Gly Pro Gln Ser Val Leu Glu Asn Ile Pro Glu Ser Tyr Leu Lys
    1040                1045                1050

Val Leu Leu Ser Ser Tyr Leu Ser Ser Thr Phe Val Tyr Gln Asn
    1055                1060                1065

Gly Ile Asp Val Asn Ile Gly Lys Phe Leu Glu Phe Ile Gly Gly
    1070                1075                1080

Leu Lys Arg Glu Ala Glu Ala Ser Ala
    1085                1090

<210> SEQ ID NO 28
<211> LENGTH: 3153
<212> TYPE: DNA
<213> ORGANISM: Neurospora crassa

<400> SEQUENCE: 28

| | |
|---|---:|
| atggattctc cttcagcccc ggtcccagcc cacaagttgg ttgatcgcct caaagatcag | 60 |
| acgcccagac atccttctcc tcagccgaca catgtcagct atcccaaggt gaacggcaac | 120 |
| gggcacaggg tgctccgctc cgcaactgtt ggatatgttg ccctgtctt ccagggaaag | 180 |
| gcagagcaga tgaagcaagt caagaatatc attgtccagg cggctggat tcccgagact | 240 |
| ctggttgacg tcagattgc gtggttctat aatgagcttg catcgacga cgtctacttc | 300 |
| caactagaaa accctcaggc ggttgcaaat catatcacat ctctctatgc ggccaaagtt | 360 |
| gctgctttct ctcgcgagga caagcgggaa gagatcagac tggatatgga agcctcggac | 420 |
| cacgccattt acatcgacac aagcgaaccc ggcatgacct ccttcgacgg tccgcgatat | 480 |
| gagcacagac tcgagtccaa gtacttggat ggcgacgata cttcgaagcg tttccgtgtc | 540 |
| gagactttca gatccccggg tgtcctgggg cagaaggaga actccaaggc agctcttcgt | 600 |
| tgctactttg tctatcagtg tctctttgtt gattctaacg ccgatcccaa ggaaactcgc | 660 |
| ctggaagtga tcagcgaccg catgttcctt gccaaggcta ccaagaacac caagcagatc | 720 |
| taccaggaca tcatccaggt tgccgtgagc cgacatggtc ccgtcattga ggttttcgac | 780 |
| atcgagggct cggaggaaat gagactggta gttgccttcc gctctcgaac agcaaagggt | 840 |
| atcttcagcg ccctcagcga cctttaccac tactacggcg tcacaagctc tcgtaagtac | 900 |
| gttgagcagt tctccaatgg tattaccgtc atgagtatct atctgcgccc tgctgcgaac | 960 |
| atcgacggca agcaccctcc tcttgagcaa tctattcacc agatcaccaa ggagatttcc | 1020 |
| ttgctgtact gccttcccca gaacaagttt cacaacatgt ttgcctctgg tgaactcagt | 1080 |
| ctgcaggaga ccatctatgc ccactgcgtc tgggtgtttg ttcagcattt cttgaaccgt | 1140 |
| cttgggacag agtacacttc gctcattgca gccctggacc caagaacaa ctcgcatgtt | 1200 |
| gagattctct ccaagatgaa gaagcgtctg cgtaccgaga cctttacacc tgactacatt | 1260 |
| cttgaaatca tcagctccca cccgcaactt gtgcgcgctc tctacgcctc attcgccagc | 1320 |
| gttcaccttc gggtcggcag cgattatgat cgccatctca ttgcgcctac gccggtcatg | 1380 |
| gaggtccttt ctgatgccag gcttaaggag aagatcacca aggacgtttc taacgagcac | 1440 |
| gaggaaatgg ttatgactgc cttccgtgta ttcaacaatg cagtcctcaa gacgaacttc | 1500 |
| ttcactccca ccaaagtcgc tttgagcttc ggcttaatc cctcgttcct tccggaagtc | 1560 |
| gagtatccca gccgctgta cggaatgttc ctcgtcatca cttccgagtc gcgaggtttc | 1620 |
| cacctccgct tcaaggatat tgcacggggt ggtattcgta ttgtcaagtc tcgaagtaag | 1680 |

-continued

```
gaggcttacc agatcaatgc ccgcaatctc tttgatgaga actacggtct tgccagcacc    1740
cagcagcgca agaacaagga tattccggag ggcggatcga agggtgtcat tctccttgac    1800
cccaagcagc aagacaggca ccgcgaggcc tttgagaagt acatcgatag tatccttgac    1860
cttcttctga aggctgagac gcctggcatc aagaacccca ttgtcgacct ctacggcaag    1920
gaggagattt tgttcatggg accggatgag aacactgctg accttgtcga ctgggccact    1980
gagcatgccc gggctcgcgg cgctccttgg tggaaatcct tcttcactgg taaatcacca    2040
cgtcttggtg catccctca cgactcctat ggcatgacaa ccttgtcggt tcgtgagtat     2100
gtcaagggta tttaccgcaa gcttgagctt gatccctcca agatcagaaa gatgcagact    2160
ggtggtcccg atggtgatct gggaagcaac gagattctgc tcagcaacga gacttacact    2220
gctatcgttg acggatccgg tgtcctctgc gaccccaacg gcattgacaa ggatgagtta    2280
cgccgtcttg ccaaggctcg tgctatgatc tcaaactttg atatcgccaa gctttccaag    2340
gatggttatc gtgtgctttg tgacgatacc aacgtcacac tccccaacgg agaggttgtg    2400
cacaatggca ctgcattccg taacacgtac catcttcgcg acaacggcat cactgatatg    2460
ttcgtgcctt gcggtggccg tcccgagtcg atcgacctct cctcagtcaa caagcttatc    2520
aaggatggaa agtcaaccat cccatatatt gttgagggtg ccaacctgtt catcactcaa    2580
gatgccaagc tcagactgga ggaagccggc tgcatcgttt acaaggatgc cagtgccaac    2640
aaaggcggtg taaccagctc atcgctcgag gtccttgcct ccctcagctt tgacgacaag    2700
ggcttcgtta cccacatgtg ccacgattcc cgcggcaatg cgcccgagtt ctaccaggcc    2760
tatgtcaagg aagtgcaaaa caagatccag gacaatgccc gcctcgagtt cgaggccatc    2820
tggcgggaac atgagcagac tggccttcct cgatctgttc tctctgacaa gttgtcattg    2880
gccatcacct ctcttgacga ggatctccag cgttcggagc tctgggacaa cgagaagatt    2940
cgcaggtccg tccttgccga tgccttgccc aaccttctca ttaacaagat cggcctcgat    3000
accatcatcg agcgtgttcc cgattcgtat ctgagggcca tctttggcag ctacctcgcc    3060
agtcgcttcg tctatgagtt tggtagctcg cccagccagt ttgctttcta tgatttcatg    3120
tcaaagagaa tgggaaacat caataaggag taa                                 3153
```

<210> SEQ ID NO 29
<211> LENGTH: 454
<212> TYPE: PRT
<213> ORGANISM: Neurospora crassa

<400> SEQUENCE: 29

```
Met Ser Asn Leu Pro Ser Glu Pro Glu Phe Glu Gln Ala Tyr Lys Glu
1               5                   10                  15

Leu Ala Tyr Thr Leu Glu Asn Ser Ser Leu Phe Gln Lys His Pro Glu
            20                  25                  30

Tyr Arg Thr Ala Leu Thr Val Ala Ser Ile Pro Glu Arg Val Ile Gln
        35                  40                  45

Phe Arg Val Val Trp Glu Asp Asp Asn Gly Asn Val Gln Val Asn Arg
    50                  55                  60

Gly Tyr Arg Val Gln Phe Asn Ser Ala Leu Gly Pro Tyr Lys Gly Gly
65                  70                  75                  80

Leu Arg Leu His Pro Ser Val Asn Leu Ser Ile Leu Lys Phe Leu Gly
                85                  90                  95

Phe Glu Gln Ile Phe Lys Asn Ala Leu Thr Gly Leu Ser Met Gly Gly
            100                 105                 110
```

Gly Lys Gly Gly Ala Asp Phe Asp Pro Lys Gly Lys Ser Asp Ala Glu
            115                 120                 125

Ile Arg Arg Phe Cys Cys Ala Phe Met Ala Glu Leu His Lys His Ile
        130                 135                 140

Gly Ala Asp Thr Asp Val Pro Ala Gly Asp Ile Gly Val Gly Gly Arg
145                 150                 155                 160

Glu Ile Gly Tyr Met Phe Gly Ala Tyr Arg Lys Ala Ala Asn Arg Phe
                165                 170                 175

Glu Gly Val Leu Thr Gly Lys Gly Leu Ser Trp Gly Gly Ser Leu Ile
            180                 185                 190

Arg Pro Glu Ala Thr Gly Tyr Gly Leu Val Tyr Val Gly His Met
        195                 200                 205

Leu Glu Tyr Ser Gly Ala Gly Ser Tyr Ala Gly Lys Arg Val Ala Leu
        210                 215                 220

Ser Gly Ser Gly Asn Val Ala Gln Tyr Ala Ala Leu Lys Leu Ile Glu
225                 230                 235                 240

Leu Gly Ala Thr Val Val Ser Leu Ser Asp Ser Lys Gly Ala Leu Val
                245                 250                 255

Ala Thr Gly Glu Ser Gly Ile Thr Val Glu Asp Ile Asn Ala Val Met
            260                 265                 270

Ala Ile Lys Glu Ala Arg Gln Ser Leu Thr Ser Phe Gln His Ala Gly
        275                 280                 285

His Leu Lys Trp Ile Glu Gly Ala Arg Pro Trp Leu His Val Gly Lys
        290                 295                 300

Val Asp Ile Ala Leu Pro Cys Ala Thr Gln Asn Glu Val Ser Lys Glu
305                 310                 315                 320

Glu Ala Glu Gly Leu Leu Ala Ala Gly Cys Lys Phe Val Ala Glu Gly
                325                 330                 335

Ser Asn Met Gly Cys Thr Leu Glu Ala Ile Glu Val Phe Glu Asn Asn
            340                 345                 350

Arg Lys Glu Lys Lys Gly Glu Ala Val Trp Tyr Ala Pro Gly Lys Ala
        355                 360                 365

Ala Asn Cys Gly Gly Val Ala Val Ser Gly Leu Glu Met Ala Gln Asn
        370                 375                 380

Ser Gln Arg Leu Asn Trp Thr Gln Ala Glu Val Asp Glu Lys Leu Lys
385                 390                 395                 400

Asp Ile Met Lys Asn Ala Phe Phe Asn Gly Leu Asn Thr Ala Lys Thr
                405                 410                 415

Tyr Val Glu Ala Ala Glu Gly Glu Leu Pro Ser Leu Val Ala Gly Ser
            420                 425                 430

Asn Ile Ala Gly Phe Val Lys Val Ala Gln Ala Met His Asp Gln Gly
        435                 440                 445

Asp Trp Trp Ser Lys Asn
    450

<210> SEQ ID NO 30
<211> LENGTH: 1371
<212> TYPE: DNA
<213> ORGANISM: Saccharomyces cerevisiae

<400> SEQUENCE: 30
atgacaagcg aaccagagtt tcagcaggct tacgatgaga tcgtttcttc tgtggaggat        60
tccaaaattt ttgaaaaatt cccacagtat aaaaaagtgt tacctattgt ttctgtcccg       120

```
gagaggatca ttcaattcag ggtcacgtgg gaaaatgata atggcgagca agaagtggct    180
caaggataca gggtgcagtt caattcagcc aagggcccct acaagggtgg cctacgcttc    240
cacccatcag tgaacctgtc tatcctaaaa tttttgggtt ttgaacagat cttcaagaat    300
gcgctcactg gctagatat gggcggtggt aagggtggcc tgtgtgtgga cttgaaaggc     360
aagtctgaca acgagatcag aaggatttgt tatgcgttca tgagagaact gagcaggcat    420
attggtaagg acacagacgt gcccgcagga gatattggtg tcggtggccg tgaaattggc    480
tacctattcg gcgcttacag atcatacaag aactcctggg aaggtgtgtt gactggtaag    540
ggtttaaact ggggtggctc acttatcagg ccggaggcca ccgggttcgg cttagtttac    600
tatacgcaag caatgatcga ttatgcaaca aacggcaagg agtcgtttga gggcaaacgt    660
gtgacaatct ccggaagtgg caatgttgcg caatatgcag ctttgaaagt gatcgagctg    720
ggtggtattg tggtgtcttt atccgattcg aagggtgca tcatctctga cgggcatt       780
acttctgagc aaattcacga tatcgcttcc gccaagatcc gtttcaagtc gttagaggaa    840
atcgttgatg aatactctac tttcagcgaa agtaagatga agtacgttgc aggagcacgc    900
ccatggacgc atgtgagcaa cgtcgacatt gccttgccct gtgccaccca aaacgaggtc    960
agtggtgacg aagccaaggc cctagtggca tctggcgtta agttcgttgc gaaggtgct   1020
aacatgggtt ctacacccga ggctatttct gttttcgaaa cagcgcgtag cactgcaacc   1080
aatgcaaagg atgcagtttg gtttgggcca ccaaaggcag ctaacctggg cggcgtggca   1140
gtatccggtc tggaaatggc tcagaattct caaaaagtaa cttggactgc gagcgggtc    1200
gatcaagaac taagaagat aatgatcaac tgcttcaacg actgcataca ggccgcacaa    1260
gagtactcta cggaaaaaaa tacaaacacc ttgccatcat tggtcaaggg ggccaacatt   1320
gccagcttcg tcatggtggc tgacgcaatg cttgaccagg gagacgttt t              1371
```

<210> SEQ ID NO 31
<211> LENGTH: 457
<212> TYPE: PRT
<213> ORGANISM: Saccharomyces cerevisiae

<400> SEQUENCE: 31

```
Met Thr Ser Glu Pro Glu Phe Gln Gln Ala Tyr Asp Glu Ile Val Ser
1               5                   10                  15

Ser Val Glu Asp Ser Lys Ile Phe Glu Lys Phe Pro Gln Tyr Lys Lys
            20                  25                  30

Val Leu Pro Ile Val Ser Val Pro Glu Arg Ile Gln Phe Arg Val
        35                  40                  45

Thr Trp Glu Asn Asp Asn Gly Glu Gln Glu Val Ala Gln Gly Tyr Arg
    50                  55                  60

Val Gln Phe Asn Ser Ala Lys Gly Pro Tyr Lys Gly Gly Leu Arg Phe
65                  70                  75                  80

His Pro Ser Val Asn Leu Ser Ile Leu Lys Phe Leu Gly Phe Glu Gln
                85                  90                  95

Ile Phe Lys Asn Ala Leu Thr Gly Leu Asp Met Gly Gly Gly Lys Gly
            100                 105                 110

Gly Leu Cys Val Asp Leu Lys Gly Lys Ser Asp Asn Glu Ile Arg Arg
        115                 120                 125

Ile Cys Tyr Ala Phe Met Arg Glu Leu Ser Arg His Ile Gly Lys Asp
    130                 135                 140

Thr Asp Val Pro Ala Gly Asp Ile Gly Val Gly Gly Arg Glu Ile Gly
145                 150                 155                 160
```

```
Tyr Leu Phe Gly Ala Tyr Arg Ser Tyr Lys Asn Ser Trp Glu Gly Val
            165                 170                 175

Leu Thr Gly Lys Gly Leu Asn Trp Gly Gly Ser Leu Ile Arg Pro Glu
        180                 185                 190

Ala Thr Gly Phe Gly Leu Val Tyr Tyr Thr Gln Ala Met Ile Asp Tyr
            195                 200                 205

Ala Thr Asn Gly Lys Glu Ser Phe Glu Gly Lys Arg Val Thr Ile Ser
        210                 215                 220

Gly Ser Gly Asn Val Ala Gln Tyr Ala Ala Leu Lys Val Ile Glu Leu
225                 230                 235                 240

Gly Gly Ile Val Val Ser Leu Ser Asp Ser Lys Gly Cys Ile Ile Ser
            245                 250                 255

Glu Thr Gly Ile Thr Ser Glu Gln Ile His Asp Ile Ala Ser Ala Lys
        260                 265                 270

Ile Arg Phe Lys Ser Leu Glu Glu Ile Val Asp Glu Tyr Ser Thr Phe
        275                 280                 285

Ser Glu Ser Lys Met Lys Tyr Val Ala Gly Ala Arg Pro Trp Thr His
        290                 295                 300

Val Ser Asn Val Asp Ile Ala Leu Pro Cys Ala Thr Gln Asn Glu Val
305                 310                 315                 320

Ser Gly Asp Glu Ala Lys Ala Leu Val Ala Ser Gly Val Lys Phe Val
            325                 330                 335

Ala Glu Gly Ala Asn Met Gly Ser Thr Pro Glu Ala Ile Ser Val Phe
            340                 345                 350

Glu Thr Ala Arg Ser Thr Ala Thr Asn Ala Lys Asp Ala Val Trp Phe
        355                 360                 365

Gly Pro Pro Lys Ala Ala Asn Leu Gly Gly Val Ala Val Ser Gly Leu
        370                 375                 380

Glu Met Ala Gln Asn Ser Gln Lys Val Thr Trp Thr Ala Glu Arg Val
385                 390                 395                 400

Asp Gln Glu Leu Lys Lys Ile Met Ile Asn Cys Phe Asn Asp Cys Ile
            405                 410                 415

Gln Ala Ala Gln Glu Tyr Ser Thr Glu Lys Asn Thr Asn Thr Leu Pro
            420                 425                 430

Ser Leu Val Lys Gly Ala Asn Ile Ala Ser Phe Val Met Val Ala Asp
        435                 440                 445

Ala Met Leu Asp Gln Gly Asp Val Phe
450                 455

<210> SEQ ID NO 32
<211> LENGTH: 6435
<212> TYPE: DNA
<213> ORGANISM: Saccharomyces cerevisiae

<400> SEQUENCE: 32
atgccagtgt tgaaatcaga caatttcgat ccattggaag aagcttacga aggtgggaca      60
attcaaaact ataacgatga acaccatctt cataaatctt gggcaaatgt gattccggac     120
aaacgaggac tttacgaccc tgattatgaa catgacgctt gtggtgtcgg tttcgtagca     180
aataagcatg gtgaacagtc tcacaagatt gttactgacg ctagatatct tttagtgaat     240
atgacacatc gtggtgccgt ctcatctgat gggaacggtg acggtgccgg tattctgcta     300
ggtattcctc acgaatttat gaaaagagaa ttcaagttag atcttgatct agacatacct     360
gagatgggca atacgccgt aggtaacgtc ttcttcaaga agaacgaaaa aaataacaag     420
```

```
aaaaatttaa ttaagtgtca gaagattttc gaggatttag ctgcatcctt caacttatcc      480
gtattaggtt ggagaaacgt ccccgtagat tctactattt taggagacgt tgcattatct      540
cgtgaaccta ctattctaca gccattattg gttccattgt atgatgaaaa acaaccggag      600
tttaatgaaa ctaaatttag aactcaattg tatcttttaa ggaaggaggc ctctcttcaa      660
ataggactgg aaaactggtt ctatgtttgt tccctaaaca ataccaccat tgtttacaag      720
ggtcaattga cgccagctca agtgtataac tactatcccg acttgactaa tgcgcatttc      780
aaatcccaca tggcgttggt ccattcaaga ttttccacta atactttccc ctcttgggat      840
agagctcaac ctttacgttg gctagctcat aatggtgaaa ttaacacctt aagaggtaac      900
aagaattgga tgcgctccag agaaggtgtg atgaattcag caactttcaa agatgagtta      960
gacaaactat acccaattat cgaagaaggt ggttctgatt cagctgcatt ggataacgtt     1020
ttagaactat tgactattaa tggcacatta tctctacctg aagctgttat gatgatggtt     1080
cctgaagcgt atcataagga tatggattct gacctaaaag catggtacga ctgggctgca     1140
tgtctgatgg aaccttggga tggtccagct ttgttaactt tcactgatgg acgttactgt     1200
ggtgctatat tggatagaaa atggtttaaga ccttgtcgtt attacatcac tagtgatgac     1260
agagttatct gtgcttcaga ggtaggtgtc attcctatcg aaaattcatt ggttgttcaa     1320
aaaggtaaac tgaagccagg tgatttattc ctagtggata ctcaattggg tgaaatggtc     1380
gatactaaaa agttaaaatc tcaaatctca aaaagacaag attttaagtc ttggttatcc     1440
aaagtcatca agtagacga cttgttatca aaaccgcta atttggttcc taaagaattt       1500
atatcacagg attcattgtc tttgaaagtt caaagtgacc cacgtctatt ggccaatggt     1560
tataccttcg aacaagtcac atttctgtta actccaatgg ctttaacagg taaagaagct     1620
ttaggttcga tgggtaacga tgcgccactg gcttgtttaa atgaaaatcc tgtcttactt     1680
tatgattatt tcagacaatt gtttgctcaa gtgaccaatc ctccaattga cccaattcgt     1740
gaagcaaatg ttatgtcgtt agaatgttat gtcggacctc aaggcaacct tttggaaatg     1800
cattcatctc aatgtgatcg tttattattg aaatctccta ttttgcattg gaatgagttc     1860
caagctttga aaaacattga agctgcttac ccatcatggt ctgtagcaga aattgatatc     1920
acattcgaca agagtgaggg tctattgggc tataccgaca caattgataa aatcactaag     1980
ttagcgagcg aagcaattga tgatggtaaa agatcttaa taattactga caggaaaatg     2040
ggtgccaacc gtgtttccat ctcctctttg attgcaattt catgtattca tcatcaccta     2100
atcagaaaca agcagcgttc ccaagttgct ttgattttgg aaacaggtga agccagagaa     2160
attcaccatt tctgtgtcct actaggttat ggttgtgatg gtgtttatcc atacttagcc     2220
atggaaactt tggtcagaat gaatagagaa ggtctacttc gtaatgtcaa caatgacaat     2280
gatacacttg aggaagggca aatactagaa aattacaagc acgctattga tgcaggtatc     2340
ttgaaggtta tgtctaaaat gggtatctcc actctagcat cctacaaagg tgctcaaatt     2400
tttgaagccc taggtttaga taactctatt gttgattgt gtttcacagg tacttcttcc      2460
agaattagag gtgtaacttt cgagtatttg gctcaagatg cctttttcttt acatgagcgt     2520 ggttatccat ccagacaaac cattagtaaa tctgttaact taccagaaag tggtaatac       2580 cactttaggg atggtggtta caaacacgtc aacgaaccaa ccgcaattgc ttcgttacaa     2640
gatactgtca gaaacaaaaa tgatgtctct tggcaattat atgtaaagaa ggaaatggaa     2700
gcaattagag actgtacact aagaggactg ttagaattag attttgaaaa ttctgtcagt     2760
```

```
atccctctag aacaagttga accatggact gaaattgcca gaagatttgc gtcaggtgca    2820
atgtcttatg gttctatttc tatggaagct cactctacat tggctattgc catgaatcgt    2880
ttaggggcca aatccaattg tggtgaaggt ggtgaagacg cagaacgttc tgctgttcaa    2940
gaaaacggtg atactatgag atctgctatc aaacaagttg cttccgctag attcggtgta    3000
acttcatact acttgtcaga tgctgatgaa atccaaatta agattgctca gggtgctaag    3060
ccgggtgaag tggtgaact accagcccac aaagtgtcta aggatatcgc aaaaaccagg    3120
cactccaccc ctaatgttgg gttaatctct cctcctcctc atcacgatat ttattccatt    3180
gaagatttga acaactgat ttatgatttg aaatgtgcta atccaagagc gggaatttct    3240
gtaaagttgg tttccgaagt tggtgttggt attgttgcct ctggtgtagc taaggctaaa    3300
gccgatcata tcttagtttc tggtcatgat ggtggtacag gtgctgcaag atggacgagt    3360
gtcaaatatg cgggtttgcc atgggaatta ggtctagctg aaactcacca gactttagtc    3420
ttgaatgatt taagacgtaa tgttgttgtc caaaccgatg gtcaattgag aactgggttt    3480
gatattgctg ttgcagtttt attaggggca gaatctttta ccttggcaac agttccatta    3540
attgctatgg gttgtgttat gttaagaaga tgtcacttga actcttgtgc tgttggtatt    3600
gccacacaag atccatattt gagaagtaag tttaaggggtc agcccgaaca tgttatcaac    3660
ttcttctatt acttgatcca agatttaaga caaatcatgg ccaagttagg attccgtacc    3720
attgacgaaa tggtgggtca ttctgaaaaa ttaaagaaaa gggacgacgt aaatgccaaa    3780
gccataaata tcgatttatc tcctattttg accccagcac atgttattcg tccaggtgtt    3840
ccaaccaagt tcactaagaa acaagaccac aaactccaca cccgtctaga taataagtta    3900
atcgatgagg ctgaagttac tttggatcgt ggcttaccag tgaatattga cgcctctata    3960
atcaatactg atcgtgcact cggttctact ttatcttaca gagtctcgaa gaaatttggt    4020
gaagatggtt tgccaaagga caccgttgtc gttaacatag aaggttcagc gggtcaatct    4080
tttggtgctt tcctagcttc tggtatcact tttatcttga atggtgatgc taatgattat    4140
gttggtaaag gtttatccgg tggtattatt gtcattaaac caccaaagga ttctaaattc    4200
aagagtgatg aaaatgtaat tgttggtaac acttgtttct atggtgctac ttctggtact    4260
gcattcattt caggtagtgc cggtgagcgt ttcggtgtca gaaactctgg tgccaccatc    4320
gttgttgaga gaattaaggg taacaatgcc tttgagtata tgactggtgg tcgtgccatt    4380
gtcttatcac aaatggaatc cctaaacgcc ttctctggtg ctactggtgg tattgcatac    4440
tgtttaactt ccgattacga cgattttgtt ggaaagatta caaagatac tgttgagtta    4500 gaatcattat gtgacccggt cgagattgcg tttgttaaga atttgatcca ggagcattgg    4560
aactacacac aatctgatct agcagccagg attctcggta atttcaacca ttatttgaaa    4620
gatttcgtta aagtcattcc aactgattat aagaaagttt tgttgaagga gaaagcagaa    4680
gctgccaagg caaaggctaa ggcaacttca gaatacttaa agaagtttag atcgaaccaa    4740
gaagttgatg acgaagtcaa tactctattg attgctaatc aaaaagctaa agagcaagaa    4800 aaaagaaga gtattactat ttcaaataag gccactttga aggagcctaa ggttgttgat    4860
ttagaagatg cagttccaga ttccaaacag ctagagaaga atagcgaaag gattgaaaaa    4920
acacgtggtt ttatgatcca caaacgtcgt catgagacac acagagatcc aagaaccaga    4980
gttaatgact ggaaagaatt tactaaccct attaccaaga aggatgccaa atatcaaact    5040
gcgagatgta tggattgtgg tacaccattc tgtttatctg ataccggttg tccctatct    5100 aacattatcc ccaagtttaa tgaattgtta ttcaagaacc aatggaagtt ggcactggac    5160
```

-continued

```
aaattgctag agacaaacaa tttcccagaa ttcactggaa gagtatgtcc agcaccctgt    5220
gagggagctt gtacactagg tattattgaa gacccagtcg gcataaaatc ggttgaaaga    5280
attatcattg acaatgcttt caaggaagga tggattaagc cttgtccacc aagtacacgc    5340
actggcttta cagtgggtgt cattggttct ggtccagcag gttagcgtg tgctgatatg     5400
ttgaaccgtg ccggacatac ggtcactgtt tatgaaagat ccgaccgttg tggtgggtta    5460
ttgatgtatg gtattccaaa catgaagttg ataaggcta tagtgcaacg tcgtattgat     5520
ctattgagtg ccgaaggtat tgactttgtt accaacaccg aaattggtaa aaccataagc    5580
atggatgagc taaagaacaa gcacaatgca gtagtgtatg ctatcggttc taccattcca    5640
cgtgacttac ctattaaggg tcgtgaattg aagaatattg attttgccat gcagttgttg    5700
gaatctaaca caaagcttt attgaacaaa gatctggaaa tcattcgtga aaagatccaa    5760
ggtaagaaag taattgttgt cggtggtggt gacacaggta acgattgttt aggtacatct    5820
gtaagacacg gtgcagcatc agttttgaat ttcgaattgt tgcctgagcc accagtggaa    5880
cgtgccaaag acaatccatg gcctcaatgg ccgcgtgtca tgagagtgga ctacggtcat    5940
gctgaagtga aagagcatta tggtagagac cctcgtgaat actgcatctt gtccaaggaa    6000
tttatcggta acgatgaggg tgaagtcact gccatcagaa ctgtgcgcgt agaatggaag    6060
aagtcacaaa gtggcgtatg gcaaatggta gaaattccca acagtgaaga gatctttgaa    6120
gccgatatca ttttgttgtc tatgggtttc gtgggtcctg aattgatcaa tggcaacgat    6180
aacgaagtta agaagacaag acgtggtacg attgccacac tcgacgactc ctcatactct    6240
attgatggag gaaagacttt tgcatgtggt gactgtagaa gagggcaatc tttgattgtc    6300
tgggccatcc aagaaggtag aaaatgtgct gcctctgtcg ataagttcct aatggacggc    6360
actacgtatc taccaagtaa tggtggtatc gttcaacgtg attacaaact attgaaagaa    6420
ttagctagtc aagtc                                                    6435
```

<210> SEQ ID NO 33
<211> LENGTH: 2145
<212> TYPE: PRT
<213> ORGANISM: Saccharomyces cerevisiae

<400> SEQUENCE: 33

```
Met Pro Val Leu Lys Ser Asp Asn Phe Asp Pro Leu Glu Glu Ala Tyr
1               5                   10                  15

Glu Gly Gly Thr Ile Gln Asn Tyr Asn Asp Glu His His Leu His Lys
            20                  25                  30

Ser Trp Ala Asn Val Ile Pro Asp Lys Arg Gly Leu Tyr Asp Pro Asp
        35                  40                  45

Tyr Glu His Asp Ala Cys Gly Val Gly Phe Val Ala Asn Lys His Gly
    50                  55                  60

Glu Gln Ser His Lys Ile Val Thr Asp Ala Arg Tyr Leu Leu Val Asn
65                  70                  75                  80

Met Thr His Arg Gly Ala Val Ser Ser Asp Gly Asn Gly Asp Gly Ala
                85                  90                  95

Gly Ile Leu Leu Gly Ile Pro His Glu Phe Met Lys Arg Glu Phe Lys
            100                 105                 110

Leu Asp Leu Asp Leu Asp Ile Pro Glu Met Gly Lys Tyr Ala Val Gly
        115                 120                 125

Asn Val Phe Phe Lys Lys Asn Glu Lys Asn Asn Lys Lys Asn Leu Ile
    130                 135                 140
```

```
Lys Cys Gln Lys Ile Phe Glu Asp Leu Ala Ala Ser Phe Asn Leu Ser
145                 150                 155                 160

Val Leu Gly Trp Arg Asn Val Pro Val Asp Ser Thr Ile Leu Gly Asp
                165                 170                 175

Val Ala Leu Ser Arg Glu Pro Thr Ile Leu Gln Pro Leu Leu Val Pro
            180                 185                 190

Leu Tyr Asp Glu Lys Gln Pro Glu Phe Asn Glu Thr Lys Phe Arg Thr
        195                 200                 205

Gln Leu Tyr Leu Leu Arg Lys Glu Ala Ser Leu Gln Ile Gly Leu Glu
    210                 215                 220

Asn Trp Phe Tyr Val Cys Ser Leu Asn Asn Thr Thr Ile Val Tyr Lys
225                 230                 235                 240

Gly Gln Leu Thr Pro Ala Gln Val Tyr Asn Tyr Tyr Pro Asp Leu Thr
                245                 250                 255

Asn Ala His Phe Lys Ser His Met Ala Leu Val His Ser Arg Phe Ser
            260                 265                 270

Thr Asn Thr Phe Pro Ser Trp Asp Arg Ala Gln Pro Leu Arg Trp Leu
        275                 280                 285

Ala His Asn Gly Glu Ile Asn Thr Leu Arg Gly Asn Lys Asn Trp Met
    290                 295                 300

Arg Ser Arg Glu Gly Val Met Asn Ser Ala Thr Phe Lys Asp Glu Leu
305                 310                 315                 320

Asp Lys Leu Tyr Pro Ile Ile Glu Glu Gly Gly Ser Asp Ser Ala Ala
                325                 330                 335

Leu Asp Asn Val Leu Glu Leu Leu Thr Ile Asn Gly Thr Leu Ser Leu
            340                 345                 350

Pro Glu Ala Val Met Met Met Val Pro Glu Ala Tyr His Lys Asp Met
        355                 360                 365

Asp Ser Asp Leu Lys Ala Trp Tyr Asp Trp Ala Ala Cys Leu Met Glu
    370                 375                 380

Pro Trp Asp Gly Pro Ala Leu Leu Thr Phe Thr Asp Gly Arg Tyr Cys
385                 390                 395                 400

Gly Ala Ile Leu Asp Arg Asn Gly Leu Arg Pro Cys Arg Tyr Tyr Ile
                405                 410                 415

Thr Ser Asp Asp Arg Val Ile Cys Ala Ser Glu Val Gly Val Ile Pro
            420                 425                 430

Ile Glu Asn Ser Leu Val Val Gln Lys Gly Lys Leu Lys Pro Gly Asp
        435                 440                 445

Leu Phe Leu Val Asp Thr Gln Leu Gly Glu Met Val Asp Thr Lys Lys
    450                 455                 460

Leu Lys Ser Gln Ile Ser Lys Arg Gln Asp Phe Lys Ser Trp Leu Ser
465                 470                 475                 480

Lys Val Ile Lys Leu Asp Asp Leu Leu Ser Lys Thr Ala Asn Leu Val
                485                 490                 495

Pro Lys Glu Phe Ile Ser Gln Asp Ser Leu Ser Lys Val Gln Ser
            500                 505                 510

Asp Pro Arg Leu Leu Ala Asn Gly Tyr Thr Phe Glu Gln Val Thr Phe
        515                 520                 525

Leu Leu Thr Pro Met Ala Leu Thr Gly Lys Glu Ala Leu Gly Ser Met
    530                 535                 540

Gly Asn Asp Ala Pro Leu Ala Cys Leu Asn Glu Asn Pro Val Leu Leu
545                 550                 555                 560
```

-continued

```
Tyr Asp Tyr Phe Arg Gln Leu Phe Ala Gln Val Thr Asn Pro Pro Ile
                565                 570                 575
Asp Pro Ile Arg Glu Ala Asn Val Met Ser Leu Glu Cys Tyr Val Gly
            580                 585                 590
Pro Gln Gly Asn Leu Leu Glu Met His Ser Ser Gln Cys Asp Arg Leu
            595                 600                 605
Leu Leu Lys Ser Pro Ile Leu His Trp Asn Glu Phe Gln Ala Leu Lys
        610                 615                 620
Asn Ile Glu Ala Ala Tyr Pro Ser Trp Ser Val Ala Glu Ile Asp Ile
625                 630                 635                 640
Thr Phe Asp Lys Ser Glu Gly Leu Leu Gly Tyr Thr Asp Thr Ile Asp
                645                 650                 655
Lys Ile Thr Lys Leu Ala Ser Glu Ala Ile Asp Asp Gly Lys Lys Ile
            660                 665                 670
Leu Ile Ile Thr Asp Arg Lys Met Gly Ala Asn Arg Val Ser Ile Ser
            675                 680                 685
Ser Leu Ile Ala Ile Ser Cys Ile His His Leu Ile Arg Asn Lys
        690                 695                 700
Gln Arg Ser Gln Val Ala Leu Ile Leu Glu Thr Gly Glu Ala Arg Glu
705                 710                 715                 720
Ile His His Phe Cys Val Leu Leu Gly Tyr Gly Cys Asp Gly Val Tyr
                725                 730                 735
Pro Tyr Leu Ala Met Glu Thr Leu Val Arg Met Asn Arg Glu Gly Leu
            740                 745                 750
Leu Arg Asn Val Asn Asn Asp Asn Asp Thr Leu Glu Glu Gly Gln Ile
            755                 760                 765
Leu Glu Asn Tyr Lys His Ala Ile Asp Ala Gly Ile Leu Lys Val Met
        770                 775                 780
Ser Lys Met Gly Ile Ser Thr Leu Ala Ser Tyr Lys Gly Ala Gln Ile
785                 790                 795                 800
Phe Glu Ala Leu Gly Leu Asp Asn Ser Ile Val Asp Leu Cys Phe Thr
                805                 810                 815
Gly Thr Ser Ser Arg Ile Arg Gly Val Thr Phe Glu Tyr Leu Ala Gln
            820                 825                 830
Asp Ala Phe Ser Leu His Glu Arg Gly Tyr Pro Ser Arg Gln Thr Ile
            835                 840                 845
Ser Lys Ser Val Asn Leu Pro Glu Ser Gly Glu Tyr His Phe Arg Asp
        850                 855                 860
Gly Gly Tyr Lys His Val Asn Glu Pro Thr Ala Ile Ala Ser Leu Gln
865                 870                 875                 880
Asp Thr Val Arg Asn Lys Asn Asp Val Ser Trp Gln Leu Tyr Val Lys
                885                 890                 895
Lys Glu Met Glu Ala Ile Arg Asp Cys Thr Leu Arg Gly Leu Leu Glu
            900                 905                 910
Leu Asp Phe Glu Asn Ser Val Ser Ile Pro Leu Glu Gln Val Glu Pro
            915                 920                 925
Trp Thr Glu Ile Ala Arg Arg Phe Ala Ser Gly Ala Met Ser Tyr Gly
        930                 935                 940
Ser Ile Ser Met Glu Ala His Ser Thr Leu Ala Ile Ala Met Asn Arg
945                 950                 955                 960
Leu Gly Ala Lys Ser Asn Cys Gly Glu Gly Gly Glu Asp Ala Glu Arg
                965                 970                 975
Ser Ala Val Gln Glu Asn Gly Asp Thr Met Arg Ser Ala Ile Lys Gln
```

-continued

```
            980                985                990
Val Ala Ser Ala Arg Phe Gly Val Thr Ser Tyr Tyr Leu Ser Asp Ala
                995                1000               1005

Asp Glu Ile Gln Ile Lys Ile Ala Gln Gly Ala Lys Pro Gly Glu
    1010            1015            1020

Gly Gly Glu Leu Pro Ala His Lys Val Ser Lys Asp Ile Ala Lys
    1025            1030            1035

Thr Arg His Ser Thr Pro Asn Val Gly Leu Ile Ser Pro Pro Pro
    1040            1045            1050

His His Asp Ile Tyr Ser Ile Glu Asp Leu Lys Gln Leu Ile Tyr
    1055            1060            1065

Asp Leu Lys Cys Ala Asn Pro Arg Ala Gly Ile Ser Val Lys Leu
    1070            1075            1080

Val Ser Glu Val Gly Val Gly Ile Val Ala Ser Gly Val Ala Lys
    1085            1090            1095

Ala Lys Ala Asp His Ile Leu Val Ser Gly His Asp Gly Gly Thr
    1100            1105            1110

Gly Ala Ala Arg Trp Thr Ser Val Lys Tyr Ala Gly Leu Pro Trp
    1115            1120            1125

Glu Leu Gly Leu Ala Glu Thr His Gln Thr Leu Val Leu Asn Asp
    1130            1135            1140

Leu Arg Arg Asn Val Val Val Gln Thr Asp Gly Gln Leu Arg Thr
    1145            1150            1155

Gly Phe Asp Ile Ala Val Ala Val Leu Leu Gly Ala Glu Ser Phe
    1160            1165            1170

Thr Leu Ala Thr Val Pro Leu Ile Ala Met Gly Cys Val Met Leu
    1175            1180            1185

Arg Arg Cys His Leu Asn Ser Cys Ala Val Gly Ile Ala Thr Gln
    1190            1195            1200

Asp Pro Tyr Leu Arg Ser Lys Phe Lys Gly Gln Pro Glu His Val
    1205            1210            1215

Ile Asn Phe Phe Tyr Tyr Leu Ile Gln Asp Leu Arg Gln Ile Met
    1220            1225            1230

Ala Lys Leu Gly Phe Arg Thr Ile Asp Glu Met Val Gly His Ser
    1235            1240            1245

Glu Lys Leu Lys Lys Arg Asp Asp Val Asn Ala Lys Ala Ile Asn
    1250            1255            1260

Ile Asp Leu Ser Pro Ile Leu Thr Pro Ala His Val Ile Arg Pro
    1265            1270            1275

Gly Val Pro Thr Lys Phe Thr Lys Lys Gln Asp His Lys Leu His
    1280            1285            1290

Thr Arg Leu Asp Asn Lys Leu Ile Asp Glu Ala Glu Val Thr Leu
    1295            1300            1305

Asp Arg Gly Leu Pro Val Asn Ile Asp Ala Ser Ile Ile Asn Thr
    1310            1315            1320

Asp Arg Ala Leu Gly Ser Thr Leu Ser Tyr Arg Val Ser Lys Lys
    1325            1330            1335

Phe Gly Glu Asp Gly Leu Pro Lys Asp Thr Val Val Val Asn Ile
    1340            1345            1350

Glu Gly Ser Ala Gly Gln Ser Phe Gly Ala Phe Leu Ala Ser Gly
    1355            1360            1365

Ile Thr Phe Ile Leu Asn Gly Asp Ala Asn Asp Tyr Val Gly Lys
    1370            1375            1380
```

-continued

```
Gly Leu Ser Gly Gly Ile Ile Val Ile Lys Pro Pro Lys Asp Ser
1385                1390                1395
Lys Phe Lys Ser Asp Glu Asn Val Ile Val Gly Asn Thr Cys Phe
1400                1405                1410
Tyr Gly Ala Thr Ser Gly Thr Ala Phe Ile Ser Gly Ser Ala Gly
1415                1420                1425
Glu Arg Phe Gly Val Arg Asn Ser Gly Ala Thr Ile Val Val Glu
1430                1435                1440
Arg Ile Lys Gly Asn Asn Ala Phe Glu Tyr Met Thr Gly Gly Arg
1445                1450                1455
Ala Ile Val Leu Ser Gln Met Glu Ser Leu Asn Ala Phe Ser Gly
1460                1465                1470
Ala Thr Gly Gly Ile Ala Tyr Cys Leu Thr Ser Asp Tyr Asp Asp
1475                1480                1485
Phe Val Gly Lys Ile Asn Lys Asp Thr Val Glu Leu Glu Ser Leu
1490                1495                1500
Cys Asp Pro Val Glu Ile Ala Phe Val Lys Asn Leu Ile Gln Glu
1505                1510                1515
His Trp Asn Tyr Thr Gln Ser Asp Leu Ala Ala Arg Ile Leu Gly
1520                1525                1530
Asn Phe Asn His Tyr Leu Lys Asp Phe Val Lys Val Ile Pro Thr
1535                1540                1545
Asp Tyr Lys Lys Val Leu Leu Lys Glu Lys Ala Glu Ala Ala Lys
1550                1555                1560
Ala Lys Ala Lys Ala Thr Ser Glu Tyr Leu Lys Lys Phe Arg Ser
1565                1570                1575
Asn Gln Glu Val Asp Asp Glu Val Asn Thr Leu Leu Ile Ala Asn
1580                1585                1590
Gln Lys Ala Lys Glu Gln Glu Lys Lys Lys Ser Ile Thr Ile Ser
1595                1600                1605
Asn Lys Ala Thr Leu Lys Glu Pro Lys Val Val Asp Leu Glu Asp
1610                1615                1620
Ala Val Pro Asp Ser Lys Gln Leu Glu Lys Asn Ser Glu Arg Ile
1625                1630                1635
Glu Lys Thr Arg Gly Phe Met Ile His Lys Arg Arg His Glu Thr
1640                1645                1650
His Arg Asp Pro Arg Thr Arg Val Asn Asp Trp Lys Glu Phe Thr
1655                1660                1665
Asn Pro Ile Thr Lys Lys Asp Ala Lys Tyr Gln Thr Ala Arg Cys
1670                1675                1680
Met Asp Cys Gly Thr Pro Phe Cys Leu Ser Asp Thr Gly Cys Pro
1685                1690                1695
Leu Ser Asn Ile Ile Pro Lys Phe Asn Glu Leu Leu Phe Lys Asn
1700                1705                1710
Gln Trp Lys Leu Ala Leu Asp Lys Leu Leu Glu Thr Asn Asn Phe
1715                1720                1725
Pro Glu Phe Thr Gly Arg Val Cys Pro Ala Pro Cys Glu Gly Ala
1730                1735                1740
Cys Thr Leu Gly Ile Ile Glu Asp Pro Val Gly Ile Lys Ser Val
1745                1750                1755
Glu Arg Ile Ile Ile Asp Asn Ala Phe Lys Glu Gly Trp Ile Lys
1760                1765                1770
```

| | | | | | | | | | | | |
|---|---|---|---|---|---|---|---|---|---|---|---|
| Pro | Cys | Pro | Pro | Ser | Thr | Arg | Thr | Gly | Phe | Thr | Val | Gly | Val | Ile |
| 1775 | | | | | 1780 | | | | | 1785 | | | | |

Gly Ser Gly Pro Ala Gly Leu Ala Cys Ala Asp Met Leu Asn Arg
1790 1795 1800

Ala Gly His Thr Val Thr Val Tyr Glu Arg Ser Asp Arg Cys Gly
1805 1810 1815

Gly Leu Leu Met Tyr Gly Ile Pro Asn Met Lys Leu Asp Lys Ala
1820 1825 1830

Ile Val Gln Arg Arg Ile Asp Leu Leu Ser Ala Glu Gly Ile Asp
1835 1840 1845

Phe Val Thr Asn Thr Glu Ile Gly Lys Thr Ile Ser Met Asp Glu
1850 1855 1860

Leu Lys Asn Lys His Asn Ala Val Val Tyr Ala Ile Gly Ser Thr
1865 1870 1875

Ile Pro Arg Asp Leu Pro Ile Lys Gly Arg Glu Leu Lys Asn Ile
1880 1885 1890

Asp Phe Ala Met Gln Leu Leu Glu Ser Asn Thr Lys Ala Leu Leu
1895 1900 1905

Asn Lys Asp Leu Glu Ile Ile Arg Glu Lys Ile Gln Gly Lys Lys
1910 1915 1920

Val Ile Val Val Gly Gly Gly Asp Thr Gly Asn Asp Cys Leu Gly
1925 1930 1935

Thr Ser Val Arg His Gly Ala Ala Ser Val Leu Asn Phe Glu Leu
1940 1945 1950

Leu Pro Glu Pro Pro Val Glu Arg Ala Lys Asp Asn Pro Trp Pro
1955 1960 1965

Gln Trp Pro Arg Val Met Arg Val Asp Tyr Gly His Ala Glu Val
1970 1975 1980

Lys Glu His Tyr Gly Arg Asp Pro Arg Glu Tyr Cys Ile Leu Ser
1985 1990 1995

Lys Glu Phe Ile Gly Asn Asp Glu Gly Glu Val Thr Ala Ile Arg
2000 2005 2010

Thr Val Arg Val Glu Trp Lys Lys Ser Gln Ser Gly Val Trp Gln
2015 2020 2025

Met Val Glu Ile Pro Asn Ser Glu Glu Ile Phe Glu Ala Asp Ile
2030 2035 2040

Ile Leu Leu Ser Met Gly Phe Val Gly Pro Glu Leu Ile Asn Gly
2045 2050 2055

Asn Asp Asn Glu Val Lys Lys Thr Arg Arg Gly Thr Ile Ala Thr
2060 2065 2070

Leu Asp Asp Ser Ser Tyr Ser Ile Asp Gly Gly Lys Thr Phe Ala
2075 2080 2085

Cys Gly Asp Cys Arg Arg Gly Gln Ser Leu Ile Val Trp Ala Ile
2090 2095 2100

Gln Glu Gly Arg Lys Cys Ala Ala Ser Val Asp Lys Phe Leu Met
2105 2110 2115

Asp Gly Thr Thr Tyr Leu Pro Ser Asn Gly Gly Ile Val Gln Arg
2120 2125 2130

Asp Tyr Lys Leu Leu Lys Glu Leu Ala Ser Gln Val
2135 2140 2145

<210> SEQ ID NO 34
<211> LENGTH: 1110
<212> TYPE: DNA

<213> ORGANISM: Saccharomyces cerevisiae

<400> SEQUENCE: 34

```
atggctgaag caagcatcga aaagactcaa attttacaaa aatatctaga actggaccaa      60
agaggtagaa taattgccga atacgtttgg atcgatggta ctggtaactt acgttccaaa     120
ggtagaactt tgaagaagag aatcacatcc attgaccaat gccagaatg gaacttcgac      180
ggttcttcta ccaaccaagc gccaggccac gactctgaca tctatttgaa acccgttgct     240
tactacccag atcccttcag gagaggtgac aacattgttg tcttggccgc atgttacaac     300
aatgacggta ctccaaacaa gttcaaccac agacacgaag ctgccaagct atttgctgct     360
cataaggatg aagaaatctg gtttggtcta gaacaagaat acactctatt tgacatgtat     420
gacgatgttt acgatggcc aaagggtggg tacccagctc cacaaggtcc ttactactgt     480
ggtgttggtg ccggtaaggt ttatgccaga gacatgatcg aagctcacta cagagcttgt     540
ttgtatgccg gattagaaat ttctggtatt aacgctgaag tcatgccatc tcaatgggaa     600
ttccaagtcg gtccatgtac cggtattgac atgggtgacc aattatggat ggccagatac     660
tttttgcaca gagtggcaga gagtttggt atcaagatct cattccatcc aaagccattg     720
aagggtgact ggaacggtgc cggttgtcac actaacgttt ccaccaagga atgagacaa      780
ccaggtggta tgaaatacat cgaacaagcc atcgagaagt tatccaagag acacgctgaa     840
cacattaagt tgtacggtag cgataacgac atgagattaa ctggtagaca tgaaaccgct     900
tccatgactg ccttttcttc tggtgtcgcc aacagaggta gctcaattag aatcccaaga     960
tccgtcgcca aggaaggtta cggttacttt gaagaccgta gaccagcttc caacatcgac    1020
ccatacttgg ttacaggtat catgtgtgaa actgtttgcg gtgctattga caatgctgac    1080
atgacgaagg aatttgaaag agaatcttca                                     1110
```

<210> SEQ ID NO 35
<211> LENGTH: 370
<212> TYPE: PRT
<213> ORGANISM: Saccharomyces cerevisiae

<400> SEQUENCE: 35

```
Met Ala Glu Ala Ser Ile Glu Lys Thr Gln Ile Leu Gln Lys Tyr Leu
1               5                   10                  15

Glu Leu Asp Gln Arg Gly Arg Ile Ile Ala Glu Tyr Val Trp Ile Asp
            20                  25                  30

Gly Thr Gly Asn Leu Arg Ser Lys Gly Arg Thr Leu Lys Lys Arg Ile
        35                  40                  45

Thr Ser Ile Asp Gln Leu Pro Glu Trp Asn Phe Asp Gly Ser Ser Thr
    50                  55                  60

Asn Gln Ala Pro Gly His Asp Ser Asp Ile Tyr Leu Lys Pro Val Ala
65                  70                  75                  80

Tyr Tyr Pro Asp Pro Phe Arg Arg Gly Asp Asn Ile Val Val Leu Ala
                85                  90                  95

Ala Cys Tyr Asn Asn Asp Gly Thr Pro Asn Lys Phe Asn His Arg His
            100                 105                 110

Glu Ala Ala Lys Leu Phe Ala Ala His Lys Asp Glu Glu Ile Trp Phe
        115                 120                 125

Gly Leu Glu Gln Glu Tyr Thr Leu Phe Asp Met Tyr Asp Asp Val Tyr
    130                 135                 140

Gly Trp Pro Lys Gly Gly Tyr Pro Ala Pro Gln Gly Pro Tyr Tyr Cys
145                 150                 155                 160
```

```
Gly Val Gly Ala Gly Lys Val Tyr Ala Arg Asp Met Ile Glu Ala His
            165                 170                 175

Tyr Arg Ala Cys Leu Tyr Ala Gly Leu Glu Ile Ser Gly Ile Asn Ala
        180                 185                 190

Glu Val Met Pro Ser Gln Trp Glu Phe Gln Val Gly Pro Cys Thr Gly
    195                 200                 205

Ile Asp Met Gly Asp Gln Leu Trp Met Ala Arg Tyr Phe Leu His Arg
210                 215                 220

Val Ala Glu Glu Phe Gly Ile Lys Ile Ser Phe His Pro Lys Pro Leu
225                 230                 235                 240

Lys Gly Asp Trp Asn Gly Ala Gly Cys His Thr Asn Val Ser Thr Lys
                245                 250                 255

Glu Met Arg Gln Pro Gly Gly Met Lys Tyr Ile Glu Gln Ala Ile Glu
            260                 265                 270

Lys Leu Ser Lys Arg His Ala Glu His Ile Lys Leu Tyr Gly Ser Asp
        275                 280                 285

Asn Asp Met Arg Leu Thr Gly Arg His Glu Thr Ala Ser Met Thr Ala
    290                 295                 300

Phe Ser Ser Gly Val Ala Asn Arg Gly Ser Ser Ile Arg Ile Pro Arg
305                 310                 315                 320

Ser Val Ala Lys Glu Gly Tyr Gly Tyr Phe Glu Asp Arg Arg Pro Ala
                325                 330                 335

Ser Asn Ile Asp Pro Tyr Leu Val Thr Gly Ile Met Cys Glu Thr Val
            340                 345                 350

Cys Gly Ala Ile Asp Asn Ala Asp Met Thr Lys Glu Phe Glu Arg Glu
        355                 360                 365

Ser Ser
    370

<210> SEQ ID NO 36
<211> LENGTH: 5505
<212> TYPE: DNA
<213> ORGANISM: Saccharomyces cerevisiae

<400> SEQUENCE: 36
atgacagtta gttccgatac aactgctgaa atatcgttag gttggtcaat ccaagactgg      60
attgatttcc acaagtcatc aagctcccag gcttcactaa ggcttcttga atcactacta     120
gactctcaaa atgttgcgcc agtcgataat gcgtggatat cgctaatttc aaaggaaaat     180
ttactgcacc aattccaaat tttaaagagc agagaaaata agaaactct acctctctac      240
ggtgtcccta ttgctgttaa ggacaacatc gacgttagag tctaccac caccgctgca      300
tgtccatcct ttgcatatga gccttccaaa gactctaaag tagtagaact actaagaaat     360
gcaggtgcga taatcgtggg taagacaaac ttggaccaat tgccacagg attagtcggc     420
acacggtctc catatgggaa acaccttgc gcttttagca aagagcatgt atctggtggt     480
tcctccgctg ggtcagcatc ggtggtcgcc agaggtatcg taccaattgc attgggtact     540
gatacagcag gttctggtag agtcccagcc gccttgaaca acctgattgg cctaaagcca     600
acaaagggcg tctttttcctg tcaaggtgta gttcccgctt gtaaatcttt agactgcgtc     660
tccatctttg cattaaacct aagtgatgct gaacgctgct ccgcatcat gtgccagcca      720
gatcctgata tgatgaata ttctagaccc tatgttccca acctttgaa aaaattttca      780
agcaatgtaa cgattgctat tcctaaaaat atcccatggt atggtgaaac caagaatcct     840
```

```
gtactgtttt ccaatgctgt cgaaaatcta tcaagaacgg gcgctaacgt catagaaatt      900
gattttgagc ctcttttaga gttagctcgc tgtttatacg aaggtacttg ggtggccgag      960
cgttatcaag ctattcaatc gttttgggac agtaaaccac caaaggaatc tttggaccct     1020
actgttattt caattataga aggggccaag aaatacagtg cagtagactg cttcagtttt     1080
gaatacaaaa gacaaggcat cttgcaaaaa gtgagacgac ttctcgaatc agtcgatgtc     1140
ttgtgtgtgc ccacatgtcc tttaaatcct actatgcaac aagttgcgga tgaaccagtc     1200
ctagtcaatt caagacaagg cacatggact aattttgtca acttggcaga tttggcagcc     1260
cttgctgttc ccgcagggtt ccgagacgat ggtttgccaa atggtattac tttaatcggt     1320
aaaaaattca cagattacgc actattagag ttggctaacc gctatttcca aaatatattc     1380
cccaacggtt ccagaacata cggtactttt acctcttctt cagtaaagcc agcaaacgat     1440
caattagtgg gaccagacta tgacccatct acgtccataa aattggctgt tgtcggtgca     1500
catcttaagg gtctgcctct acattggcaa ttggaaaagg tcaatgcaac atatttatgt     1560
acaacaaaaa catcaaaagc ttaccagctt tttgctttgc ccaaaaatgg accagtttta     1620
aaacctggtt tgagaagagt tcaagatagc aatggctctc aaatcgaatt agaagtgtac     1680
agtgttccaa aagaactgtt cggtgctttt atttccatgg ttcctgaacc attaggaata     1740
ggttcagtgg agttagaatc tggtgaatgg atcaaatcct ttatttgtga agaatctggt     1800
tacaaagcca aaggtacagt tgatatcaca agtatggtg gatttagagc atattttgaa      1860
atgttgaaga aaaagagtc ccaaaagaag aagttatttg ataccgtgtt aattgccaat      1920
agaggtgaaa ttgccgttcg tattatcaag acattaaaaa aattgggtat tagatcagtt     1980
gcagtttatt ccgaccctga taaatattct caacacgtta ctgatgcaga tgtttctgta     2040 cccttcatg gcacaaccgc agcccaaact tatttagaca tgaataagat catagatgcc      2100
gctaagcaaa ctaatgcaca ggccattatt cctggttatg gtttcttgtc ggaaaatgcg     2160 gattttctg atgcgtgcac cagtgctggc attacctttg ttggtccttc gggagatatt      2220
atcagaggtt tagggttaaa acattctgct agacagattg cacagaaggc tggcgttcct     2280
ctagtgccag gctctttgct tatcacatca gttgaagagg ctaagaaagt cgcagcggaa     2340
ttggaatacc cagttatggt gaagtcaact gctggtggcg gtggtattgg tttgcagaaa     2400
gtcgattctg aagaggacat cgagcatatt tttgagactg tgaaacatca aggtgaaaca     2460 ttttcggtg acgctggtgt atttctggaa cggtttatcg aaaatgccag gcatgttgaa      2520
gtccaactta tgggagatgg ttttggtaag gccattgctt tgggcgaacg tgattgttct     2580
ttacagcgtc gtaaccaaaa agttatcgaa gaaactcctg caccaaattt gccagaaaag     2640
acgaggttgg cgttaagaaa ggcagctgaa agtttgggat cttttattgaa ttacaagtgt      2700 gctggtacgg ttgaatttat ttacgatgag aaaaaggacg agttttactt tttagaagtt     2760
aatacaagat tacaagttga acatccaata acagaaatgg ttacagggtt agacttggtc     2820
gagtggatga tcaggattgc cgctaatgat gcacctgatt ttgattctac aaaggtagaa     2880
gtcaatgggg tttcaatgga ggcacgttta tatgctgaaa atccattgaa aaatttcaga     2940
ccttctccag gtttacttgt cgatgtgaaa tttcctgatt gggcaagagt ggatacttgg     3000
gttaagaaag gtactaatat ttctcccgaa tatgatccaa cattggccaa aattatcgtt     3060
catgggaaag accgtgatga tgcaatttcc aagttaaatc aagcgttaga agaaacaaaa     3120
gtttacggat gtattactaa cattgactac ctgaagtcta tcattaccag tgatttcttt     3180
gctaaagcaa aagtttctac aaacattttg aactcttatc aatatgagcc taccgccatc     3240
```

```
gaaattactt tgcccggtgc acacactagt attcaggatt accccggtag agttgggtac      3300
tggagaattg gtgttccgcc ctctggtcca acggacgcat attcgtttag attggcgaac      3360
agaattgttg gtaatgacta caggactcct gccattgaag taacgttgac tggtccatcc      3420
atcgttttcc attgtgaaac tgtcattgcc attactggtg gtaccgctct atgtacatta      3480
gacggccaag aaattcccca acacaaaccg gtcgaagtta agaggggatc tactttatcc      3540
attggcaagt tgacaagcgg ctgtagagca tacttaggta tcaggggtgg cattgatgtg      3600
cctaaatact tgggctctta ttctactttc actctaggaa atgtcggtgg atacaatgga      3660
agggtgctaa aacttggaga cgtactattc ttaccaagca atgaagaaaa taaatcagtt      3720
gagtgccttc cacagaatat tcctcaatca ttaattcctc aaatttccga aactaaggaa      3780
tggagaattg gtgtaacatg tggtccccat gggtctccag attttttttaa acctgagtcc      3840
atcgaagaat ttttcagtga gaagtggaag gttcattaca actccaatag atttggtgtc      3900
cgtttgattg gacctaaacc taagtgggca agaagtaatg gtggtgaagg tggtatgcat      3960
ccttcaaaca ctcacgatta cgtttattct ctgggtgcaa ttaatttcac gggtgatgag      4020
ccagttatta ttacttgcga tggtccttcc ttaggtggtt ttgtgtgtca agctgttgtc      4080
ccagaagcag aactgtggaa ggttggacag gttaaacccg gtgattccat tcagtttgtg      4140
ccactttctt acgaaagctc gagatcctta aaggaatctc aggatgttgc aattaaatca      4200
ttggatggta ctaagttaag gcgcttagac tctgtttcaa ttttaccatc attcgaaacg      4260
cctattcttg cacaaatgga aaagtgaat gagctttcac caaaggttgt atacagacaa      4320
gcaggtgatc gttatgtttt ggtggaatac ggtgataatg aaatgaattt taatatttcc      4380
tatagaattg aatgcctgat ctcccttgtg aaaagaata agactattgg tattgttgaa      4440
atgtcccaag gtgttagatc tgtattgata gaatttgatg gttacaaagt cactcaaaaa      4500
gaattgctta agtattggt ggcatatgaa acagaaatcc agtttgatga aaattggaag      4560
ataacttcta atataataag attaccgatg gctttcgaag actcgaagac tttggcatgt      4620
gttcaaaggt atcaagaaac aattcgttcg tctgctccat ggttgccaaa taacgttgat      4680
ttcattgcca atgtaaatgg aatttcaagg aatgaagttt atgatatgtt gtattctgcc      4740
agatttatgg ttttaggttt aggtgatgtc ttcctagggt cgccttgtgc tgttccatta      4800
gatcctcgtc acagattttt gggaagcaag tacaacccaa gtagaacata tacagaaaga      4860
ggtgcagtcg gtattggcgg tatgtatatg tgcatatatg ctgctaacag tcctggtggg      4920
taccaattag tgggtagaac aataccaatt tgggacaaac tatgtctggc cgcatcttct      4980
gaggttccgt ggttgatgaa cccatttgac caagtcgaat tttacccagt ttctgaagaa      5040
gatttggata aaatgactga agattgtgat aatggtgttt ataaagtcaa tatcgaaaag      5100
agtgttttg atcatcaaga atacttgaga tggatcaacg caaacaaaga ttccatcaca      5160
gcattccagg agggccagct tggtgaaaga gcagaggaat ttgccaaatt gattcaaaat      5220
gcaaactctg aactaaaaga aagtgtcaca gtcaaacctg acgaggaaga agacttccca      5280
gaaggtgcag aaattgtata ttctgagtat tctgggcgtt tttggaaatc catagcatct      5340
gttggagatg ttattgaagc aggtcaaggg ctactaatta ttgaagccat gaaagcggaa      5400
atgattatat ccgctcctaa atcgggtaag attatcaaga tttgccatgg caatggtgat      5460
atggttgatt ctggtgacat agtggccgtc atagagacat tggca                     5505
```

<210> SEQ ID NO 37

<211> LENGTH: 1835
<212> TYPE: PRT
<213> ORGANISM: Saccharomyces cerevisiae

<400> SEQUENCE: 37

Met Thr Val Ser Ser Asp Thr Thr Ala Glu Ile Ser Leu Gly Trp Ser
1               5                   10                  15

Ile Gln Asp Trp Ile Asp Phe His Lys Ser Ser Ser Gln Ala Ser
            20                  25                  30

Leu Arg Leu Leu Glu Ser Leu Leu Asp Ser Gln Asn Val Ala Pro Val
        35                  40                  45

Asp Asn Ala Trp Ile Ser Leu Ile Ser Lys Glu Asn Leu Leu His Gln
    50                  55                  60

Phe Gln Ile Leu Lys Ser Arg Glu Asn Lys Glu Thr Leu Pro Leu Tyr
65                  70                  75                  80

Gly Val Pro Ile Ala Val Lys Asp Asn Ile Asp Val Arg Gly Leu Pro
                85                  90                  95

Thr Thr Ala Ala Cys Pro Ser Phe Ala Tyr Glu Pro Ser Lys Asp Ser
            100                 105                 110

Lys Val Val Glu Leu Leu Arg Asn Ala Gly Ala Ile Ile Val Gly Lys
        115                 120                 125

Thr Asn Leu Asp Gln Phe Ala Thr Gly Leu Val Gly Thr Arg Ser Pro
    130                 135                 140

Tyr Gly Lys Thr Pro Cys Ala Phe Ser Lys Glu His Val Ser Gly Gly
145                 150                 155                 160

Ser Ser Ala Gly Ser Ala Ser Val Val Ala Arg Gly Ile Val Pro Ile
                165                 170                 175

Ala Leu Gly Thr Asp Thr Ala Gly Ser Gly Arg Val Pro Ala Ala Leu
            180                 185                 190

Asn Asn Leu Ile Gly Leu Lys Pro Thr Lys Gly Val Phe Ser Cys Gln
        195                 200                 205

Gly Val Val Pro Ala Cys Lys Ser Leu Asp Cys Val Ser Ile Phe Ala
    210                 215                 220

Leu Asn Leu Ser Asp Ala Glu Arg Cys Phe Arg Ile Met Cys Gln Pro
225                 230                 235                 240

Asp Pro Asp Asn Asp Glu Tyr Ser Arg Pro Tyr Val Ser Asn Pro Leu
                245                 250                 255

Lys Lys Phe Ser Ser Asn Val Thr Ile Ala Ile Pro Lys Asn Ile Pro
            260                 265                 270

Trp Tyr Gly Glu Thr Lys Asn Pro Val Leu Phe Ser Asn Ala Val Glu
        275                 280                 285

Asn Leu Ser Arg Thr Gly Ala Asn Val Ile Glu Ile Asp Phe Glu Pro
    290                 295                 300

Leu Leu Glu Leu Ala Arg Cys Leu Tyr Glu Gly Thr Trp Val Ala Glu
305                 310                 315                 320

Arg Tyr Gln Ala Ile Gln Ser Phe Leu Asp Ser Lys Pro Pro Lys Glu
                325                 330                 335

Ser Leu Asp Pro Thr Val Ile Ser Ile Ile Glu Gly Ala Lys Lys Tyr
            340                 345                 350

Ser Ala Val Asp Cys Phe Ser Phe Glu Tyr Lys Arg Gln Gly Ile Leu
        355                 360                 365

Gln Lys Val Arg Arg Leu Leu Glu Ser Val Asp Val Leu Cys Val Pro
    370                 375                 380

Thr Cys Pro Leu Asn Pro Thr Met Gln Gln Val Ala Asp Glu Pro Val

```
            385                 390                 395                 400
        Leu Val Asn Ser Arg Gln Gly Thr Trp Thr Asn Phe Val Asn Leu Ala
                        405                 410                 415

Asp Leu Ala Ala Leu Ala Val Pro Ala Gly Phe Arg Asp Asp Gly Leu
                    420                 425                 430

Pro Asn Gly Ile Thr Leu Ile Gly Lys Lys Phe Thr Asp Tyr Ala Leu
                    435                 440                 445

Leu Glu Leu Ala Asn Arg Tyr Phe Gln Asn Ile Phe Pro Asn Gly Ser
                450                 455                 460

Arg Thr Tyr Gly Thr Phe Thr Ser Ser Val Lys Pro Ala Asn Asp
        465                 470                 475                 480

Gln Leu Val Gly Pro Asp Tyr Asp Pro Ser Thr Ser Ile Lys Leu Ala
                        485                 490                 495

Val Val Gly Ala His Leu Lys Gly Leu Pro Leu His Trp Gln Leu Glu
                    500                 505                 510

Lys Val Asn Ala Thr Tyr Leu Cys Thr Thr Lys Thr Ser Lys Ala Tyr
                    515                 520                 525

Gln Leu Phe Ala Leu Pro Lys Asn Gly Pro Val Leu Lys Pro Gly Leu
                530                 535                 540

Arg Arg Val Gln Asp Ser Asn Gly Ser Gln Ile Glu Leu Glu Val Tyr
        545                 550                 555                 560

Ser Val Pro Lys Glu Leu Phe Gly Ala Phe Ile Ser Met Val Pro Glu
                        565                 570                 575

Pro Leu Gly Ile Gly Ser Val Glu Leu Glu Ser Gly Glu Trp Ile Lys
                    580                 585                 590

Ser Phe Ile Cys Glu Glu Ser Gly Tyr Lys Ala Lys Gly Thr Val Asp
                    595                 600                 605

Ile Thr Lys Tyr Gly Gly Phe Arg Ala Tyr Phe Glu Met Leu Lys Lys
                610                 615                 620

Lys Glu Ser Gln Lys Lys Lys Leu Phe Asp Thr Val Leu Ile Ala Asn
        625                 630                 635                 640

Arg Gly Glu Ile Ala Val Arg Ile Ile Lys Thr Leu Lys Lys Leu Gly
                        645                 650                 655

Ile Arg Ser Val Ala Val Tyr Ser Asp Pro Asp Lys Tyr Ser Gln His
                    660                 665                 670

Val Thr Asp Ala Asp Val Ser Val Pro Leu His Gly Thr Thr Ala Ala
                    675                 680                 685

Gln Thr Tyr Leu Asp Met Asn Lys Ile Ile Asp Ala Ala Lys Gln Thr
                690                 695                 700

Asn Ala Gln Ala Ile Ile Pro Gly Tyr Gly Phe Leu Ser Glu Asn Ala
        705                 710                 715                 720

Asp Phe Ser Asp Ala Cys Thr Ser Ala Gly Ile Thr Phe Val Gly Pro
                        725                 730                 735

Ser Gly Asp Ile Ile Arg Gly Leu Gly Leu Lys His Ser Ala Arg Gln
                    740                 745                 750

Ile Ala Gln Lys Ala Gly Val Pro Leu Val Pro Gly Ser Leu Leu Ile
                    755                 760                 765

Thr Ser Val Glu Glu Ala Lys Lys Val Ala Ala Glu Leu Glu Tyr Pro
                770                 775                 780

Val Met Val Lys Ser Thr Ala Gly Gly Gly Ile Gly Leu Gln Lys
        785                 790                 795                 800

Val Asp Ser Glu Glu Asp Ile Glu His Ile Phe Glu Thr Val Lys His
                        805                 810                 815
```

```
Gln Gly Glu Thr Phe Phe Gly Asp Ala Gly Val Phe Leu Glu Arg Phe
            820                 825                 830

Ile Glu Asn Ala Arg His Val Glu Val Gln Leu Met Gly Asp Gly Phe
            835                 840                 845

Gly Lys Ala Ile Ala Leu Gly Glu Arg Asp Cys Ser Leu Gln Arg Arg
    850                 855                 860

Asn Gln Lys Val Ile Glu Glu Thr Pro Ala Pro Asn Leu Pro Glu Lys
865                 870                 875                 880

Thr Arg Leu Ala Leu Arg Lys Ala Ala Glu Ser Leu Gly Ser Leu Leu
                885                 890                 895

Asn Tyr Lys Cys Ala Gly Thr Val Glu Phe Ile Tyr Asp Glu Lys Lys
            900                 905                 910

Asp Glu Phe Tyr Phe Leu Glu Val Asn Thr Arg Leu Gln Val Glu His
            915                 920                 925

Pro Ile Thr Glu Met Val Thr Gly Leu Asp Leu Val Glu Trp Met Ile
    930                 935                 940

Arg Ile Ala Ala Asn Asp Ala Pro Asp Phe Asp Ser Thr Lys Val Glu
945                 950                 955                 960

Val Asn Gly Val Ser Met Glu Ala Arg Leu Tyr Ala Glu Asn Pro Leu
                965                 970                 975

Lys Asn Phe Arg Pro Ser Pro Gly Leu Leu Val Asp Val Lys Phe Pro
            980                 985                 990

Asp Trp Ala Arg Val Asp Thr Trp Val Lys Lys Gly Thr Asn Ile Ser
            995                1000                1005

Pro Glu Tyr Asp Pro Thr Leu Ala Lys Ile Ile Val His Gly Lys
   1010                1015                1020

Asp Arg Asp Asp Ala Ile Ser Lys Leu Asn Gln Ala Leu Glu Glu
   1025                1030                1035

Thr Lys Val Tyr Gly Cys Ile Thr Asn Ile Asp Tyr Leu Lys Ser
   1040                1045                1050

Ile Ile Thr Ser Asp Phe Phe Ala Lys Ala Lys Val Ser Thr Asn
   1055                1060                1065

Ile Leu Asn Ser Tyr Gln Tyr Glu Pro Thr Ala Ile Glu Ile Thr
   1070                1075                1080

Leu Pro Gly Ala His Thr Ser Ile Gln Asp Tyr Pro Gly Arg Val
   1085                1090                1095

Gly Tyr Trp Arg Ile Gly Val Pro Pro Ser Gly Pro Met Asp Ala
   1100                1105                1110

Tyr Ser Phe Arg Leu Ala Asn Arg Ile Val Gly Asn Asp Tyr Arg
   1115                1120                1125

Thr Pro Ala Ile Glu Val Thr Leu Thr Gly Pro Ser Ile Val Phe
   1130                1135                1140

His Cys Glu Thr Val Ile Ala Ile Thr Gly Gly Thr Ala Leu Cys
   1145                1150                1155

Thr Leu Asp Gly Gln Glu Ile Pro Gln His Lys Pro Val Glu Val
   1160                1165                1170

Lys Arg Gly Ser Thr Leu Ser Ile Gly Lys Leu Thr Ser Gly Cys
   1175                1180                1185

Arg Ala Tyr Leu Gly Ile Arg Gly Gly Ile Asp Val Pro Lys Tyr
   1190                1195                1200

Leu Gly Ser Tyr Ser Thr Phe Thr Leu Gly Asn Val Gly Gly Tyr
   1205                1210                1215
```

```
Asn Gly Arg Val Leu Lys Leu Gly Asp Val Leu Phe Leu Pro Ser
1220                1225                1230

Asn Glu Glu Asn Lys Ser Val Glu Cys Leu Pro Gln Asn Ile Pro
1235                1240                1245

Gln Ser Leu Ile Pro Gln Ile Ser Glu Thr Lys Glu Trp Arg Ile
1250                1255                1260

Gly Val Thr Cys Gly Pro His Gly Ser Pro Asp Phe Phe Lys Pro
1265                1270                1275

Glu Ser Ile Glu Glu Phe Phe Ser Glu Lys Trp Lys Val His Tyr
1280                1285                1290

Asn Ser Asn Arg Phe Gly Val Arg Leu Ile Gly Pro Lys Pro Lys
1295                1300                1305

Trp Ala Arg Ser Asn Gly Gly Glu Gly Gly Met His Pro Ser Asn
1310                1315                1320

Thr His Asp Tyr Val Tyr Ser Leu Gly Ala Ile Asn Phe Thr Gly
1325                1330                1335

Asp Glu Pro Val Ile Ile Thr Cys Asp Gly Pro Ser Leu Gly Gly
1340                1345                1350

Phe Val Cys Gln Ala Val Val Pro Glu Ala Glu Leu Trp Lys Val
1355                1360                1365

Gly Gln Val Lys Pro Gly Asp Ser Ile Gln Phe Val Pro Leu Ser
1370                1375                1380

Tyr Glu Ser Ser Arg Ser Leu Lys Glu Ser Gln Asp Val Ala Ile
1385                1390                1395

Lys Ser Leu Asp Gly Thr Lys Leu Arg Arg Leu Asp Ser Val Ser
1400                1405                1410

Ile Leu Pro Ser Phe Glu Thr Pro Ile Leu Ala Gln Met Glu Lys
1415                1420                1425

Val Asn Glu Leu Ser Pro Lys Val Val Tyr Arg Gln Ala Gly Asp
1430                1435                1440

Arg Tyr Val Leu Val Glu Tyr Gly Asp Asn Glu Met Asn Phe Asn
1445                1450                1455

Ile Ser Tyr Arg Ile Glu Cys Leu Ile Ser Leu Val Lys Lys Asn
1460                1465                1470

Lys Thr Ile Gly Ile Val Glu Met Ser Gln Gly Val Arg Ser Val
1475                1480                1485

Leu Ile Glu Phe Asp Gly Tyr Lys Val Thr Gln Lys Glu Leu Leu
1490                1495                1500

Lys Val Leu Val Ala Tyr Glu Thr Glu Ile Gln Phe Asp Glu Asn
1505                1510                1515

Trp Lys Ile Thr Ser Asn Ile Ile Arg Leu Pro Met Ala Phe Glu
1520                1525                1530

Asp Ser Lys Thr Leu Ala Cys Val Gln Arg Tyr Gln Glu Thr Ile
1535                1540                1545

Arg Ser Ser Ala Pro Trp Leu Pro Asn Asn Val Asp Phe Ile Ala
1550                1555                1560

Asn Val Asn Gly Ile Ser Arg Asn Glu Val Tyr Asp Met Leu Tyr
1565                1570                1575

Ser Ala Arg Phe Met Val Leu Gly Leu Gly Asp Val Phe Leu Gly
1580                1585                1590

Ser Pro Cys Ala Val Pro Leu Asp Pro Arg His Arg Phe Leu Gly
1595                1600                1605

Ser Lys Tyr Asn Pro Ser Arg Thr Tyr Thr Glu Arg Gly Ala Val
```

```
                      1610                1615                1620
Gly Ile Gly Gly Met Tyr Met Cys Ile Tyr Ala Ala Asn Ser Pro
     1625                1630                1635

Gly Gly Tyr Gln Leu Val Gly Arg Thr Ile Pro Ile Trp Asp Lys
     1640                1645                1650

Leu Cys Leu Ala Ala Ser Ser Glu Val Pro Trp Leu Met Asn Pro
     1655                1660                1665

Phe Asp Gln Val Glu Phe Tyr Pro Val Ser Glu Glu Asp Leu Asp
     1670                1675                1680

Lys Met Thr Glu Asp Cys Asp Asn Gly Val Tyr Lys Val Asn Ile
     1685                1690                1695

Glu Lys Ser Val Phe Asp His Gln Glu Tyr Leu Arg Trp Ile Asn
     1700                1705                1710

Ala Asn Lys Asp Ser Ile Thr Ala Phe Gln Glu Gly Gln Leu Gly
     1715                1720                1725

Glu Arg Ala Glu Glu Phe Ala Lys Leu Ile Gln Asn Ala Asn Ser
     1730                1735                1740

Glu Leu Lys Glu Ser Val Thr Val Lys Pro Asp Glu Glu Glu Asp
     1745                1750                1755

Phe Pro Glu Gly Ala Glu Ile Val Tyr Ser Glu Tyr Ser Gly Arg
     1760                1765                1770

Phe Trp Lys Ser Ile Ala Ser Val Gly Asp Val Ile Glu Ala Gly
     1775                1780                1785

Gln Gly Leu Leu Ile Ile Glu Ala Met Lys Ala Glu Met Ile Ile
     1790                1795                1800

Ser Ala Pro Lys Ser Gly Lys Ile Ile Lys Ile Cys His Gly Asn
     1805                1810                1815

Gly Asp Met Val Asp Ser Gly Asp Ile Val Ala Val Ile Glu Thr
     1820                1825                1830

Leu Ala
     1835

<210> SEQ ID NO 38
<211> LENGTH: 2205
<212> TYPE: DNA
<213> ORGANISM: Saccharomyces cerevisiae

<400> SEQUENCE: 38
atgggagaat ttaaacctcc gctacctcaa ggcgctgggt acgctattgt attgggccta      60
ggggccgtat ttgcaggaat gatggttttg accactattt tactgaaacg ttatcaaaag     120
gaaatcatca cagcagaaga attcaccacc gccggtagat ctgtaaaaac cggcttagtg     180
gctgcagccg tggtttctag ttggatctgg tgttctacat tgttaacgtc gtcaacaaag     240
gaatatgcag acggtatatt tggcggttat gcgtacgctg ctggcgcatg cttccaaatt     300
attgcattcg caattttggc aattaaaacc aagcaaatgg ctcccaatgc gcacacatat     360
ttagaattag tgagaacaag atatggtaag atcggccatg gttgctactt gttttatgcc     420
atcgcgacga atattttagt cacttcaatg cttttaactt caggttctgc tgtctttagt     480
gatttaaccg ggatgaacac tatcgcatca tgttttttac tgcctgtggg tgttgttgtt     540
tatactctat tggtgggat taaagcaact ttcttaacgg actatatgca cacatgtgtc     600
attatcatca ttgtcctcgt atttgccttt aaagtttatg cgactagtga tgttttaggc     660
tcaccgggaa aagtttatga cttagttcgt gaagccgcca agaggcatcc agtagacggt     720
```

-continued

```
aactatcagg gtgaatatat gaccatgaca tccaaatccg ctggtatttt attaattatt    780
aacctgattg gaaatttcgg caccgttttc cttgataatg gttattggaa taaagcgatt    840
tctgctagtc ccgcagcgag tttgaaagca tatgccatcg gtgggttagc atggtttgca    900
gtaccttctt tgatttcatt gaccatggga ttagcatgtc ttgcggtgga aacgtctccg    960
aacttcccca cctatcctga tccacttact tcgttccagg caaattctgg gttagtcttg   1020
ccggcagctg caattgctat catgggtaag ggggtgctg tggcatcgct gctaatgatt    1080
ttcatggccg tcacatctgc tatgtctgct gaactaattg ccgtttcatc tgttttcact   1140
tacgatatct atagagaata tattgatcct cgtgcaagcg gtaagaaatt gatttacaca   1200
tcacacgttg cttgtatctt ttttggtctt gccatgagtg gattttcggt tggtttatac   1260
tatggtggta tttctatggg ttatatctat gaaatgatgg gtataattat tagtagtgca   1320
gtattacctg tcgttttgac cttatgttcc aaagacatga atttggtggc cgctgtagtg   1380
tcgcctattt tgggcacagg actggctata atgtcatggc ttgtctgtac caaatcccct   1440
tataaagaat tgaccgtgga tactacgttc atggattatc aatgttaac aggtaacttg     1500
gtggctttgc tatccagc cattttttatt cctattttaa cgtatgtgtt taagccacaa    1560
aattttgact gggagaaaat gaaagatatt actagagttg acgaaactgc agagttagtt   1620
caggctgacc ctgatatcca gctttacgat gctgaagcta acgataagga acaagaagaa   1680
gaaacaaatt ctctggtctc agatagtgaa aaaaacgatg ttagagtaaa taatgaaaaa   1740
ttgattgagc ctaaccttgg tgttgtaata agtaatgcca ttttttcaaga agatgacaca   1800
cagttacaaa atgaattaga cgaagaacaa agagaactag cacgtggttt aaaaattgca   1860
tacttcctat gtgttttttt cgctttggca ttttttggtag tttggcccat gcccatgtat   1920
ggttccaaat atatcttcag taaaaaattc tttaccggtt gggttgttgt gatgatcatc   1980
tggctttttt tcagtgcgtt tgccgtttgt atttatccac tctgggaagg taggcatggt   2040
atatatacca ctttgcgagg cctttactgg gatctatctg gtcaaactta taaattaagg   2100
gaatggcaaa attcgaaccc acaagatctg catgtagtaa caagccaaat tagtgcgaga   2160
gcacatagac aatcatcaca tttcggacaa gttgatgaaa taatt                  2205
```

<210> SEQ ID NO 39
<211> LENGTH: 735
<212> TYPE: PRT
<213> ORGANISM: Saccharomyces cerevisiae

<400> SEQUENCE: 39

```
Met Gly Glu Phe Lys Pro Pro Leu Pro Gln Gly Ala Gly Tyr Ala Ile
1               5                   10                  15

Val Leu Gly Leu Gly Ala Val Phe Ala Gly Met Met Val Leu Thr Thr
            20                  25                  30

Tyr Leu Leu Lys Arg Tyr Gln Lys Glu Ile Ile Thr Ala Glu Glu Phe
        35                  40                  45

Thr Thr Ala Gly Arg Ser Val Lys Thr Gly Leu Val Ala Ala Ala Val
    50                  55                  60

Val Ser Ser Trp Ile Trp Cys Ser Thr Leu Leu Thr Ser Ser Thr Lys
65                  70                  75                  80

Glu Tyr Ala Asp Gly Ile Phe Gly Gly Tyr Ala Tyr Ala Ala Gly Ala
                85                  90                  95

Cys Phe Gln Ile Ile Ala Phe Ala Ile Leu Ala Ile Lys Thr Lys Gln
            100                 105                 110
```

```
Met Ala Pro Asn Ala His Thr Tyr Leu Glu Leu Val Arg Thr Arg Tyr
            115                 120                 125

Gly Lys Ile Gly His Gly Cys Tyr Leu Phe Tyr Ala Ile Ala Thr Asn
        130                 135                 140

Ile Leu Val Thr Ser Met Leu Leu Thr Ser Gly Ser Ala Val Phe Ser
145                 150                 155                 160

Asp Leu Thr Gly Met Asn Thr Ile Ala Ser Cys Phe Leu Leu Pro Val
                165                 170                 175

Gly Val Val Val Tyr Thr Leu Phe Gly Ile Lys Ala Thr Phe Leu
            180                 185                 190

Thr Asp Tyr Met His Thr Cys Val Ile Ile Ile Val Leu Val Phe
            195                 200                 205

Ala Phe Lys Val Tyr Ala Thr Ser Asp Val Leu Gly Ser Pro Gly Lys
    210                 215                 220

Val Tyr Asp Leu Val Arg Glu Ala Ala Lys Arg His Pro Val Asp Gly
225                 230                 235                 240

Asn Tyr Gln Gly Glu Tyr Met Thr Met Thr Ser Lys Ser Ala Gly Ile
                245                 250                 255

Leu Leu Ile Ile Asn Leu Ile Gly Asn Phe Gly Thr Val Phe Leu Asp
            260                 265                 270

Asn Gly Tyr Trp Asn Lys Ala Ile Ser Ala Ser Pro Ala Ala Ser Leu
        275                 280                 285

Lys Ala Tyr Ala Ile Gly Gly Leu Ala Trp Phe Ala Val Pro Ser Leu
        290                 295                 300

Ile Ser Leu Thr Met Gly Leu Ala Cys Leu Ala Val Glu Thr Ser Pro
305                 310                 315                 320

Asn Phe Pro Thr Tyr Pro Asp Pro Leu Thr Ser Phe Gln Ala Asn Ser
                325                 330                 335

Gly Leu Val Leu Pro Ala Ala Ile Ala Ile Met Gly Lys Gly Gly
            340                 345                 350

Ala Val Ala Ser Leu Leu Met Ile Phe Met Ala Val Thr Ser Ala Met
        355                 360                 365

Ser Ala Glu Leu Ile Ala Val Ser Ser Val Phe Thr Tyr Asp Ile Tyr
    370                 375                 380

Arg Glu Tyr Ile Asp Pro Arg Ala Ser Gly Lys Lys Leu Ile Tyr Thr
385                 390                 395                 400

Ser His Val Ala Cys Ile Phe Phe Gly Leu Ala Met Ser Gly Phe Ser
                405                 410                 415

Val Gly Leu Tyr Tyr Gly Gly Ile Ser Met Gly Tyr Ile Tyr Glu Met
            420                 425                 430

Met Gly Ile Ile Ile Ser Ser Ala Val Leu Pro Val Val Leu Thr Leu
        435                 440                 445

Cys Ser Lys Asp Met Asn Leu Val Ala Ala Val Ser Pro Ile Leu
450                 455                 460

Gly Thr Gly Leu Ala Ile Met Ser Trp Leu Val Cys Thr Lys Ser Leu
465                 470                 475                 480

Tyr Lys Glu Leu Thr Val Asp Thr Thr Phe Met Asp Tyr Pro Met Leu
                485                 490                 495

Thr Gly Asn Leu Val Ala Leu Leu Ser Pro Ala Ile Phe Ile Pro Ile
            500                 505                 510

Leu Thr Tyr Val Phe Lys Pro Gln Asn Phe Asp Trp Glu Lys Met Lys
        515                 520                 525

Asp Ile Thr Arg Val Asp Glu Thr Ala Glu Leu Val Gln Ala Asp Pro
```

```
                530             535              540
Asp Ile Gln Leu Tyr Asp Ala Glu Ala Asn Asp Lys Glu Gln Glu Glu
545                 550                 555                 560

Glu Thr Asn Ser Leu Val Ser Asp Ser Glu Lys Asn Asp Val Arg Val
                565                 570                 575

Asn Asn Glu Lys Leu Ile Glu Pro Asn Leu Gly Val Val Ile Ser Asn
                580                 585                 590

Ala Ile Phe Gln Glu Asp Asp Thr Gln Leu Gln Asn Glu Leu Asp Glu
                595                 600                 605

Glu Gln Arg Glu Leu Ala Arg Gly Leu Lys Ile Ala Tyr Phe Leu Cys
610                 615                 620

Val Phe Phe Ala Leu Ala Phe Leu Val Val Trp Pro Met Pro Met Tyr
625                 630                 635                 640

Gly Ser Lys Tyr Ile Phe Ser Lys Lys Phe Phe Thr Gly Trp Val Val
                645                 650                 655

Val Met Ile Ile Trp Leu Phe Phe Ser Ala Phe Ala Val Cys Ile Tyr
                660                 665                 670

Pro Leu Trp Glu Gly Arg His Gly Ile Tyr Thr Thr Leu Arg Gly Leu
                675                 680                 685

Tyr Trp Asp Leu Ser Gly Gln Thr Tyr Lys Leu Arg Glu Trp Gln Asn
690                 695                 700

Ser Asn Pro Gln Asp Leu His Val Val Thr Ser Gln Ile Ser Ala Arg
705                 710                 715                 720

Ala His Arg Gln Ser Ser His Phe Gly Gln Val Asp Glu Ile Ile
                725                 730                 735

<210> SEQ ID NO 40
<211> LENGTH: 1134
<212> TYPE: DNA
<213> ORGANISM: Zea mays

<400> SEQUENCE: 40
atggcgagag cgctgccgct ggtgctcgcg gcgtccgtcc tgctggcggc cgccgcgctg      60
ctgctggccg cggcgccggc gccggcggcc gcaggtcgac ttcggcgcgg aggacctggc     120
gtcgagagga ggcgctgtgg cgctgtacg agcgctggcg cggccgccac gcggtggcgc     180
gggacctggg cgacaaggcg cgccgtcttc aacgtcttca aggccaacgt gcgcctcatc     240
cacgagttca accgccggga cgagccctac aagctccgcc tcaaccgctt cggcgacatg     300
accgccgacg agttccgacg ccactacgcg ggctccaggg tcgcgcacca ccgcatgttc     360
cgcggcgaca ggcagggctc ctcggcgtcg gcgtcgttca tgtacgccga cgcgcgcgac     420
gtcccggcct ccgtcgactg gaggcagaag ggcgccgtca ccgacgtcaa ggaccagggc     480
cagtgcggta gctgctgggc gttctcgacg atcgccgccg tggagggcat caacgcgatc     540
aagaccaaga acctgacgtc gctgtcggag cagcagctgg tggactgcga caccaaggcc     600
aacgccggct gcaacggggg cctcatggac tacgcgttcc agtacatcgc caagcacggc     660
ggggtggcgg cggaggacgc gtacccgtac agagcgcgcc aggcgtcctg caagaagtcg     720
ccggccccgt cgtcaccat cgacggctac gaggacgtgc cggccaacga cgagtcggcg     780
ctcaagaagg cggtggcgca ccagccgtg tccgtcgcca tcgaggccag tggctcgcac     840
ttccagttct actccgaggg ggtcttctcc ggcaggtgcg ggacggagct ggaccacggc     900 gtcgcggcg tcgctacgg ggtcaccgcg gacggcacca gtactggct ggtcaagaac     960 tcgtggggcc ccgagtgggg cgagaagggg tacatccgca tggcgcgcga cgtggccgcc    1020
```

-continued

```
aaggagggac actgcggcat cgccatggag gcatcctacc ccgtcaagac ctcgcccaac    1080
cccaaggtcc acgccgtcgt cgacgaggac ggctccagcc acgacgagct ctga          1134
```

<210> SEQ ID NO 41
<211> LENGTH: 376
<212> TYPE: PRT
<213> ORGANISM: Zea mays

<400> SEQUENCE: 41

| | | | | | | | | | | | | | | |
|---|---|---|---|---|---|---|---|---|---|---|---|---|---|---|
| Met | Ala | Arg | Ala | Leu | Pro | Leu | Val | Leu | Ala | Ser | Val | Leu | Leu | Ala |
| 1 | | | | 5 | | | | | 10 | | | | | 15 |
| Ala | Ala | Leu | Leu | Leu | Leu | Ala | Phe | Ala | Pro | Ala | Pro | Ala | Ala | Val |
| | | | 20 | | | | | 25 | | | | | 30 | |
| Asp | Phe | Gly | Ala | Glu | Asp | Leu | Ala | Ser | Glu | Glu | Ala | Leu | Trp | Ala | Leu |
| | | | 35 | | | | | 40 | | | | | 45 | | |
| Tyr | Glu | Arg | Trp | Arg | Gly | Arg | His | Ala | Leu | Ala | Arg | Asp | Leu | Gly | Asp |
| | 50 | | | | | 55 | | | | | 60 | | | | |
| Lys | Ala | Arg | Arg | Phe | Asn | Val | Phe | Lys | Ala | Asn | Val | Arg | Leu | Ile | His |
| 65 | | | | | 70 | | | | | 75 | | | | | 80 |
| Glu | Phe | Asn | Arg | Arg | Asp | Glu | Pro | Tyr | Lys | Leu | Arg | Leu | Asn | Arg | Phe |
| | | | | 85 | | | | | 90 | | | | | 95 | |
| Gly | Asp | Met | Thr | Ala | Asp | Glu | Phe | Arg | Arg | His | Tyr | Ala | Gly | Ser | Arg |
| | | | 100 | | | | | 105 | | | | | 110 | | |
| Val | Ala | His | His | Arg | Met | Phe | Arg | Gly | Asp | Arg | Gln | Gly | Ser | Ser | Ala |
| | | 115 | | | | | 120 | | | | | 125 | | | |
| Ser | Ala | Ser | Phe | Met | Tyr | Ala | Asp | Ala | Arg | Asp | Val | Pro | Ala | Ser | Val |
| 130 | | | | | 135 | | | | | 140 | | | | | |
| Asp | Trp | Arg | Gln | Lys | Gly | Ala | Val | Thr | Asp | Val | Lys | Asp | Gln | Gly | Gln |
| 145 | | | | | 150 | | | | | 155 | | | | | 160 |
| Cys | Gly | Ser | Cys | Trp | Ala | Phe | Ser | Thr | Ile | Ala | Ala | Val | Glu | Gly | Ile |
| | | | | 165 | | | | | 170 | | | | | 175 | |
| Asn | Ala | Ile | Lys | Thr | Lys | Asn | Leu | Thr | Ser | Leu | Ser | Glu | Gln | Gln | Leu |
| | | | 180 | | | | | 185 | | | | | 190 | | |
| Val | Asp | Cys | Asp | Thr | Lys | Ala | Asn | Ala | Gly | Cys | Asn | Gly | Gly | Leu | Met |
| | | 195 | | | | | 200 | | | | | 205 | | | |
| Asp | Tyr | Ala | Phe | Gln | Tyr | Ile | Ala | Lys | His | Gly | Gly | Val | Ala | Ala | Glu |
| | 210 | | | | | 215 | | | | | 220 | | | | |
| Asp | Ala | Tyr | Pro | Tyr | Arg | Ala | Arg | Gln | Ala | Ser | Cys | Lys | Lys | Ser | Pro |
| 225 | | | | | 230 | | | | | 235 | | | | | 240 |
| Ala | Pro | Val | Val | Thr | Ile | Asp | Gly | Tyr | Glu | Asp | Val | Pro | Ala | Asn | Asp |
| | | | | 245 | | | | | 250 | | | | | 255 | |
| Glu | Ser | Ala | Leu | Lys | Lys | Ala | Val | Ala | His | Gln | Pro | Val | Ser | Val | Ala |
| | | | 260 | | | | | 265 | | | | | 270 | | |
| Ile | Glu | Ala | Ser | Gly | Ser | His | Phe | Gln | Phe | Tyr | Ser | Glu | Gly | Val | Phe |
| | | 275 | | | | | 280 | | | | | 285 | | | |
| Ser | Gly | Arg | Cys | Gly | Thr | Glu | Leu | Asp | His | Gly | Val | Thr | Ala | Val | Gly |
| | 290 | | | | | 295 | | | | | 300 | | | | |
| Tyr | Gly | Val | Thr | Ala | Asp | Gly | Thr | Lys | Tyr | Trp | Leu | Val | Lys | Asn | Ser |
| 305 | | | | | 310 | | | | | 315 | | | | | 320 |
| Trp | Gly | Pro | Glu | Trp | Gly | Glu | Lys | Gly | Tyr | Ile | Arg | Met | Ala | Arg | Asp |
| | | | | 325 | | | | | 330 | | | | | 335 | |
| Val | Ala | Lys | Glu | Gly | His | Cys | Gly | Ile | Ala | Met | Glu | Ala | Ser | Tyr |
| | | | 340 | | | | | 345 | | | | | 350 | | |

Pro Val Lys Thr Ser Pro Asn Pro Lys Val His Ala Val Val Asp Glu
        355                 360                 365

Asp Gly Ser Ser His Asp Glu Leu
        370                 375

<210> SEQ ID NO 42
<211> LENGTH: 1413
<212> TYPE: DNA
<213> ORGANISM: Zea mays

<400> SEQUENCE: 42

```
atggctgctc tgggccgtgg cctgcccctc ctcctcctgc tcctcctcct cgccgtatcg      60
ggggccgcca acgccgcggc ggcgcccggc ggcatgtcca tcatcaccta caacgaggag     120
cacggcgcgc gggggctgga gcggacggag ccggaggtgc gggccatgta cgacctctgg     180
ctcgcggagc acgccgcgc ctacaacgcg ctgggcgagg gcgagggcga gcgcgaccgc      240
cgcttcctcg tcttctggga caacctccgc ttcgtcgacg cgcacaacga gcgcgccggc     300
gcccgcggct tccgcctcgg gatgaaccag ttcgccgacc tcaccaacga cgagttccgc     360
gccgcgtacc tcggcgccat ggtccccgcc gcccgccggg gagccgtcgt ggggagagg      420
taccgccacg acgcgccgc cgaggagctg ccggagagcg tcgactggag ggagaagggc      480
gccgtcgcgc ccgtcaagaa ccagggkcaa tgcggaagtt gctgggcttt ctctgcagta     540
agctcagtgg aaagcgttaa ccagatcgtc accggtgaga tggtgacact gtctgaacag     600
gagctcgtag agtgctcgac tgacggaggg aacagcggct gcaacggcgg gctcatggac     660
gccgctttcg atttcatcat aaagaacggg ggcatcgata ccgaagatga ctacccttac     720
agagccgtgg acgggaagtg cgacatgaac aggaaaaatg ccagggttgt gagcatcgat     780
ggctttgaag acgtgcctga aacgacgag aagtcgctgc agaaggcggt tgctcaccag      840
ccagttagcg ttgccattga ggccggaggc cgggagttcc agctctacaa atcgggtgtc     900
ttcagcggaa gctgcaccac gaaccttgac catggtgtcg tcgcggtcgg ctacggcgcc     960
gagaacggga aggactactg gatcgtccgc aactcgtggg gcccgaagtg gggcgaggct    1020
ggttacatcc gtatggagag gaacgtcaac gccagcactg ggaagtgcgg gatcgcgatg    1080
atggcgtcct acccgacgaa gaagggcgcg aaccctccca ggccgtctcc aaccccgcca    1140
acaccgccgg ctgcccctga caatgtctgc gacgagaact tctcgtgctc cgcgggcagc    1200
acctgctgct gcgcgtttgg cttcaggaac gtctgcttgg tctggggctg ctgcccggtc    1260
gagggcgcca cctgctgcaa ggatcacgcc agctgctgcc cgccgggcta ccctgtctgc    1320
aacgtcagag ctggaacttg ctcggtgagc aagaacagcc cactgagcgt caaggccttg    1380
aagcgcactc tcgccaagct gagcaccgca tga                                  1413
```

<210> SEQ ID NO 43
<211> LENGTH: 470
<212> TYPE: PRT
<213> ORGANISM: Zea mays

<400> SEQUENCE: 43

Met Ala Ala Leu Gly Arg Gly Leu Pro Leu Leu Leu Leu Leu Leu
1               5                   10                  15

Leu Ala Val Ser Gly Ala Ala Asn Ala Ala Ala Ala Pro Gly Gly Met
                20                  25                  30

Ser Ile Ile Thr Tyr Asn Glu Glu His Gly Ala Arg Gly Leu Glu Arg
        35                  40                  45

```
Thr Glu Pro Glu Val Arg Ala Met Tyr Asp Leu Trp Leu Ala Glu His
 50                  55                  60

Gly Arg Ala Tyr Asn Ala Leu Gly Glu Gly Gly Glu Arg Asp Arg
 65              70                  75                  80

Arg Phe Leu Val Phe Trp Asp Asn Leu Arg Phe Val Asp Ala His Asn
                 85                  90                  95

Glu Arg Ala Gly Ala Arg Gly Phe Arg Leu Gly Met Asn Gln Phe Ala
                100                 105                 110

Asp Leu Thr Asn Asp Glu Phe Arg Ala Ala Tyr Leu Gly Ala Met Val
             115                 120                 125

Pro Ala Ala Arg Arg Gly Ala Val Val Gly Arg Tyr Arg His Asp
130                 135                 140

Gly Ala Ala Glu Glu Leu Pro Glu Ser Val Asp Trp Arg Glu Lys Gly
145                 150                 155                 160

Ala Val Ala Pro Val Lys Asn Gln Gly Gln Cys Gly Ser Cys Trp Ala
                 165                 170                 175

Phe Ser Ala Val Ser Ser Val Glu Ser Val Asn Gln Ile Val Thr Gly
             180                 185                 190

Glu Met Val Thr Leu Ser Glu Gln Glu Leu Val Glu Cys Ser Thr Asp
             195                 200                 205

Gly Gly Asn Ser Gly Cys Asn Gly Gly Leu Met Asp Ala Ala Phe Asp
210                 215                 220

Phe Ile Ile Lys Asn Gly Gly Ile Asp Thr Glu Asp Tyr Pro Tyr
225                 230                 235                 240

Arg Ala Val Asp Gly Lys Cys Asp Met Asn Arg Lys Asn Ala Arg Val
                 245                 250                 255

Val Ser Ile Asp Gly Phe Glu Asp Val Pro Glu Asn Asp Glu Lys Ser
             260                 265                 270

Leu Gln Lys Ala Val Ala His Gln Pro Val Ser Val Ala Ile Glu Ala
         275                 280                 285

Gly Gly Arg Glu Phe Gln Leu Tyr Lys Ser Gly Val Phe Ser Gly Ser
290                 295                 300

Cys Thr Thr Asn Leu Asp His Gly Val Val Ala Val Gly Tyr Gly Ala
305                 310                 315                 320

Glu Asn Gly Lys Asp Tyr Trp Ile Val Arg Asn Ser Trp Gly Pro Lys
             325                 330                 335

Trp Gly Glu Ala Gly Tyr Ile Arg Met Glu Arg Asn Val Asn Ala Ser
             340                 345                 350

Thr Gly Lys Cys Gly Ile Ala Met Met Ala Ser Tyr Pro Thr Lys Lys
             355                 360                 365

Gly Ala Asn Pro Pro Arg Pro Ser Pro Thr Pro Thr Pro Pro Ala
370                 375                 380

Ala Pro Asp Asn Val Cys Asp Glu Asn Phe Ser Cys Ser Ala Gly Ser
385                 390                 395                 400

Thr Cys Cys Cys Ala Phe Gly Phe Arg Asn Val Cys Leu Val Trp Gly
                 405                 410                 415

Cys Cys Pro Val Glu Gly Ala Thr Cys Cys Lys Asp His Ala Ser Cys
             420                 425                 430

Cys Pro Pro Gly Tyr Pro Val Cys Asn Val Arg Ala Gly Thr Cys Ser
         435                 440                 445

Val Ser Lys Asn Ser Pro Leu Ser Val Lys Ala Leu Lys Arg Thr Leu
450                 455                 460

Ala Lys Leu Ser Thr Ala
```

<210> SEQ ID NO 44
<211> LENGTH: 1512
<212> TYPE: DNA
<213> ORGANISM: Zea mays

<400> SEQUENCE: 44

| | | | | | |
|---|---|---|---|---|---|
| atggctgcct | ccaccacggc | ggcggcggcg | ctgctgctgc | tcctcctgtc | gctcgccgcg | 60 |
| gcggcggaca | tgtcgatcgt | gtcctacggg | gagcgcagck | wcgaggaggc | gcggcggatg | 120 |
| tacgcggagt | ggatggcggc | gcacggccgg | acctacaacg | ccgtcggcga | ggaggagcgg | 180 |
| cggtaccagg | tgttccggga | caacctccgc | tacatcgacg | cgcacaacgc | cgccgccgac | 240 |
| gcggcgtcc | actccttccg | cctcggcctc | aaccgcttcg | ccgacctcac | caacgacgag | 300 |
| taccgcgcca | cctacctcgg | cgccaggacc | aggccgcaga | gggagaggaa | gctcggcgcc | 360 |
| aggtaccacg | ccgccgacaa | cgaggacctg | ccggagtccg | tcgactggag | ggccaagggc | 420 |
| gccgtcgccg | aggtcaagga | ccaggcagc | tgcgggagct | gttgggcttt | ctcaacaata | 480 |
| gcagctgtgg | aaggcatcaa | ccagattgtt | acaggcgact | tgatctcctt | gtctgagcaa | 540 |
| gagcttgtcg | actgtgacac | ttcgtacaat | caggggtgca | atggaggtct | gatggactat | 600 |
| gcgtttgagt | tcatcatcaa | caatggcgga | atcgacaccg | agaaggatta | cccttacaaa | 660 |
| ggcacggacg | gacgatgtga | tgtcaacagg | aaaaacgcga | aggttgtcac | tattgacagc | 720 |
| tacgaagatg | taccagcgaa | cgatgagaag | agtctgcaga | aggcagttgc | aaaccagcct | 780 |
| gtcagtgtcg | caattgaggc | tgctggcaca | gcatttcagc | tctacagctc | gggtatcttc | 840 |
| actggaagct | gtggaacagc | gctagaccat | ggtgtcacgg | ccgtcggcta | cggcacagag | 900 |
| aacggcaagg | actactggat | cgtgaagaac | tcatggggca | gcagctgggg | cgagtccggg | 960 |
| tacgtgagga | tggagcgcaa | catcaaggcg | tccagcggca | agtgcggtat | cgcggttgag | 1020 |
| ccgtcatacc | cgttgaagga | gggcgctaac | ccgccgaacc | ctggccccag | cccgccgtcc | 1080 |
| ccgaccccgg | cgcccgccgt | ctgcgacaac | tactactcgt | gccctgacag | caccacctgc | 1140 |
| tgctgcatct | acgagtacgg | caagtactgc | ttcgcctggg | gctgctgccc | gctcgagggc | 1200 |
| gccacctgct | gcgacgatca | ctacagctgc | tgccccatg | actaccccat | ctgcaacgtc | 1260 |
| aggcagggaa | cctgcctcat | gggcaaggac | agcccactgt | cactgtcagt | gaaggctacg | 1320 |
| aagcgaaccc | tggccaagcc | gcactgggct | ttctccggca | acacagctga | cggcatgaag | 1380 |
| agcagcgcat | gagaaaacgt | gggcaaggac | agcccactgt | cactgtcagt | gaaggctacg | 1440 |
| aagcgaaccc | tggccaagcc | gcactgggct | ttctccggca | acacagctga | cggcatgaag | 1500 |
| agcagcgcat | ga | | | | | 1512 |

<210> SEQ ID NO 45
<211> LENGTH: 463
<212> TYPE: PRT
<213> ORGANISM: Zea mays
<220> FEATURE:
<221> NAME/KEY: misc_feature
<222> LOCATION: (34)..(34)
<223> OTHER INFORMATION: Xaa can be any naturally occurring amino acid

<400> SEQUENCE: 45

Met Ala Ala Ser Thr Thr Ala Ala Ala Leu Leu Leu Leu Leu Leu
1               5                   10                  15

Ser Leu Ala Ala Ala Ala Asp Met Ser Ile Val Ser Tyr Gly Glu Arg
            20                  25                  30

```
Ser Xaa Glu Glu Ala Arg Arg Met Tyr Ala Glu Trp Met Ala Ala His
    35                      40                      45

Gly Arg Thr Tyr Asn Ala Val Gly Glu Glu Glu Arg Arg Tyr Gln Val
    50                      55                      60

Phe Arg Asp Asn Leu Arg Tyr Ile Asp Ala His Asn Ala Ala Ala Asp
65                      70                      75                      80

Ala Gly Val His Ser Phe Arg Leu Gly Leu Asn Arg Phe Ala Asp Leu
                85                      90                      95

Thr Asn Asp Glu Tyr Arg Ala Thr Tyr Leu Gly Ala Arg Thr Arg Pro
                100                     105                     110

Gln Arg Glu Arg Lys Leu Gly Ala Arg Tyr His Ala Ala Asp Asn Glu
                115                     120                     125

Asp Leu Pro Glu Ser Val Asp Trp Arg Ala Lys Gly Ala Val Ala Glu
                130                     135                     140

Val Lys Asp Gln Gly Ser Cys Gly Ser Cys Trp Ala Phe Ser Thr Ile
145                     150                     155                     160

Ala Ala Val Glu Gly Ile Asn Gln Ile Val Thr Gly Asp Leu Ile Ser
                165                     170                     175

Leu Ser Glu Gln Glu Leu Val Asp Cys Asp Thr Ser Tyr Asn Gln Gly
                180                     185                     190

Cys Asn Gly Gly Leu Met Asp Tyr Ala Phe Glu Phe Ile Ile Asn Asn
                195                     200                     205

Gly Gly Ile Asp Thr Glu Lys Asp Tyr Pro Tyr Lys Gly Thr Asp Gly
                210                     215                     220

Arg Cys Asp Val Asn Arg Lys Asn Ala Lys Val Val Thr Ile Asp Ser
225                     230                     235                     240

Tyr Glu Asp Val Pro Ala Asn Asp Glu Lys Ser Leu Gln Lys Ala Val
                245                     250                     255

Ala Asn Gln Pro Val Ser Val Ala Ile Glu Ala Ala Gly Thr Ala Phe
                260                     265                     270

Gln Leu Tyr Ser Ser Gly Ile Phe Thr Gly Ser Cys Gly Thr Ala Leu
                275                     280                     285

Asp His Gly Val Thr Ala Val Gly Tyr Gly Thr Glu Asn Gly Lys Asp
                290                     295                     300

Tyr Trp Ile Val Lys Asn Ser Trp Gly Ser Ser Trp Gly Glu Ser Gly
305                     310                     315                     320

Tyr Val Arg Met Glu Arg Asn Ile Lys Ala Ser Ser Gly Lys Cys Gly
                325                     330                     335

Ile Ala Val Glu Pro Ser Tyr Pro Leu Lys Glu Gly Ala Asn Pro Pro
                340                     345                     350

Asn Pro Gly Pro Ser Pro Pro Ser Pro Thr Pro Ala Pro Ala Val Cys
                355                     360                     365

Asp Asn Tyr Tyr Ser Cys Pro Asp Ser Thr Thr Cys Cys Cys Ile Tyr
                370                     375                     380

Glu Tyr Gly Lys Tyr Cys Phe Ala Trp Gly Cys Cys Pro Leu Glu Gly
385                     390                     395                     400

Ala Thr Cys Cys Asp Asp His Tyr Ser Cys Cys Pro His Asp Tyr Pro
                405                     410                     415

Ile Cys Asn Val Arg Gln Gly Thr Cys Leu Met Gly Lys Asp Ser Pro
                420                     425                     430

Leu Ser Leu Ser Val Lys Ala Thr Lys Arg Thr Leu Ala Lys Pro His
                435                     440                     445
```

Trp Ala Phe Ser Gly Asn Thr Ala Asp Gly Met Lys Ser Ser Ala
        450                 455                 460

<210> SEQ ID NO 46
<211> LENGTH: 1359
<212> TYPE: DNA
<213> ORGANISM: Neurospora crassa

<400> SEQUENCE: 46

| | | | | | |
|---|---|---|---|---|---|
| atggatcttg | acggcatccc | ttctctcaac | aacggaagcc | ttcgccattc gacaaaagca | 60 |
| agatgcagat | accccaaaga | tggtggatac | tatgtcaatg | tgaccattgg tacacccgga | 120 |
| aggaatcttt | ccctacatct | cgacacaggc | tcaagtgata | cttgggtgaa ttctcccagt | 180 |
| tcgattcttt | gtcaagatga | agacaaacca | tgcgaatact | ccggcaccta cctagccaat | 240 |
| gactcgtcta | cttatgagta | catcagcaat | catttcgaca | tcaagtatgt ggatgggtct | 300 |
| ggcgccagag | gggactatgc | ctccgatact | ttcacaatcg | gcaacaccaa actgaaccgg | 360 |
| ctgcagtttg | gcattggcta | ctcttcaact | aacgcgcagg | gactgctcgg tatagggtac | 420 |
| accctgagcg | aagtgcaaac | ccgtgccggg | ttgccagcct | ataacaacct tccggcgcaa | 480 |
| atggtcgccg | acggcttgat | caactccaac | gcctactcca | tctggctcaa tgacctcgat | 540 |
| gccctcacgg | gtaccattct | cttcggcggc | gtcgacgccg | ccaagtacga gggcgacctg | 600 |
| ctcaccctac | ccgttcaaac | cccagaaaag | ggcacgtaca | agaacctcat ggtcaccatg | 660 |
| accggcctgt | ctctatctca | gtcccagtcc | tcctccagcg | acaagggcaa cggtgatgac | 720 |
| accacccaga | tctccaaaga | caacctcgcc | cttgccgttc | tcttggacac cggctcaacc | 780 |
| ctcagttatc | tccccagtga | gctcgtcaaa | ccgctctacg | acgcgatcgg tatcgaatac | 840 |
| ataacagacc | ccgacggcaa | agtagatggc | tacgcgccct | gccatctcat gtcctcgtcg | 900 |
| caatccgtca | tgttctcctt | ctcctccccg | cttcagattg | ccgtgcccat gaacgagctc | 960 |
| atcgtcaacc | ggaccttcca | cggaaaactc | ccacgcatgc | cggacggcgt cacagacgcc | 1020 |
| tgcatctttg | gcatccaaga | acgtaatggc | acgggagcaa | acaccttggg cgacacgttc | 1080 |
| ctgcgcagcg | cgtatgttgt | gtttgatttg | acaacaacg | agatctcgat ggcgcagacg | 1140 |
| aggtttaatg | ccacggcgac | ggacctgaag | gagattaaga | agggcaaagg tggggtgccg | 1200 |
| ggcgcgaagg | cggtggaaaa | tcctgtggag | gccacgagcg | gcctgtctgg taatgaaggg | 1260 |
| gggatatatg | tgaatggggc | ggcgtgtgaa | ttgaatgtgg | gtatgggaat ggcttggggt | 1320 |
| ttgttggttg | gtgctacgat | ggtggttttg | gggttgtga | | 1359 |

<210> SEQ ID NO 47
<211> LENGTH: 452
<212> TYPE: PRT
<213> ORGANISM: Neurospora crassa

<400> SEQUENCE: 47

Met Asp Leu Asp Gly Ile Pro Ser Leu Asn Asn Gly Ser Leu Arg His
1               5                   10                  15

Ser Thr Lys Ala Arg Cys Arg Tyr Pro Lys Asp Gly Tyr Tyr Val
            20                  25                  30

Asn Val Thr Ile Gly Thr Pro Gly Arg Asn Leu Ser Leu His Leu Asp
            35                  40                  45

Thr Gly Ser Ser Asp Thr Trp Val Asn Ser Ser Ile Leu Cys
        50                  55                  60

Gln Asp Glu Asp Lys Pro Cys Glu Tyr Ser Gly Thr Tyr Leu Ala Asn
65                  70                  75                  80

-continued

Asp Ser Ser Thr Tyr Glu Tyr Ile Ser Asn His Phe Asp Ile Lys Tyr
                85                  90                  95

Val Asp Gly Ser Gly Ala Arg Gly Asp Tyr Ala Ser Asp Thr Phe Thr
                100                 105                 110

Ile Gly Asn Thr Lys Leu Asn Arg Leu Gln Phe Gly Ile Gly Tyr Ser
                115                 120                 125

Ser Thr Asn Ala Gln Gly Leu Leu Gly Ile Gly Tyr Thr Leu Ser Glu
        130                 135                 140

Val Gln Thr Arg Ala Gly Leu Pro Ala Tyr Asn Asn Leu Pro Ala Gln
145                 150                 155                 160

Met Val Ala Asp Gly Leu Ile Asn Ser Asn Ala Tyr Ser Ile Trp Leu
                165                 170                 175

Asn Asp Leu Asp Ala Leu Thr Gly Thr Ile Leu Phe Gly Gly Val Asp
                180                 185                 190

Ala Ala Lys Tyr Glu Gly Asp Leu Leu Thr Leu Pro Val Gln Thr Pro
                195                 200                 205

Glu Lys Gly Thr Tyr Lys Asn Leu Met Val Thr Met Thr Gly Leu Ser
        210                 215                 220

Leu Ser Gln Ser Gln Ser Ser Ser Asp Lys Gly Asn Gly Asp Asp
225                 230                 235                 240

Thr Thr Gln Ile Ser Lys Asp Asn Leu Ala Leu Ala Val Leu Leu Asp
                245                 250                 255

Thr Gly Ser Thr Leu Ser Tyr Leu Pro Ser Glu Leu Val Lys Pro Leu
                260                 265                 270

Tyr Asp Ala Ile Gly Ile Glu Tyr Ile Thr Asp Pro Asp Gly Lys Val
                275                 280                 285

Asp Gly Tyr Ala Pro Cys His Leu Met Ser Ser Ser Gln Ser Val Met
        290                 295                 300

Phe Ser Phe Ser Ser Pro Leu Gln Ile Ala Val Pro Met Asn Glu Leu
305                 310                 315                 320

Ile Val Asn Arg Thr Phe His Gly Lys Leu Pro Arg Met Pro Asp Gly
                325                 330                 335

Val Thr Asp Ala Cys Ile Phe Gly Ile Gln Glu Arg Asn Gly Thr Gly
                340                 345                 350

Ala Asn Thr Leu Gly Asp Thr Phe Leu Arg Ser Ala Tyr Val Val Phe
        355                 360                 365

Asp Leu Asp Asn Asn Glu Ile Ser Met Ala Gln Thr Arg Phe Asn Ala
370                 375                 380

Thr Ala Thr Asp Leu Lys Glu Ile Lys Lys Gly Lys Gly Val Pro
385                 390                 395                 400

Gly Ala Lys Ala Val Glu Asn Pro Val Glu Ala Thr Ser Gly Leu Ser
                405                 410                 415

Gly Asn Glu Gly Gly Ile Tyr Val Asn Gly Ala Ala Cys Glu Leu Asn
        420                 425                 430

Val Gly Met Gly Met Ala Trp Gly Leu Leu Val Gly Ala Thr Met Val
        435                 440                 445

Val Leu Gly Leu
    450

<210> SEQ ID NO 48
<211> LENGTH: 1443
<212> TYPE: DNA
<213> ORGANISM: Podospora anserina

<400> SEQUENCE: 48

```
atgaagacag ccacttctct tttggttgtt gcagcctcgc ttgcgggtca gacgatagac    60
gctctctctt tgccatcgac gacgccaaca caacaacaac aacgaagaga tggaagtgga   120
ccgagggttg tggggatgga tattcagagg aggacgccca aaaacccatt acatcgagat   180
catctaagaa agagagggag cgtggaggtc gatttggaca atcaggaaac cctctacttc   240
atcaacggca caatcggcac cccaccaaaa tccctccgtc tacacctcga caccggctcg   300
tccgacctct gggtcaacac cccatcctcc tccctatgca cccagtcctc agcgccctgt   360
aaatacgccg gcacttactc ggccaacggc tcaagcacgt acgagtacat cggctcctgg   420
ttcaacatct cctacgtcga cggctccggc gcctcggggg attacgtttc cgacaccgtc   480
acctttggcg acgccacgct ggacaggttg cagtttggca taggatactc gtccaacaac   540
gcccagggca tcctcgggat agggtacccg atcaacgaag tccaagtcgg cagggcagga   600
atgagacctt acaacaacct ccccgcgcaa atggtggccg acgggctgat ccaaacaaac   660
gcttattccc tgtggctgaa cgacctcgac gctgacacgg gaatattcct gtttggcggt   720
gtcgacacgg aaaagtttgt tccccgttg atgtccctcc cggtggaatc cgaggcgggg   780
gtgtacgccg agtttatgat cacgttgacg aaagtcgagc tcggctcggc gcaggtaggc   840
ggcgatctcg ccttggctgt gctgttggat accggcagca gcttgacgta cctccccgac   900
cggatggtgc aagatatttt cgaccttgtc gacgcgcagt acgatcctga ggctaacgcg   960
gcgtatgttc cttgctcgct tgccgacaat gagactgctg ttttgtcgtt acgtttacg   1020
gagccgacga tcaatgtggg gatggatgag cttgtgctcg accttgtgac gagctcgggg   1080
aggaggccgg tttttagtga cgggacggag gcgtgcctgt ttgggattgc gccggcgggg   1140
gaggggacga atgtgctggg ggatacgttt ttgaggagtg cgtatgtggt ttatgacttg   1200
gagaataacg agatttcgtt ggcggcgacg aggttcaaca gtacggggac gagggttgag   1260
gagatagggag aggggagggg ggggtgccg ggggcgacga aggtggagaa tccgaccaag   1320
gcgacggagg ggttggatgg gccgaatggt ttgggggga taagtgctgg gaataagagg   1380
ggtttggagg ttggggtggt gtggttggtg gcgggtatgg tgggagtttt gctggtggtc   1440
taa                                                                 1443
```

<210> SEQ ID NO 49
<211> LENGTH: 480
<212> TYPE: PRT
<213> ORGANISM: Podospora anserina

<400> SEQUENCE: 49

```
Met Lys Thr Ala Thr Ser Leu Leu Val Val Ala Ala Ser Leu Ala Gly
1               5                   10                  15

Gln Thr Ile Asp Ala Leu Ser Leu Pro Ser Thr Thr Pro Thr Gln Gln
            20                  25                  30

Gln Gln Arg Arg Asp Gly Ser Gly Pro Arg Val Gly Met Asp Ile
        35                  40                  45

Gln Arg Arg Thr Pro Lys Asn Pro Leu His Arg Asp His Leu Arg Lys
    50                  55                  60

Arg Gly Ser Val Glu Val Asp Leu Asp Asn Gln Glu Thr Leu Tyr Phe
65                  70                  75                  80

Ile Asn Gly Thr Ile Gly Thr Pro Pro Lys Ser Leu Arg Leu His Leu
                85                  90                  95

Asp Thr Gly Ser Ser Asp Leu Trp Val Asn Thr Pro Ser Ser Ser Leu
```

```
                100             105             110
Cys Thr Gln Ser Ser Ala Pro Cys Lys Tyr Ala Gly Thr Tyr Ser Ala
            115                 120                 125
Asn Gly Ser Ser Thr Tyr Glu Tyr Ile Gly Ser Trp Phe Asn Ile Ser
        130                 135                 140
Tyr Val Asp Gly Ser Gly Ala Ser Gly Asp Tyr Val Ser Asp Thr Val
145                 150                 155                 160
Thr Phe Gly Asp Ala Thr Leu Asp Arg Leu Gln Phe Gly Ile Gly Tyr
                165                 170                 175
Ser Ser Asn Asn Ala Gln Gly Ile Leu Gly Ile Gly Tyr Pro Ile Asn
            180                 185                 190
Glu Val Gln Val Gly Arg Ala Gly Met Arg Pro Tyr Asn Asn Leu Pro
        195                 200                 205
Ala Gln Met Val Ala Asp Gly Leu Ile Gln Thr Asn Ala Tyr Ser Leu
    210                 215                 220
Trp Leu Asn Asp Leu Asp Ala Asp Thr Gly Asn Ile Leu Phe Gly Gly
225                 230                 235                 240
Val Asp Thr Glu Lys Phe Val Pro Pro Leu Met Ser Leu Pro Val Glu
                245                 250                 255
Ser Glu Ala Gly Val Tyr Ala Glu Phe Met Ile Thr Leu Thr Lys Val
            260                 265                 270
Glu Leu Gly Ser Ala Gln Val Gly Gly Asp Leu Ala Leu Ala Val Leu
        275                 280                 285
Leu Asp Thr Gly Ser Ser Leu Thr Tyr Leu Pro Asp Arg Met Val Gln
    290                 295                 300
Asp Ile Phe Asp Leu Val Asp Ala Gln Tyr Asp Pro Glu Ala Asn Ala
305                 310                 315                 320
Ala Tyr Val Pro Cys Ser Leu Ala Asp Asn Glu Thr Ala Val Leu Ser
                325                 330                 335
Phe Thr Phe Thr Glu Pro Thr Ile Asn Val Gly Met Asp Glu Leu Val
            340                 345                 350
Leu Asp Leu Val Thr Ser Ser Gly Arg Arg Pro Val Phe Ser Asp Gly
        355                 360                 365
Thr Glu Ala Cys Leu Phe Gly Ile Ala Pro Ala Gly Glu Gly Thr Asn
    370                 375                 380
Val Leu Gly Asp Thr Phe Leu Arg Ser Ala Tyr Val Val Tyr Asp Leu
385                 390                 395                 400
Glu Asn Asn Glu Ile Ser Leu Ala Ala Thr Arg Phe Asn Ser Thr Gly
                405                 410                 415
Thr Arg Val Glu Glu Ile Gly Lys Gly Glu Gly Val Pro Gly Ala
            420                 425                 430
Thr Lys Val Glu Asn Pro Thr Lys Ala Thr Glu Gly Leu Asp Gly Pro
        435                 440                 445
Asn Gly Leu Gly Gly Ile Ser Ala Gly Asn Lys Arg Gly Leu Glu Val
    450                 455                 460
Gly Val Val Trp Leu Val Ala Gly Met Val Gly Val Leu Leu Val Val
465                 470                 475                 480

<210> SEQ ID NO 50
<211> LENGTH: 1425
<212> TYPE: DNA
<213> ORGANISM: Magnaporthe oryzae

<400> SEQUENCE: 50
```

-continued

```
atgaggttaa tagcatcact ggccttggcg gcatcactgg cctcttcaat cacaaatgga     60
tcaacgatac cgaggagggc ctcgggcaca ccagctgcgc cgagggtaat tggcctggag    120
acggaaaggc agcacatccc gaatcccttg gagcgggaca ggttaaggag gagagccgcc    180
gtcatggcta ctctcgacaa cgagcagacg ctgtactttg tcaacgtctc catcggcacg    240
ccaccgcaga agctacgtct tcaccttgac accggcagca gtgacctgtg ggtcaacacg    300
cccgactcga aactctgttc cgtctcgtcg cagccgtgca gatttgccgg aacctttagc    360
gcaaacagct cctctacata tcaatacatc aacagtgtct tcaacatctc gtacgttgac    420
ggctcaggcg ccaatggcga ctatgtctcc gatatggtca cggtgggcaa caccaagatc    480
gaccgcctcc agttcggaat cggatacacg agcagttcgg cgcagggaat tctgggcgtc    540
ggttatgagg ccaacgaggt gcaggtcgga cgtgctcagc tcaagccgta ccgcaacctc    600
ccctcgcgca tggtcgagga gggcctgatc gcttccaacg cctacagcct ttacctcaat    660
gacctgcagt ccaacaaggg cagcatcctg tttggtggca tcgacacgga gcagtacacg    720
ggaacgctgc agaccgtccc gatccagccc aacggtggcc gcatggccga gtttctcatc    780
accttgacct ctgtctcctt gacctcggca agcattggcg gtgacaagct ggccctggcc    840
gtgctgctcg actcgggttc ctcgctcacc tacctgcccg acgacatcgt aaagaacatg    900
tacagcgccg tgggcgccca gtacgacagc aacgagggcg ccgcatacgt cccctgctcc    960
ctcgccaggg accaggccaa ctcgttgacc tttagctttt ccggcatccc catcgtcgtg   1020
cccatgaacg agctcgtctt ggacctggta acttccaacg gccgccggcc ctcgttccgc   1080
aacggcgtcc ccgcctgcct gtttggcgtc gccccggccg gcaagggcac caatgttcta   1140
ggtgacacgt tcctccgctc cgcctacgtc gtctacgacc tcgaaaacaa cgccatctcg   1200
ctcgctcaga ccagcttcaa cgctaccaag agcaacgtca aggagatcgg caagggcagc   1260
aaccctgttc ccggcgccgt tgccgtctcg cagcccgtcg ctgccacttc gggcctgtcg   1320
cagaacggcg gcaacaggtc tggctctggc gccatcgccc gggccgttcc gactctcttg   1380
ctcgtcggag gaatcttctc cggttcgttg ttgactctgt tctag                    1425
```

<210> SEQ ID NO 51
<211> LENGTH: 474
<212> TYPE: PRT
<213> ORGANISM: Magnaporthe oryzae

<400> SEQUENCE: 51

```
Met Arg Leu Ile Ala Ser Leu Ala Leu Ala Ala Ser Leu Ala Ser Ser
1               5                   10                  15

Ile Thr Asn Gly Ser Thr Ile Pro Arg Arg Ala Ser Gly Thr Pro Ala
            20                  25                  30

Ala Pro Arg Val Ile Gly Leu Glu Thr Glu Arg Gln His Ile Pro Asn
        35                  40                  45

Pro Leu Glu Arg Asp Arg Leu Arg Arg Arg Ala Ala Val Met Ala Thr
    50                  55                  60

Leu Asp Asn Glu Gln Thr Leu Tyr Phe Val Asn Val Ser Ile Gly Thr
65                  70                  75                  80

Pro Pro Gln Lys Leu Arg Leu His Leu Asp Thr Gly Ser Ser Asp Leu
                85                  90                  95

Trp Val Asn Thr Pro Asp Ser Lys Leu Cys Ser Val Ser Ser Gln Pro
            100                 105                 110

Cys Arg Phe Ala Gly Thr Phe Ser Ala Asn Ser Ser Ser Thr Tyr Gln
        115                 120                 125
```

Tyr Ile Asn Ser Val Phe Asn Ile Ser Tyr Val Asp Gly Ser Gly Ala
130                 135                 140

Asn Gly Asp Tyr Val Ser Asp Met Val Thr Val Gly Asn Thr Lys Ile
145                 150                 155                 160

Asp Arg Leu Gln Phe Gly Ile Gly Tyr Thr Ser Ser Ala Gln Gly
            165                 170                 175

Ile Leu Gly Val Gly Tyr Glu Ala Asn Glu Val Gln Val Gly Arg Ala
                180                 185                 190

Gln Leu Lys Pro Tyr Arg Asn Leu Pro Ser Arg Met Val Glu Gly
            195                 200                 205

Leu Ile Ala Ser Asn Ala Tyr Ser Leu Tyr Leu Asn Asp Leu Gln Ser
210                 215                 220

Asn Lys Gly Ser Ile Leu Phe Gly Gly Ile Asp Thr Glu Gln Tyr Thr
225                 230                 235                 240

Gly Thr Leu Gln Thr Val Pro Ile Gln Pro Asn Gly Gly Arg Met Ala
                245                 250                 255

Glu Phe Leu Ile Thr Leu Thr Ser Val Ser Leu Thr Ser Ala Ser Ile
            260                 265                 270

Gly Gly Asp Lys Leu Ala Leu Ala Val Leu Leu Asp Ser Gly Ser Ser
            275                 280                 285

Leu Thr Tyr Leu Pro Asp Asp Ile Val Lys Asn Met Tyr Ser Ala Val
290                 295                 300

Gly Ala Gln Tyr Asp Ser Asn Glu Gly Ala Ala Tyr Val Pro Cys Ser
305                 310                 315                 320

Leu Ala Arg Asp Gln Ala Asn Ser Leu Thr Phe Ser Phe Ser Gly Ile
                325                 330                 335

Pro Ile Val Val Pro Met Asn Glu Leu Val Leu Asp Leu Val Thr Ser
            340                 345                 350

Asn Gly Arg Arg Pro Ser Phe Arg Asn Gly Val Pro Ala Cys Leu Phe
            355                 360                 365

Gly Val Ala Pro Ala Gly Lys Gly Thr Asn Val Leu Gly Asp Thr Phe
370                 375                 380

Leu Arg Ser Ala Tyr Val Val Tyr Asp Leu Glu Asn Asn Ala Ile Ser
385                 390                 395                 400

Leu Ala Gln Thr Ser Phe Asn Ala Thr Lys Ser Asn Val Lys Glu Ile
                405                 410                 415

Gly Lys Gly Ser Asn Pro Val Pro Gly Ala Val Ala Val Ser Gln Pro
            420                 425                 430

Val Ala Ala Thr Ser Gly Leu Ser Gln Asn Gly Gly Asn Arg Ser Gly
            435                 440                 445

Ser Gly Ala Ile Ala Arg Ala Val Pro Thr Leu Leu Leu Val Gly Gly
    450                 455                 460

Ile Phe Ser Gly Ser Leu Leu Thr Leu Phe
465                 470

<210> SEQ ID NO 52
<211> LENGTH: 1806
<212> TYPE: DNA
<213> ORGANISM: Saccharomyces cerevisiae

<400> SEQUENCE: 52
atgagtaata cttcttcgta cgagaagaat aatccagata atctgaaaca caatggtatt      60
accatagatt ctgagtttct aactcaggag ccaataacca ttccctcaaa tggctccgct     120

-continued

```
gtttctattg acgaaacagg ttcagggtcc aaatggcaag actttaaaga ttctttcaaa    180
agggtaaaac ctattgaagt tgatcctaat ctttcagaag ctgaaaaagt ggctatcatc    240
actgcccaaa ctccattgaa gcaccacttg aagaatagac atttgcaaat gattgccatc    300
ggtggtgcca tcggtactgg tctgctggtt gggtcaggta ctgcactaag aacaggtggt    360
cccgcttcgc tactgattgg atgggggtct acaggtacca tgatttacgc tatggttatg    420
gctctgggtg agttggctgt tatcttccct atttcgggtg ggttcaccac gtacgctacc    480
agatttattg atgagtcctt tggttacgct aataatttca attatatgtt acaatggttg    540
gttgtgctac cattggaaat tgtctctgca tctattactg taaatttctg gggtacagat    600
ccaaagtata gagatgggtt tgttgcgttg ttttggcttg caattgttat catcaatatg    660
tttggtgtca aaggttatgg tgaagcagaa ttcgtctttt catttatcaa ggtcatcact    720
gttgttgggt tcatcatctt aggtatcatt ctaaactgtg gtggtggtcc aacaggtggt    780
tacattgggg gcaagtactg gcatgatcct ggtgcctttg ctggtgacac tccaggtgct    840
aaattcaaag gtgtttgttc tgtcttcgtc accgctgcct tttcttttgc cggttcagaa    900
ttggttggtc ttgctgccag tgaatccgta gagcctagaa agtccgttcc taaggctgct    960
aaacaagttt tctggagaat caccctattt tatattctgt cgctattaat gattggtctt   1020
ttagtcccat acaacgataa aagtttgatt ggtgcctcct ctgtggatgc tgctgcttca   1080
cccttcgtca ttgccattaa gactcacggt atcaagggtt gccaagtgt tgtcaacgtc   1140
gttatcttga ttgccgtgtt atctgtcggt aactctgcca tttatgcatg ttccagaaca   1200
atggttgccc tagctgaaca gagatttctg ccagaaatct tttcctacgt tgaccgtaag   1260
ggtagaccat tggtgggaat tgctgtcaca tctgcattcg gtcttattgc gtttgttgcc   1320
gcctccaaaa aggaaggtga agttttcaac tggttactag ccttgtctgg gttgtcatct   1380
ctattcacat ggggtggtat ctgtatttgt cacattcgtt tcagaaaggc attggccgcc   1440
caaggaagag gcttggatga attgtctttc aagtctccta ccggtgtttg gggttcctac   1500
tgggggttat ttatggttat tattatgttc attgcccaat tctacgttgc tgtattcccc   1560
gtgggagatt ctccaagtgc ggaaggtttc ttcgaagctt atctatcctt cccacttgtt   1620
atggttatgt acatcggaca caagatctat aagaggaatt ggaagctttt catcccagca   1680
gaaaagatgg acattgatac gggtagaaga gaagtcgatt tagatttgtt gaaacaagaa   1740
attgcagaag aaaaggcaat tatggccaca aagccaagat ggtatagaat ctggaatttc   1800
tggtgt                                                               1806
```

<210> SEQ ID NO 53
<211> LENGTH: 602
<212> TYPE: PRT
<213> ORGANISM: Saccharomyces cerevisiae

<400> SEQUENCE: 53

```
Met Ser Asn Thr Ser Ser Tyr Glu Lys Asn Asn Pro Asp Asn Leu Lys
 1               5                  10                  15

His Asn Gly Ile Thr Ile Asp Ser Glu Phe Leu Thr Gln Glu Pro Ile
            20                  25                  30

Thr Ile Pro Ser Asn Gly Ser Ala Val Ser Ile Asp Glu Thr Gly Ser
        35                  40                  45

Gly Ser Lys Trp Gln Asp Phe Lys Asp Ser Phe Lys Arg Val Lys Pro
    50                  55                  60

Ile Glu Val Asp Pro Asn Leu Ser Glu Ala Glu Lys Val Ala Ile Ile
```

```
                65                  70                  75                  80
Thr Ala Gln Thr Pro Leu Lys His His Leu Lys Asn Arg His Leu Gln
                    85                  90                  95
Met Ile Ala Ile Gly Ala Ile Gly Thr Gly Leu Leu Val Gly Ser
                100                 105                 110
Gly Thr Ala Leu Arg Thr Gly Pro Ala Ser Leu Leu Ile Gly Trp
            115                 120                 125
Gly Ser Thr Gly Thr Met Ile Tyr Ala Met Val Met Ala Leu Gly Glu
    130                 135                 140
Leu Ala Val Ile Phe Pro Ile Ser Gly Gly Phe Thr Thr Tyr Ala Thr
145                 150                 155                 160
Arg Phe Ile Asp Glu Ser Phe Gly Tyr Ala Asn Asn Phe Asn Tyr Met
                165                 170                 175
Leu Gln Trp Leu Val Val Leu Pro Leu Glu Ile Val Ser Ala Ser Ile
            180                 185                 190
Thr Val Asn Phe Trp Gly Thr Asp Pro Lys Tyr Arg Asp Gly Phe Val
        195                 200                 205
Ala Leu Phe Trp Leu Ala Ile Val Ile Asn Met Phe Gly Val Lys
    210                 215                 220
Gly Tyr Gly Glu Ala Glu Phe Val Phe Ser Phe Ile Lys Val Ile Thr
225                 230                 235                 240
Val Val Gly Phe Ile Ile Leu Gly Ile Ile Leu Asn Cys Gly Gly Gly
                245                 250                 255
Pro Thr Gly Gly Tyr Ile Gly Gly Lys Tyr Trp His Asp Pro Gly Ala
            260                 265                 270
Phe Ala Gly Asp Thr Pro Gly Ala Lys Phe Lys Gly Val Cys Ser Val
        275                 280                 285
Phe Val Thr Ala Ala Phe Ser Phe Ala Gly Ser Glu Leu Val Gly Leu
    290                 295                 300
Ala Ala Ser Glu Ser Val Glu Pro Arg Lys Ser Val Pro Lys Ala Ala
305                 310                 315                 320
Lys Gln Val Phe Trp Arg Ile Thr Leu Phe Tyr Ile Leu Ser Leu Leu
                325                 330                 335
Met Ile Gly Leu Leu Val Pro Tyr Asn Asp Lys Ser Leu Ile Gly Ala
            340                 345                 350
Ser Ser Val Asp Ala Ala Ala Ser Pro Phe Val Ile Ala Ile Lys Thr
        355                 360                 365
His Gly Ile Lys Gly Leu Pro Ser Val Asn Val Val Ile Leu Ile
    370                 375                 380
Ala Val Leu Ser Val Gly Asn Ser Ala Ile Tyr Ala Cys Ser Arg Thr
385                 390                 395                 400
Met Val Ala Leu Ala Glu Gln Arg Phe Leu Pro Glu Ile Phe Ser Tyr
                405                 410                 415
Val Asp Arg Lys Gly Arg Pro Leu Val Gly Ile Ala Val Thr Ser Ala
            420                 425                 430
Phe Gly Leu Ile Ala Phe Val Ala Ala Ser Lys Lys Glu Gly Glu Val
        435                 440                 445
Phe Asn Trp Leu Leu Ala Leu Ser Gly Leu Ser Ser Leu Phe Thr Trp
    450                 455                 460
Gly Gly Ile Cys Ile Cys His Ile Arg Phe Arg Lys Ala Leu Ala Ala
465                 470                 475                 480
Gln Gly Arg Gly Leu Asp Glu Leu Ser Phe Lys Ser Pro Thr Gly Val
                485                 490                 495
```

Trp Gly Ser Tyr Trp Gly Leu Phe Met Val Ile Ile Met Phe Ile Ala
        500                 505                 510

Gln Phe Tyr Val Ala Val Phe Pro Val Gly Asp Ser Pro Ser Ala Glu
        515                 520                 525

Gly Phe Phe Glu Ala Tyr Leu Ser Phe Pro Leu Val Met Val Met Tyr
        530                 535                 540

Ile Gly His Lys Ile Tyr Lys Arg Asn Trp Lys Leu Phe Ile Pro Ala
545                 550                 555                 560

Glu Lys Met Asp Ile Asp Thr Gly Arg Arg Glu Val Asp Leu Asp Leu
                565                 570                 575

Leu Lys Gln Glu Ile Ala Glu Glu Lys Ala Ile Met Ala Thr Lys Pro
        580                 585                 590

Arg Trp Tyr Arg Ile Trp Asn Phe Trp Cys
        595                 600

<210> SEQ ID NO 54
<211> LENGTH: 1062
<212> TYPE: DNA
<213> ORGANISM: Saccharomyces cerevisiae

<400> SEQUENCE: 54

```
atgatgaata caacggcaa ccaagtgtcg aatctctcca atgcgctccg tcaagtaaac      60
ataggaaaca ggaacagtaa tacaaccacc gatcaaagta atataaattt tgaattttca    120
acaggtgtaa ataataataa taataacaat agcagtagta ataacaataa tgttcaaaac    180
aataacagcg gccgcaatgg tagccaaaat aatgataacg agaataatat caagaatacc    240
ttagaacaac atcgacaaca acaacaggca ttttcggata tgagtcacgt ggagtattcc    300
agaattacaa aattttttca agaacaacca ctggagggat atacccttt ctctcacagg     360
tctgcgccta atggattcaa agttgctata gtactaagtg aacttggatt tcattataac    420
acaatcttcc tagatttcaa tcttggcgaa catagggccc ccgaatttgt gtctgtgaac    480
cctaatgcaa gagttccagc tttaatcgat catggtatgg acaacttgtc tatttgggaa    540
tcaggggcga ttttattaca tttggtaaat aaatattaca aagagactgg taatccatta    600
ctctggtccg atgatttagc tgaccaatca caaatcaacg catggttgtt cttccaaacg    660
tcagggcatg cgccaatgat tggacaagct ttacatttca gatacttcca ttcacaaaag    720
atagcaagtg ctgtagaaag atatacggat gaggttagaa gagtttacgg tgtagtggag    780
atggccttgg ctgaacgtag agaagcgctg gtgatggaat tagacacgga aaatgcggct    840
gcatactcag ctggtacaac accaatgtca caaagtcgtt tctttgatta tcccgtatgg    900
cttgtaggag ataaattaac tatagcagat ttggcctttg tcccatggaa taatgtcgtg    960
gatagaattg gcattaatat caaaattgaa tttccagaag tttacaaatg gacgaagcat   1020
atgatgagaa gacccgcggt catcaaggca ttgcgtggtg aa                      1062
```

<210> SEQ ID NO 55
<211> LENGTH: 354
<212> TYPE: PRT
<213> ORGANISM: Saccharomyces cerevisiae

<400> SEQUENCE: 55

Met Met Asn Asn Asn Gly Asn Gln Val Ser Asn Leu Ser Asn Ala Leu
1               5                   10                  15

Arg Gln Val Asn Ile Gly Asn Arg Asn Ser Asn Thr Thr Asp Gln
            20                  25                  30

Ser Asn Ile Asn Phe Glu Phe Ser Thr Gly Val Asn Asn Asn Asn
             35                  40                  45

Asn Asn Ser Ser Ser Asn Asn Asn Val Gln Asn Asn Ser Gly
 50                  55                  60

Arg Asn Gly Ser Gln Asn Asn Asp Asn Glu Asn Asn Ile Lys Asn Thr
 65                  70                  75                  80

Leu Glu Gln His Arg Gln Gln Gln Ala Phe Ser Asp Met Ser His
                 85                  90                  95

Val Glu Tyr Ser Arg Ile Thr Lys Phe Phe Gln Glu Gln Pro Leu Glu
                100                 105                 110

Gly Tyr Thr Leu Phe Ser His Arg Ser Ala Pro Asn Gly Phe Lys Val
                115                 120                 125

Ala Ile Val Leu Ser Glu Leu Gly Phe His Tyr Asn Thr Ile Phe Leu
130                 135                 140

Asp Phe Asn Leu Gly Glu His Arg Ala Pro Glu Phe Val Ser Val Asn
145                 150                 155                 160

Pro Asn Ala Arg Val Pro Ala Leu Ile Asp His Gly Met Asp Asn Leu
                165                 170                 175

Ser Ile Trp Glu Ser Gly Ala Ile Leu Leu His Leu Val Asn Lys Tyr
                180                 185                 190

Tyr Lys Glu Thr Gly Asn Pro Leu Leu Trp Ser Asp Leu Ala Asp
                195                 200                 205

Gln Ser Gln Ile Asn Ala Trp Leu Phe Phe Gln Thr Ser Gly His Ala
                210                 215                 220

Pro Met Ile Gly Gln Ala Leu His Phe Arg Tyr Phe His Ser Gln Lys
225                 230                 235                 240

Ile Ala Ser Ala Val Glu Arg Tyr Thr Asp Glu Val Arg Arg Val Tyr
                245                 250                 255

Gly Val Val Glu Met Ala Leu Ala Glu Arg Glu Ala Leu Val Met
                260                 265                 270

Glu Leu Asp Thr Glu Asn Ala Ala Ala Tyr Ser Ala Gly Thr Thr Pro
                275                 280                 285

Met Ser Gln Ser Arg Phe Phe Asp Tyr Pro Val Trp Leu Val Gly Asp
                290                 295                 300

Lys Leu Thr Ile Ala Asp Leu Ala Phe Val Pro Trp Asn Asn Val Val
305                 310                 315                 320

Asp Arg Ile Gly Ile Asn Ile Lys Ile Glu Phe Pro Glu Val Tyr Lys
                325                 330                 335

Trp Thr Lys His Met Met Arg Arg Pro Ala Val Ile Lys Ala Leu Arg
                340                 345                 350

Gly Glu

<210> SEQ ID NO 56
<211> LENGTH: 282
<212> TYPE: DNA
<213> ORGANISM: Saccharomyces cerevisiae

<400> SEQUENCE: 56
atggaccgat ctttgcaagt atatatctgt atgtatccat atttagatgg cagcaagcaa      60
tatagatttg atgagcttat atcatttat cgtccttgtc caaaaagtct tgataacatt     120
aaaagtcact accgtcaaat ccatcatcaa atccgccgtc gaacccacca gcatcatcaa     180
atccgccgtc ggacccacca gcatcatcac cgtagtaatt gttctcgaca acgacagtgt     240

```
ctggtccgtc atagttgtgg tcgtcaaatg cgtgttctag ca                   282
```

<210> SEQ ID NO 57
<211> LENGTH: 94
<212> TYPE: PRT
<213> ORGANISM: Saccharomyces cerevisiae

<400> SEQUENCE: 57

```
Met Asp Arg Ser Leu Gln Val Tyr Ile Cys Met Tyr Pro Tyr Leu Asp
1               5                   10                  15

Gly Ser Lys Gln Tyr Arg Phe Asp Glu Leu Ile Ser Phe Tyr Arg Pro
            20                  25                  30

Cys Pro Lys Ser Leu Asp Asn Ile Lys Ser His Tyr Arg Gln Ile His
        35                  40                  45

His Gln Ile Arg Arg Arg Thr His Gln His Gln Ile Arg Arg Arg
    50                  55                  60

Thr His Gln His His His Arg Ser Asn Cys Ser Arg Gln Arg Gln Cys
65                  70                  75                  80

Leu Val Arg His Ser Cys Gly Arg Gln Met Arg Val Leu Ala
                85                  90
```

<210> SEQ ID NO 58
<211> LENGTH: 499
<212> TYPE: DNA
<213> ORGANISM: Saccharomyces cerevisiae

<400> SEQUENCE: 58

```
gggcgccata accaaggtat ctatagaccg ccaatcagca aactacctcc gtacattcct    60
gttgcaccca cacatttata cacccagacc gcgacaaatt acccataagg ttgtttgtga   120
cggcgtcgta caagagaacg tgggaacttt ttaggctcac caaaaaagaa aggaaaaata   180
cgagttgctg acagaagcct caagaaaaaa aaaattcttc ttcgactatg ctggagccag   240
agatgatcga gccggtagtt aactatatat agctaaattg gttccatcac cttcttttct   300
ggtgtcgctc cttctagtgc tatttctggc ttttcctatt tttttttttc cattttttctt   360 tctctctttc taatatataa attctcttgc attttctatt tttctctcta tctattctac   420
ttgtttattc ccttcaaggt ttttttttaag gactacttgt ttttagaata tacggtcaac   480
gaactataat taactaaac                                                 499
```

<210> SEQ ID NO 59
<211> LENGTH: 449
<212> TYPE: DNA
<213> ORGANISM: Saccharomyces cerevisiae

<400> SEQUENCE: 59

```
ccagaaaggc aacgcaaaat ttttttttcca gggaataaac tttctatgac ccactacttc    60
tcgtaggaac aatttcgggc ccctgcgtgt tcttctgagg ttcatctttt acatttgctt   120
ctgctggata attttcagag gcaacaagga aaaattagat ggcaaaaagt cgtctttcaa   180
ggaaaaatcc ccaccatcct tcgagatccc ctgtaactta ttggcaactg aaagaatgaa   240
aaggaggaaa atacaaaata tactagaact gaaaaaaaaa agtataaata gagacgtat   300 atgccaatac ttcacaatgt tcgaatccat tcttcatttg cagctattgt aaaataataa   360
aacatcaaga acaacaagc tcaacttgtc ttttctaaga acaagaata aacacaaaaa   420 caaaagttt tttaattttt aatcaaaaa                                     449
```

<210> SEQ ID NO 60
<211> LENGTH: 749
<212> TYPE: DNA
<213> ORGANISM: Saccharomyces cerevisiae

<400> SEQUENCE: 60

| | | |
|---|---|---|
| cgatttttt ctaaaccgtg gaatatttcg gatatccttt tgttgtttcc gggtgtacaa | 60 |
| tatggacttc ctcttttctg gcaaccaaac ccatacatcg ggattcctat aataccttcg | 120 |
| ttggtctccc taacatgtag gtggcggagg ggagatatac aatagaacag ataccagaca | 180 |
| agacataatg ggctaaacaa gactacacca attacactgc ctcattgatg gtggtacata | 240 |
| acgaactaat actgtagccc tagacttgat agccatcatc atatcgaagt ttcactaccc | 300 |
| ttttccatt tgccatctat tgaagtaata ataggcgcat gcaacttctt ttctttttt | 360 |
| ttcttttctc tctccccgt tgttgtctca ccatatccgc aatgacaaaa aaatgatgga | 420 |
| agacactaaa ggaaaaaatt aacgacaaag acagcaccaa cagatgtcgt tgttccagag | 480 |
| ctgatgaggg gtatctcgaa gcacgcgaaa cttttttcctt ccttcattca cgcacactac | 540 |
| tctctaatga gcaacggtat acggccttcc ttccagttac ttgaatttga aataaaaaaa | 600 |
| gtttgctgtc ttgctatcaa gtaaaatag acctgcaatt attaatcttt tgtttcctcg | 660 |
| tcattgttct cgttcccttt cttccttgtt tcttttctg cacaatattt caagctatac | 720 |
| caagcataca atcaactatc tcatataca | 749 |

<210> SEQ ID NO 61
<211> LENGTH: 450
<212> TYPE: DNA
<213> ORGANISM: Saccharomyces cerevisiae

<400> SEQUENCE: 61

| | | |
|---|---|---|
| ctacttattc ccttcgagat tatatctagg aacccatcag gttggtggaa gattacccgt | 60 |
| tctaagactt ttcagcttcc tctattgatg ttacacctgg acacccctt tctggcatcc | 120 |
| agtttttaat cttcagtggc atgtgagatt ctccgaaatt aattaaagca atcacacaat | 180 |
| tctctcggat gccacctcgg ttgaaactga caggtggttt gttacgcatg ctaatgcaaa | 240 |
| ggagcctata taccttggc tcggctgctg taacagggaa tataaagggc agcataattt | 300 |
| aggagtttag tgaacttgca acatttacta ttttcccttc ttacgtaaat attttctttt | 360 |
| ttaattctaa atcaatcttt ttcaattttt tgtttgtatt cttttcttgc ttaaatctat | 420 |
| aactacaaaa aacacataca taaactaaag | 450 |

<210> SEQ ID NO 62
<211> LENGTH: 500
<212> TYPE: DNA
<213> ORGANISM: Saccharomyces cerevisiae
<220> FEATURE:
<221> NAME/KEY: misc_feature
<222> LOCATION: (368)..(368)
<223> OTHER INFORMATION: n is a, c, g, or t
<220> FEATURE:
<221> NAME/KEY: misc_feature
<222> LOCATION: (452)..(453)
<223> OTHER INFORMATION: n is a, c, g, or t

<400> SEQUENCE: 62

| | | |
|---|---|---|
| gttaattcaa attaattgat atagttttt aatgagtatt gaatctgttt agaaataatg | 60 |
| gaatattatt tttatttatt tatttatatt attggtcggc tctttctc tgaaggtcaa | 120 |
| tgacaaaatg atatgaagga aataatgatt tctaaaatta tacaacgtaa gatattttta | 180 |

| | |
|---|---|
| caagagccta gctcatcttt tgtcatgcac tattttactc acgcttgaaa ttaacggcca | 240 |
| gttcactgcg gagtcatttc aaagtcatcc taatcgatct atcgttttg atagctcatt | 300 |
| ttggagttcg cgattgtctt ctgttattca caactgtttt aatttttatt tcattctgga | 360 |
| actcttcnag ttctttgtaa agtctttcat agtagcttac tttatcctcc aacatattta | 420 |
| acttcatgtc aatttcggct cttaaatttt cnncatcatc aagttcaaca tcatctttta | 480 |
| acttgaattt attctctagc | 500 |

<210> SEQ ID NO 63
<211> LENGTH: 491
<212> TYPE: DNA
<213> ORGANISM: Saccharomyces cerevisiae

<400> SEQUENCE: 63

| | |
|---|---|
| gcgatttaat ctctaattat tagttaaagt tttataagca ttttttatgta acgaaaaata | 60 |
| aattggttca tattattact gcactgtcac ttaccatgga aagaccagac aagaagttgc | 120 |
| cgacagtctg ttgaattggc ttaagtctgg gtccgctcct ttctaaattt gaagaatttc | 180 |
| tcttaaacga tatgtatatt cttttcgttg gaaagatgt cttccaaaaa aaaaaaaccg | 240 |
| atgaattagt ggaaccaagg aaaaaaaaga ggtatccttg attaaggaac actgtttaaa | 300 |
| cagtgtggtt tccaaaaacc tgaaactgca ttagcgtaat agaagactag acacctcgat | 360 |
| acaataatg gttactcaat tcaaaactgc cagcgaattc gactctgcaa ttgctcaaga | 420 |
| caagctagtt gtcgtagatt tctacgccac ttggtgcggt ccatgtaaaa tgattgctcc | 480 |
| aatgattgaa a | 491 |

<210> SEQ ID NO 64
<211> LENGTH: 504
<212> TYPE: DNA
<213> ORGANISM: Saccharomyces cerevisiae

<400> SEQUENCE: 64

| | |
|---|---|
| tcctgttgaa gtagcattta atcataattt ttgtcacatt ttaatcaact tgattttct | 60 |
| ggtttaattt ttctaatttt aattttaatt tttttatcaa tgggaactga tacactaaaa | 120 |
| agaattagga gccaacaaga ataagccgct tatttcctac tagagtttac ttaaaatttc | 180 |
| atctcgaatt gtcattctaa tatttatcc acacacacac acaccttaaa attttagat | 240 |
| taaatggcat caactcttag cttcacacac acacacacac cgaagctggt tgttttattt | 300 |
| gatttgatat aattggtttc tctggatggt acttttcctt tcttggttat ttcctatttt | 360 |
| aaaatatgaa acgcacacaa gtcataatta ttctaataga gcacaattca caacacgcac | 420 |
| atttcaactt taatatttt ttagaaacac tttatttagt ctaattctta attttaata | 480 |
| tatataatgc acacacacta attt | 504 |

<210> SEQ ID NO 65
<211> LENGTH: 500
<212> TYPE: DNA
<213> ORGANISM: Saccharomyces cerevisiae

<400> SEQUENCE: 65

| | |
|---|---|
| tagcgtgtta cgcacccaaa cttttatga aagtctttgt ttataatgat gaggtttata | 60 |
| aatatatagt ggagcaaaga ttaatcacta aatcaagaag cagtaccagt atttttttta | 120 |
| tatcaagtag tgataatgga aatagcccaa atttggcttc cgtcggcaca tagcacgttt | 180 |
| gagagacatt atcaccatca agcatcgagc cgcccaaacc taactgtata agttttttca | 240 |

```
cgttttgat     ttttccttgc     acacttcgat     attactctca     cgataaaagg     gccgaagaga      300
atatttttct    tgaacatcca     gaattttaat     tcggagaaat     ttcacaagcc     gccgatttaa      360
gggtcctgtg    ttcttaataa     tcagcctctc     tcaaagcagg     taagaggcag     tctttctttt      420
aacaatagga    gacattcgaa     ctaaaacatc     agccccaaaa     atgcgcttga     aggtcattag      480
gatttggatt    tcttcctcat                                                                  500
```

<210> SEQ ID NO 66
<211> LENGTH: 23
<212> TYPE: DNA
<213> ORGANISM: Artificial Sequence
<220> FEATURE:
<223> OTHER INFORMATION: X14961

<400> SEQUENCE: 66

```
gcagttacct    tttagcaccc     aac                                                          23
```

<210> SEQ ID NO 67
<211> LENGTH: 24
<212> TYPE: DNA
<213> ORGANISM: Artificial Sequence
<220> FEATURE:
<223> OTHER INFORMATION: X14966

<400> SEQUENCE: 67

```
ggtgtaggta    agcagaatga     ggag                                                         24
```

<210> SEQ ID NO 68
<211> LENGTH: 59
<212> TYPE: DNA
<213> ORGANISM: Artificial Sequence
<220> FEATURE:
<223> OTHER INFORMATION: X15464

<400> SEQUENCE: 68

```
gtccatgtaa    aatgattgct     ccaatgattg     aaagaggttt     agacattggc     tcttcattg       59
```

<210> SEQ ID NO 69
<211> LENGTH: 59
<212> TYPE: DNA
<213> ORGANISM: Artificial Sequence
<220> FEATURE:
<223> OTHER INFORMATION: X15465

<400> SEQUENCE: 69

```
ctaagctcaa    tgaagagcca     atgtctaaac     ctctttcaat     cattggagca     atcattta        59
```

<210> SEQ ID NO 70
<211> LENGTH: 60
<212> TYPE: DNA
<213> ORGANISM: Artificial Sequence
<220> FEATURE:
<223> OTHER INFORMATION: X18846

<400> SEQUENCE: 70

```
gtccatgtaa    aatgattgct     ccaatgattg     aaaagcacgc     agcacgctgt     atttacgtat      60
```

<210> SEQ ID NO 71
<211> LENGTH: 59
<212> TYPE: DNA
<213> ORGANISM: Artificial Sequence
<220> FEATURE:
<223> OTHER INFORMATION: X18847

<400> SEQUENCE: 71
aattaaatac gtaaatacag cgtgctgcgt gcttttcaat cattggagca atcatttta       59

<210> SEQ ID NO 72
<211> LENGTH: 60
<212> TYPE: DNA
<213> ORGANISM: Artificial Sequence
<220> FEATURE:
<223> OTHER INFORMATION: X18858

<400> SEQUENCE: 72
agccagctta aagagttaaa aatttcatag ctactactta ttcccttcga gattatatct      60

<210> SEQ ID NO 73
<211> LENGTH: 59
<212> TYPE: DNA
<213> ORGANISM: Artificial Sequence
<220> FEATURE:
<223> OTHER INFORMATION: X18859

<400> SEQUENCE: 73
gttcctagat ataatctcga agggaataag tagtagctat gaaattttta actctttaa       59

<210> SEQ ID NO 74
<211> LENGTH: 60
<212> TYPE: DNA
<213> ORGANISM: Artificial Sequence
<220> FEATURE:
<223> OTHER INFORMATION: X18860

<400> SEQUENCE: 74
acatcatctt ttaacttgaa tttattctct agcagcacgc agcacgctgt atttacgtat      60

<210> SEQ ID NO 75
<211> LENGTH: 59
<212> TYPE: DNA
<213> ORGANISM: Artificial Sequence
<220> FEATURE:
<223> OTHER INFORMATION: X18861

<400> SEQUENCE: 75
aattaaatac gtaaatacag cgtgctgcgt gctgctagag aataaattca agttaaaag       59

<210> SEQ ID NO 76
<211> LENGTH: 30
<212> TYPE: DNA
<213> ORGANISM: Artificial Sequence
<220> FEATURE:
<223> OTHER INFORMATION: X18869

<400> SEQUENCE: 76
agatcctgtg gtagtgctgt ctgaacagaa                                       30

<210> SEQ ID NO 77
<211> LENGTH: 59
<212> TYPE: DNA
<213> ORGANISM: Artificial Sequence
<220> FEATURE:
<223> OTHER INFORMATION: X18955

<400> SEQUENCE: 77
ataaaattaa atacgtaaat acagcgtgct gcgtgctcga ttttttttcta aaccgtgga      59

<210> SEQ ID NO 78
<211> LENGTH: 60

<212> TYPE: DNA
<213> ORGANISM: Artificial Sequence
<220> FEATURE:
<223> OTHER INFORMATION: X19513

<400> SEQUENCE: 78
acttggtgcg gtccatgtaa aatgattgct ccaatgattg aaaatgagga agaaatccaa    60

<210> SEQ ID NO 79
<211> LENGTH: 60
<212> TYPE: DNA
<213> ORGANISM: Artificial Sequence
<220> FEATURE:
<223> OTHER INFORMATION: X19514

<400> SEQUENCE: 79
tgaaggtcat taggatttgg atttcttcct cattttcaat cattggagca atcattttac    60

<210> SEQ ID NO 80
<211> LENGTH: 59
<212> TYPE: DNA
<213> ORGANISM: Artificial Sequence
<220> FEATURE:
<223> OTHER INFORMATION: X19551

<400> SEQUENCE: 80
agccagctta aagagttaaa aatttcatag ctagggcgcc ataaccaagg tatctatag    59

<210> SEQ ID NO 81
<211> LENGTH: 60
<212> TYPE: DNA
<213> ORGANISM: Artificial Sequence
<220> FEATURE:
<223> OTHER INFORMATION: X19552

<400> SEQUENCE: 81
tggcggtcta tagatacctt ggttatggcg ccctagctat gaaattttta actctttaag    60

<210> SEQ ID NO 82
<211> LENGTH: 59
<212> TYPE: DNA
<213> ORGANISM: Artificial Sequence
<220> FEATURE:
<223> OTHER INFORMATION: X19721

<400> SEQUENCE: 82
aaagaaatgt cagagccaga atttcaacaa gctaagcttt ctaactgatc tatccaaaa    59

<210> SEQ ID NO 83
<211> LENGTH: 60
<212> TYPE: DNA
<213> ORGANISM: Artificial Sequence
<220> FEATURE:
<223> OTHER INFORMATION: X19722

<400> SEQUENCE: 83
ttttcagttt tggatagatc agttagaaag cttagcttgt tgaaattctg gctctgacat    60

<210> SEQ ID NO 84
<211> LENGTH: 60
<212> TYPE: DNA
<213> ORGANISM: Artificial Sequence
<220> FEATURE:
<223> OTHER INFORMATION: X19726

<400> SEQUENCE: 84

```
atccgaaata ttccacggtt tagaaaaaaa tcggatgcta tgtttgacca aggtgatgta    60
```

<210> SEQ ID NO 85
<211> LENGTH: 60
<212> TYPE: DNA
<213> ORGANISM: Artificial Sequence
<220> FEATURE:
<223> OTHER INFORMATION: X19727

<400> SEQUENCE: 85

```
ttaaaataca tcaccttggt caaacatagc atccgatttt tttctaaacc gtggaatatt    60
```

<210> SEQ ID NO 86
<211> LENGTH: 60
<212> TYPE: DNA
<213> ORGANISM: Artificial Sequence
<220> FEATURE:
<223> OTHER INFORMATION: X19948

<400> SEQUENCE: 86

```
aaagaaatgt cagagccaga atttcaacaa gctgatgcta tgtttgacca aggtgatgta    60
```

<210> SEQ ID NO 87
<211> LENGTH: 60
<212> TYPE: DNA
<213> ORGANISM: Artificial Sequence
<220> FEATURE:
<223> OTHER INFORMATION: X19949

<400> SEQUENCE: 87

```
ttaaaataca tcaccttggt caaacatagc atcagcttgt tgaaattctg gctctgacat    60
```

<210> SEQ ID NO 88
<211> LENGTH: 60
<212> TYPE: DNA
<213> ORGANISM: Artificial Sequence
<220> FEATURE:
<223> OTHER INFORMATION: X19950

<400> SEQUENCE: 88

```
atccgaaata ttccacggtt tagaaaaaaa tcgagcacgc agcacgctgt atttacgtat    60
```

<210> SEQ ID NO 89
<211> LENGTH: 60
<212> TYPE: DNA
<213> ORGANISM: Artificial Sequence
<220> FEATURE:
<223> OTHER INFORMATION: X19967

<400> SEQUENCE: 89

```
tgaaggtcat taggatttgg atttcttcct cataaattag tgtgtgtgca ttatatatat    60
```

<210> SEQ ID NO 90
<211> LENGTH: 60
<212> TYPE: DNA
<213> ORGANISM: Artificial Sequence
<220> FEATURE:
<223> OTHER INFORMATION: X19968

<400> SEQUENCE: 90

```
tttttaatat atataatgca cacacactaa tttatgagga agaaatccaa atcctaatga    60
```

<210> SEQ ID NO 91
<211> LENGTH: 59
<212> TYPE: DNA
<213> ORGANISM: Artificial Sequence -continued

```
<220> FEATURE:
<223> OTHER INFORMATION: X19969

<400> SEQUENCE: 91
aattaaatac gtaaatacag cgtgctgcgt gctccagaaa ggcaacgcaa aatttttt        59

<210> SEQ ID NO 92
<211> LENGTH: 60
<212> TYPE: DNA
<213> ORGANISM: Artificial Sequence
<220> FEATURE:
<223> OTHER INFORMATION: X19970

<400> SEQUENCE: 92
ccctggaaaa aaaattttgc gttgcctttc tggagcacgc agcacgctgt atttacgtat       60

<210> SEQ ID NO 93
<211> LENGTH: 32
<212> TYPE: DNA
<213> ORGANISM: Artificial Sequence
<220> FEATURE:
<223> OTHER INFORMATION: X20022

<400> SEQUENCE: 93
aggtagacgc tacagtcaca ggtgtcacaa ct                                    32

<210> SEQ ID NO 94
<211> LENGTH: 60
<212> TYPE: DNA
<213> ORGANISM: Artificial Sequence
<220> FEATURE:
<223> OTHER INFORMATION: X20023

<400> SEQUENCE: 94
ggacgaggca agctaaacag atctctagac ctattggtgt acaacttaat ttgcagctta      60

<210> SEQ ID NO 95
<211> LENGTH: 60
<212> TYPE: DNA
<213> ORGANISM: Artificial Sequence
<220> FEATURE:
<223> OTHER INFORMATION: X20024

<400> SEQUENCE: 95
ccgtttcttt tctttggact atcatgtagt ctcaggctgc tttaaaaaca agaaagaaag      60

<210> SEQ ID NO 96
<211> LENGTH: 32
<212> TYPE: DNA
<213> ORGANISM: Artificial Sequence
<220> FEATURE:
<223> OTHER INFORMATION: X20025

<400> SEQUENCE: 96
gagtgggatg cgcatatagt gcatgaacct at                                    32

<210> SEQ ID NO 97
<211> LENGTH: 60
<212> TYPE: DNA
<213> ORGANISM: Artificial Sequence
<220> FEATURE:
<223> OTHER INFORMATION: X20026

<400> SEQUENCE: 97
ttgttttaag ctgcaaatta agttgtacac caaaggctgc tttaaaaaca agaaagaaag      60
```

```
<210> SEQ ID NO 98
<211> LENGTH: 60
<212> TYPE: DNA
<213> ORGANISM: Artificial Sequence
<220> FEATURE:
<223> OTHER INFORMATION: X20027

<400> SEQUENCE: 98
cttcttcttt ctttcttgtt tttaaagcag cctttggtgt acaacttaat ttgcagctta      60

<210> SEQ ID NO 99
<211> LENGTH: 60
<212> TYPE: DNA
<213> ORGANISM: Artificial Sequence
<220> FEATURE:
<223> OTHER INFORMATION: X20028

<400> SEQUENCE: 99
ttgttttaag ctgcaaatta agttgtacac caataggtct agagatctgt ttagcttgcc      60

<210> SEQ ID NO 100
<211> LENGTH: 60
<212> TYPE: DNA
<213> ORGANISM: Artificial Sequence
<220> FEATURE:
<223> OTHER INFORMATION: X20029

<400> SEQUENCE: 100
cttcttcttt ctttcttgtt tttaaagcag cctgagacta catgatagtc caaagaaaag      60

<210> SEQ ID NO 101
<211> LENGTH: 59
<212> TYPE: DNA
<213> ORGANISM: Artificial Sequence
<220> FEATURE:
<223> OTHER INFORMATION: X20043

<400> SEQUENCE: 101
ataaaattaa atacgtaaat acagcgtgct gcgtgctatg aggaagaaat ccaaatcct       59

<210> SEQ ID NO 102
<211> LENGTH: 59
<212> TYPE: DNA
<213> ORGANISM: Artificial Sequence
<220> FEATURE:
<223> OTHER INFORMATION: X20044

<400> SEQUENCE: 102
tgaaggtcat taggatttgg atttcttcct catagcacgc agcacgctgt atttacgta       59

<210> SEQ ID NO 103
<211> LENGTH: 60
<212> TYPE: DNA
<213> ORGANISM: Artificial Sequence
<220> FEATURE:
<223> OTHER INFORMATION: X20282

<400> SEQUENCE: 103
agccagctta aagagttaaa aatttcatag ctaccagaaa ggcaacgcaa aattttttt       60

<210> SEQ ID NO 104
<211> LENGTH: 60
<212> TYPE: DNA
<213> ORGANISM: Artificial Sequence
<220> FEATURE:
<223> OTHER INFORMATION: X20283
```

```
<400> SEQUENCE: 104
ccctggaaaa aaaatttttgc gttgcctttc tggtagctat gaaattttta actctttaag     60

<210> SEQ ID NO 105
<211> LENGTH: 60
<212> TYPE: DNA
<213> ORGANISM: Artificial Sequence
<220> FEATURE:
<223> OTHER INFORMATION: X20284

<400> SEQUENCE: 105
tttttaatat atataatgca cacacactaa tttagcacgc agcacgctgt atttacgtat     60

<210> SEQ ID NO 106
<211> LENGTH: 60
<212> TYPE: DNA
<213> ORGANISM: Artificial Sequence
<220> FEATURE:
<223> OTHER INFORMATION: X20285

<400> SEQUENCE: 106
aattaaatac gtaaatacag cgtgctgcgt gctaaattag tgtgtgtgca ttatatatat     60

<210> SEQ ID NO 107
<211> LENGTH: 60
<212> TYPE: DNA
<213> ORGANISM: Artificial Sequence
<220> FEATURE:
<223> OTHER INFORMATION: X20286

<400> SEQUENCE: 107
agccagctta aagagttaaa aatttcatag ctatgtggta gaattcaaaa gactatgtga     60

<210> SEQ ID NO 108
<211> LENGTH: 60
<212> TYPE: DNA
<213> ORGANISM: Artificial Sequence
<220> FEATURE:
<223> OTHER INFORMATION: X20287

<400> SEQUENCE: 108
atggcatcac atagtctttt gaattctacc acatagctat gaaattttta actctttaag     60

<210> SEQ ID NO 109
<211> LENGTH: 60
<212> TYPE: DNA
<213> ORGANISM: Artificial Sequence
<220> FEATURE:
<223> OTHER INFORMATION: X20288

<400> SEQUENCE: 109
ttttaatatt gcttttcaat tactgttatt aaaagcacgc agcacgctgt atttacgtat     60

<210> SEQ ID NO 110
<211> LENGTH: 60
<212> TYPE: DNA
<213> ORGANISM: Artificial Sequence
<220> FEATURE:
<223> OTHER INFORMATION: X20289

<400> SEQUENCE: 110
aattaaatac gtaaatacag cgtgctgcgt gcttttaata acagtaattg aaaagcaata     60

<210> SEQ ID NO 111
```

<211> LENGTH: 32
<212> TYPE: DNA
<213> ORGANISM: Artificial Sequence
<220> FEATURE:
<223> OTHER INFORMATION: X20620

<400> SEQUENCE: 111
ggtgattgga atggttatgg ttccggaatc gc                          32

<210> SEQ ID NO 112
<211> LENGTH: 60
<212> TYPE: DNA
<213> ORGANISM: Artificial Sequence
<220> FEATURE:
<223> OTHER INFORMATION: X20621

<400> SEQUENCE: 112
ggacgaggca agctaaacag atctctagac ctatatacta catagaaagc aattaaaaga  60

<210> SEQ ID NO 113
<211> LENGTH: 60
<212> TYPE: DNA
<213> ORGANISM: Artificial Sequence
<220> FEATURE:
<223> OTHER INFORMATION: X20622

<400> SEQUENCE: 113
ccgtttcttt tctttggact atcatgtagt ctcctccacc taacaaaccc gcaccaacac  60

<210> SEQ ID NO 114
<211> LENGTH: 32
<212> TYPE: DNA
<213> ORGANISM: Artificial Sequence
<220> FEATURE:
<223> OTHER INFORMATION: X20623

<400> SEQUENCE: 114
gtcatatggc ctcttaacgt ggtcctttgt gg                          32

<210> SEQ ID NO 115
<211> LENGTH: 60
<212> TYPE: DNA
<213> ORGANISM: Artificial Sequence
<220> FEATURE:
<223> OTHER INFORMATION: X20630

<400> SEQUENCE: 115
tttttatctt ttaattgctt tctatgtagt ataggtct agagatctgt ttagcttgcc   60

<210> SEQ ID NO 116
<211> LENGTH: 60
<212> TYPE: DNA
<213> ORGANISM: Artificial Sequence
<220> FEATURE:
<223> OTHER INFORMATION: X20631

<400> SEQUENCE: 116
tacttggtgt tggtgcgggt tgttaggtg gaggagacta catgatagtc caaagaaaag   60

<210> SEQ ID NO 117
<211> LENGTH: 60
<212> TYPE: DNA
<213> ORGANISM: Artificial Sequence
<220> FEATURE:
<223> OTHER INFORMATION: X20632

<400> SEQUENCE: 117

```
tttttatctt ttaattgctt tctatgtagt atactccacc taacaaaccc gcaccaacac    60
```

<210> SEQ ID NO 118
<211> LENGTH: 60
<212> TYPE: DNA
<213> ORGANISM: Artificial Sequence
<220> FEATURE:
<223> OTHER INFORMATION: X20633

<400> SEQUENCE: 118

```
tacttggtgt tggtgcgggt ttgttaggtg gagtatacta catagaaagc aattaaaaga    60
```

<210> SEQ ID NO 119
<211> LENGTH: 36
<212> TYPE: DNA
<213> ORGANISM: Artificial Sequence
<220> FEATURE:
<223> OTHER INFORMATION: X21123

<400> SEQUENCE: 119

```
gcgacatgtg atgagattgc atgcacctcc acagaa                              36
```

<210> SEQ ID NO 120
<211> LENGTH: 60
<212> TYPE: DNA
<213> ORGANISM: Artificial Sequence
<220> FEATURE:
<223> OTHER INFORMATION: X21124

<400> SEQUENCE: 120

```
ggacgaggca agctaaacag atctctagac ctatctttat tcttttattt gttgtgaatt    60
```

<210> SEQ ID NO 121
<211> LENGTH: 60
<212> TYPE: DNA
<213> ORGANISM: Artificial Sequence
<220> FEATURE:
<223> OTHER INFORMATION: X21125

<400> SEQUENCE: 121

```
ccgtttcttt tctttggact atcatgtagt ctcgcttcaa taaaattgtt ttgtataaat    60
```

<210> SEQ ID NO 122
<211> LENGTH: 35
<212> TYPE: DNA
<213> ORGANISM: Artificial Sequence
<220> FEATURE:
<223> OTHER INFORMATION: X21126

<400> SEQUENCE: 122

```
ggcagctatc tctactatcc cgtttagtac tatcc                               35
```

<210> SEQ ID NO 123
<211> LENGTH: 60
<212> TYPE: DNA
<213> ORGANISM: Artificial Sequence
<220> FEATURE:
<223> OTHER INFORMATION: X21127

<400> SEQUENCE: 123

```
atattaaatt cacaacaata aaaagaataa agataggtct agagatctgt ttagcttgcc    60
```

<210> SEQ ID NO 124
<211> LENGTH: 60
<212> TYPE: DNA

```
<213> ORGANISM: Artificial Sequence
<220> FEATURE:
<223> OTHER INFORMATION: X21128

<400> SEQUENCE: 124
gaactaattt atacaaaaca attttattga agcgagacta catgatagtc caaagaaaag     60

<210> SEQ ID NO 125
<211> LENGTH: 59
<212> TYPE: DNA
<213> ORGANISM: Artificial Sequence
<220> FEATURE:
<223> OTHER INFORMATION: X21133

<400> SEQUENCE: 125
atattaaatt cacaacaata aaaagaataa agagcttcaa taaaattgtt ttgtataaa      59

<210> SEQ ID NO 126
<211> LENGTH: 34
<212> TYPE: DNA
<213> ORGANISM: Artificial Sequence
<220> FEATURE:
<223> OTHER INFORMATION: X21135

<400> SEQUENCE: 126
gcattgattg tctatcagag catatcaagg tggt                                 34

<210> SEQ ID NO 127
<211> LENGTH: 60
<212> TYPE: DNA
<213> ORGANISM: Artificial Sequence
<220> FEATURE:
<223> OTHER INFORMATION: X21136

<400> SEQUENCE: 127
ggacgaggca agctaaacag atctctagac ctacggtgac tgttgctact tccctatata     60

<210> SEQ ID NO 128
<211> LENGTH: 60
<212> TYPE: DNA
<213> ORGANISM: Artificial Sequence
<220> FEATURE:
<223> OTHER INFORMATION: X21137

<400> SEQUENCE: 128
ccgtttcttt tctttggact atcatgtagt ctcccgtaag cgctattttc tttttgttcg     60

<210> SEQ ID NO 129
<211> LENGTH: 35
<212> TYPE: DNA
<213> ORGANISM: Artificial Sequence
<220> FEATURE:
<223> OTHER INFORMATION: X21138

<400> SEQUENCE: 129
ggctaggacc ccgtaaggag gaaagaatag gcaag                                35

<210> SEQ ID NO 130
<211> LENGTH: 60
<212> TYPE: DNA
<213> ORGANISM: Artificial Sequence
<220> FEATURE:
<223> OTHER INFORMATION: X21139

<400> SEQUENCE: 130
tatatatata tagggaagta gcaacagtca ccgtaggtct agagatctgt ttagcttgcc     60
```

<210> SEQ ID NO 131
<211> LENGTH: 60
<212> TYPE: DNA
<213> ORGANISM: Artificial Sequence
<220> FEATURE:
<223> OTHER INFORMATION: X21140

<400> SEQUENCE: 131
tagttacgaa caaaaagaaa atagcgctta cgggagacta catgatagtc caaagaaaag    60

<210> SEQ ID NO 132
<211> LENGTH: 60
<212> TYPE: DNA
<213> ORGANISM: Artificial Sequence
<220> FEATURE:
<223> OTHER INFORMATION: X21147

<400> SEQUENCE: 132
tatatatata tagggaagta gcaacagtca ccgccgtaag cgctattttc tttttgttcg    60

<210> SEQ ID NO 133
<211> LENGTH: 60
<212> TYPE: DNA
<213> ORGANISM: Artificial Sequence
<220> FEATURE:
<223> OTHER INFORMATION: X21148

<400> SEQUENCE: 133
tagttacgaa caaaaagaaa atagcgctta cggcggtgac tgttgctact tccctatata    60

<210> SEQ ID NO 134
<211> LENGTH: 60
<212> TYPE: DNA
<213> ORGANISM: Artificial Sequence
<220> FEATURE:
<223> OTHER INFORMATION: X21179

<400> SEQUENCE: 134
ttgttttaag ctgcaaatta agttgtacac caagggcgcc ataaccaagg tatctataga    60

<210> SEQ ID NO 135
<211> LENGTH: 60
<212> TYPE: DNA
<213> ORGANISM: Artificial Sequence
<220> FEATURE:
<223> OTHER INFORMATION: X21180

<400> SEQUENCE: 135
tggcggtcta tagatacctt ggttatggcg cccttggtgt acaacttaat ttgcagctta    60

<210> SEQ ID NO 136
<211> LENGTH: 60
<212> TYPE: DNA
<213> ORGANISM: Artificial Sequence
<220> FEATURE:
<223> OTHER INFORMATION: X21181

<400> SEQUENCE: 136
cttcttcttt ctttcttgtt tttaaagcag cctcgatttt tttctaaacc gtggaatatt    60

<210> SEQ ID NO 137
<211> LENGTH: 60
<212> TYPE: DNA
<213> ORGANISM: Artificial Sequence
<220> FEATURE:

<223> OTHER INFORMATION: X21182

<400> SEQUENCE: 137
atccgaaata ttccacggtt tagaaaaaaa tcgaggctgc tttaaaaaca agaaagaaag        60

<210> SEQ ID NO 138
<211> LENGTH: 60
<212> TYPE: DNA
<213> ORGANISM: Artificial Sequence
<220> FEATURE:
<223> OTHER INFORMATION: X21289

<400> SEQUENCE: 138
aaagaaatgt cagagccaga atttcaacaa gctaggtcta gagatctgtt tagcttgcct        60

<210> SEQ ID NO 139
<211> LENGTH: 60
<212> TYPE: DNA
<213> ORGANISM: Artificial Sequence
<220> FEATURE:
<223> OTHER INFORMATION: X21290

<400> SEQUENCE: 139
ttaaaataca tcaccttggt caaacatagc atcgagacta catgatagtc caaagaaaag        60

<210> SEQ ID NO 140
<211> LENGTH: 60
<212> TYPE: DNA
<213> ORGANISM: Artificial Sequence
<220> FEATURE:
<223> OTHER INFORMATION: X21291

<400> SEQUENCE: 140
gggacgaggc aagctaaaca gatctctaga cctagcttgt tgaaattctg gctctgacat        60

<210> SEQ ID NO 141
<211> LENGTH: 59
<212> TYPE: DNA
<213> ORGANISM: Artificial Sequence
<220> FEATURE:
<223> OTHER INFORMATION: X21292

<400> SEQUENCE: 141
ccgtttcttt tctttggact atcatgtagt ctcgatgcta tgtttgacca aggtgatgt         59

<210> SEQ ID NO 142
<211> LENGTH: 60
<212> TYPE: DNA
<213> ORGANISM: Artificial Sequence
<220> FEATURE:
<223> OTHER INFORMATION: X21319

<400> SEQUENCE: 142
ttgttttaag ctgcaaatta agttgtacac caacgatttt tttctaaacc gtggaatatt        60

<210> SEQ ID NO 143
<211> LENGTH: 60
<212> TYPE: DNA
<213> ORGANISM: Artificial Sequence
<220> FEATURE:
<223> OTHER INFORMATION: X21320

<400> SEQUENCE: 143
atccgaaata ttccacggtt tagaaaaaaa tcgttggtgt acaacttaat ttgcagctta        60

```
<210> SEQ ID NO 144
<211> LENGTH: 60
<212> TYPE: DNA
<213> ORGANISM: Artificial Sequence
<220> FEATURE:
<223> OTHER INFORMATION: X21321

<400> SEQUENCE: 144
ttttcagttt tggatagatc agttagaaag cttaggctgc tttaaaaaca agaaagaaag    60

<210> SEQ ID NO 145
<211> LENGTH: 60
<212> TYPE: DNA
<213> ORGANISM: Artificial Sequence
<220> FEATURE:
<223> OTHER INFORMATION: X21322

<400> SEQUENCE: 145
cttcttcttt ctttcttgtt tttaaagcag cctaagcttt ctaactgatc tatccaaaac    60

<210> SEQ ID NO 146
<211> LENGTH: 60
<212> TYPE: DNA
<213> ORGANISM: Artificial Sequence
<220> FEATURE:
<223> OTHER INFORMATION: X21507

<400> SEQUENCE: 146
gaactaattt atacaaaaca attttattga agctctttat tcttttttatt gttgtgaatt    60

<210> SEQ ID NO 147
<211> LENGTH: 60
<212> TYPE: DNA
<213> ORGANISM: Artificial Sequence
<220> FEATURE:
<223> OTHER INFORMATION: X21735

<400> SEQUENCE: 147
agccagctta aagagttaaa aatttcatag ctacgatttt tttctaaacc gtggaatatt    60

<210> SEQ ID NO 148
<211> LENGTH: 60
<212> TYPE: DNA
<213> ORGANISM: Artificial Sequence
<220> FEATURE:
<223> OTHER INFORMATION: X21736

<400> SEQUENCE: 148
atccgaaata ttccacggtt tagaaaaaaa tcgtagctat gaaattttta actctttaag    60

<210> SEQ ID NO 149
<211> LENGTH: 31
<212> TYPE: DNA
<213> ORGANISM: Artificial Sequence
<220> FEATURE:
<223> OTHER INFORMATION: X21754

<400> SEQUENCE: 149
gccaaagtgg attctcctac tcaagctttg c                                    31

<210> SEQ ID NO 150
<211> LENGTH: 60
<212> TYPE: DNA
<213> ORGANISM: Artificial Sequence
<220> FEATURE:
<223> OTHER INFORMATION: X23319
```

```
<400> SEQUENCE: 150
aaagaaatgt cagagccaga atttcaacaa gctcgatttt tttctaaacc gtggaatatt      60

<210> SEQ ID NO 151
<211> LENGTH: 60
<212> TYPE: DNA
<213> ORGANISM: Artificial Sequence
<220> FEATURE:
<223> OTHER INFORMATION: X23320

<400> SEQUENCE: 151
atccgaaata ttccacggtt tagaaaaaaa tcgagcttgt tgaaattctg gctctgacat      60

<210> SEQ ID NO 152
<211> LENGTH: 60
<212> TYPE: DNA
<213> ORGANISM: Artificial Sequence
<220> FEATURE:
<223> OTHER INFORMATION: X23321

<400> SEQUENCE: 152
gtccatgtaa aatgattgct ccaatgattg aaagatgcta tgtttgacca aggtgatgta      60

<210> SEQ ID NO 153
<211> LENGTH: 60
<212> TYPE: DNA
<213> ORGANISM: Artificial Sequence
<220> FEATURE:
<223> OTHER INFORMATION: X23322

<400> SEQUENCE: 153
ttaaaataca tcaccttggt caaacatagc atctttcaat cattggagca atcattttac      60

<210> SEQ ID NO 154
<211> LENGTH: 60
<212> TYPE: DNA
<213> ORGANISM: Artificial Sequence
<220> FEATURE:
<223> OTHER INFORMATION: X23408

<400> SEQUENCE: 154
ttttcagttt tggatagatc agttagaaag ctttagctat gaattttta actctttaag       60

<210> SEQ ID NO 155
<211> LENGTH: 60
<212> TYPE: DNA
<213> ORGANISM: Artificial Sequence
<220> FEATURE:
<223> OTHER INFORMATION: X23409

<400> SEQUENCE: 155
agccagctta aagagttaaa aatttcatag ctaaagcttt ctaactgatc tatccaaaac      60

<210> SEQ ID NO 156
<211> LENGTH: 730
<212> TYPE: PRT
<213> ORGANISM: Saccharomyces cerevisiae

<400> SEQUENCE: 156

Met Gln Asp Asp Pro Glu Asn Ser Lys Leu Tyr Asp Leu Leu Asn Ser
 1               5                  10                  15

His Leu Asp Val His Gly Arg Ser Asn Glu Glu Pro Arg Gln Thr Gly
            20                  25                  30

Asp Ser Arg Ser Gln Ser Ser Gly Asn Thr Gly Glu Asn Glu Glu Asp
```

```
                35                  40                  45
Ile Ala Phe Ala Ser Gly Leu Asn Gly Gly Thr Phe Asp Ser Met Leu
 50                  55                  60
Glu Ala Leu Pro Asp Asp Leu Tyr Phe Thr Asp Phe Val Ser Pro Phe
 65                  70                  75                  80
Thr Ala Ala Ala Thr Thr Ser Val Thr Thr Lys Thr Val Lys Asp Thr
                 85                  90                  95
Thr Pro Ala Thr Asn His Met Asp Asp Asp Ile Ala Met Phe Asp Ser
                100                 105                 110
Leu Ala Thr Thr Gln Pro Ile Asp Ile Ala Ala Ser Asn Gln Gln Asn
                115                 120                 125
Gly Glu Ile Ala Gln Leu Trp Asp Phe Asn Val Asp Gln Phe Asn Met
                130                 135                 140
Thr Pro Ser Asn Ser Ser Gly Ser Ala Thr Ile Ser Ala Pro Asn Ser
145                 150                 155                 160
Phe Thr Ser Asp Ile Pro Gln Tyr Asn His Gly Ser Leu Gly Asn Ser
                165                 170                 175
Val Ser Lys Ser Ser Leu Phe Pro Tyr Asn Ser Ser Thr Ser Asn Ser
                180                 185                 190
Asn Ile Asn Gln Pro Ser Ile Asn Asn Asn Ser Asn Thr Asn Ala Gln
                195                 200                 205
Ser His His Ser Phe Asn Ile Tyr Lys Leu Gln Asn Asn Asn Ser Ser
                210                 215                 220
Ser Ser Ala Met Asn Ile Thr Asn Asn Asn Ser Asn Asn Ser Asn
225                 230                 235                 240
Ile Gln His Pro Phe Leu Lys Lys Ser Asp Ser Ile Gly Leu Ser Ser
                245                 250                 255
Ser Asn Thr Thr Asn Ser Val Arg Lys Asn Ser Leu Ile Lys Pro Met
                260                 265                 270
Ser Ser Thr Ser Leu Ala Asn Phe Lys Arg Ala Ala Ser Val Ser Ser
                275                 280                 285
Ser Ile Ser Asn Met Glu Pro Ser Gly Gln Asn Lys Lys Pro Leu Ile
                290                 295                 300
Gln Cys Phe Asn Cys Lys Thr Phe Lys Thr Pro Leu Trp Arg Arg Ser
305                 310                 315                 320
Pro Glu Gly Asn Thr Leu Cys Asn Ala Cys Gly Leu Phe Gln Lys Leu
                325                 330                 335
His Gly Thr Met Arg Pro Leu Ser Leu Lys Ser Asp Val Ile Lys Lys
                340                 345                 350
Arg Ile Ser Lys Lys Arg Ala Lys Gln Thr Asp Pro Asn Ile Ala Gln
                355                 360                 365
Asn Thr Pro Ser Ala Pro Ala Thr Ala Ser Thr Ser Val Thr Thr Thr
                370                 375                 380
Asn Ala Lys Pro Ile Arg Ser Arg Lys Lys Ser Leu Gln Gln Asn Ser
385                 390                 395                 400
Leu Ser Arg Val Ile Pro Glu Glu Ile Ile Arg Asp Asn Ile Gly Asn
                405                 410                 415
Thr Asn Asn Ile Leu Asn Val Asn Arg Gly Tyr Asn Phe Asn Ser
                420                 425                 430
Val Pro Ser Pro Val Leu Met Asn Ser Gln Ser Tyr Asn Ser Ser Asn
                435                 440                 445
Ala Asn Phe Asn Gly Ala Ser Asn Ala Asn Leu Asn Ser Asn Asn Leu
                450                 455                 460
```

```
Met Arg His Asn Ser Asn Thr Val Thr Pro Asn Phe Arg Arg Ser Ser
465                 470                 475                 480
Arg Arg Ser Ser Thr Ser Ser Asn Thr Ser Ser Ser Lys Ser Ser
                485                 490                 495
Ser Arg Ser Val Val Pro Ile Leu Pro Lys Pro Ser Pro Asn Ser Ala
            500                 505                 510
Asn Ser Gln Gln Phe Asn Met Asn Met Asn Leu Met Asn Thr Thr Asn
                515                 520                 525
Asn Val Ser Ala Gly Asn Ser Val Ala Ser Ser Pro Arg Ile Ile Ser
        530                 535                 540
Ser Ala Asn Phe Asn Ser Asn Ser Pro Leu Gln Gln Asn Leu Leu Ser
545                 550                 555                 560
Asn Ser Phe Gln Arg Gln Gly Met Asn Ile Pro Arg Arg Lys Met Ser
                565                 570                 575
Arg Asn Ala Ser Tyr Ser Ser Ser Phe Met Ala Ala Ser Leu Gln Gln
            580                 585                 590
Leu His Glu Gln Gln Gln Val Asp Val Asn Ser Asn Thr Asn Thr Asn
                595                 600                 605
Ser Asn Arg Gln Asn Trp Asn Ser Ser Asn Ser Val Ser Thr Asn Ser
        610                 615                 620
Arg Ser Ser Asn Phe Val Ser Gln Lys Pro Asn Phe Asp Ile Phe Asn
625                 630                 635                 640
Thr Pro Val Asp Ser Pro Ser Val Ser Arg Pro Ser Ser Arg Lys Ser
                645                 650                 655
His Thr Ser Leu Leu Ser Gln Gln Leu Gln Asn Ser Glu Ser Asn Ser
            660                 665                 670
Phe Ile Ser Asn His Lys Phe Asn Asn Arg Leu Ser Ser Asp Ser Thr
                675                 680                 685
Ser Pro Ile Lys Tyr Glu Ala Asp Val Ser Ala Gly Gly Lys Ile Ser
        690                 695                 700
Glu Asp Asn Ser Thr Lys Gly Ser Ser Lys Glu Ser Ser Ala Ile Ala
705                 710                 715                 720
Asp Glu Leu Asp Trp Leu Lys Phe Gly Ile
                725                 730
```

<210> SEQ ID NO 157
<211> LENGTH: 2193
<212> TYPE: DNA
<213> ORGANISM: Saccharomyces cerevisiae

<400> SEQUENCE: 157

```
atgcaagacg acccccgaaaa ttcgaagctg tacgacctgc tgaatagtca tctggacgtg      60
catggtcgaa gtaatgaaga gccgagacaa actggtgaca gtaggagcca gagtagtggc     120
aacaccggtg aaaacgagga ggatatagca tttgccagtg gattaaacgg cggcacattc     180
gactcaatgc tggaggcact gcccgatgat ttatatttta cggacttcgt gtctcctttt     240
acagcagctg ccacgaccag cgtgactact aagacggtca aggacaccac accagctacc     300
aatcatatgg atgatgatat tgcgatgttt gattcacttg ccacaactca gcccatcgac     360
atagccgcat ccaaccaaca aaatggtgaa attgcacaac tttgggactt taacgtggac     420
caattcaaca tgacgcccag caactcgagc ggttcagcta ctattagtgc tcctaacagc     480
tttacttccg acataccgca atacaaccac ggttccctcg caacagcgt ctccaaatcc     540
tcactgttcc cgtataattc cagcacgtcc aacagcaaca tcaaccagcc atctatcaat     600
```

```
aacaactcaa atactaatgc gcagtcccac cattccttca acatctacaa actacaaaac      660
aacaactcat cttcatccgc tatgaacatt accaataata ataatagcaa caatagtaat      720
atccagcatc cttttctgaa gaagagcgat tcgataggat tatcttcatc caacacaaca      780
aattctgtaa gaaaaaactc acttatcaag ccaatgtcgt ccacgtccct ggccaatttc      840
aaaagagctg cctcagtatc ttccagtata tccaatatgg aaccatcagg acaaaataaa      900
aaacctctga tacaatgttt caattgtaaa actttcaaga caccgctttg gaggagaagc      960
ccagagggga atactctttg caatgcctgc ggtcttttcc agaaattaca tggtaccatg     1020
aggccattat ccttaaaatc ggacgttatc aaaaagagga tttcaaagaa gagagccaaa     1080
caaacggacc caaacattgc acaaaatact ccaagtgcac ctgcaactgc ctcaacttca     1140
gtaaccacta caaatgctaa acccatacga tcgaggaaaa aatcactaca acaaaactct     1200
ttatctagag tgatacctga agaaatcatt agagacaaca tcggtaatac taataatatc     1260
cttaatgtaa atagggagg ctataacttc aactcagtcc cctccccggt cctcatgaac     1320
agccaatcgt ataatagtag taacgcaaat tttaatggag caagcaatgc aaatttgaat     1380
tctaataact taatgcgtca caattcgaac actgttactc ctaattttag aaggtcttca     1440
agacgaagta gtacttcatc gaacacctca agttccagta atcttcatc cagatctgtt     1500 gttccgatat taccaaaacc ttcacctaat agcgctaatt cacagcagtt caacatgaac     1560
atgaacctaa tgaacacaac aaataatgta agtgcaggaa atagtgtcgc atcctcacca     1620
agaattatat cgtccgcaaa ctttaactca aatagtcctc tacagcagaa tctattatca     1680
aattctttcc aacgtcaagg aatgaatata ccaagaagaa agatgtcgcg caatgcatcg     1740
tactcctcat cgtttatggc tgcgtctttg caacaactgc acgaacagca acaagtggac     1800
gtgaattcca acacaaacac gaattcgaat agacagaatt ggaattcaag caatagcgtt     1860
tcaacaaatt caagatcatc aaattttgtc tctcaaaagc caaattttga tattttaat     1920 actcctgtag attcaccgag tgtctcaaga ccttcttcaa gaaaatcaca tacctcattg     1980
ttatcacaac aattgcagaa ctcggagtcg aattcgttta tctcaaatca caaatttaac     2040
aatagattat caagtgactc tacttcacct ataaatatg aagcagatgt gagtgcaggc     2100
ggaaagatca gtgaggataa ttccacaaaa ggatcttcta agaaagttc agcaattgct     2160 gacgaattgg attggttaaa atttggtata tga                                 2193

<210> SEQ ID NO 158
<211> LENGTH: 753
<212> TYPE: DNA
<213> ORGANISM: Saccharomyces cerevisiae

<400> SEQUENCE: 158
atgcctttga ccacaaaacc tttatctttg aaaatcaacg ccgctctatt cgatgttgac       60
ggtaccatca tcatctctca accagccatt gctgctttct ggagagattt cggtaaagac      120
aagccttact tcgatgccga acacgttatt cacatctctc acggttggag aacttacgat      180
gccattgcca gttcgctcc agactttgct gatgaagaat acgttaacaa gctagaaggt      240
gaaatcccag aaaagtacgg tgaacactcc atcgaagttc aggtgctgt caagttgtgt      300 aatgctttga acgccttgcc aaaggaaaaa tgggctgtcg ccacctctgg tacccgtgac      360
atggccaaga atggttcga cattttgaag atcaagagac cagaatactt catcaccgcc      420
aatgatgtca agcaaggtaa gcctcaccca gaaccatact taagggtag aaacggtttg      480
```

```
ggtttcccaa ttaatgaaca agacccatcc aaatctaagg ttgttgtctt tgaagacgca    540
ccagctggta ttgctgctgg taaggctgct ggctgtaaaa tcgttggtat tgctaccact    600
ttcgatttgg acttcttgaa ggaaaagggt tgtgacatca ttgtcaagaa ccacgaatct    660
atcagagtcg gtaatacaa cgctgaaacc gatgaagtcg aattgatctt tgatgactac    720
ttatacgcta aggatgactt gttgaaatgg taa                                753

<210> SEQ ID NO 159
<211> LENGTH: 250
<212> TYPE: PRT
<213> ORGANISM: Saccharomyces cerevisiae

<400> SEQUENCE: 159

Met Pro Leu Thr Thr Lys Pro Leu Ser Leu Lys Ile Asn Ala Ala Leu
1               5                   10                  15

Phe Asp Val Asp Gly Thr Ile Ile Ile Ser Gln Pro Ala Ile Ala Ala
            20                  25                  30

Phe Trp Arg Asp Phe Gly Lys Asp Lys Pro Tyr Phe Asp Ala Glu His
        35                  40                  45

Val Ile His Ile Ser His Gly Trp Arg Thr Tyr Asp Ala Ile Ala Lys
    50                  55                  60

Phe Ala Pro Asp Phe Ala Asp Glu Glu Tyr Val Asn Lys Leu Glu Gly
65                  70                  75                  80

Glu Ile Pro Glu Lys Tyr Gly Glu His Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Lys Lys Trp Phe Asp Ile
        115                 120                 125

Leu Lys Ile Lys Arg Pro Glu Tyr Phe Ile Thr Ala Asn Asp Val Lys
    130                 135                 140

Gln Gly Lys Pro His Pro Glu Pro Tyr Leu Lys Gly Arg Asn Gly Leu
145                 150                 155                 160

Gly Phe Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Val Gly Ile Ala Thr Thr Phe Asp Leu Asp Phe Leu Lys Glu
        195                 200                 205

Lys Gly Cys Asp Ile Ile Val Lys Asn His Glu Ser Ile Arg Val Gly
    210                 215                 220

Glu Tyr Asn Ala Glu Thr Asp Glu Val Glu Leu Ile Phe Asp Asp Tyr
225                 230                 235                 240

Leu Tyr Ala Lys Asp Asp Leu Leu Lys Trp
                245                 250

<210> SEQ ID NO 160
<211> LENGTH: 753
<212> TYPE: DNA
<213> ORGANISM: Saccharomyces cerevisiae

<400> SEQUENCE: 160
atgggattga ctactaaacc tctatctttg aaagttaacg ccgctttgtt cgacgtcgac     60
ggtaccatta tcatctctca accagccatt gctgcattct ggagggattt cggtaaggac    120
aaaccttatt tcgatgctga acacgttatc caagtctcgc atggttggag aacgtttgat    180
```

```
gccattgcta agttcgctcc agactttgcc aatgaagagt atgttaacaa attagaagct      240
gaaattccgg tcaagtacgg tgaaaaatcc attgaagtcc caggtgcagt taagctgtgc      300
aacgctttga acgctctacc aaaagagaaa tgggctgtgg caacttccgg tacccgtgat      360
atggcacaaa aatggttcga gcatctggga atcaggagac caaagtactt cattaccgct      420
aatgatgtca aacagggtaa gcctcatcca gaaccatatc tgaagggcag gaatggctta      480
ggatatccga tcaatgagca agaccettcc aaatctaagg tagtagtatt tgaagacgct      540
ccagcaggta ttgccgccgg aaaagccgcc ggttgtaaga tcattggtat tgccactact      600
ttcgacttgg acttcctaaa ggaaaaaggc tgtgacatca ttgtcaaaaa ccacgaatcc      660
atcagagttg gcggctacaa tgccgaaaca gacgaagttg aattcatttt tgacgactac      720
ttatatgcta aggacgatct gttgaaatgg taa                                    753

<210> SEQ ID NO 161
<211> LENGTH: 250
<212> TYPE: PRT
<213> ORGANISM: Saccharomyces cerevisiae

<400> SEQUENCE: 161

Met Gly Leu Thr Thr Lys Pro Leu Ser Leu Lys Val Asn Ala Ala Leu
1               5                   10                  15

Phe Asp Val Asp Gly Thr Ile Ile Ile Ser Gln Pro Ala Ile Ala Ala
                20                  25                  30

Phe Trp Arg Asp Phe Gly Lys Asp Lys Pro Tyr Phe Asp Ala Glu His
            35                  40                  45

Val Ile Gln Val Ser His Gly Trp Arg Thr Phe Asp Ala Ile Ala Lys
        50                  55                  60

Phe Ala Pro Asp Phe Ala Asn Glu Glu Tyr Val Asn Lys Leu Glu Ala
65                  70                  75                  80

Glu Ile Pro Val Lys Tyr Gly Glu Lys Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Gln Lys Trp Phe Glu His
        115                 120                 125

Leu Gly Ile Arg Arg Pro Lys Tyr Phe Ile Thr Ala Asn Asp Val Lys
    130                 135                 140

Gln Gly Lys Pro His Pro Glu Pro Tyr Leu Lys Gly Arg Asn Gly Leu
145                 150                 155                 160

Gly Tyr Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Ile Gly Ile Ala Thr Thr Phe Asp Leu Asp Phe Leu Lys Glu
        195                 200                 205

Lys Gly Cys Asp Ile Ile Val Lys Asn His Glu Ser Ile Arg Val Gly
    210                 215                 220

Gly Tyr Asn Ala Glu Thr Asp Glu Val Glu Phe Ile Phe Asp Asp Tyr
225                 230                 235                 240

Leu Tyr Ala Lys Asp Asp Leu Leu Lys Trp
                245                 250

<210> SEQ ID NO 162
```

<211> LENGTH: 1548
<212> TYPE: DNA
<213> ORGANISM: Saccharomycopsis fibuligera

<400> SEQUENCE: 162

```
atgatcagat tgaccgtttt cttgaccgct gttttgctg ctgttgcttc ttgtgttcca      60
gttgaattgg ataagagaaa caccggtcat ttccaagctt attctggtta taccgttgct     120
agatctaact tcacccaatg gattcatgaa caaccagctg tttcttggta ctacttgttg     180
caaaacatcg attcccaga aggtcaattc aaatctgcta accaggtgt tgttgttgct       240
tctccatcta catctgaacc agattacttc taccaatgga ctagagatac cgctattacc     300
ttcttgtcct tgattgctga agttgaagat cattcttct ccaacactac cttggctaag      360
gttgtcgaat attacatttc caacacctac accttgcaaa gagtttctaa tccatccggt     420
aacttcgatt ctccaaatca tgatggtttg ggtgaaccta agttcaacgt tgatgatact     480
gcttatacag cttcttgggg tagaccacaa aatgatggtc cagctttgag agcttacgct     540
atttctagat acttgaacgc tgttgctaag cacaacaacg taaattatt attggccggt      600
caaaacggta ttccttattc ttctgcttcc gatatctact ggaagattat taagccagac    660
ttgcaacatg tttctactca ttggtctacc tctggttttg atttgtggga agaaaatcaa    720
ggtactcatt tcttcaccgc tttggttcaa ttgaaggctt tgtcttacgg tattccattg    780
tctaagacct acaatgatcc aggtttcact tcttggttgg aaaaacaaaa ggatgccttg    840
aactcctaca ttaactcttc cggtttcgtt aactctggta aaagcacat cgttgaatct     900
ccacaattgt catctagagg tggtttggat tctgctactt atattgctgc cttgatcacc    960
catgatatcg gtgatgatga tacttacacc ccattcaatg ttgataactc ctacgttttg   1020
aactccttgt attacctatt ggtcgacaac aagaacagat acaagatcaa cggtaactac   1080
aaagctggtg ctgctgttgg tagatatcct gaagatgttt acaacggtgt tggtacttct   1140
gaaggtaatc catggcaatt ggctactgct tatgctggtc aaacttttta caccttggcc   1200
tacaattcct tgaagaacaa gaagaacttg gtcatcgaaa agttgaacta cgacttgtac   1260
aactccttca ttgctgattt gtccaagatt gattcttcct acgcttctaa ggattctttg   1320
actttgacct acggttccga taactacaag aacgttatca agtccttgtt gcaattcggt   1380
gactcattct tgaaggtttt gttggatcac atcgatgaca acggtcaatt gactgaagaa   1440
atcaacagat acaccggttt tcaagctggt gcagtttctt tgacttggtc atctggttct   1500
ttgttgtctg ctaatagagc cagaaacaag ttgatcgaat tattgtaa                1548
```

<210> SEQ ID NO 163
<211> LENGTH: 515
<212> TYPE: PRT
<213> ORGANISM: Saccharomycopsis fibuligera

<400> SEQUENCE: 163

```
Met Ile Arg Leu Thr Val Phe Leu Thr Ala Val Phe Ala Ala Val Ala
1               5                   10                  15

Ser Cys Val Pro Val Glu Leu Asp Lys Arg Asn Thr Gly His Phe Gln
            20                  25                  30

Ala Tyr Ser Gly Tyr Thr Val Arg Ser Asn Phe Thr Gln Trp Ile
        35                  40                  45

His Glu Gln Pro Ala Val Ser Trp Tyr Leu Leu Gln Asn Ile Asp
    50                  55                  60

Tyr Pro Glu Gly Gln Phe Lys Ser Ala Lys Pro Gly Val Val Val Ala
```

```
            65                  70                  75                  80
        Ser Pro Ser Thr Ser Glu Pro Asp Tyr Phe Tyr Gln Trp Thr Arg Asp
                        85                  90                  95
        Thr Ala Ile Thr Phe Leu Ser Leu Ile Ala Glu Val Glu Asp His Ser
                        100                 105                 110
        Phe Ser Asn Thr Thr Leu Ala Lys Val Val Glu Tyr Tyr Ile Ser Asn
                        115                 120                 125
        Thr Tyr Thr Leu Gln Arg Val Ser Asn Pro Ser Gly Asn Phe Asp Ser
                    130                 135                 140
        Pro Asn His Asp Gly Leu Gly Glu Pro Lys Phe Asn Val Asp Asp Thr
        145                 150                 155                 160
        Ala Tyr Thr Ala Ser Trp Gly Arg Pro Gln Asn Asp Gly Pro Ala Leu
                        165                 170                 175
        Arg Ala Tyr Ala Ile Ser Arg Tyr Leu Asn Ala Val Ala Lys His Asn
                        180                 185                 190
        Asn Gly Lys Leu Leu Leu Ala Gly Gln Asn Gly Ile Pro Tyr Ser Ser
                        195                 200                 205
        Ala Ser Asp Ile Tyr Trp Lys Ile Lys Pro Asp Leu Gln His Val
                    210                 215                 220
        Ser Thr His Trp Ser Thr Ser Gly Phe Asp Leu Trp Glu Glu Asn Gln
        225                 230                 235                 240
        Gly Thr His Phe Phe Thr Ala Leu Val Gln Leu Lys Ala Leu Ser Tyr
                        245                 250                 255
        Gly Ile Pro Leu Ser Lys Thr Tyr Asn Asp Pro Gly Phe Thr Ser Trp
                        260                 265                 270
        Leu Glu Lys Gln Lys Asp Ala Leu Asn Ser Tyr Ile Asn Ser Ser Gly
                    275                 280                 285
        Phe Val Asn Ser Gly Lys Lys His Ile Val Glu Ser Pro Gln Leu Ser
                    290                 295                 300
        Ser Arg Gly Gly Leu Asp Ser Ala Thr Tyr Ile Ala Ala Leu Ile Thr
        305                 310                 315                 320
        His Asp Ile Gly Asp Asp Asp Thr Tyr Thr Pro Phe Asn Val Asp Asn
                        325                 330                 335
        Ser Tyr Val Leu Asn Ser Leu Tyr Tyr Leu Val Asp Asn Lys Asn
                        340                 345                 350
        Arg Tyr Lys Ile Asn Gly Asn Tyr Lys Ala Gly Ala Ala Val Gly Arg
                    355                 360                 365
        Tyr Pro Glu Asp Val Tyr Asn Gly Val Gly Thr Ser Glu Gly Asn Pro
                    370                 375                 380
        Trp Gln Leu Ala Thr Ala Tyr Ala Gly Gln Thr Phe Tyr Thr Leu Ala
        385                 390                 395                 400
        Tyr Asn Ser Leu Lys Asn Lys Lys Asn Leu Val Ile Glu Lys Leu Asn
                        405                 410                 415
        Tyr Asp Leu Tyr Asn Ser Phe Ile Ala Asp Leu Ser Lys Ile Asp Ser
                    420                 425                 430
        Ser Tyr Ala Ser Lys Asp Ser Leu Thr Leu Thr Tyr Gly Ser Asp Asn
                    435                 440                 445
        Tyr Lys Asn Val Ile Lys Ser Leu Leu Gln Phe Gly Asp Ser Phe Leu
                    450                 455                 460
        Lys Val Leu Leu Asp His Ile Asp Asp Asn Gly Gln Leu Thr Glu Glu
        465                 470                 475                 480
        Ile Asn Arg Tyr Thr Gly Phe Gln Ala Gly Ala Val Ser Leu Thr Trp
                        485                 490                 495
```

-continued

```
Ser Ser Gly Ser Leu Leu Ser Ala Asn Arg Ala Arg Asn Lys Leu Ile
        500                 505                 510

Glu Leu Leu
    515
```

METHODS FOR REGULATING NITROGEN METABOLISM DURING THE PRODUCTION OF ETHANOL FROM CORN BY METABOLICALLY ENGINEERED YEAST STRAINS

CROSS REFERENCE TO RELATED APPLICATIONS

The present application is a '371 U.S. national phase application of PCT/US2014/025460, filed Mar. 13, 2014, entitled "METHODS FOR REGULATING NITROGEN METABOLISM DURING THE PRODUCTION OF ETHANOL FROM CORN BY METABOLICALLY ENGINEERED YEAST STRAINS," which claims priority to U.S. Provisional Application No. 61/800,323, filed Mar. 15, 2013, each application of which is hereby incorporated by reference in its entirety.

REFERENCE TO SEQUENCE LISTING SUBMITTED ELECTRONICALLY VIA EFS-WEB

The content of the electronically submitted sequence listing (Name: 115235-202SeqList.txt; Size: 276,936 bytes; Date of Creation: Aug. 31, 2015) is in accordance with 37 C.F.R. § 1.821-1.825, and is incorporated by reference in its entirety.

BACKGROUND OF THE INVENTION

Energy conversion, utilization and access underlie many of the great challenges of our time, including those associated with sustainability, environmental quality, security, and poverty. New applications of emerging technologies are required to respond to these challenges. Biotechnology, one of the most powerful of the emerging technologies, can give rise to important new energy conversion processes. Plant biomass and derivatives thereof are a resource for the biological conversion of energy to forms useful to humanity.

Among forms of plant biomass, both grain-based biomass and lignocellulosic biomass (collectively "biomass") are well-suited for energy applications. Each feedstock has advantages and disadvantages. For example, because of its large-scale availability, low cost, and environmentally benign production lignocellulosic biomass has gained attention as a viable feed source for biofuel production. In particular, many energy production and utilization cycles based on cellulosic biomass have near-zero greenhouse gas emissions on a life-cycle basis.

However, grain-based feed stocks are more readily converted to fuels by existing microorganisms, although grain-based feed stock is more expensive than lignocellulosic feed stock and conversion to fuel competes with alternative uses for the grain.

Biomass processing schemes involving enzymatic or microbial hydrolysis commonly involve four biologically mediated transformations: (1) the production of saccharolytic enzymes (cellulases and hemicellulases); (2) the hydrolysis of carbohydrate components present in pretreated biomass to sugars; (3) the fermentation of hexose sugars (e.g., glucose, mannose, and galactose); and (4) the fermentation of pentose sugars (e.g., xylose and arabinose). These four transformations can occur in a single step in a process configuration called consolidated bioprocessing ("CBP"), which is distinguished from other less highly integrated configurations in that it does not involve a dedicated process step for cellulase and/or hemicellulase production.

CBP offers the potential for lower cost and higher efficiency than processes featuring dedicated cellulase production. The benefits result in part from avoided capital costs, substrate and other raw materials, and utilities associated with cellulase production. In addition, several factors support the realization of higher rates of hydrolysis, and hence reduced reactor volume and capital investment using CBP, including enzyme-microbe synergy and the use of thermophilic organisms and/or complexed cellulase systems. Moreover, cellulose-adherent cellulolytic microorganisms are likely to compete successfully for products of cellulose hydrolysis with non-adhered microbes, e.g., contaminants. Successful competition of desirable microbes increases the stability of industrial processes based on microbial cellulose utilization. Progress in developing CBP-enabling microorganisms is being made through two strategies: engineering naturally occurring cellulolytic microorganisms to improve product-related properties, such as yield and titer; and engineering non-cellulolytic organisms that exhibit high product yields and titers to express a heterologous cellulase and hemicellulase system enabling cellulose and hemicellulose utilization.

One way to meet the demand for ethanol production is to convert sugars found in biomass, i.e., materials such as agricultural wastes, corn hulls, corncobs, cellulosic materials, and the like to produce ethanol. Efficient biomass conversion in large-scale industrial applications requires a microorganism that is able to tolerate high concentrations of sugar and ethanol, and which is able to ferment more than one sugar simultaneously.

Bakers' yeast (*Saccharomyces cerevisiae*) is the preferred microorganism for the production of ethanol (Hahn-Hagerdat, B., et al., Adv. Biochem. Hiotechnol.73, 53- 84 (2001)). Attributes in favor of this microbe are (i) high productivity at close to theoretical yields (0.51 g ethanol produced/g glucose used), (ii) high osmo- and ethanol tolerance, (in) natural robustness in industrial processes, also (iv) being generally regarded as safe (GRAS) due to its long association with wine and bread making, and beer brewing. Furthermore, S. cerevisiae exhibits tolerance to inhibitors commonly found in hydrolysates resulting from biomass pretreatment. Exemplary metabolic pathways for the production of ethanol are depicted in FIG. 1. However, S. cerevisiae does not naturally break, down components of cellulose, nor does it efficiently use pentose sugars, Glycerol is a metabolic end-product of native yeast ethanolic fermentation (FIG. 1). During anaerobic growth on carbohydrates, production of ethanol and carbon dioxide is redox neutral, while the reactions that create cell biomass and associated carbon dioxide are more oxidized relative to carbohydrates. The production of glycerol, which is more reduced relative to carbohydrates, functions as an electron sink to off-set cell biomass formation, so that overall redox neutrality is conserved. This is essential from a theoretical consideration of conservation of mass, and in practice strains unable to produce glycerol are unable (or only very poorly able) to grow under anaerobic conditions.

There is a strong commercial incentive not to produce glycerol as a byproduct because it represents lost ethanol yield. In industrial corn ethanol fermentations, this yield loss can be up to 6% of theoretical, for a market of ~14 billion gallons/yr. At selling price of $2.50/gal, this is a total market value of $2 B/yr.

Strategies from the literature to address this problem include decreasing glycerol formation by engineering ammonia fixation to function with NADH instead of NADPH via up-regulation of GLN1, encoding glutamine synthetase, or GLT1, encoding glutamate synthase with deletion of GDH1, encoding the NADPH-dependent glutamate dehydrogenase. (Nissen, T. L., et al., *Metabolic Engineering* 2: 69-77 (2000)). Another strategy engineering cells to produce excess NADPH during glycolysis via expression of a NADPH linked glyceraldehyde-3-phosphate dehydrogenase. (Bro, C., et al., *Metabolic Engineering* 8: 102-111 (2006)). Another strategy contained a deletion of GDH1, and over-expression of glutamate synthase (GLT1) and glutamine synthase (GLN1), which also resulted in reduced glycerol formation. However, growth rates and biomass formation were well below the control strain and improvements on the initial performance have not been demonstrated. Additionally, industrially relevant yields, titers and fermentation rates were never demonstrated. (U.S. Pat. No. 7,018,829). Another strategy describes deletion of only GDH1 without overexpression of GDH2 or GLT1/GLN1. However, the strategy was dependent on the use of an industrial polyploid yeast strain capable of tolerating high ethanol concentrations. It is noted in the patent that GDH1 was the only deletion, and that there are no heterologous DNA sequences in the genome. Additionally, the maximum reduction in glycerol production seen was 12.04%, and the technology was not demonstrated on an industrially relevant substrate (U.S. Pat. No. 7,935,514). Most glycerol reduction strategies either only partially reduce the requirement for glycerol formation, or create a by-product other than ethanol. The present invention overcomes the shortcomings of these other strategies.

Corn mash contains free amino nitrogen. However the amount is too low to enable yeast biomass formation sufficient to meet the needs of the process. Nitrogen is added to industrial corn ethanol fermentations to promote yeast growth, most commonly in the form of urea and ammonia. Excess nitrogen can improve the fermentation kinetics of conventional yeasts; however ethanol yields are often lower due to excess biomass and glycerol formation. Typically, urea is added to industrial corn fermentations in concentrations that range from 500 ppm to 1000 ppm.

Yeast take up and assimilate ammonium as its preferred nitrogen source, followed by amino acids, and finally urea (FIGS. 2-4) (extensively reviewed by Lungdhal et al., (*Genetics* 190: 885-929 (2012)). The mechanism of nitrogen catabolite repression (NCR) control is established by transcription factors which control the expression of ammonium, amino acid and urea transporters. These transcription factors also control expression of proteins responsible for degradation and assimilation of nitrogen containing molecules. It has been shown that de-repression of non-preferred nitrogen source assimilation pathways can improve fermentation kinetics (Salmon, J. M., and Barre, P., *Appl. Environ. Microbiol.* 64:3831-3837 (1998)); however, effects on ethanol productivity were not measured.

*S. cerevisiae* contains three known ammonium transporters, MEP1, MEP2 and MEP3. MEP1 and MEP2 are high affinity transporters while MEP3 is a low affinity transporter. *S. cerevisiae* breaks down urea through the enzymatic action of a urea-amido lyase (EC 6.3.4.6). This activity is encoded by the enzyme DUR1/2 in *S. cerevisiae* (FIGS. 2-4). Over-expression of DUR1/2 in wine yeasts has been shown to enhance urea degradation rates during fermentation of grape must (Coulon, J., et al., *Am. J. Enol. Vitic.* 57:2 (2006)). There are two known urea transporters in *S. cerevisiae*, DUR3 and DUR4 (FIGS. 2-4). It has been shown that overexpression of DUR3 resulted in improved urea degradation rates during wine fermentation (Dahabieh, M. S., el al., *Am. J. Enol. Vitic.* 60:4 (2009)). U.S. Patent Publ. No. 2011/0129566 describes the expression of DUR1/2 and DUR3 in wine yeasts.

Industrial corn mash substrates contain as much as 3% protein (w/v); however, much of the amino acid content contained in these proteins is unavailable to *S. cerevisiae*. Expression of one or more proteases would release amino acids that could serve as a nitrogen source for yeast. Additionally, the use of amino acids as a nitrogen source for *S. cerevisiae* in corn ethanol fermentations would improve yield through a reduction in the surplus NADH generated from in vivo amino acid synthesis during anaerobic growth.

Guo et al. engineered *S. cerevisiae* to express a heterologous protease for the purpose of improving ethanol yield (Guo, Z-p, et al., *Enzyme and Microbial Technology* 48: 148-154 (2011)). However, the work was conducted in a wild type yeast background that had not been previously engineered for reduced glycerol formation, and the activity of the expressed endoprotease primarily breaks protein into short polypeptides which are not transported by *S. cerevisiae*.

One aspect of the present invention relates to improved fermentation performance through co-expression of an exo-protease to release single amino acids. Additionally, corn kernel protein is primarily a class of storage proteins known as zeins. Zeins have been shown to be recalcitrant to hydrolysis by many proteases and it is possible that expression of zein specific proteases would result in improved proteolysis. Thus, another aspect of the present invention relates to expressing zein-specific proteases to improve corn protein hydrolysis and amino acid utilization by the yeast.

Amino acids are transported by a large family of amino acid permeases. One aspect of this invention relates to deregulation or over-expression of a specific or general amino acid permease to complement protease expression or metabolic engineering by improving the uptake rate of free amino acids released during proteolysis. For example, expression of the general amino acid permease GAP1 is negatively regulated by AUA1. One aspect of this invention relates to the deletion of AUA1 or over expression of GAP1 that could result in improved amino acid uptake rates.

PCT/US2012/032443, which is incorporated herein by reference, teaches a method of eliminating glycerol formation through the production of formate. The formate production pathway can also be combined with strains engineered for reduced activity of the native glycerol production pathway. These combinations can be designed such that strains are built with different degrees of glycerol reduction as shown in FIG. 5. Several embodiments of the current invention relate to a combination of those or related genetic modifications described in PCT/US2012/032443, with additional genetic modifications that are designed to alter nitrogen transport and assimilation.

One aspect of this invention relates to strains of *S. cerevisiae* with reduced glycerol production that get a kinetic benefit from higher nitrogen concentration without sacrificing ethanol yield. A second aspect of the invention relates to metabolic modifications resulting in altered transport and/or intracellular metabolism of nitrogen sources present in corn mash.

BRIEF SUMMARY OF THE INVENTION

Some embodiments are direct to a recombinant microorganism comprising: at least one engineered genetic modification that leads to the up-regulation or down-regulation of one or more native and/or heterologous enzymes that function in one or more ethanol production pathways; at least one engineered genetic modification that leads to the down-regulation of an enzyme in a glycerol-production pathway; and at least one engineered genetic modification that leads to the up-regulation or down-regulation of an enzyme in a nitrogen-assimilation pathway.

In some embodiments of the invention, the down-regulated enzyme in the nitrogen-assimilation pathway is glutamate dehydrogenase (Gdh) (EC 1.4.1.4).

In some embodiments of the invention, the microorganism further comprises least one genetic modification that leads to the up-regulation of an enzyme in a nitrogen-assimilation pathway.

In some embodiments of the invention, the up-regulated enzyme in the nitrogen-assimilation pathway is at least one enzyme selected from the group consisting of glutamate dehydrogenase (Gdh) (EC 1.4.1.2), glutamate synthase (Glt) (EC 1.4.1.14), and glutamine synthase (Gln) (EC 6.3.1.2). In some embodiments of the invention, the up-regulated enzyme in the nitrogen-assimilation pathway is a native ammonium transporter. In some embodiments of the invention, the up-regulated enzyme in the nitrogen-assimilation pathway is a MEP protein from the genus *Saccharomyces*. In some embodiments of the invention, the up-regulated enzyme in the nitrogen assimilation pathway is a urea-amido lyase (EC 6.3.4.6). In some embodiments of the invention, the up-regulated enzyme in the nitrogen assimilation pathway is a urea transporter. In some embodiments of the invention, the up-regulated enzyme in the nitrogen assimilation pathway is Gln3.

In some embodiments of the invention, the enzyme in the glycerol-production pathway is encoded by at least one enzyme selected from the group consisting of: a glycerol-3-phosphate dehydrogenase 1 polynucleotide (GPD1) (EC 1.1.1.8), a glycerol-3-phosphate dehydrogenase 1 polypeptide (Gpd1) (EC 1.1.1.8), a glycerol-3-phosphate dehydrogenase 2 polynucleotide (GPD2) (EC 1.1.1.8), a glycerol-3-phosphate dehydrogenase 2 polypeptide (Gpd2) (EC 1.1.1.8), a glycerol-3-phosphate phosphatase 1 polynucleotide (GPP1) (EC 3.1.3.21), a glycerol-3-phosphate phosphatase polypeptide 1 (Gpp1) (EC 3.1.3.21), a glycerol-3-phosphate phosphatase 2 polynucleotide (GPP2) (EC 3.1.3.21), and a glycerol-3-phosphate phosphatase polypeptide 2 (Gpp2) (EC 3.1.3.21).

In some embodiments of the invention, up-regulated enzyme that acts in an ethanol production pathway is pyruvate formate lyase (EC 2.3.1.54). In some embodiments of the invention, the up-regulated enzyme that acts in the ethanol production pathway is pyruvate formate lyase activating enzyme (EC 1.91.1.4).

In some embodiments of the invention, the up-regulated enzyme that acts in the ethanol production pathway is bifunctional acetaldehyde-alcohol dehydrogenase selected from a group of enzymes having both of the following Enzyme Commission Numbers: EC 1.2.1.10 and 1.1.1.1.

In some embodiments of the invention, the up-regulated enzyme that acts in the ethanol production pathway is an NADPH-dependent bifunctional acetaldehyde-alcohol dehydrogenase selected from a group of enzymes having both of the following Enzyme Commission Numbers: EC 1.2.1.10 and 1.1.1.2.

In some embodiments, the microorganism further comprises a down-regulation in one or more native enzymes encoded by a formate dehydrogenase enzyme selected from the group consisting of: EC 1.2.1.43 and EC 1.2.1.2.

In some embodiments of the invention, the recombinant microorganism further comprises a heterologous GPD1 polynucleotide operably linked to a native GPD2 promoter. In some embodiments of the invention, the recombinant microorganism further comprises a heterologous GPD2 polynucleotide operably linked to a native GPD1 promoter.

In some embodiments of the invention, the microorganism further comprises an up-regulation or down-regulation of a regulatory element. In some embodiments the regulatory element is selected from the group consisting of: Ure2 and Aua1.

In some embodiments of the invention, the microorganism further comprises at least one additional up-regulated enzyme. In some embodiments of the invention, the additional up-regulated enzyme is a glucoamylase enzyme with EC number 3.2.1.3. In some embodiments of the invention, the additional up-regulated enzyme is a permease. In some embodiments of the invention, the additional up-regulated enzyme is a protease with EC number: 3.4.23.41.

In some embodiments of the invention, the up-regulated or down-regulated enzymes are under the control of a heterologous promoter. In some embodiments of the invention, the heterologous promoter is selected from a group consisting of: TEF2 (SEQ ID NO: 58), HXT7 (SEQ ID NO: 59), ADH1 (SEQ ID NO: 60), and TPI (SEQ ID NO: 61).

In some embodiments, the microorganism is a yeast. In some embodiments, the yeast is from the genus *Saccharomyces*. In some embodiments, the yeast is *Saccharomyces cerevisiae*. In some embodiments, the microorganism produces ethanol at a higher yield than an otherwise identical microorganism lacking the genetic modifications. In some embodiments, the microorganism produces an ethanol titer about 1% to about 10% more than an otherwise identical microorganism lacking the genetic modifications. In some embodiments, the microorganism produces an ethanol titer of at least about 125 g/L.

In some embodiments, the microorganism produces glycerol at a lower yield than an otherwise identical microorganism lacking the genetic modifications. In some embodiments, the microorganism produces a glycerol titer of about 10 to about 100% less than an otherwise identical microorganism lacking the genetic modifications.

In some embodiments, the invention relates to a composition comprising any recombinant microorganism herein, and a carbon-containing feedstock.

Some embodiments of the invention are directed to a method of producing a fermentation product using any composition herein, wherein the recombinant microorganism is capable of fermenting the carbon containing feedstock to yield the fermentation product.

Some embodiments of the invention are directed to a method of producing a fermentation product comprising: any composition provided herein; contacting the composition with a carbon containing feedstock, wherein the recombinant microorganism is capable of fermenting the carbon containing feedstock to yield the fermentation product; and, optionally recovering the fermentation production Some embodiments of the invention are directed to a method of producing ethanol comprising: providing any recombinant microorganism herein; culturing the recombinant microorganism in the presence of a carbon containing feedstock for sufficient time to produce ethanol; and, optionally, extracting the ethanol.

Some embodiments of the invention are directed to a co-culture comprising at least two host cells, wherein one of the host cells comprises any recombinant microorganism herein; and another host cell that is genetically distinct from the recombinant microorganism.

Some embodiments of the invention are directed to a recombinant microorganism comprising: down-regulated Gpd1, down-regulated Gpd2, down-regulated Fdh1, down-regulated Fdh2, down-regulated Gdh1, up-regulated AdhE, up-regulated pyruvate formate lyase, an up-regulated pyruvate formate lyase-activating enzyme, GPD1 under the control of the GPD2 promoter, GPD2 under the control of the GPD1 promoter, and up-regulated Gdh2.

Some embodiments of the invention are directed to a recombinant microorganism comprising: down-regulated Gpd1, down-regulated Gpd2, down-regulated Fdh1, down-regulated Fdh2, down-regulated Gdh1, up-regulated AdhE, up-regulated pyruvate formate lyase, an up-regulated pyruvate formate lyase-activating enzyme, GPD1 under the control of the GPD2 promoter, GPD2 under the control of the GPD1 promoter, up-regulated Glt1 and up-regulated Gln1.

Some embodiments of the invention are directed to a recombinant microorganism comprising: down-regulated Gpd1, down-regulated Fdh1, down-regulated Fdh2, down-regulated Gdh1, up-regulated AdhE, up-regulated pyruvate formate lyase, an up-regulated pyruvate formate lyase-activating enzyme, GPD1 under the control of the GPD2 promoter, GPD2 under the control of the GPD1 promoter, up-regulated Glt1 and up-regulated Gln1.

Some embodiments of the invention are directed to a recombinant microorganism comprising: down-regulated Gpd2, down-regulated Fdh1, down-regulated Fdh2, down-regulated Gdh1, up-regulated AdhE, up-regulated pyruvate formate lyase, and an up-regulated pyruvate formate lyase-activating enzyme.

Some embodiments of the invention are directed to a recombinant microorganism comprising: down-regulated Gpd1, down-regulated Fdh1, down-regulated Fdh2, down-regulated Gdh1, up-regulated AdhE, up-regulated pyruvate formate lyase, an up-regulated pyruvate formate lyase-activating enzyme, and GPD2 under the control of the GPD1 promoter.

Some embodiments of the invention are directed to a recombinant microorganism comprising: down-regulated Gpd1, down-regulated Fdh1, down-regulated Fdh2, down-regulated Gdh1, up-regulated AdhE, up-regulated pyruvate formate lyase, and an up-regulated pyruvate formate lyase-activating enzyme.

Some embodiments of the invention are directed to a recombinant microorganism comprising: down-regulated Gpd1, down-regulated Fdh1, down-regulated Fdh2, up-regulated AdhE, up-regulated pyruvate formate lyase, an up-regulated pyruvate formate lyase-activating enzyme, upregulated-DUR2, and GPD2 under the control of the GPD1 promoter.

Some embodiments of the invention are directed to a recombinant microorganism comprising: down-regulated Gpd1, down-regulated Fdh1, down-regulated Fdh2, up-regulated AdhE, up-regulated pyruvate formate lyase, an up-regulated pyruvate formate lyase-activating enzyme, and up-regulated-DUR/12.

Some embodiments of the invention are directed to a recombinant microorganism comprising: down-regulated Gpd1, down-regulated Gpd2, down-regulated Fdh1, down-regulated Fdh2, down-regulated Ure2, up-regulated AdhE, up-regulated pyruvate formate lyase, an up-regulated pyruvate formate lyase-activating enzyme, GPD1 under the control of the (GPD2 promoter, and GPD2 under the control of the GPD1 promoter.

Some embodiments of the invention are directed to a recombinant microorganism comprising: down-regulated Gpd1, down-regulated Gpd2, down-regulated Fdh1, down-regulated Fdh2, up-regulated AdhE, up-regulated pyruvate formate lyase, an up-regulated pyruvate formate lyase-activating enzyme, up-regulated GDH2, GPD1 under the control of the GPD2 promoter, and GPD2 under the control of the GPD1 promoter.

BRIEF DESCRIPTION OF THE DRAWINGS/FIGURES

FIG. 1 depicts simplified carbon and redox pathways utilized by wildtype *S. cerevisiae* during anaerobic growth. Ethanol formation is redox neutral while cell biomass formation generates net NADH, which is balanced by glycerol formation.

FIG. 2 depicts urea transport and intracellular catabolism. The enzymes Dur3 and Dur4 are known transporters of urea. Once inside the cell, urea is broken down into 2 ammonia molecules and 2 carbon dioxide molecules in a reaction catalyzed by Dur1,2.

Figure 45:
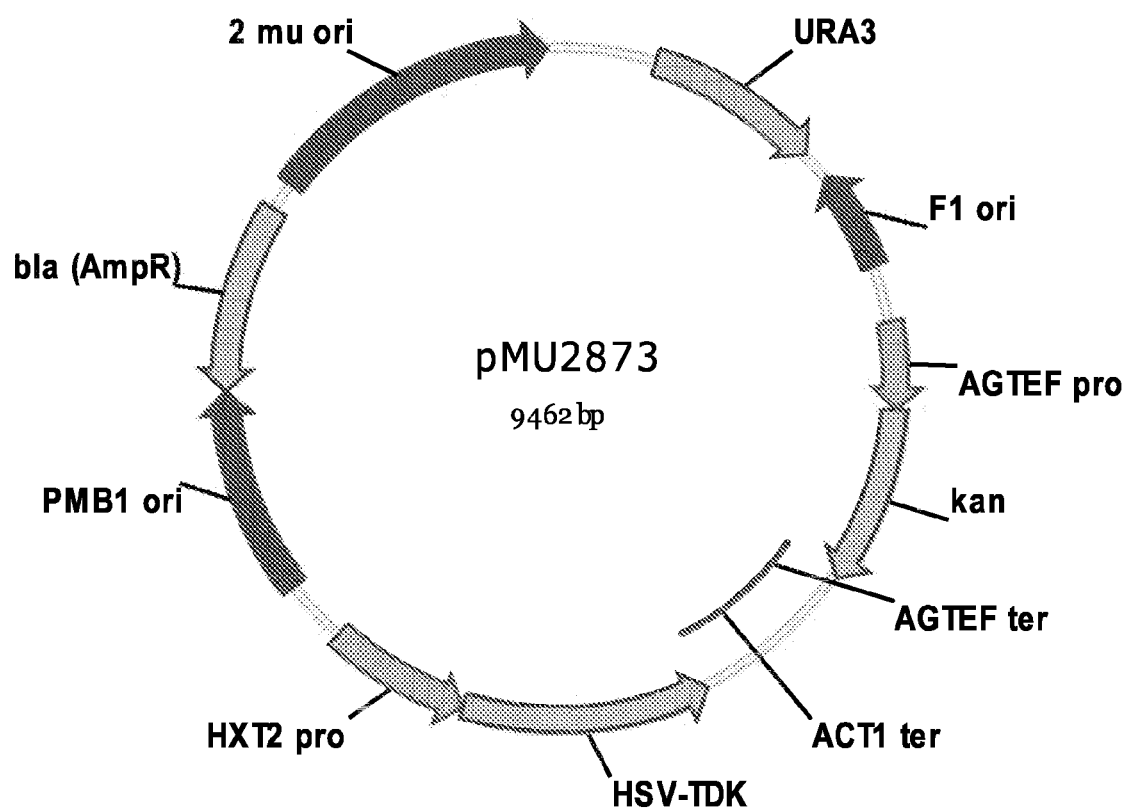
Figure 46:
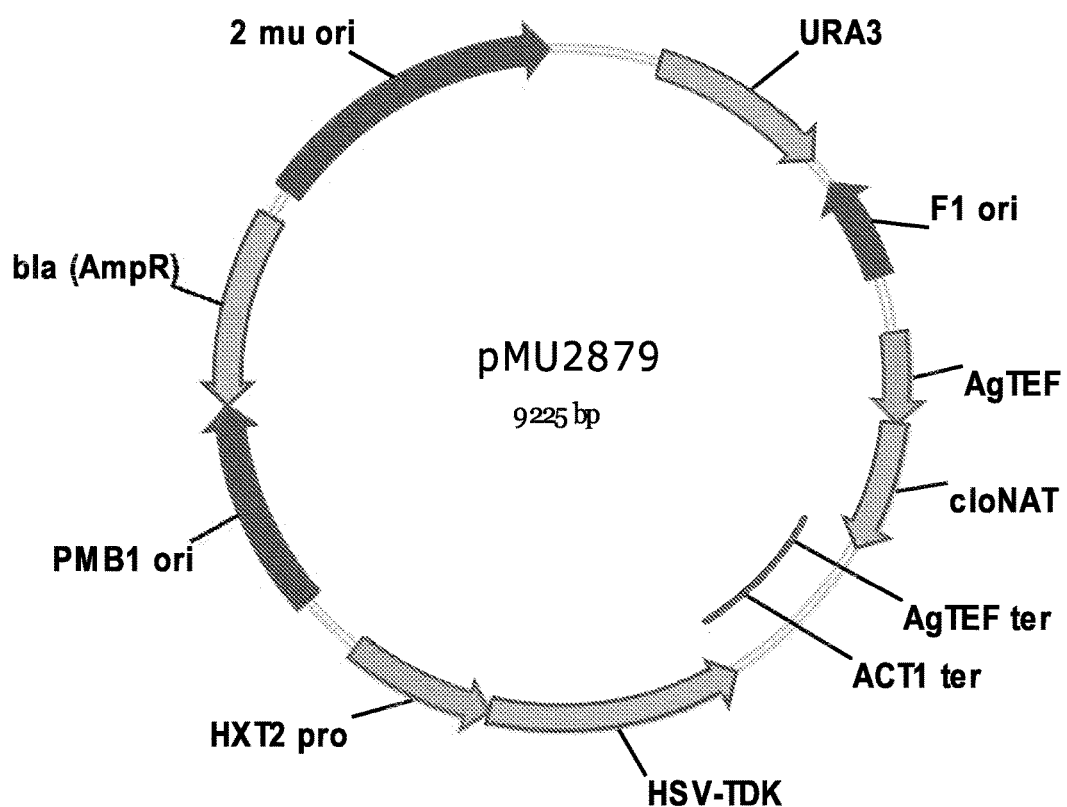
Figure 47:
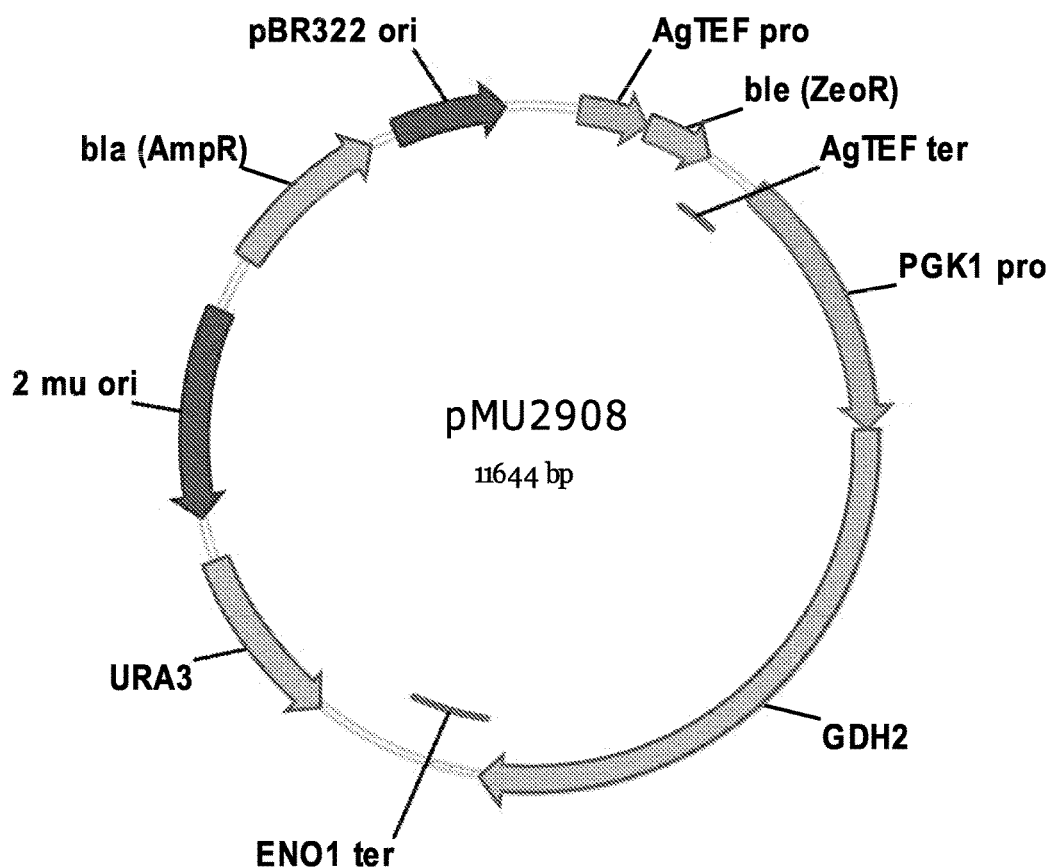
Figure 48:
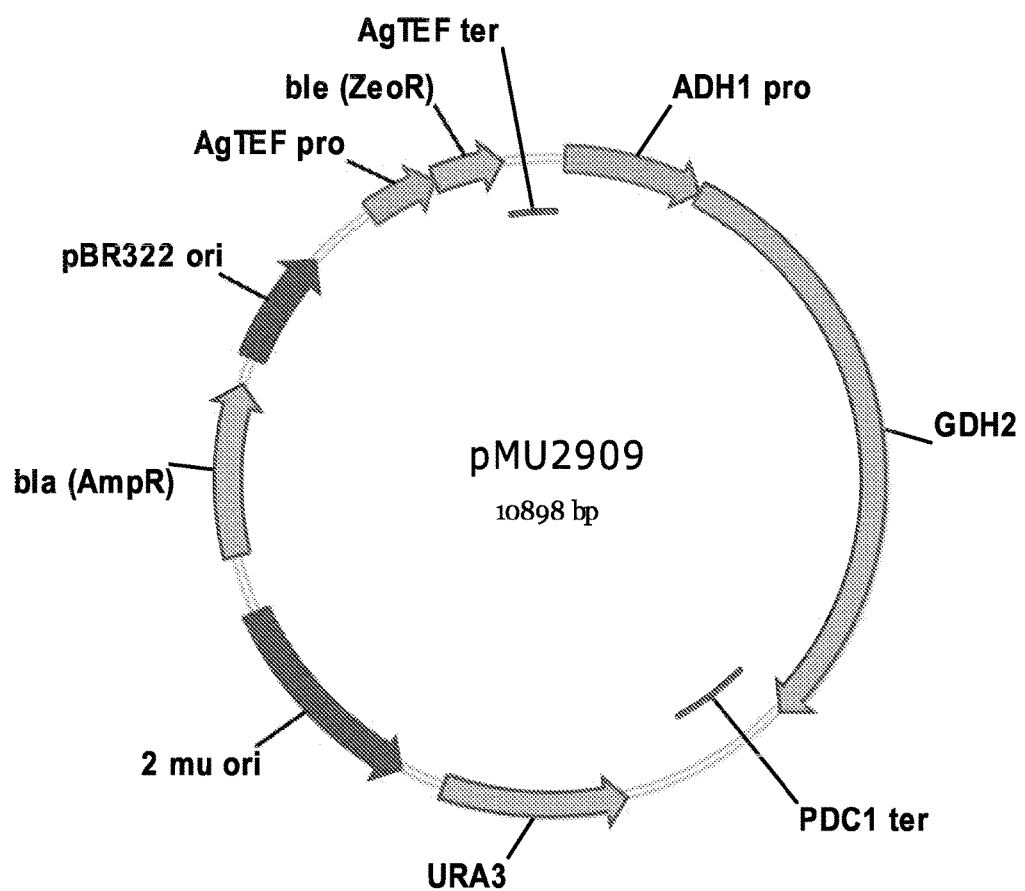
Figure 49:
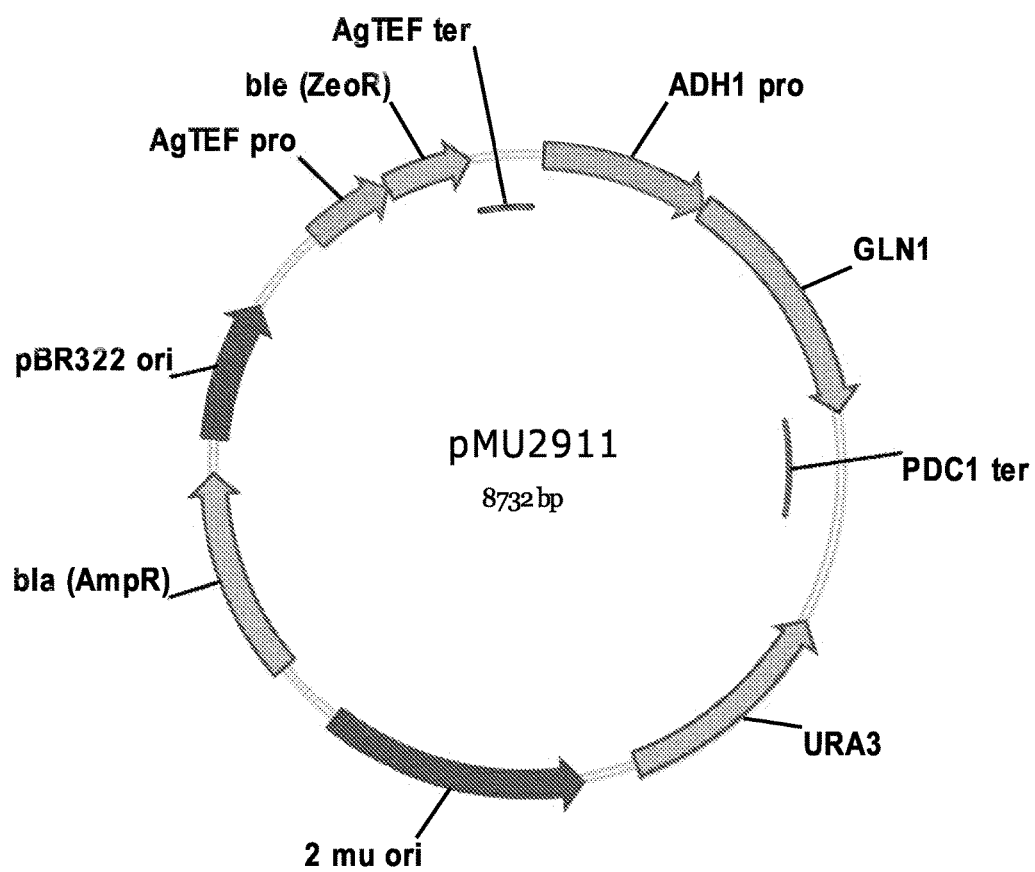
Figure 50:
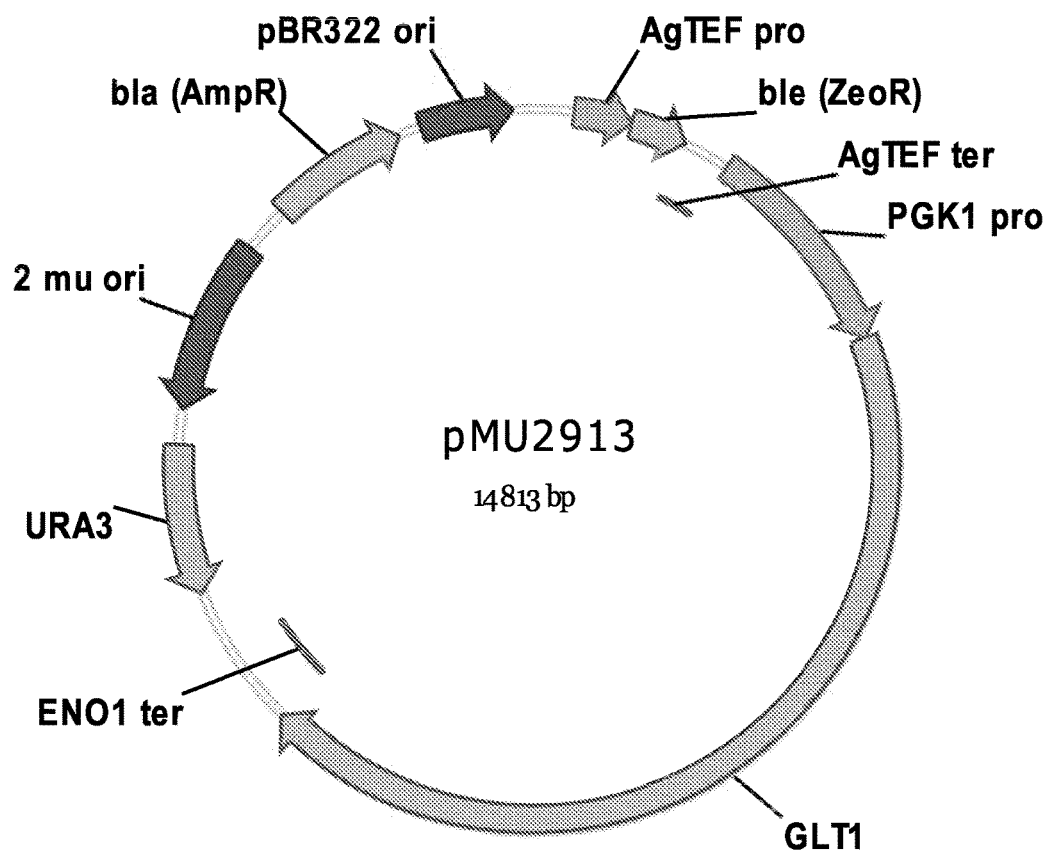
Figure 51:
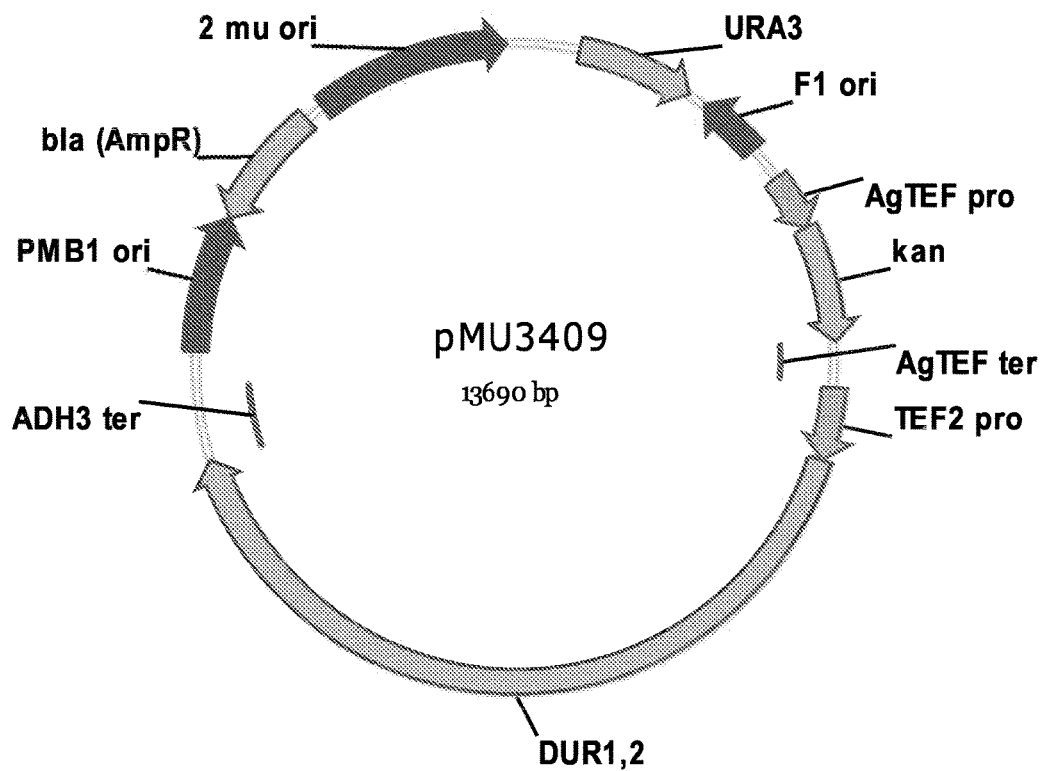
Figure 52:
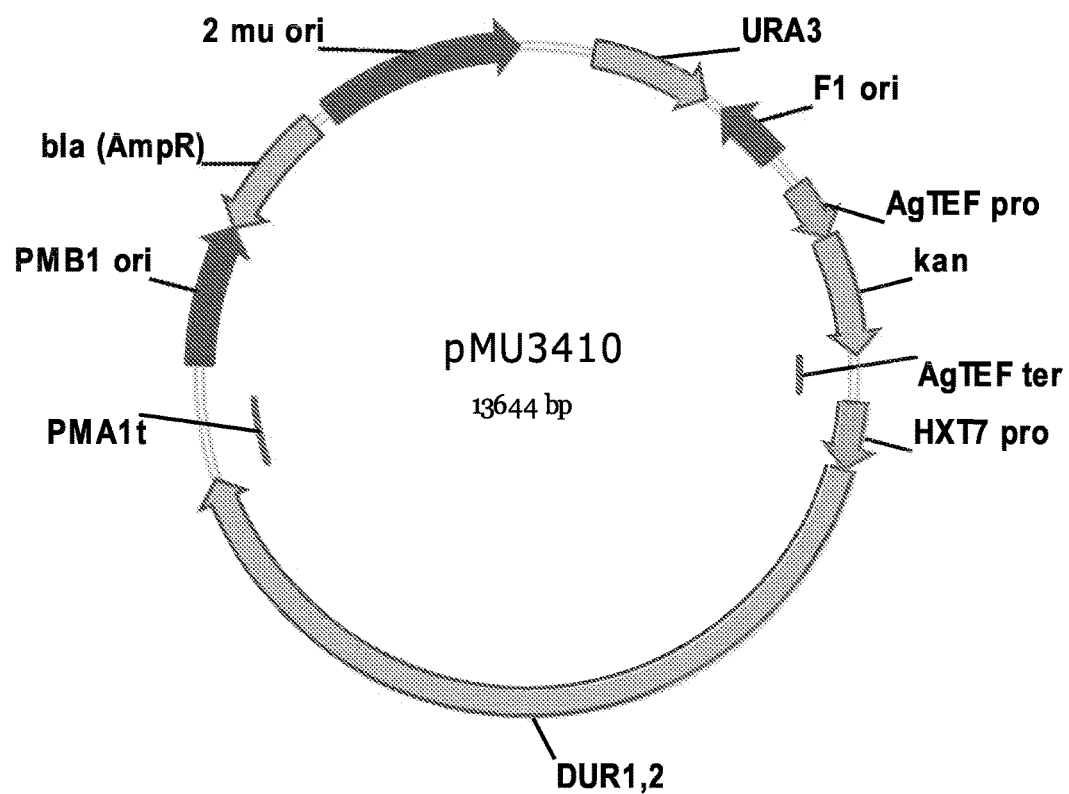
Figure 53:
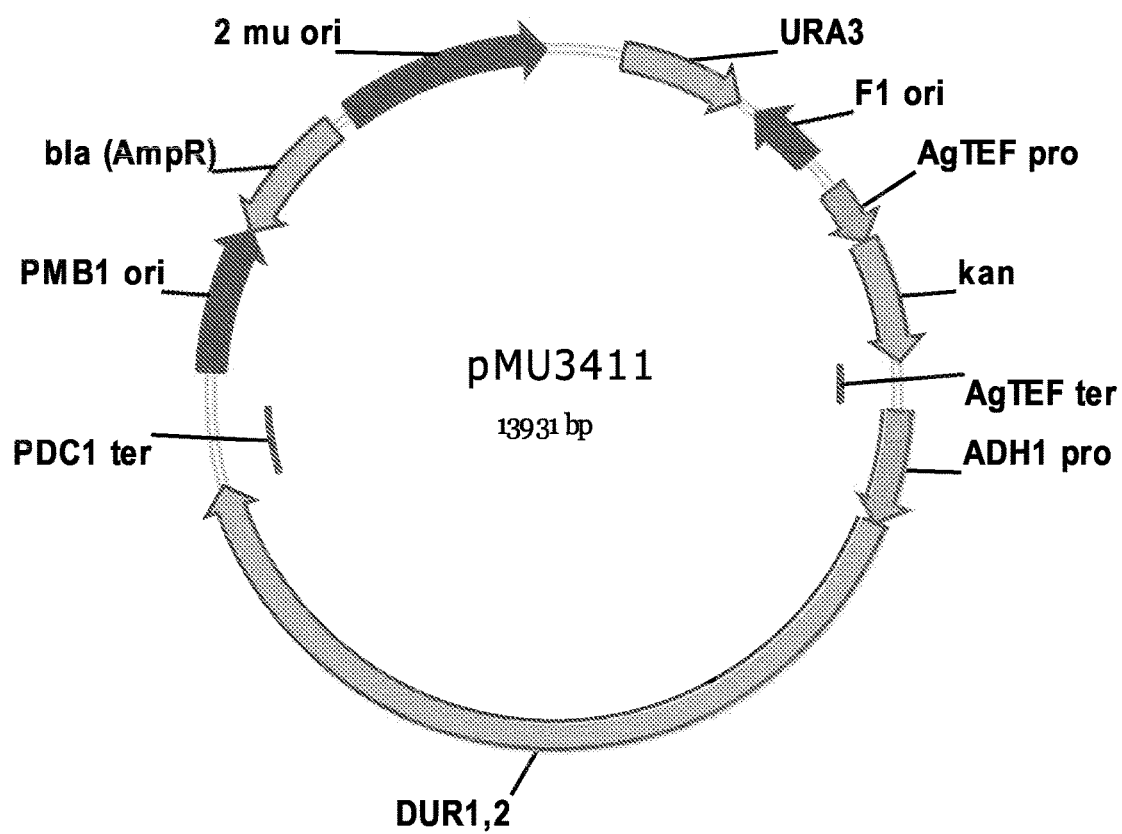
Figure 54:
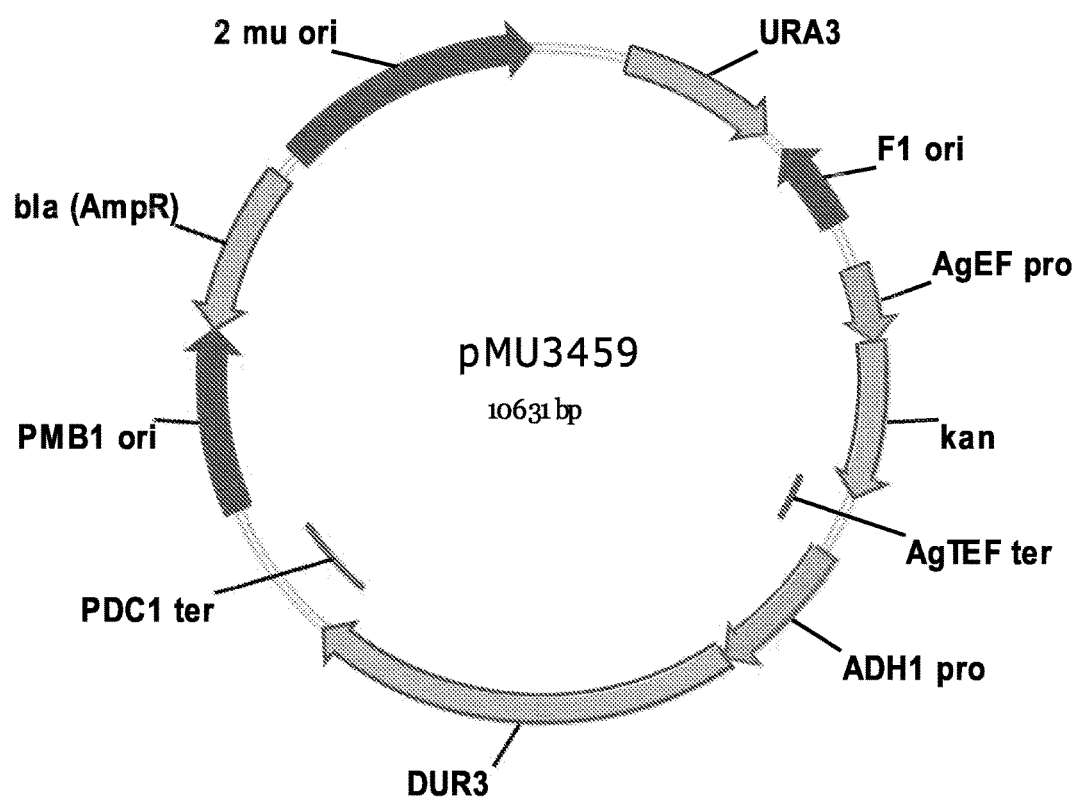
Figure 55:
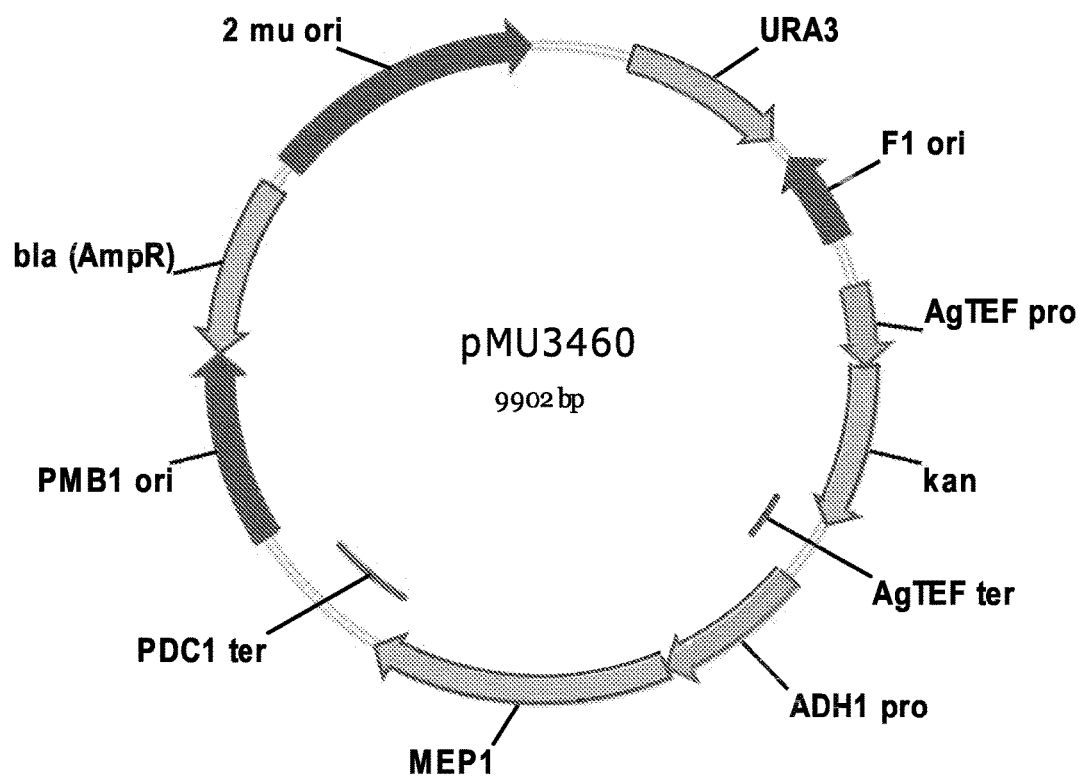
Figure 56:
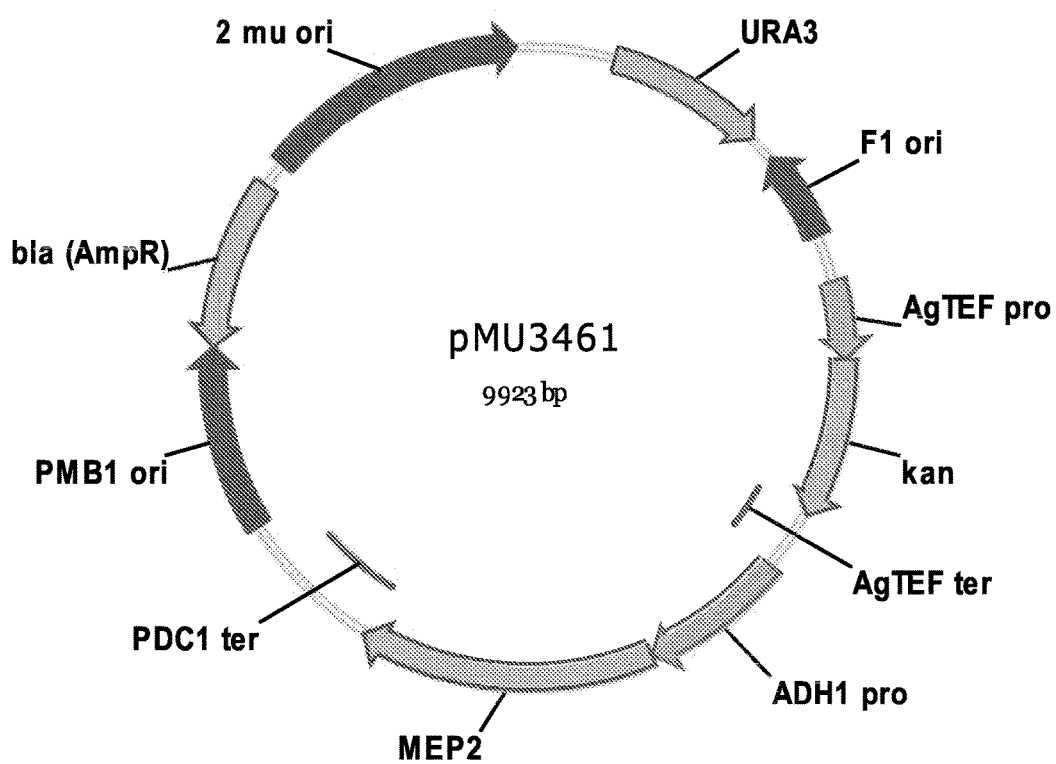
Figure 57:
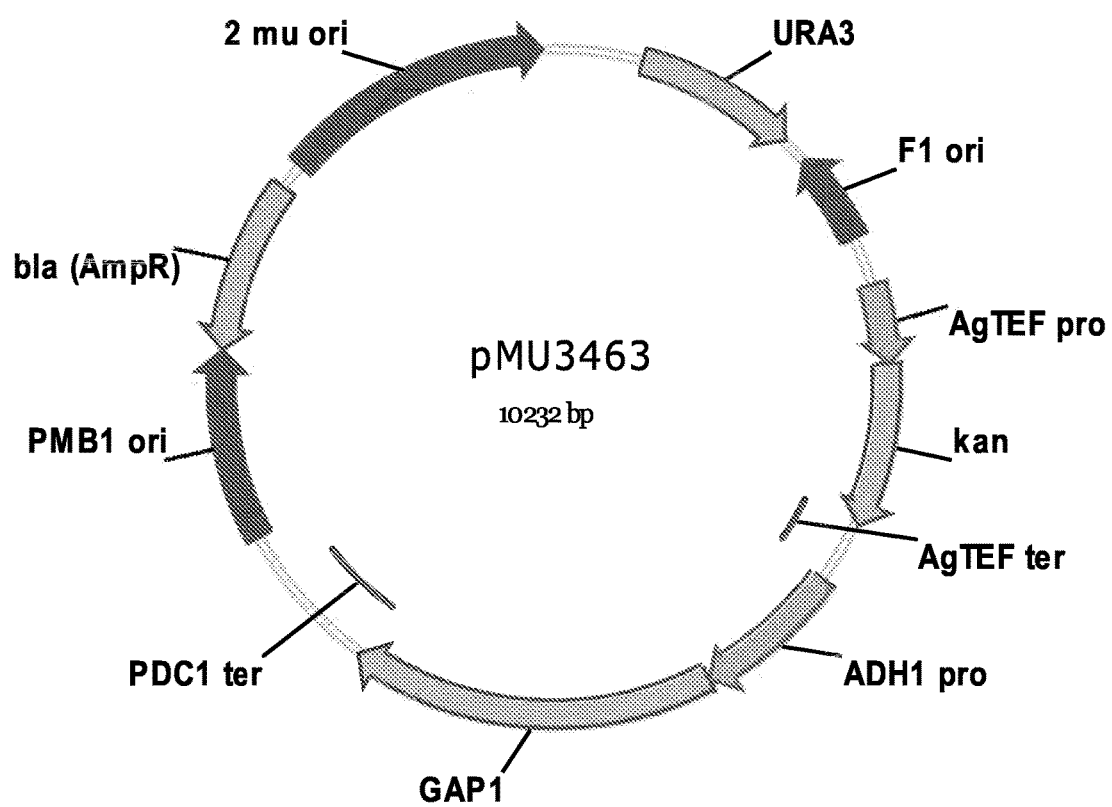
Figure 58:
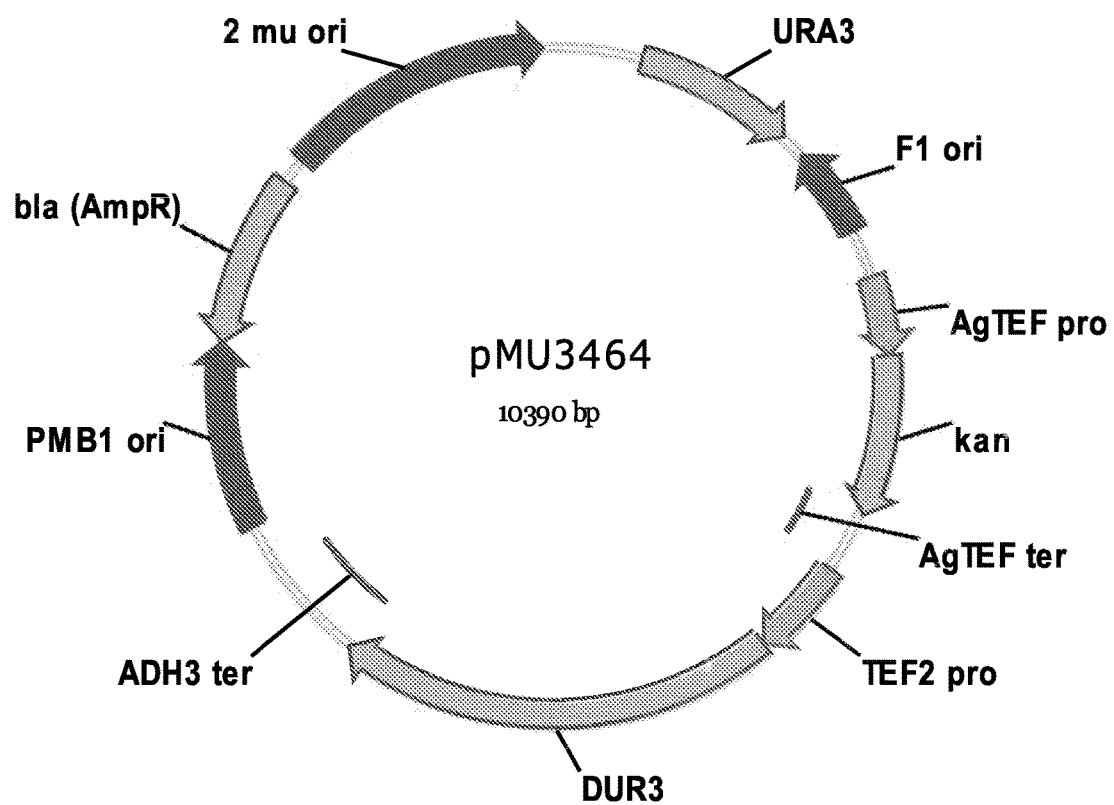
Figure 59:
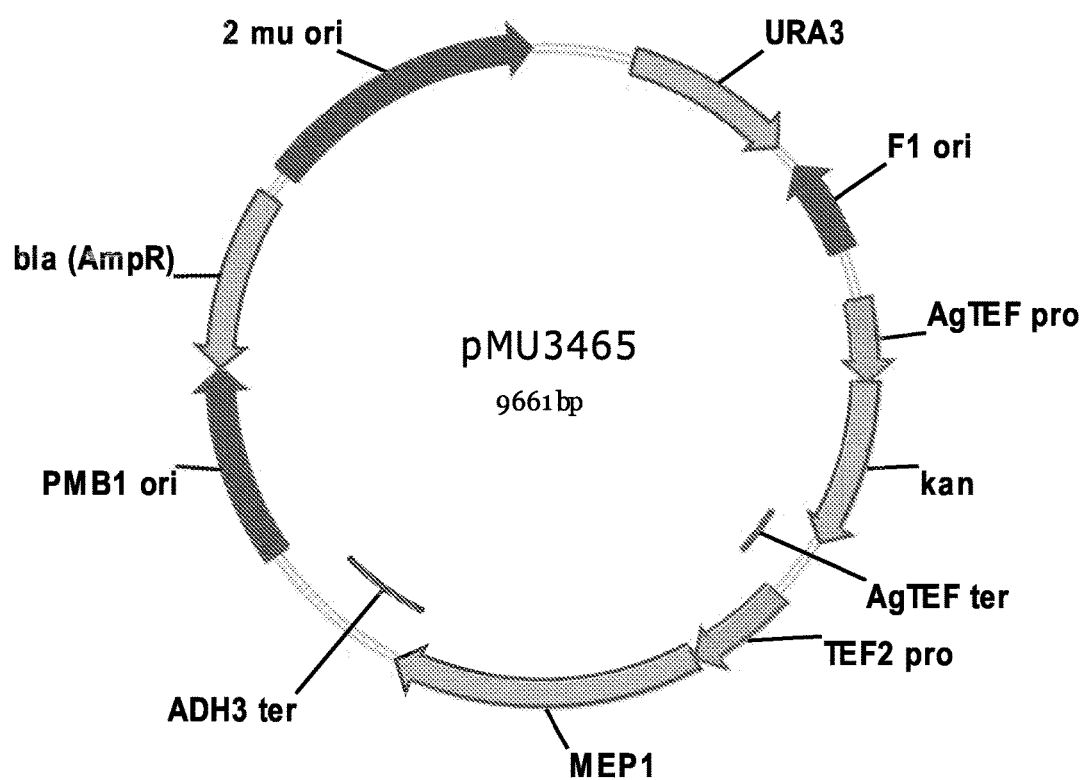
Figure 60:
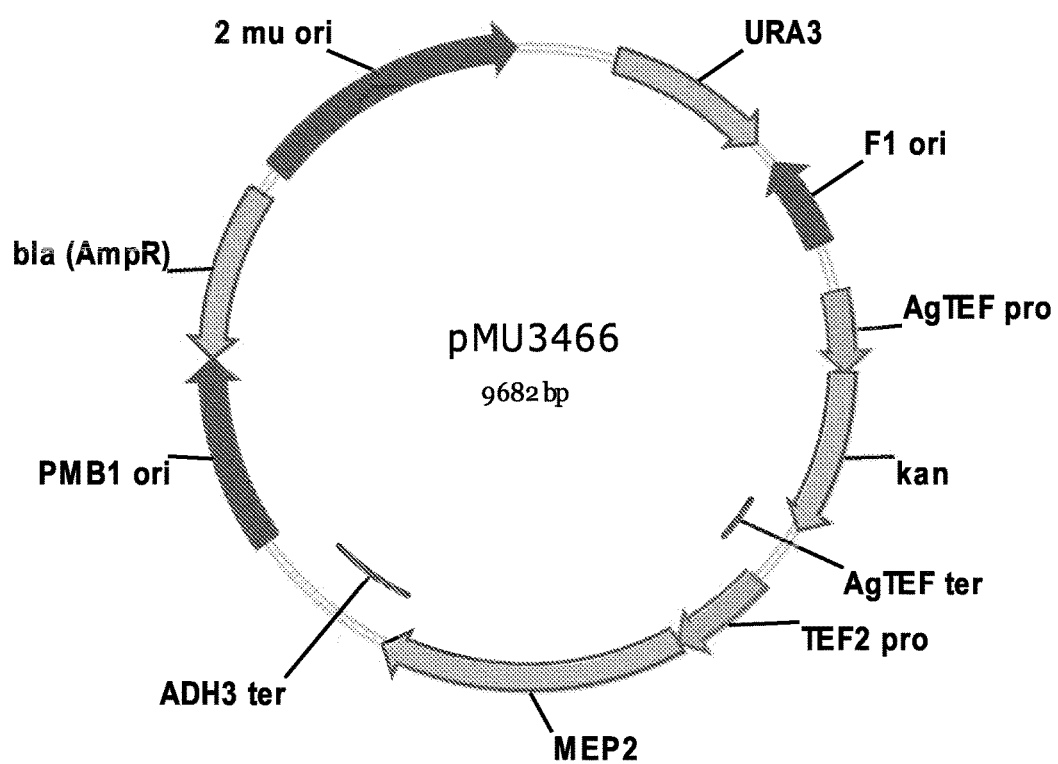
Figure 61:
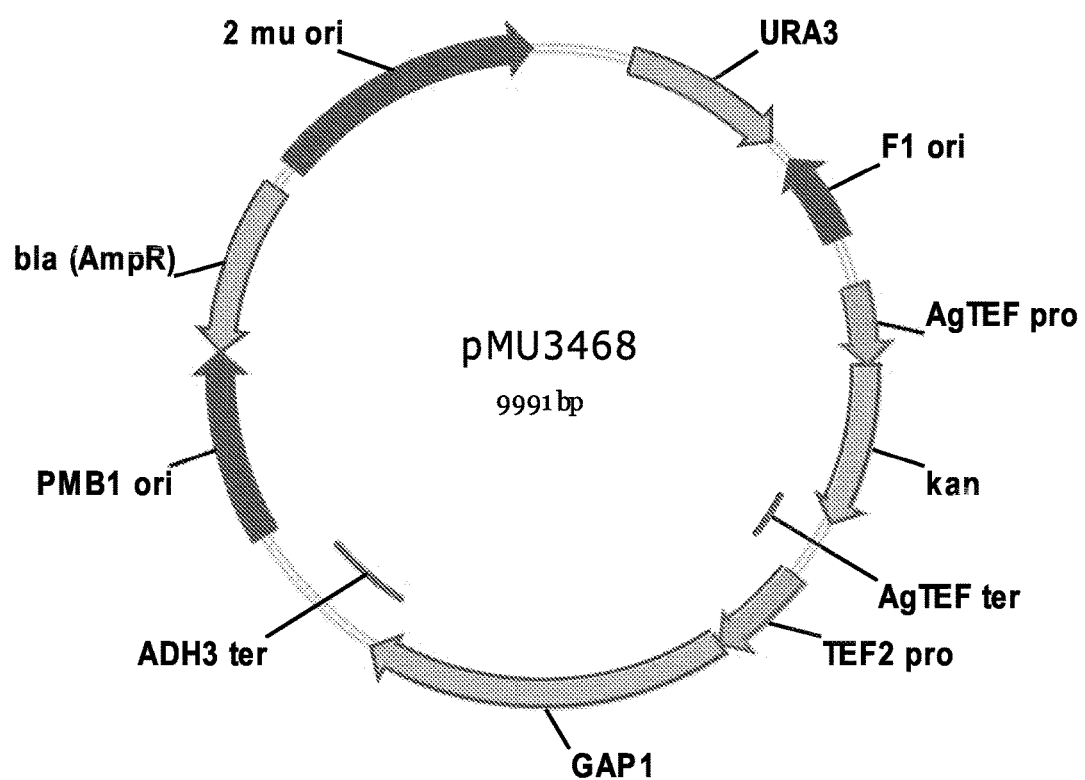
Figure 62:
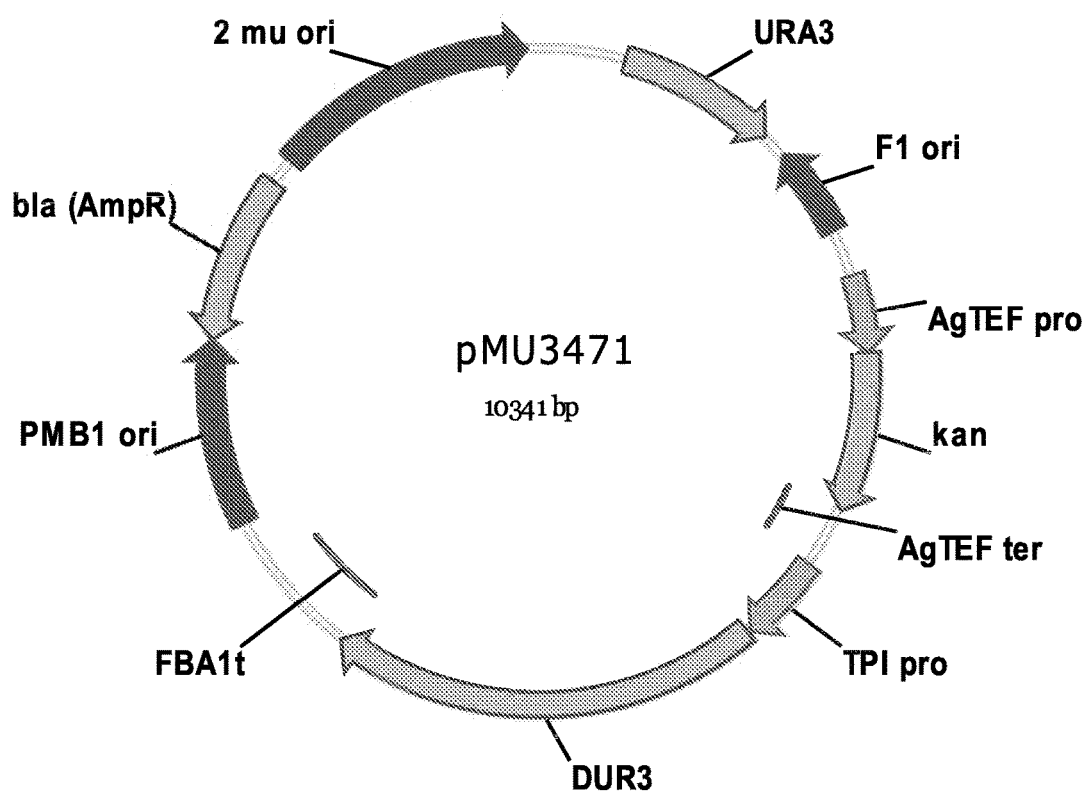
Figure 63:
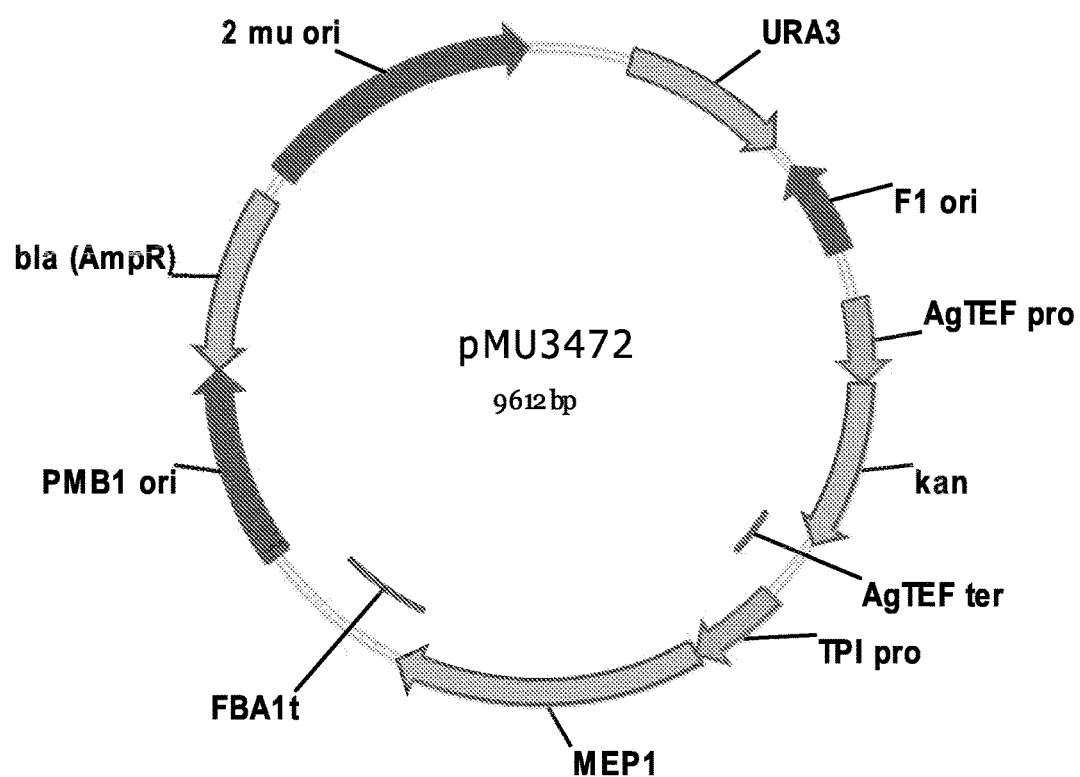
Figure 64:
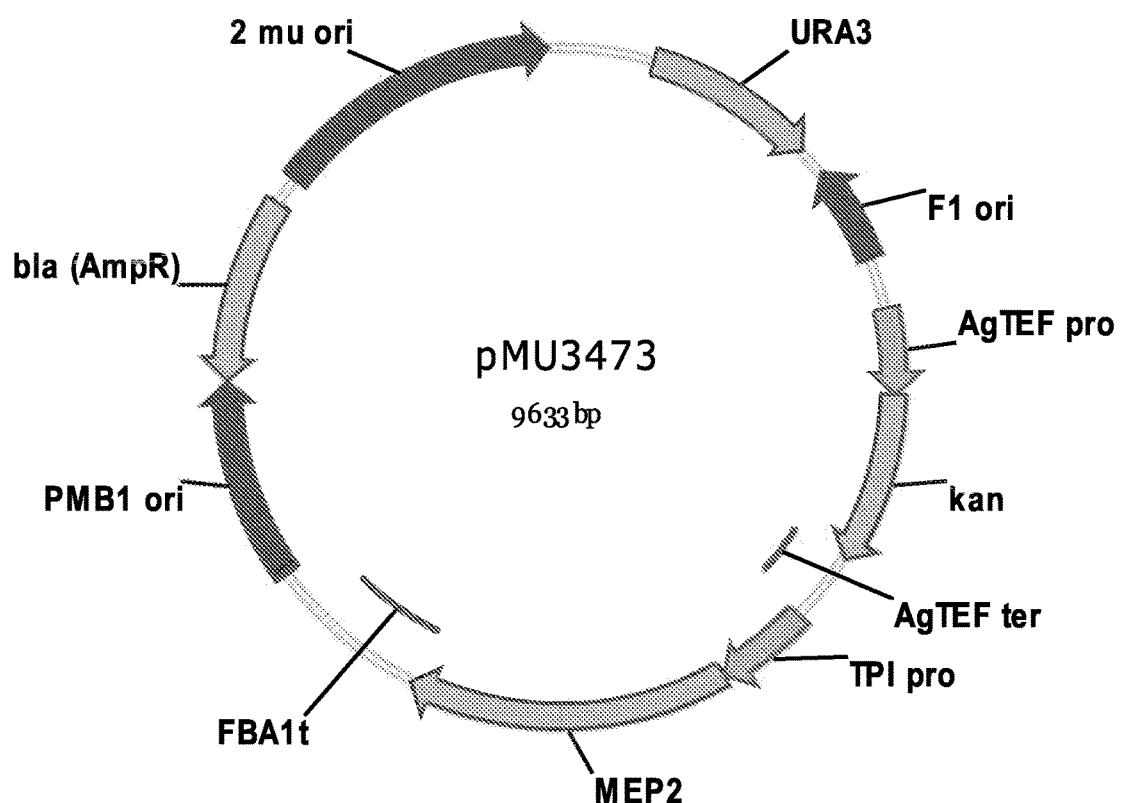
Figure 65:
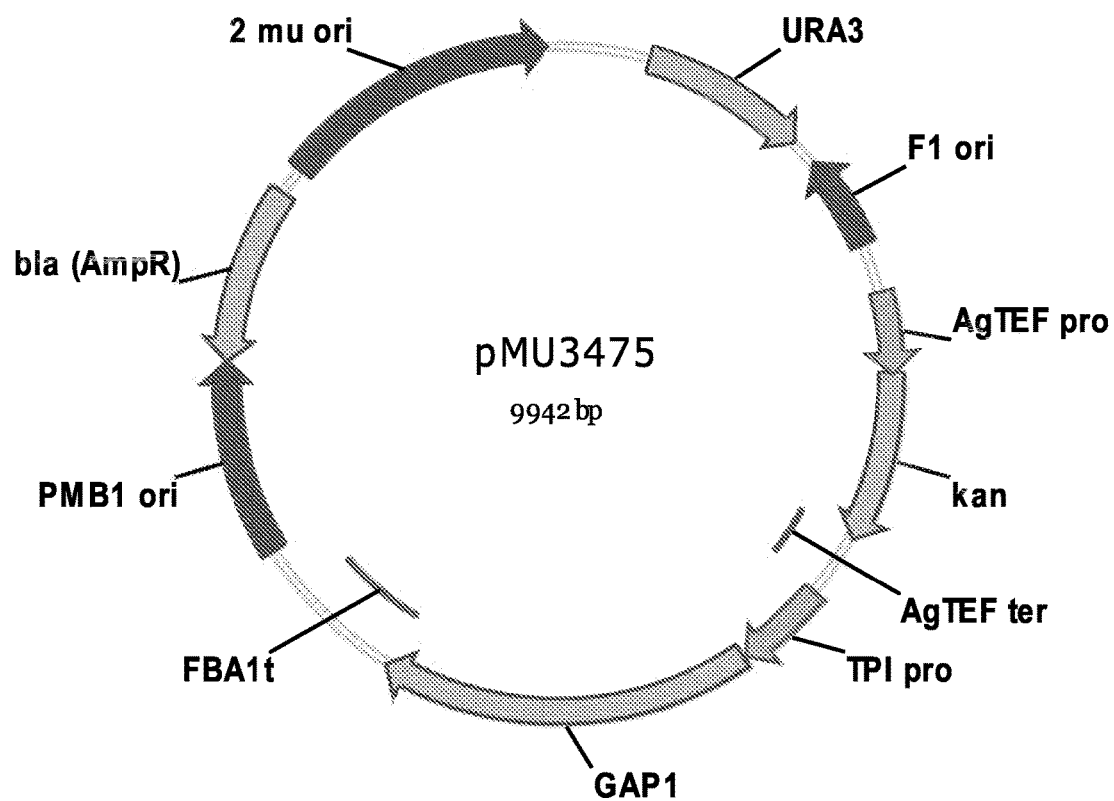
Figure 66:
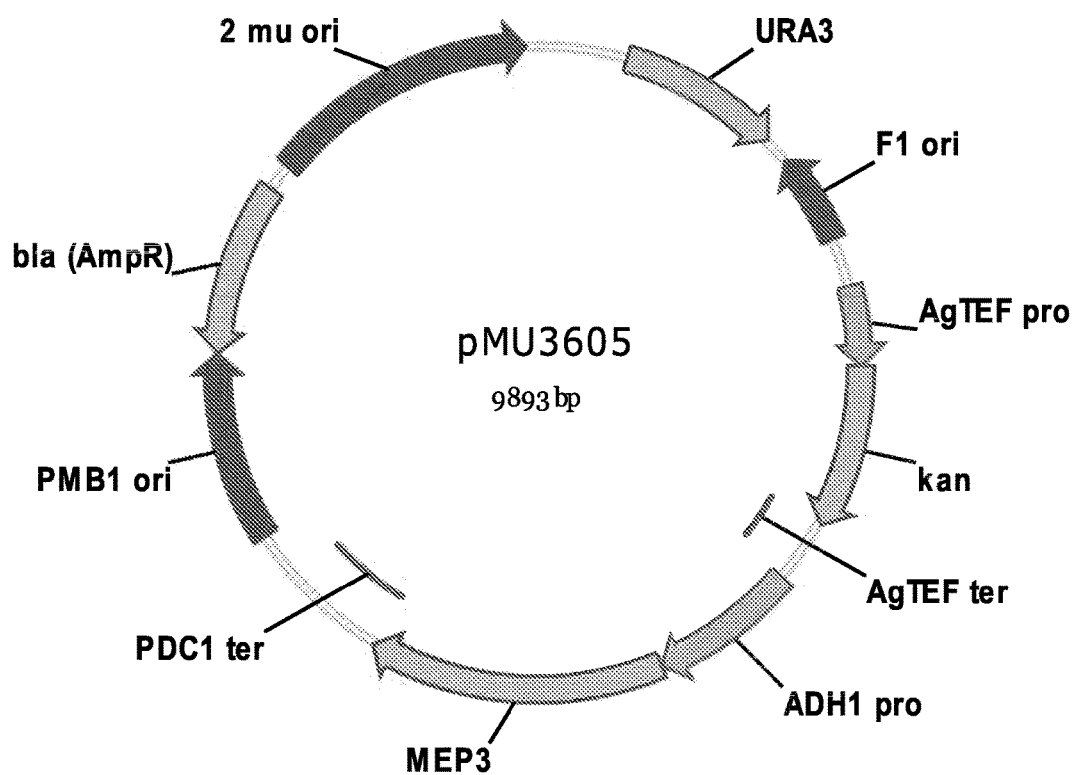
Figure 67:
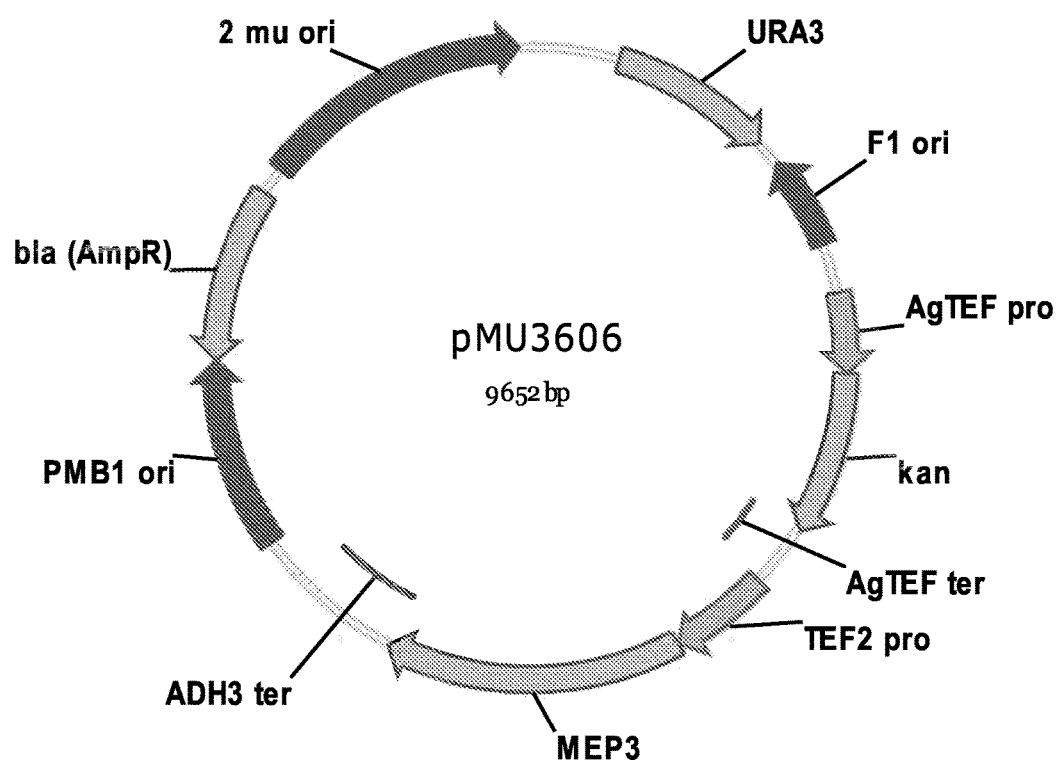
Figure 68:
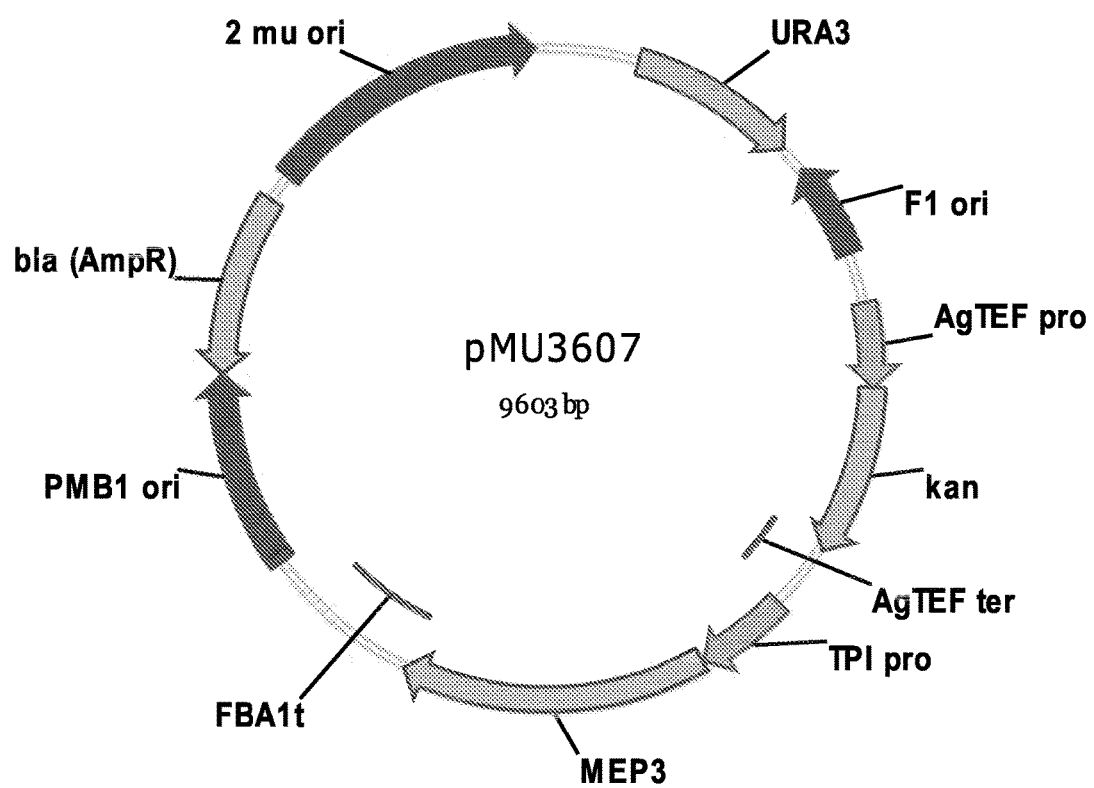

FIG. 45 depicts a plasmid map for pMU2873.
FIG. 46 depicts a plasmid map for pMU2879.
FIG. 47 depicts a plasmid map for pMU2908.
FIG. 48 depicts a plasmid map for pMU2909.
FIG. 49 depicts a plasmid map for pMU2911.
FIG. 50 depicts a plasmid map for pMU2913.
FIG. 51 depicts a plasmid map for pMU3409.
FIG. 52 depicts a plasmid map for pMU3410.
FIG. 53 depicts a plasmid map for pMU3411.
FIG. 54 depicts a plasmid map for pMU3459.
FIG. 55 depicts a plasmid map for pMU3460.
FIG. 56 depicts a plasmid map for pMU3461.
FIG. 57 depicts a plasmid map for pMU3463.
FIG. 58 depicts a plasmid map for pMU3464.
FIG. 59 depicts a plasmid map for pMU3465.
FIG. 60 depicts a plasmid map for pMU3466.
FIG. 61 depicts a plasmid map for pMU3468.
FIG. 62 depicts a plasmid map for pMU3471.
FIG. 63 depicts a plasmid map for pMU3472.
FIG. 64 depicts a plasmid map for pMU3473.
FIG. 65 depicts a plasmid map for pMU3475.
FIG. 66 depicts a plasmid map for pMU3605.
FIG. 67 depicts a plasmid map for pMU3606.
FIG. 68 depicts a plasmid map for pMU3607.

Figure 69:
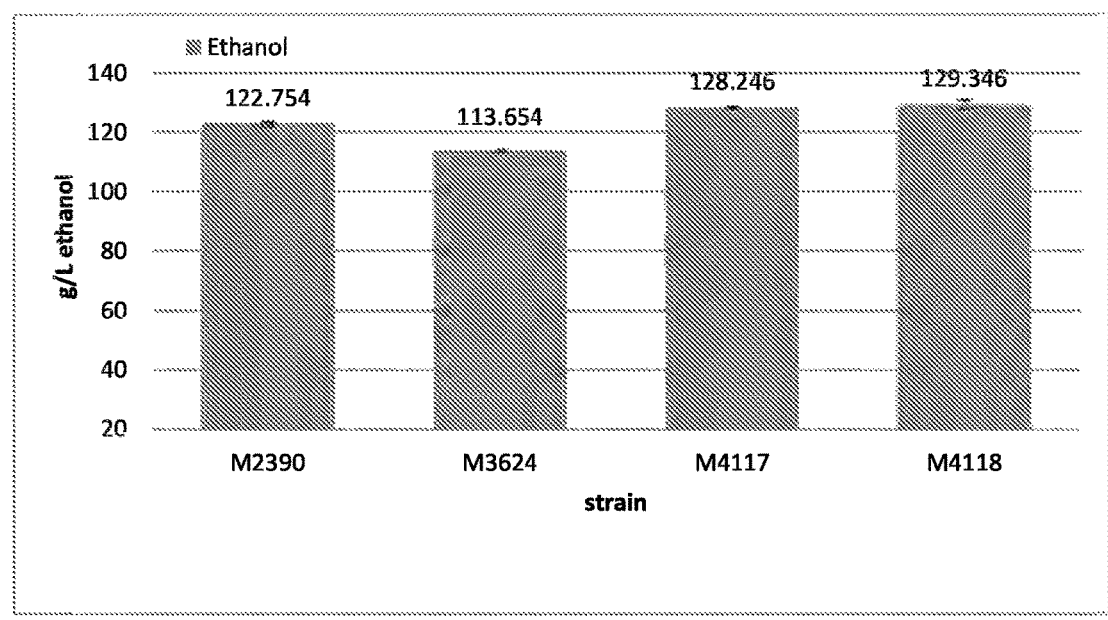

FIG. 69 depicts the final ethanol titers measured following fermentation of 31% solids corn mash in wildtype cells (M2390), a glycerol reduction strain containing the formate pathway (M3624), and 2 strains with modification of the ammonium assimilation pathway (M4117, which contains a deletion of gdh1 and an over-expression of Gdh2, and M4118, which contains a deletion of gdh1 and an over-expression of Glt1 and Gln1).

Figure 70:
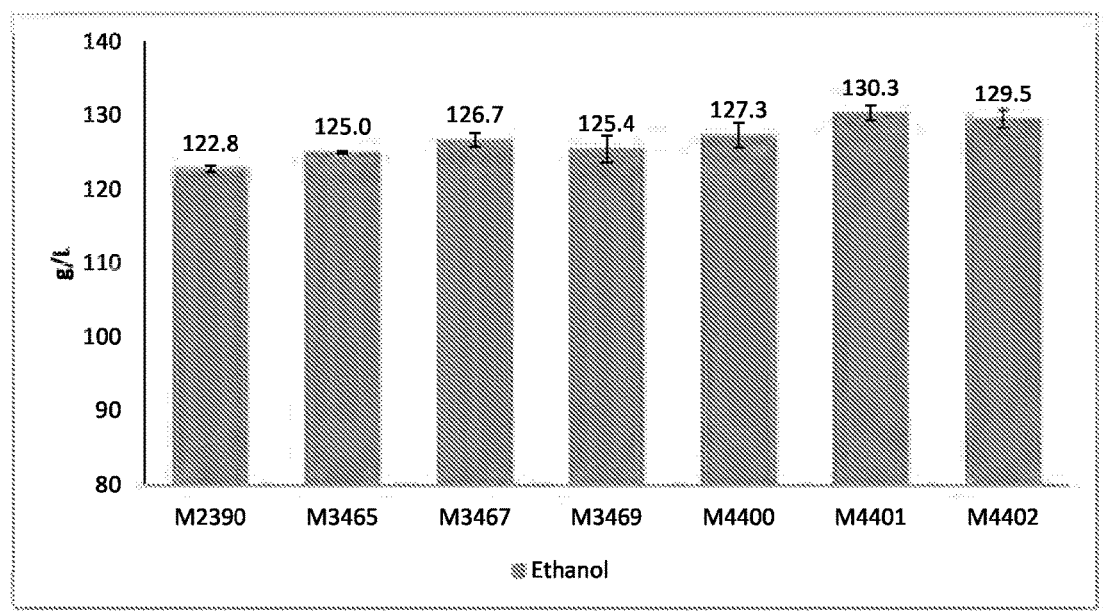

FIG. 70 depicts the ethanol titers measured following fermentation of 31% solids corn mash for glycerol reduction strains containing the formate pathway (M3465, M3467, M3469) that additionally have a deletion of gdh1 (M4400, M4401, M4402). M2390 was a parental control.

Figure 71:
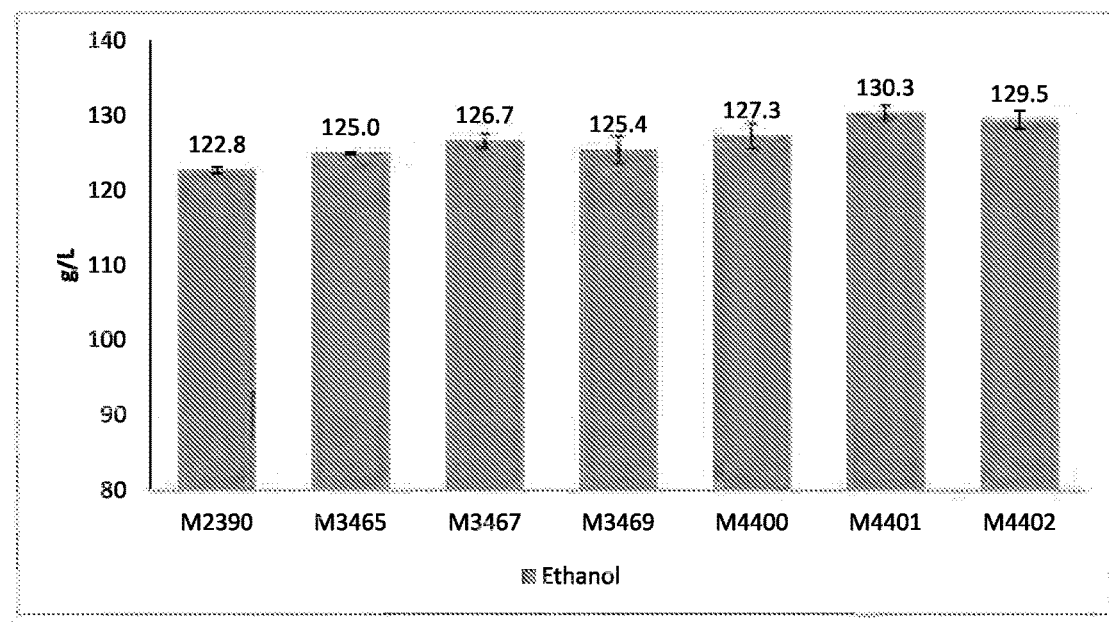

FIG. 71 depicts the ethanol titers measured following fermentation of 31% solids corn mash for M2390, M3467, M3469, M4427 (M3467 parent strain: expression of DUR1/2 driven by the TEF2 promoter), M4428 (M3467 parent strain: expression of DUR1/2 driven by the HXT7 promoter), M4429 (M3467 parent strain: expression of DUR1/2 driven by the ADH1 promoter), M4430 (M3467 parent strain: expression of DUR1/2 driven by the HXT7/TEF2 promoters), M4431 (M3469 parent strain: expression of DUR1/2 driven by the TEF2 promoter), M4432 (M3469 parent strain: expression of DUR1/2 driven by the HXT7 promoter), M4433 (M3469 parent strain: expression of DUR1/2 driven by the ADH1 promoter), and M4434 (M3469 parent strain: expression of DUR1/2 driven by the HXT7/TEF2 promoters)

Figure 72:
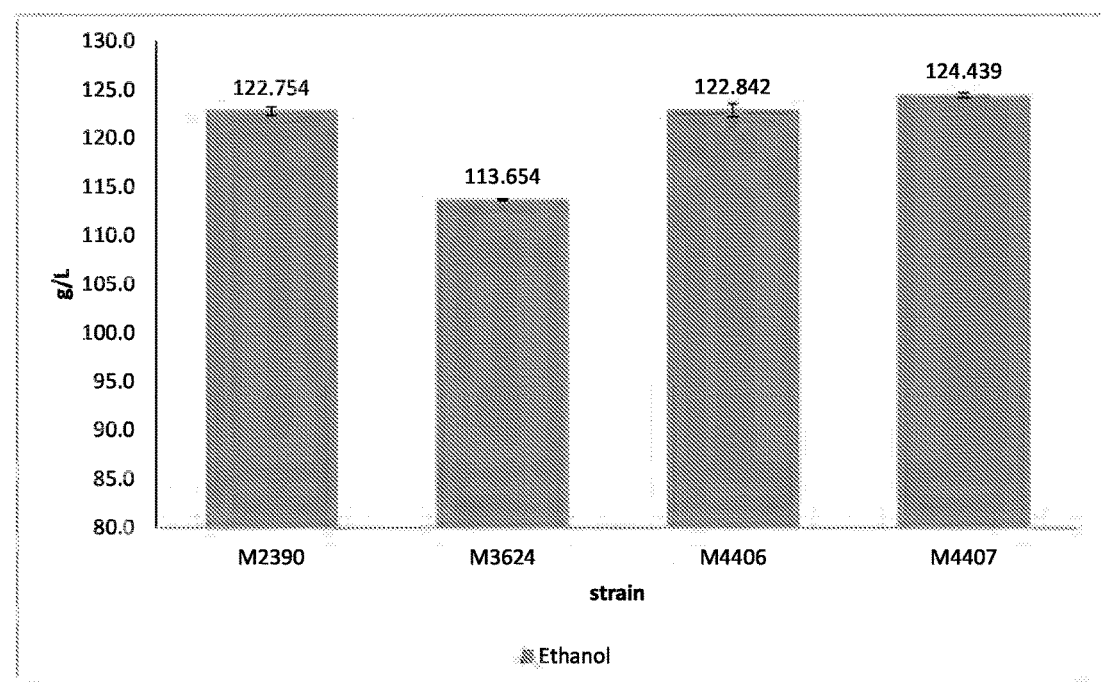

FIG. 72 depicts the ethanol titers measured following fermentation of 31% solids corn mash for M2390, M3624, M4406, and M4407.

Figure 73:
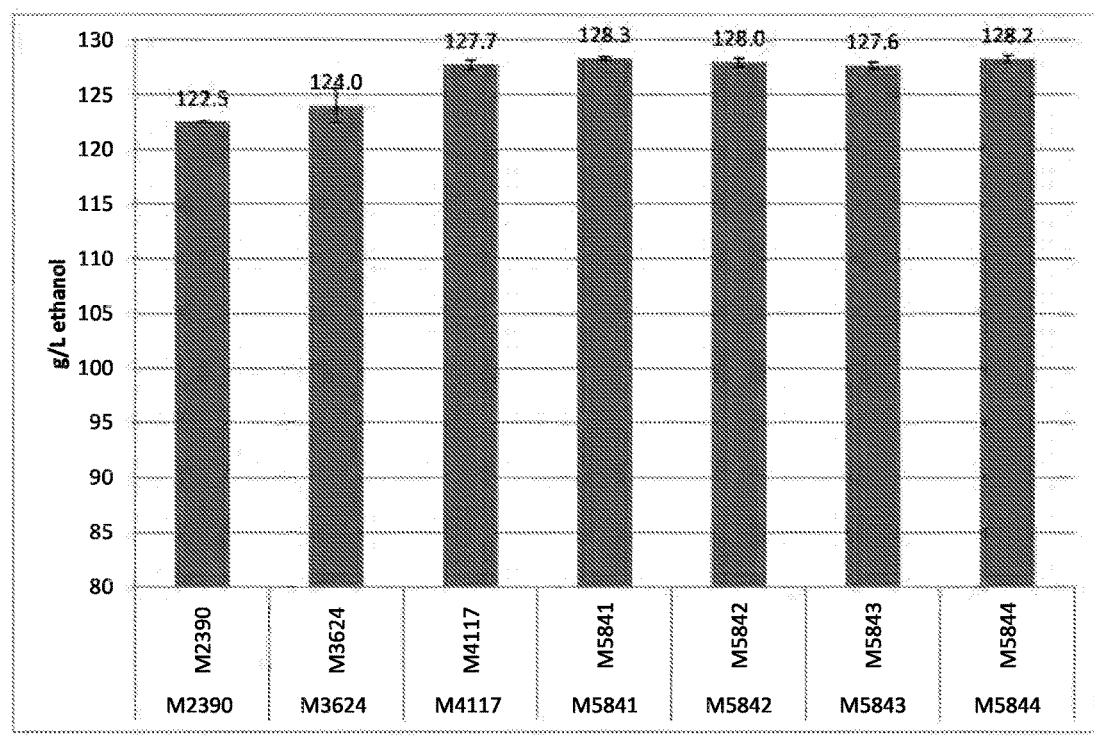

FIG. 73 depicts the ethanol titers produced after 68 hrs fermentation in mini-vials for strains M2390, M3624, M4117, M5841, M5842, M5843, and M5844.

Figure 74:
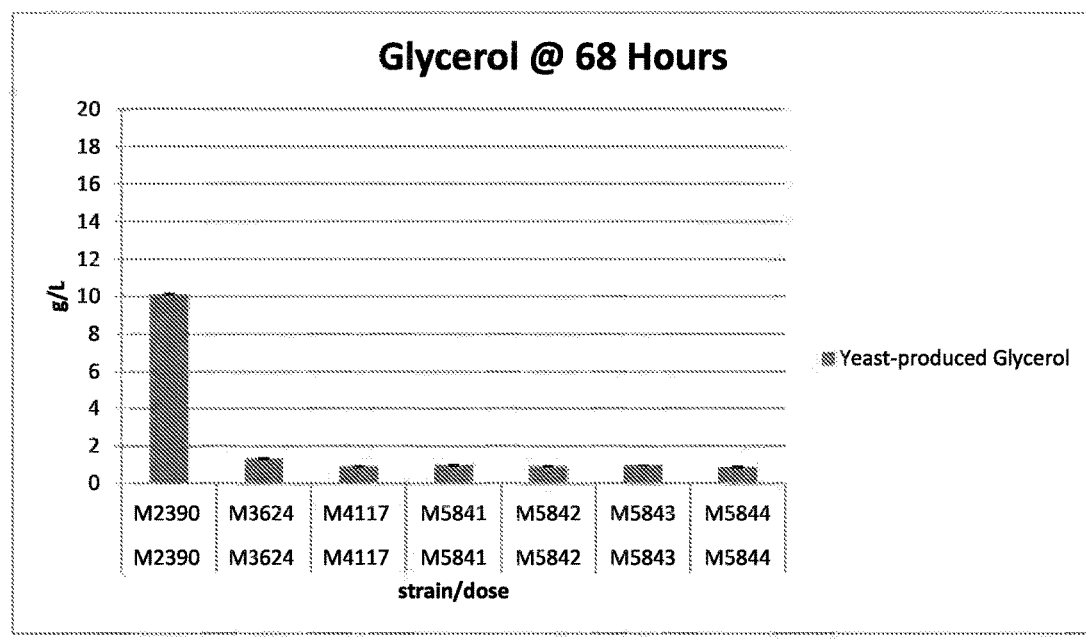

FIG. 74 depicts the glycerol titers produced after 68 hrs fermentation in mini-vials for strains M2390, M3624, M4117, M5841, M5842, M5843, and M5844.

DETAILED DESCRIPTION OF THE INVENTION

Definitions

Unless defined otherwise, all technical and scientific terms used herein have the same meaning as commonly understood to one of ordinary skill in the art of microbial metabolic engineering. Although methods and materials similar or equivalent to those described herein can be used in the practice of the disclosed methods and compositions, exemplary methods, devices and materials are described herein.

The embodiments described, and references in the specification to "one embodiment", "an embodiment", "an example embodiment", etc., indicate that the embodiments described can include a particular feature, structure, or characteristic, but every embodiment does not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

The description of "a" or "an" item herein may refer to a single item or multiple items. It is understood that wherever embodiments are described herein with the language "comprising," otherwise analogous embodiments described in terms of "consisting of" and/or "consisting essentially of" are also provided. Thus, for example, reference to "a polynucleotide" includes a plurality of such polynucleotides and reference to "the microorganism" includes reference to one or more microorganisms, and so forth.

The term "heterologous" is used in reference to a polynucleotide or a gene not normally found in the host organism. "Heterologous" includes up-regulated or down-regulated endogenous genes. "Heterologous" also includes a native coding region, or portion thereof, that is reintroduced into the source organism in a form that is different from the corresponding native gene, e.g., not in its natural location in the organism's genome. "Heterologous" also includes any gene that has been modified and placed into an organism. A heterologous gene may include a native coding region that is a portion of a chimeric gene including a non-native regulatory region that is reintroduced into the native host or modifications to the native regulatory sequences that affect the expression level of the gene. Foreign genes can comprise native genes inserted into a non-native organism, or chimeric genes. A heterologous polynucleotide, gene, polypeptide, or an enzyme may be derived or isolated from any source, e.g., eukaryotes, prokaryotes, viruses, or synthetic polynucleotide fragments, and includes up-regulated endogenous genes.

The terms "gene(s)" or "polynucleotide" or "nucleic acid" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. Also, the terms are intended to include a specific gene for a selected purpose. The gene may be endogenous to the host cell or may be recombinantly introduced into the host cell, e.g., as a plasmid maintained episomally or a plasmid (or fragment thereof) that is stably integrated into the genome. In addition to the plasmid form, a gene may, for example, be in the form of linear DNA or RNA. The term "gene" is also intended to cover multiple copies of a particular gene, e.g., all of the DNA sequences in a cell encoding a particular gene product. A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native" or "endogenous" refers to a gene as found in nature with its own regulatory sequences.

A "nucleic acid," "polynucleotide," or "nucleic acid molecule" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

An "isolated nucleic acid molecule" or "isolated nucleic acid fragment" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

The term "expression" is intended to include the expression of a gene at least at the level of mRNA production, generally subsequently translated into a protein product. The term "expression," refers to the transcription and stable accumulation of sense (mRNA) or antisense RNA derived from the nucleic acid fragment of the invention. Expression may also refer to translation of mRNA into a polypeptide.

As used herein, an "expression vector" is a vector capable of directing the expression of genes to which it is operably linked.

A "vector," e.g., a "plasmid" or "YAC" (yeast artificial chromosome) refers to an extrachromosomal element often carrying one or more genes that are not part of the central metabolism of the cell, and is usually in the form of a circular double-stranded DNA molecule. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. Preferably, the plasmids or vectors of the present invention are stable and self-replicating.

The term "integrated" as used herein refers to genetic elements that are placed, through molecular biology techniques, into a chromosome of a host cell. For example, genetic elements can be placed into the chromosomes of the host cell as opposed to in a vector such as a plasmid carried by the host cell. Methods for integrating genetic elements into the genome of a host cell are well known in the art and include homologous recombination.

The term "domain" as used herein refers to a part of a molecule or structure that shares common physical or chemical features, for example hydrophobic, polar, globular, helical domains or properties, e.g., a DNA binding domain or an ATP binding domain. Domains can be identified by their homology to conserved structural or functional motifs. Examples of cellobiohydrolase (CBH) domains include the catalytic domain (CD) and the cellulose binding domain (CBD).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL., Second Edition, Cold Spring Harbor Laboratory Press, Cold Spring Harbor (1989), particularly Chapter 11 and Table 11.1 therein (hereinafter "Maniatis", entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see, e.g., Maniatis at 9.50-9.51). For hybridizations with shorter nucleic acids, i.e., oligonucleotides, the position of mismatches becomes more important, and the length of the oligonucleotide determines its specificity (see, e.g., Maniatis, at 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences.

As known in the art, "similarity" between two polypeptides is determined by comparing the amino acid sequence and conserved amino acid substitutes thereto of the polypeptide to the sequence of a second polypeptide.

"Identity" and "similarity" can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993), Computer Analysis of Sequence Data, Part I (Griffin, A. M., and Griffin, H. G., eds.) Humana Press, N.J. (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PENALTY=0). Default parameters for pairwise alignments using the Clustal method were KTUPLE 1, GAP PENALTY=3, WINDOW=5 and DIAGONALS SAVED=5.

Suitable nucleic acid sequences or fragments thereof (isolated polynucleotides of the present invention) encode polypeptides that are at least about 70% to about 75% identical to the amino acid sequences reported herein, at least about 80%, about 85%, or about 90% identical to the amino acid sequences reported herein, or at least about 95%, about 96%, about 97%, about 98%, about 99%, or about 100% identical to the amino acid sequences reported herein. Suitable nucleic acid fragments are at least about 70%, about 75%, or about 80% identical to the nucleic acid sequences reported herein, at least about 80%, about 85%, or about 90% identical to the nucleic acid sequences reported herein, or at least about 95%, about 96%, about 97%, about 98%, about 99%, or about 100%/o identical to the nucleic acid sequences reported herein. Suitable nucleic acid fragments not only have the above identities/similarities but typically encode a polypeptide having at least 50 amino acids, at least 100 amino acids, at least 150 amino acids, at least 200 amino acids, or at least 250 amino acids.

A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

An "isoform" is a protein that has the same function as another protein but which is encoded by a different gene and may have small differences in its sequence.

A "paralogue" is a protein encoded by a gene related by duplication within a genome.

An "orthologue" is gene from a different species that has evolved from a common ancestral gene by speciation. Normally, orthologues retain the same function in the course of evolution as the ancestral gene.

"Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

"Promoter" refers to a DNA fragment capable of controlling the expression of a coding sequence or functional RNA. In general, a coding region is located 3' to a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of cellular development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of RNA polymerase.

A coding region is "under the control" of transcriptional and translational control elements in a cell when RNA polymerase transcribes the coding region into mRNA, which is then trans-RNA spliced (if the coding region contains introns) and translated into the protein encoded by the coding region.

"Transcriptional and translational control regions" are DNA regulatory regions, such as promoters, enhancers, terminators, and the like, that provide for the expression of a coding region in a host cell. In eukaryotic cells, polyadenylation signals are control regions.

The term "operably associated" refers to the association of nucleic acid sequences on a single nucleic acid fragment so that the function of one is affected by the other. For example, a promoter is operably associated with a coding region when it is capable of affecting the expression of that coding region (i.e., that the coding region is under the transcriptional control of the promoter). Coding regions can be operably associated to regulatory regions in sense or antisense orientation.

As used herein, the term "anaerobic" refers to an organism, biochemical reaction or process that is active or occurs under conditions of an absence of gaseous $O_2$.

"Anaerobic conditions" are defined as conditions under which the oxygen concentration in the fermentation medium is too low for the microorganism to use as a terminal electron acceptor. Anaerobic conditions may be achieved by sparging a fermentation medium with an inert gas such as nitrogen until oxygen is no longer available to the microorganism as a terminal electron acceptor. Alternatively, anaerobic conditions may be achieved by the microorganism consuming the available oxygen of fermentation until oxygen is unavailable to the microorganism as a terminal electron acceptor.

"Aerobic metabolism" refers to a biochemical process in which oxygen is used as a terminal electron acceptor to convert energy, typically in the form of ATP, from carbohydrates. Aerobic metabolism typically occurs, for example, via the electron transport chain in mitochondria in eukaryotes, wherein a single glucose molecule is metabolized completely into carbon dioxide in the presence of oxygen.

In contrast, "anaerobic metabolism" refers to a biochemical process in which oxygen is not the final acceptor of electrons generated. Anaerobic metabolism can be divided into anaerobic respiration, in which compounds other than oxygen serve as the terminal electron acceptor, and substrate level phosphorylation, in which no exogenous electron acceptor is used and products of an intermediate oxidation state are generated via a "fermentative pathway."

In "fermentative pathways", the amount of NAD(P)H generated by glycolysis is balanced by the consumption of the same amount of NAD(P)H in subsequent steps. For example, in one of the fermentative pathways of certain yeast strains, NAD(P)H generated through glycolysis donates its electrons to acetaldehyde, yielding ethanol. Fermentative pathways are usually active under anaerobic conditions but may also occur under aerobic conditions, under conditions where NADH is not fully oxidized via the respiratory chain.

As used herein, the term "end-product" refers to a chemical compound that is not or cannot be used by a cell, and so is excreted or allowed to diffuse into the extracellular environment. Common examples of end-products from anaerobic fermentation include, but are not limited to, ethanol, acetic acid, formic acid, lactic acid, hydrogen and carbon dioxide.

As used herein, "cofactors" are compounds involved in biochemical reactions that are recycled within the cells and remain at approximately steady state levels. Common examples of cofactors involved in anaerobic fermentation include, but are not limited to, $NAD^+$ and $NADP^+$. In metabolism, a cofactor can act in oxidation-reduction reactions to accept or donate electrons. When organic compounds are broken down by oxidation in metabolism, their energy can be transferred to $NAD^+$ by its reduction to NADH, to $NADP^+$ by its reduction to NADPH, or to another cofactor, $FAD^+$, by its reduction to $FADH_2$. The reduced cofactors can then be used as a substrate for a reductase.

As used herein, a "pathway" is a group of biochemical reactions that together can convert one compound into another compound in a step-wise process. A product of the first step in a pathway may be a substrate for the second step, and a product of the second step may be a substrate for the third, and so on. Pathways of the present invention include, but are not limited to, the pyruvate metabolism pathway the lactate production pathway, the ethanol production pathway, the glycerol-production pathway, the nitrogen assimilation pathway, and the ammonium assimilation pathway.

The term "recombination" or "recombinant" refers to the physical exchange of DNA between two identical (homologous), or nearly identical, DNA molecules. Recombination can be used for targeted gene deletion or to modify the sequence of a gene. The term "recombinant microorganism" and "recombinant host cell" are used interchangeably herein and refer to microorganisms that have been genetically modified to express or over-express endogenous polynucleotides, or to express heterologous polynucleotides, such as those included in a vector, or which have a modification in expression of an endogenous gene.

By "expression modification" it is meant that the expression of the gene, or level of a RNA molecule or equivalent RNA molecules encoding one or more polypeptides or polypeptide subunits, or activity of one or more polypeptides or polypeptide subunits is up regulated or down-regulated, such that expression, level, or activity, is greater than or less than that observed in the absence of the modification.

In one aspect of the invention, genes or particular polynucleotide sequences are partially, substantially, or completely deleted, silenced, inactivated, or down-regulated in order to inactivate the enzymatic activity they encode. Complete deletions provide maximum stability because there is no opportunity for a reverse mutation to restore function. Alternatively, genes can be partially, substantially, or completely deleted, silenced, inactivated, or down-regulated by insertion, deletion, removal or substitution of nucleic acid sequences that disrupt the function and/or expression of the gene.

As used herein, the term "down-regulate" includes the deletion or mutation of a genetic sequence, or insertion of a disrupting genetic element, coding or non-coding, such that the production of a gene product is lessened by the deletion, mutation, or insertion. It includes a decrease in the expression level (i.e., molecular quantity) of an mRNA or protein. "Delete" or "deletion" as used herein refers to a removal of a genetic element such that a corresponding gene is completely prevented from being expressed. In some embodiments, deletion refers to a complete gene deletion. Down-regulation can also occur by engineering the repression of genetic elements by chemical or other environmental means, for example by engineering a chemically-responsive promoter element (or other type of conditional promoter) to control the expression of a desired gene product. Down-regulation can also occur through use of a weak promoter.

As used herein, the term "up-regulate" includes the insertion, reintroduction, mutation, or increased expression of a genetic sequence, such that the production of a gene product is increased by the insertion, reintroduction, or mutation. It includes an increase in the expression level (i.e., molecular quantity) of an mRNA or protein. "Insert" or "insertion" as used herein refers to an introduction of a genetic element such that a corresponding gene is expressed. Up-regulation can also occur by causing the increased expression of genetic elements through an alteration of the associated regulatory sequence. Up-regulation can occur by engineering the expression of genetic elements by chemical or other environmental means, for example by engineering a chemically-responsive promoter element (or other type of conditional promoter) to control the expression of a desired gene product. Up-regulation can also occur through use of a strong promoter.

As used herein, the term "glycerol-production pathway" refers to the collection of biochemical pathways that produce glycerol from DHAP. Components of the pathway consist of all substrates, cofactors, byproducts, intermediates, end-products, and enzymes in the pathway.

As used herein, the term "ethanol production pathway" refers the collection of biochemical pathways that produce ethanol from a carbohydrate source. Components of the pathway consist of all substrates, cofactors, byproducts, intermediates, end-products, and enzymes in the pathway.

As used herein, the term "nitrogen assimilation pathway" refers to the collection of biochemical pathways that result in the formation of organic nitrogen containing compounds from inorganic nitrogen compounds. Components of the pathway consist of all substrates, cofactors, byproducts, intermediates, end-products, and enzymes in the pathway.

As used herein, the term "ammonium assimilation pathway" refers to the collection of biochemical pathways that assimilate ammonia or ammonium ($NH_4^+$) into glutamate and/or glutamine. The ammonium assimilation pathway is part of the larger nitrogen assimilation pathway. Components of the pathway consist of all substrates, cofactors, byproducts, intermediates, end-products, and enzymes in the pathway.

As used herein, the term "glycolysis" or "glycolytic pathway" refers to the canonical pathway of basic metabolism in which a sugar such as glucose is broken down into more oxidized products, converting energy and compounds required for cell growth. Components of the pathway consist of all substrates, cofactors, byproducts, intermediates end-products, and enzymes in the pathway.

As used herein, the term "alcohol dehydrogenase" or "ADH" is intended to include the enzymes that catalyze the conversion of ethanol into acetylaldehyde. Very commonly, the same enzyme catalyzes the reverse reaction from acetaldehyde to ethanol, which is the direction more relevant to fermentation. Alcohol dehydrogenase includes those enzymes that correspond to EC 1.1.1.1 and 1.1.1.2 and exemplified by the enzymes disclosed in GenBank Accession No. U49975.

As used herein, the term "aldehyde dehydrogenase", "ALD" or "A LDH" is intended to include the enzymes that catalyze the oxidation of aldehydes. Aldehyde dehydrogenase enzymes include "acetaldehyde dehydrogenase", which catalyzes the conversion of acetaldehyde into acetyl-CoA. Very commonly, the same enzyme catalyzes the reverse reaction from acetyl-CoA to acetaldehyde, which is the direction more relevant to fermentation. Aldehyde dehydrogenase includes those enzymes that correspond to EC 1.2.1.3, 1.2.1.4 and 1.2.1.10.

As used herein, the term "glycerol-3-phosphate dehydrogenase" or "GPD" is intended to include those enzymes capable of converting dihydroxyacetone phosphate to glycerol-3-phosphate. GPD includes those enzymes that correspond to EC 1.1.1.8. In some embodiments, the GPD is GPD1 and/or GPD2 from *S. cerevisiae* (GDP1: SEQ ID NO: 4 and 5, GDP2: SEQ ID NO: 6 and 7).

As used herein, the term "glycerol-3-phosphate phosphatase" or "GPP" is intended to include those enzymes capable of converting glycerol-1-phosphate to glycerol. Glycerol-3-phosphate is intended to include those enzymes that correspond to EC 3.1.3.21. (GPP1: SEQ ID NO: 158 and 159, GPP2: SEQ ID NO 160 and 161)

As used herein, the term "formate dehydrogenase" or "FDH" is intended to include those enzymes capable of converting formate to bicarbonate (carbon dioxide). Formate dehydrogenase includes those enzymes that correspond to EC 1.2.1.43 and EC 1.2.1.2. In some embodiments, the FDH is from *S. cerevisiae* (FDH1: SEQ ID NO: 1 and 2, FDH2: SEQ ID NO: 3).

As used herein, the term "bifunctional" is intended to include enzymes that catalyze more than one biochemical reaction step. A specific example of a bifunctional enzyme used herein is an enzyme (adhE) that catalyzes both the alcohol dehydrogenase and acetaldehyde dehydrogenase reactions, and includes those enzymes that correspond to EC 1.2.1.10 and 1.1.1.1. In some embodiments, the bifunctional acetaldehyde-alcohol dehydrogenase is from *B. adolescentis* (adhE: SEQ ID NO: 12 and 13). In some embodiments, the bifunctional enzyme is a NADPH specific bifunctional acetaldehyde-alcohol dehydrogenase, and includes those enzymes that correspond to EC 1.2.1.10 and 1.1.1.2. In some embodiments, the NADPH specific bifunctional acetaldehyde-alcohol dehydrogenase is from *L. mesenteroides* (SEQ ID NO: 14 and 15) or *O. oenii* (SEQ ID NO: 16 and 17).

As used herein, the term "pyruvate formate lyase" or "PFL" is intended to include the enzymes capable of converting pyruvate to formate and acetyl-CoA. PFL includes those enzymes that correspond to EC 2.3.1.54 and exemplified by SEQ ID NO: 8 and 9.

As used herein, the term "PFL-activating enzymes" is intended to include those enzymes capable of aiding in the activation of PFL. PFL-activating enzymes include those enzymes that correspond to EC 1.97.1.4 and are exemplified by SEQ ID NO: 10 and 11.

As used herein, the term "glutamate dehydrogenase", "GDH", or "GLDH" is intended to include those enzymes that convert glutamate to α-ketoglutarate, as well as those enzymes that catalyze the reverse reaction. The glutamate dehydrogenase can be NADPH-dependent (e.g. GDH1 or GDH3 in S. cerevisiae). The glutamate dehydrogenase can be NADH-dependent (e.g. GDH2 in S. cerevisiae). Glutamate dehydrogenases include those enzymes that correspond to EC 1.4.1.2 and EC 1.4.1.4. Glutamate dehydrogenases include those enzymes that correspond to accession numbers: M10590, S66436, S 66039.1, U12980, NP_015020, NP_010066, S66039.1 and AAC04972. In some embodiments, the glutamate dehydrogenase is from S. cerevisiae (GDH1: SEQ ID NOs: 25 and 25; GDH2: SEQ ID NOs: 26 and 27; GDH3: SEQ ID NOs: 30 and 31.) or N. crassa (GDH2: SEQ ID NOs: 28 29).

As used herein, the term "glutamate synthase" or "GLT" is intended to include those enzymes that convert L-glutamine and 2-oxoglutarate to L-glutamate, as well as those enzymes that catalyze the reverse reaction. Glutamate synthases include those enzymes that correspond to EC 1.4.1.14 and EC 1.4.1.13. In some embodiments, the glutamate synthase is GLT1 from S. cerevisiae (SEQ ID NOs: 32 and 33; accession numbers: X89221 and NP_010110.1).

As used herein, the term "glutamine synthase", "glutamine synthetase", or "GLN" is intended to include those enzymes that convert glutamate to glutamine. Glutamine synthases include those enzymes that correspond to EC 6.3.1.2. In some embodiments, the glutamine synthase is GLN1 from S. cerevisiae (SEQ ID NOs: 34 and 35; accession numbers: M65157 and NP_015360.2).

As used herein, the term "urea-amido lyase" is intended to include those enzymes that convert urea to urea-1-carboxylate. Urea-amido lyases include those enzymes that correspond to EC 6.3.4.6. In some embodiments, the urea-amido lyase is DUR1/2 (DUR1,2) from S. cerevisiae (SEQ ID NOs: 36 and 37; accession numbers: M64926 and NP_009767.1)

As used herein, the term "urea transporter" is a membrane protein that transports urea across a cellular membrane. In some embodiments, the urea transporter is Dur3 or Dur4 from S. cerevisiae (DUR3: SEQ ID NOs: 38 and 39; accession numbers: AY693170 and NP_011847.1).

As used herein, the term "protease" is any enzyme that hydrolyzes the peptide bonds between amino acids together in a protein. An exoprotease is a protease that breaks the peptide bonds of terminal amino acids in a protein. An endoprotease is a protease that breaks the peptide bonds of non-terminal amino acids in a protein. Proteases include those enzymes that correspond to EC 3.4.23.41. Proteases include those enzymes that correspond to accession numbers: NP_001151278, NP_001150196, NP_001148706, NCU00338, XP_001908191, XP_369812, EU970094.1, NM_001156724, NM_001155234.1, XP_957809.2, XM_001908156.1, and XM_003717209.1. In some embodiments, the protease is from Z. mays (SEQ ID NOs: 40-45), N. crassa (SEQ ID NOs: 46-47), P. anserine (SEQ ID NOs: 48-49), or M. oryzae (SEQ ID NOs: 50-51).

As used herein, the term "glucoamylase" or "γ-amylase" refers to an amylase that acts on α-1,6-glycosidic bonds. Glucoamylases include those enzymes that correspond to EC 3.2.1.3. In some embodiments, the glucoamylase is S. fibuligera glucoamylase (glu-0111-CO) (SEQ ID NO: 162 and 163).

As used herein, the term "permease" refers to a membrane transport protein that facilitates the diffusion of a molecule through the use of passive transport in or out of a cell. In some embodiments, the permease is the amino acid permease GAP1 from S. cerevisiae. (SEQ ID NO: 52 and 53).

As used herein, the term "ammonium transporter" refers to permeases, and is intended to include the enzymes that are involved in the transport of ammonium and ammonia, and are exemplified by the S. cerevisiae MEP1, MEP2 and MEP3 enzymes (MEP 1: SEQ ID NOs: 18 and 19; MEP2: SEQ ID NOs: 20 and 21; MEP3: SEQ ID NOs: 22 and 23). Ammonium transporters include those enzymes that correspond to accession numbers: X77608, X83608, AY692775, NP_011636.3, NP_014257.1, and NP_015464.1.

As used herein, the term "URE2" refers to transcription factor known in the art by that name that represses the nitrogen catabolism of glutamate by controlling the transcription factor. URE2 is a regulator of GLN3. In some embodiments, the URE2 is from S. cerevisiae (SEQ ID NOs: 54 and 55).

As used herein, "AUA1" refers to a transcription factor known in the art by that name which is required for the negative regulation of Gap1. In some embodiments, the AUA1 is from S. cerevisiae (SEQ ID NOs: 56 and 57).

As used herein, "GLN3" refers to a transcription factor known in the art by that name that activates genes that are regulated by nitrogen catabolite metabolism. In some embodiments, the GLN3 is from S. cerevisiae (SEQ ID NOs: 156 and 157). The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a product in a fermentation process. A feedstock can contain nutrients other than a carbon source.

Biomass can include any type of biomass known in the art or described herein. The terms "lignocellulosic material," "lignocellulosic substrate" and "cellulosic biomass" mean any type of carbon containing feed stock including woody biomass, such as recycled wood pulp fiber, sawdust, hardwood, softwood, grasses, sugar-processing residues, agricultural wastes, such as, but not limited to, rice straw, rice hulls, barley straw, corn cobs, cereal straw, wheat straw, canola straw, oat straw, oat hulls, corn fiber, stover, succulents, agave, or any combination thereof.

The term "yield" is defined as the amount of product obtained per unit weight of raw material and may be expressed as gram product per gram substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product. For example, the theoretical yield for one typical conversion of glucose to ethanol is 0.51 g EtOH per 1 g glucose. As such, a yield of 4.8 g ethanol from 10 g of glucose would be expressed as 94% of theoretical or 94% theoretical yield.

The term "titer" is defined as the strength of a solution or the concentration of a substance in solution. For example, the titer of a product in a fermentation broth is described as gram of product in solution per liter of fermentation broth (g/L) or as g/kg broth.

As used herein, the term "flux" is the rate of flow of molecules through a metabolic pathway, akin to the flow of material in a process.

"Bacteria", or "eubacteria", refers to a domain of prokaryotic organisms. Bacteria include gram-positive (gram+) bacteria and gram-negative (gram−) bacteria.

"Yeast" refers to a domain of eukaryotic organisms that are unicellular fungi.

The terms "derivative" and "analog" refer to a polypeptide differing from the enzymes of the invention, but retaining essential properties thereof. Generally, derivatives and analogs are overall closely similar, and, in many regions, identical to the enzymes of the invention. The terms "derived from", "derivative" and "analog" when referring to enzymes of the invention include any polypeptides which retain at least some of the activity of the corresponding native polypeptide or the activity of its catalytic domain.

Derivatives of enzymes disclosed herein are polypeptides which may have been altered so as to exhibit features not found on the native polypeptide. Derivatives can be covalently modified by substitution (e.g. amino acid substitution), chemical, enzymatic, or other appropriate means with a moiety other than a naturally occurring amino acid (e.g., a detectable moiety such as an enzyme or radioisotope). Examples of derivatives include fusion proteins, or proteins which are based on a naturally occurring protein sequence, but which have been altered. For example, proteins can be designed by knowledge of a particular amino acid sequence, and/or a particular secondary, tertiary, and quaternary structure. Derivatives include proteins that are modified based on the knowledge of a previous sequence, natural or synthetic, which is then optionally modified, often, but not necessarily to confer some improved function. These sequences, or proteins, are then said to be derived from a particular protein or amino acid sequence. In some embodiments of the invention, a derivative must retain at least about 50% identity, at least about 60% identity, at least about 70% identity, at least about 80% identity, at least about 90% identity, at least about 95% identity, at least about 97% identity, or at least about 99% identity to the sequence the derivative is "derived from." In some embodiments of the invention, an enzyme is said to be derived from an enzyme naturally found in a particular species if, using molecular genetic techniques, the DNA sequence for part or all of the enzyme is amplified and placed into a new host cell.

"Isolated" from, as used herein, refers to a process whereby, using molecular biology techniques, genetic material is harvested from a particular organism often with the end goal of putting the general material into a non-native environment.

The term "percent identity", as known in the art, is a relationship between two or more polypeptide sequences or two or more polynucleotide sequences, as determined by comparing the sequences. In the an, "identity" also means the degree of sequence relatedness between polypeptide or polynucleotide sequences, as the case may be, as determined by the match between strings of such sequences.

As known in the art, "similarity" between two polypeptides is determined by comparing the amino acid sequence and conserved amino acid substitutes thereto of the polypeptide to the sequence of a second polypeptide.

"Identity" and "similarity" can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, N.J. (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid sequences or fragments thereof (isolated polynucleotides of the present invention) encode polypeptides that are at least about 70% to 75% identical to the amino acid sequences disclosed herein, at least about 80%, at least about 85%, or at least about 90% identical to the amino acid sequences disclosed herein, or at least about 95%, at least about 96%, at least about 97%, at least about 98%, at least about 99%, or at least about 100% identical to the amino acid sequences disclosed herein. Suitable nucleic acid fragments are at least about 70%, at least about 75%, or at least about 80% identical to the nucleic acid sequences disclosed herein, at least about 80%, at least about 85%, or at least about 900/% identical to the nucleic acid sequences disclosed herein, or at least about 95%, at least about 96%, at least about 97%, at least about 98%, at least about 99%, or at least about 100% identical to the nucleic acid sequences disclosed herein. Suitable nucleic acid fragments not only have the above identities/similarities but typically encode a polypeptide having at least about 50 amino acids, at least about 100 amino acids, at least about 150 amino acids, at least about 200 amino acids, or at least about 250 amino acids.

Codon Optimization

In some embodiments of the present invention, exogenous genes may be codon-optimized in order to express the polypeptide they encode most efficiently in the host cell. Methods of codon optimization are well known in the art. (See, e.g. Welch et al. "Designing genes for successful protein expression." *Methods Enymol.* 2011, 498:43-66.)

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The Codon Adaptation Index is described in more detail in Sharp et al., "The Codon Adaptation Index: a Measure of Directional Synonymous Codon Usage Bias, and Its Potential Applications." *Nucleic Acids Research* (1987) 15: 1281-1295, which is incorporated by reference herein in its entirety.

A codon optimized sequence may be further modified for expression in a particular organism, depending on that organism's biological constraints. For example, large runs of "As" or "Ts" (e.g., runs greater than 3, 4, 5, 6, 7, 8, 9, or 10 consecutive bases) can effect transcription negatively. Therefore, it can be useful to remove a run by, for example, replacing at least one nucleotide in the run with another nucleotide. Furthermore, specific restriction enzyme sites may be removed for molecular cloning purposes by replacing at least one nucleotide in the restriction site with another nucleotide. Examples of such restriction enzyme sites include PacI, AscI, BamHI, BglII, EcoRI and XhoI. Additionally, the DNA sequence can be checked for direct repeats, inverted repeats and mirror repeats with lengths of about 5, 6, 7, 8, 9 or 10 bases or longer. Runs of "As" or "Ts", restriction sites and/or repeats can be modified by replacing at least one codon within the sequence with the "second best" codons, i.e., the codon that occurs at the second highest frequency for a particular amino acid within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six triplets each, whereas tryptophan and methionine are coded for by just one triplet. This degeneracy allows for DNA base composition to vary over a wide range without altering the amino acid sequence of the proteins encoded by the DNA.

TABLE 1

The Standard Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA Ter | TGA Ter |
| | TTG Leu (L) | TCG Ser (S) | TAG Ter | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Host Cells

In some embodiments of the invention, the host cell is a eukaryotic microorganism. In some embodiments, the host cell is a yeast. In some embodiments, the host cell is able to digest and ferment cellulose. In some embodiments, the host cell is from the genus *Saccharomyces*. In some embodiments, the host cell is *Saccharomyces cerevisiae*.

In some embodiments, the host cells of the invention are cultured at a temperature above about 20° C., above about 25° C., above about 27° C., above about 30° C., above about 33° C., above about 35° C., above about 37° C., above about 40° C., above about 43° C., above about 45° C., or above about 47° C. In some embodiments, the host cells of the invention contain genetic constructs that lead to the down-regulation of one or more genes encoding a polypeptide at least about 80%, at least about 85%, at least about 90%, at least about 95%, at least about 96%, at least about 97%, at least about 98%, at least about 99%, or about 100% identical to one or more of the polypeptides encoded SEQ ID NOs: 2, 5, 7, 25, 31, 55, 57, 159 and 161, and the polynucleotide sequence encoded by SEQ ID NO: 3. In some embodiments, the host cells of the invention contain genetic constructs that lead to the expression or up-regulation of a polypeptide encoding the activity associated with EC Nos.: 1.1.1.8, 3.1.3.21, 1.2.1.43, 1.2.1.2, 1.4.1.2, and 1.4.1.4.

In some embodiments, the host cells of the invention contain genetic constructs that lead to the expression or up-regulation of one or more genes encoding a polypeptide at least about 80%, at least about 85%, at least about 90%, at least about 95%, at least about 96%, at least about 97%, at least about 98%, at least about 99%, or about 100% identical to one or more of the polypeptides encoded by SEQ ID NOs: 9, 11, 13, 15, 17, 19, 21, 23, 27, 33, 35, 37, 39, 41, 43, 45, 47, 49, 51, 53, 157, and 163. In some embodiments, the host cells of the invention contain genetic constructs that lead to the expression or up-regulation of a polypeptide encoding the activity associated with EC Nos.: 1.1.1.1, 1.1.1.2, 1.2.1.3, 1.2.1.4, 1.2.1.10, 2.3.1.54, 1.97.1.4, 1.4.1.2, 1.4.1.4, 1.1.1.14, 1.4.1.13, 6.3.1.2, 6.3.4.6, and 3.2.1.3.

In some embodiments, bifunctional acetaldehyde-alcohol dehydrogenase is up-regulated. In some embodiments, the up-regulated bifunctional acetaldehyde-alcohol dehydrogenase is from an enzyme that corresponds to an EC number selected from the group consisting of: EC 1.2.1.0 and 1.1.1.1. In some embodiments, the bifunctional acetaldehyde-alcohol dehydrogenase is a NADPH dependent bifunctional acetaldehyde-alcohol dehydrogenase selected from a group of enzymes having the following Enzyme Commission Numbers: EC 1.2.1.10 and 1.1.1.2. In some embodiments, the bifunctional acetaldehyde-alcohol dehydrogenase corresponds to a polypeptide selected from the group consisting of SEQ ID NOs: 13, 15, and 17. In some embodiments, the bifunctional acetaldehyde-alcohol dehydrogenase is adhE.

In some embodiments, pyruvate formate lyase is up-regulated. In some embodiments, the up-regulated pyruvate formate lyase is from an enzyme that corresponds to EC 2.3.1.54. In some embodiments, the pyruvate formate lyase corresponds to a polypeptide encoded by SEQ ID NO: 2. In some embodiments, pyruvate formate lyase activating enzyme is up-regulated. In some embodiments, the up-regulated pyruvate formate lyase activating enzyme is from an enzyme that corresponds to EC 1.97.1.4. In some embodiments, the pyruvate formate lyase activating enzyme corresponds to a polynucleotide encoded by SEQ ID NO: 3.

In some embodiments, glutamate dehydrogenase is up-regulated. In some embodiments, the glutamate dehydrogenase that is up-regulated is NADH-dependent. In some embodiments, the up-regulated glutamate dehydrogenase corresponds to EC 1.4.1.2. In some embodiments, glutamate dehydrogenase from *S. cerevisiae* is up-regulated. In some embodiments, the glutamate dehydrogenase that is up-regulated is from *S. cerevisiae* is GDH2 and corresponds to a polypeptide corresponding to SEQ ID NO: 29. In some embodiments, glutamate synthase is up-regulated. In some embodiments, the up-regulated glutamate synthase corresponds to EC 1.4.1.14. In some embodiments, glutamate synthase from *S. cerevisiae* is up-regulated. In some embodiments, the glutamate dehydrogenase that is up-regulated is from *S. cerevisiae* is GLT1 and corresponds to a polypeptide corresponding to SEQ ID NO: 33. In some embodiments, glutamine synthase is up-regulated. In some embodiments, the up-regulated glutamine synthase corresponds to EC 6.3.1.2. In some embodiments, glutamine synthase from *S. cerevisiae* is up-regulated. In some embodiments, the glutamine dehydrogenase that is up-regulated is from *S. cerevisiae* is GLN1 and corresponds to a polypeptide corresponding to SEQ ID NO: 35.

In some embodiments, a urea-amido lyase is up-regulated. In some embodiments, the up-regulated urea-amido lyase corresponds to EC 6.3.4.6. In some embodiments, urea-amido lyase from *S. cerevisiae* is up-regulated. In some embodiments, the urea-amido lyase that is up-regulated is from *S. cerevisiae* is DUR1/2 and corresponds to a polypeptide corresponding to SEQ ID NO: 37.

In some embodiments, a protease is up-regulated. In some embodiments, the up-regulated protease corresponds to EC 3.4.23.41. In some embodiments, the protease is an endoprotease. In some embodiments, the protease is an exoprotease. In some embodiments, a protease from *Z. mays, N. crassa, P. anserine,* or *M. oryzae* is up-regulated. In some embodiments, the protease that is up-regulated corresponds to a polypeptide corresponding to SEQ ID NOs: 41, 43, 45, 47, 49 or 51. In some embodiments, a permease is up-regulated. In some embodiments, a permease from *S. cerevisiae* is up-regulated. In some embodiments, the permease that is up-regulated is GAP1 and corresponds to a polypeptide corresponding to SEQ ID NO: 53.

In some embodiments, a glucoamylase is up-regulated. In some embodiments, the up-regulated glucoamylase corresponds to EC 3.2.1.3. In some embodiments, a glucoamylase from *S. fibuligera* is up-regulated. In some embodiments, the glucoamylase from *S. fibuligera* that is up-regulated corresponds to a polypeptide corresponding to SEQ ID NO: 163.

In some embodiments, an ammonium transporter is up-regulated. In some embodiments, an ammonium transporter from *S. cerevisiae* is up-regulated. In some embodiments, the ammonium transporter that is up-regulated is MEP1, MEP2, or MEP3 from *S. cerevisiae* and corresponds to a polypeptide corresponding to SEQ ID NOs: 19, 21, and 23. In some embodiments, a urea transporter is up-regulated. In some embodiments, a urea transporter from is from *S. cerevisiae*. In some embodiments, the urea transporter that is up-regulated is DUR3 or DUR4 from *S. cerevisiae* and corresponds to a polypeptide corresponding to SEQ ID NOs: 39.

In some embodiments, glycerol-3-phosphate dehydrogenase is down-regulated. In some embodiments, the down-regulated Gpd is from an enzyme that corresponds to EC 1.1.1.8. In some embodiments, the glycerol-3-phosphate dehydrogenase is selected from the group consisting of glycerol-3-phosphate dehydrogenase 1 ("Gpd1"), glycerol-3-phosphate dehydrogenase 2 ("Gpd2"), and combinations thereof. In some embodiments, the Gpd1 is from *S. cerevisiae* and corresponds to a polypeptide encoded by SEQ ID NO: 5. In some embodiments, the Gpd2 is from *S. cerevisiae* and corresponds to a polypeptide encoded by SEQ ID NO: 7. In some embodiments, formate dehydrogenase is down-regulated. In some embodiments, the down-regulated formate dehydrogenase corresponds to an EC number selected from the group consisting of: EC 1.2.1.43 and EC 1.2.1.2. In some embodiments, formate dehydrogenase from *S. cerevisiae* is down-regulated. In some embodiments, the formate dehydrogenase from *S. cerevisiae* corresponds to a polypeptide corresponding to SEQ ID NO: 2 or a polynucleotide corresponding to SEQ ID NO: 3. In some embodiments, glycerol-3-phosphate phosphatase is down-regulated. In some embodiments, the down-regulated glycerol-3-phosphate phosphatase corresponds to EC 3.1.3.21. In some embodiments, the down-regulated glycerol-3-phosphate phosphatase corresponds to a polynucleotide corresponding to SEQ ID NOs 158 or 160 or a polypeptide corresponding to SEQ ID NOs 159 or 161.

In some embodiments, glutamate dehydrogenase is down-regulated. In some embodiments, the glutamate dehydrogenase that is down-regulated is NADPH-dependent. In some embodiments, the down-regulated glutamate dehydrogenase corresponds to EC 1.4.1.4. In some embodiments, glutamate dehydrogenase that is down-regulated is from *S. cerevisiae*. In some embodiments, the glutamate dehydrogenase is from *S. cerevisiae* is GDH1 and corresponds to a polypeptide corresponding to SEQ ID NO: 25.

In some embodiments, a regulatory element is down-regulated. In some embodiments, the regulatory element that is down-regulated is from *S. cerevisiae*. In some embodiments, the regulatory element from *S. cerevisiae* is Ure2 and corresponds to a polypeptide corresponding to SEQ ID NO: 55. In some embodiments, the regulatory element from *S. cerevisiae* is Aua1 and corresponds to a polypeptide corresponding to SEQ ID NO: 57.

In some embodiments, bifunctional acetaldehyde-alcohol dehydrogenase (AdhE), *B. adolescentis* pyruvate formate lyase, and *B. adolescentis* pyruvate formate lyase activating enzyme are up-regulated, and Gpd1 and Gpd2 are down-regulated. In some embodiments, AdhE, *B. adolescentis* pyruvate formate lyase, and *B. adolescentis* pyruvate formate lyase activating enzyme are up-regulated, and Gpd1, Gpd2, Fdh1 and Fdh2 are down-regulated. In some embodiments, AdhE, *B. adolescentis* pyruvate formate lyase, and *B. adolescentis* pyruvate formate lyase activating enzyme are up-regulated, Gpd1, Gpd2, Fdh1 and Fdh2 are down-regulated, Gil1 is expressed under the control of the GPID2 promoter, and GPD2 is expressed under the control of the GPD1 promoter. In some embodiments, AdhE, *B. adolescentis* pyruvate formate lyase, and *B. adolescentis* pyruvate formate lyase activating enzyme are up-regulated, Gpd1, Gpd2, Fdh1, Fdh2, Gdh1 are down-regulated, GPD1 is expressed under the control of the GPD2 promoter, and GPD2 is expressed under the control of the GPD1 promoter. In some embodiments, AdhE, *B. adolescentis* pyruvate formate lyase, and *B. adolescentis* pyruvate formate lyase activating enzyme, and Glt1 are up-regulated, Gpd1, Gpd2, Fdh1, Fdh2, Gdh1 are down-regulated, GPD1 is expressed under the control of the (GPD2 promoter, and GPD2 is expressed under the control of the GPD1 promoter. In some embodiments, AdhE, *B. adolescentis* pyruvate formate lyase, and *B. adolescentis* pyruvate formate lyase activating enzyme, and Gln are up-regulated, Gpd1, Gpd2, Fdh1, Fdh2, Gdh1 are down-regulated, GPD1 is expressed under the control of the GPD2 promoter, and GPD2 is expressed under the control of the GPD1 promoter. In some embodiments, AdhE, *B. adolescentis* pyruvate formate lyase, and *B. adolescentis* pyruvate formate lyase activating enzyme, Gln1 and Glt1 are up-regulated, Gpd1, Gpd2, Fdh1, Fdh2, Gdh1 are down-regulated, GPD1 is expressed under the control of the GPD2 promoter, and GPD2 is expressed under the control of the GPD1 promoter. In some embodiments, the regulatory element Ure2 is down-regulated. In some embodiments, the regulatory element Aua1 is down-regulated. In some embodiments, Gln3 is up-regulated.

In some embodiments, AdhE, *B. adolescentis* pyruvate formate lyase, and *B. adolescentis* pyruvate formate lyase activating enzyme are up-regulated, and Gpd2, Fdh1, and Fdh2 are down-regulated. In some embodiments, AdhE, *B. adolescentis* pyruvate formate lyase, and *B. adolescentis* pyruvate formate lyase activating enzyme are up-regulated, and Gpd2, Fdh1, Fdh2, and Gdh1 are down-regulated. In some embodiments, AdhE, *B. adolescentis* pyruvate formate lyase, and *B. adolescentis* pyruvate formate lyase activating enzyme are up-regulated, and Gpd1, Fdh1, and Fdh2 are down-regulated. In some embodiments, AdhE, *B. adolescentis* pyruvate formate lyase, and *B. adolescentis* pyruvate formate lyase activating enzyme are up-regulated, and Gpd1, Fdh1, Fdh2, and Gdh1 are down-regulated. In some embodiments, Dur1/2 is additionally expressed. In some embodiments, Dur1/2 is expressed from the TEF2 promoter. In some embodiments, Dur1/2 is expressed from the HXT7 promoter. In some embodiments, Dur1/2 is expressed from the GPM1 promoter. In some embodiments, Dur1/2 is expressed from the ADH1 promoter. In some embodiments, Dur1/2 is expressed from the HXT7/TEF2 promoters. In some embodiments, Gln3 is up-regulated. In some embodiments, GPD1 is expressed from the GPD2 promoter. In some embodiments, GPD2 is expressed from a GPD1 promoter.

Ethanol Production

For a microorganism to produce ethanol most economically, it is desired to produce a high yield. In one embodiment, the only product produced is ethanol. Extra products lead to a reduction in product yield and an increase in capital and operating costs, particularly if the extra products have little or no value. Extra products also require additional capital and operating costs to separate these products from ethanol.

Ethanol production can be measured using any method known in the art. For example, the quantity of ethanol in fermentation samples can be assessed using HPLC analysis. Additionally, many ethanol assay kits are commercially available, for example, alcohol oxidase enzyme based assays. Methods of determining ethanol production are within the scope of those skilled in the art from the teachings herein.

In some embodiments of the invention where redirected carbon flux generates increased ethanol production, the ethanol output can be improved by growth-coupled selection. For example, continuous culture or serial dilution cultures can be performed to select for cells that grow faster and/or produce ethanol (or any desired product) more efficiently on a desired feedstock.

One embodiment of the present invention relates to a method of producing ethanol using a microorganism described herein wherein the microorganism is cultured in the presence of a carbon containing feedstock for sufficient time to produce ethanol and, optionally, extracting the ethanol. In some embodiments, nitrogen is added to the culture containing the recombinant microorganism and the feedstock.

Ethanol may be extracted by methods known in the art. (See, e.g., U.S. Appl. Pub. No. 2011/0171709, which is incorporated herein by reference in its entirety.)

Another embodiment of the present invention relates to a method of producing ethanol using a co-culture composed of at least two microorganisms in which at least one of the organisms is an organism described herein, and at least one of the organisms is a genetically distinct microorganism. In some embodiments, the genetically distinct microorganism is a yeast or bacterium. In some embodiments the genetically distinct microorganism is any organism from the genus *Issatchenkia, Pichia, Clavispora, Candida, Hansemula, Kluyveromyces, Saccharomyces, Trichoderma, Thermoascus, Escherichia, Closiridium, Caldicellulosiruptor, Thermoanaerobacter* and *Thermoanaerobacierium*.

In some embodiments, the recombinant microorganism produces about 2% to about 3% higher ethanol titer than a wildtype, non-recombinant organism; at least about 1% to at least about 2% higher ethanol titer than a wildtype, non-recombinant organism; at least about 1% to at least about 5% higher ethanol titer than a wildtype, non-recombinant organism; at least about 1% to at least about 7% higher ethanol titer than a wildtype, non-recombinant organism; at least about 1% to at least about 10% higher ethanol titer than a wildtype, non-recombinant organism; at least about 1% to at least about 15% higher ethanol titer than a wildtype, non-recombinant organism; at least about 1% to at least about 20% higher ethanol titer than a wildtype, non-recombinant organism; at least about 1% to at least about 30% higher ethanol titer than a wildtype, non-recombinant organism; at least about 1% to at least about 50% higher ethanol titer than a wildtype, non-recombinant organism; at least about 1% to at least about 75% higher ethanol titer than a wildtype, non-recombinant organism; at least about 1% to at least about 100% higher ethanol titer than a wildtype, non-recombinant organism. In some embodiments, the recombinant microorganism produces at least about 0.5 g/L ethanol to at least about 2 g/L ethanol, at least about 0.5 g/L ethanol to at least about 3 g/L ethanol, at least about 0.5 g/L ethanol to at least about 5 g/L ethanol, at least about 0.5 g/L ethanol to at least about 7 g/L ethanol, at least about 0.5 g/L ethanol to at least about 10 g/L ethanol, at least about 0.5 g/L ethanol to at least about 15 g/L ethanol, at least about 0.5 g/L ethanol to at least about 20 g/L ethanol, at least about 0.5 g/L ethanol to at least about 30 g/L ethanol, at least about 0.5 g/L ethanol to at least about 40 g/L ethanol, at least about 0.5 g/L ethanol to at least about 50 g/L ethanol, at least about 0.5 g/L ethanol to at least about 75 g/L ethanol, at least about 0.5 g/L ethanol to at least about 99 g/L ethanol, at least about 0.5 g/L ethanol to at least about 125 g/L ethanol, or at least about 0.5 g/L to at least about 150 g/L ethanol per at least about 24 hour, at least about 48 hour, or at least about 72 hour incubation on a carbon-containing feed stock, such as corn mash.

In some embodiments, the recombinant microorganism produces ethanol at least about 55% to at least about 75% of theoretical yield, at least about 50% to at least about 80% of theoretical yield, at least about 45% to at least about 85% of theoretical yield, at least about 40% to at least about 90% of theoretical yield, at least about 35% to at least about 95% of theoretical yield, at least about 30% to at least about 99% of theoretical yield, or at least about 25% to at least about 99% of theoretical yield. In some embodiments, methods of producing ethanol can comprise contacting a biomass feedstock with a host cell or co-culture of the invention and additionally contacting the biomass feedstock with externally produced saccharolytic enzymes. In some embodiments, the host cells are genetically engineered (e.g., transduced, transformed, or transfected) with the polynucleotides encoding saccharolytic enzymes.

An "amylolytic enzyme" can be any enzyme involved in amylase digestion, metabolism and/or hydrolysis. The term "amylase" refers to an enzyme that breaks starch down into sugar. Amylase is present in human saliva, where it begins the chemical process of digestion. Foods that contain much starch but little sugar, such as rice and potato, taste slightly sweet as they are chewed because amylase turns some of their starch into sugar in the mouth. The pancreas also makes amylase (α-amylase) to hydrolyse dietary starch into disaccharides and trisaccharides which are converted by other enzymes to glucose to supply the body with energy. Plants and some bacteria also produce amylase. All amylases are glycoside hydrolases and act on α-1,4-glycosidic bonds. Some amylases, such as γ-amylase (glucoamylase), also act on α-1,6-glycosidic bonds. Amylase enzymes include α-amylase (EC 3.2.1.1), β-amylase (EC 3.2.1.2), and γ-amylase (EC 3.2.1.3). The α-amylases are calcium metalloenzymes, unable to function in the absence of calcium. By acting at random locations along the starch chain, α-amylase breaks down long-chain carbohydrates, ultimately yielding maltotriose and maltose from amylose, or maltose, glucose and "limit dextrin" from amylopectin. Because it can act anywhere on the substrate, α-amylase tends to be faster-acting than β-amylase. In animals, it is a major digestive enzyme and its optimum pH1 is about 6.7-7.0. Another form of amylase, β-amylase is also synthesized by bacteria, fungi, and plants. Working from the non-reducing end, β-amylase catalyzes the hydrolysis of the second α-1,4 glycosidic bond, cleaving off two glucose units (maltose) at a time. Many microbes produce amylase to degrade extracellular starches. In addition to cleaving the last α(1-4) glycosidic linkages at the nonreducing end of amylose and amylopectin, yielding glucose, γ-amylase will cleave α(1-6) glycosidic linkages. Another amylolytic enzyme is alpha-glucosidase that acts on maltose and other short malto-oligosaccharides produced by alpha-, beta-, and gamma-amylases, converting them to glucose. Another amylolytic enzyme is pullulanase. Pullulanase is a specific kind of glucanase, an amylolytic exoenzyme, that degrades pullulan. Pullulan is regarded as a chain of maltotriose units linked by alpha-1,6-glycosidic bonds. Pullulanase (EC 3.2.1.41) is also known as pullulan-6-glucanohydrolase (debranching enzyme). Another amylolytic enzyme, isopullulanase, hydrolyses pullulan to isopanose (6-alpha-maltosylglucose). Isopullulanase (EC 3.2.1.57) is also known as pullulan 4-glucanohydrolase. An "amylase" can be any enzyme involved in amylase digestion, metabolism and/or hydrolysis, including α-amylase, β-amylase, glucoamylase, pullulanase, isopullulanase, and alpha-glucosidase.

In some embodiments, the recombinant microorganisms of the invention further comprise one or more native and/or heterologous enzymes which encodes a saccharolytic enzyme, including amylases, cellulases, hemicellulases, cellulolytic and amylolytic accessory enzymes, inulinases, levanases, and pentose sugar utilizing enzymes. In one aspect, the saccharolytic enzyme is an amylase, where the amylase is selected from *H. grisea*, *T. aurantiacus*, *T. emersonii*, *T. reesei*, *C. lacteus*, *C. formosanus*, *N. takasagoensis*, *C. acinaciformis*, *M. darwinensis*, *V. walkeri*, *S. flidigera*, *C. luckowense R. speratus*, *Thermobfida fusca*, *Clostridum thermocellum*, *Clostridium cellulolyticum*, *Clostridum josni*, *Bacillus pumilis*, *Cellulomonas fimi*, *Saccharophagus degradans*, *Piromyces equii*, *Neocallimastir patricarum* or *Arabidopsis thaliana*. In another aspect, the saccharolytic enzyme is a glucoamylase (glu-0111-CO) from *S. fibuligera*.

The term "xylanolytic activity" is intended to include the ability to hydrolyze glycosidic linkages in oligopentoses and polypentoses. The term "xylanase" is the name given to a class of enzymes which degrade the linear polysaccharide beta-1,4-xylan into xylose, thus breaking down hemicellulose, one of the major components of plant cell walls. As such, it plays a major role in micro-organisms thriving on plant sources (mammals, conversely, do not produce xylanase). Additionally, xylanases are present in fungi for the degradation of plant matter into usable nutrients. Xylanases include those enzymes that correspond to E.C. Number 3.2.1.8. A "xylose metabolizing enzyme" can be any enzyme involved in xylose digestion, metabolism and/or hydrolysis, including a xylose isomerase, xylulokinase, xylose reductase, xylose dehydrogenase, xylitol dehydrogenase, xylonate dehydratase, xylose transketolase, and a xylose transaldolase protein.

The term "pectinase" is a general term for enzymes, such as pectolyase, pectozyme and polygalacturonase, commonly referred to in brewing as pectic enzymes. These enzymes break down pectin, a polysaccharide substrate that is found in the cell walls of plants. One of the most studied and widely used commercial pectinases is polygalacturonase. Pectinases are commonly used in processes involving the degradation of plant materials, such as speeding up the extraction of fruit juice from fruit, including apples and sapota. Pectinases have also been used in wine production since the 1960s.

A "saccharolytic enzyme" can be any enzyme involved in carbohydrate digestion, metabolism and/or hydrolysis, including amylases, cellulases, hemicellulases, cellulolytic and amylolytic accessory enzymes, inulinases, levanases, and pentose sugar utilizing enzymes.

A "pentose sugar utilizing enzyme" can be any enzyme involved in pentose sugar digestion, metabolism and/or hydrolysis, including xylanase, arabinase, arabinoxylanase, arabinosidase, arabinofuranosidase, arabinoxylanase, arabinosidase, and arabinofuranosidase, arabinose isomerase, ribulose-5-phosphate 4-epimerase, xylose isomerase, xylulokinase, xylose reductase, xylose dehydrogenase, xylitol dehydrogenase, xylonate dehydratase, xylose transketolase, and/or xylose transaldolase.

Glycerol Production

In some embodiments of the invention where redirected carbon flux generates increased ethanol production, the glycerol output can be decreased by growth-coupled selection. For example, continuous culture or serial dilution cultures can be performed to select for cells that produce less glycerol on a desired feedstock. Glycerol can be measured, for example, by HPLC analysis of metabolite concentrations.

In some embodiments, the recombinant microorganism produces at least about 20% to at least about 30% less glycerol than a wildtype, non-recombinant organism; at least about 30% to at least about 50% less glycerol than a wildtype, non-recombinant organism; at least about 40% to at least about 60% less glycerol than a wildtype, non-recombinant organism; at least about 50% to at least about 70% less glycerol than a wildtype, non-recombinant organism; at least about 60% to at least about 80% less glycerol than a wildtype, non-recombinant organism; at least about 70% to at least about 90% less glycerol than a wildtype, non-recombinant organism; at least about 75% to at least about 95% less glycerol than a wildtype, non-recombinant organism; at least about 70% to at least about 99% less glycerol than a wildtype, non-recombinant organism; at least about 15% to at least about 30% less glycerol than a wildtype, non-recombinant organism; at least about 10% to at least about 40% less glycerol than a wildtype, non-recombinant organism; at least about 10% to at least about 50% less glycerol than a wildtype, non-recombinant organism; at least about 10% to at least about 60% less glycerol than a wildtype, non-recombinant organism, at least about 10% to at least about 70% less glycerol than a wildtype, non-recombinant organism; at least about 10% to at least about 80% less glycerol than a wildtype, non-recombinant organism; at least about 10% to at least about 90% less glycerol than a wildtype, non-recombinant organism; at least about 10% to at least about 99% less glycerol than a wildtype, non-recombinant organism; at least about 10% to at least about 100% less glycerol than a wildtype, non-recombinant organism; at least about 5% to at least about 100% less glycerol than a wildtype, non-recombinant organism; at least about 1% to at least about 100% less glycerol than a wildtype, non-recombinant organism. In some embodiments, the recombinant microorganism produces no glycerol. In some embodiments, the recombinant microorganism has a growth rate at least about 1/2 to at least about equal to the growth rate of a wildtype, non-recombinant organism, at least about 1/4 to at least about equal to the growth rate of a wildtype, non-recombinant organism, at least about 1/8 to at least about equal to the growth rate of a wildtype, non-recombinant organism, at least about 1/10to at least about equal to the growth rate of a wildtype, non-recombinant organism, at least about 1/25 to at least about equal to the growth rate of a wildtype, non-recombinant organism, at least about 1/50 to at least about equal to the growth rate of a wildtype, non-recombinant organism or at least about 1/100 th to at least about equal to the growth rate of a wildtype, non-recombinant organism.

A wildtype-non-recombinant organism produces glycerol at a rate of at least about 8-11 mM glycerol per gram dry cell weight (DCW) during anaerobic growth. In some embodiments, glycerol production is reduced to a rate of between 1-10 mM glycerol per gram dry cell weight during anaerobic growth.

EXAMPLES

Strains used in the following examples were created using Mascoma Assemblies ("MAs"). Schematic diagrams of the MAs can be seen in FIGS. 6-44. Plasmids used to make the MAs can be seen in FIGS. 45-68 and Table 2. Primers used to create the MAs can be seen in Table 3 below and in SEQ ID NOs: 66-155. Strains used in the invention can be seen in Table 4 below. For a general description of molecular methods that could be used to create the strains, see U.S. Application No. 61/728,450, which is incorporated herein by reference.

TABLE 2

Plasmids used to make the MAs.

| Plasmid ID | Description |
| --- | --- |
| pMU2873 | AGTEF pro-KAN-AGTEF ter/HXT2 pro-TDK-ACT1 ter |
| pMU2879 | AGTEF pro-cloNAT-AGTEF ter/HXT2 pro-TDK-ACT1 ter |
| pMU2908 | PGK1 pro-S. cerevisiae GDH2-ENO1 ter |
| pMU2909 | ADH1 pro-S. cerevisiae GDH2-PDC1 ter |
| pMU2911 | ADH1 pro-GLN1-PDC1 ter |
| pMU2913 | PGK1 pro-GLT1-ENO1 ter |
| pMU3409 | TEF2 pro-DUR1,2-ADH3 ter |
| pMU3410 | HXT7 pro-DUR1,2-PMA1t |
| pMU3411 | ADH1 pro-DUR1,2-PDC1 ter |
| pMU3459 | ADH1 pro-DUR3-PDC1 ter |
| pMU3460 | ADH1 pro-MEP1-PDC1 ter |
| pMU3461 | ADH1 pro-MEP2-PDC1 ter |
| pMU3463 | ADH1 pro-GAP1-PDC1 ter |
| pMU3464 | TEF2 pro-DUR3-ADH3 ter |
| pMU3465 | TEF2 pro-MEP1-ADH3 ter |
| pMU3466 | TEF2 pro-MEP2-ADH3 ter |
| pMU3468 | TEF2 pro-GAP1-ADH3 ter |
| pMU3471 | TPI pro-DUR3-FBA1 ter |
| PMU3472 | TPI pro-MEP1-FBA1 ter |
| pMU3473 | TPI pro-MEP2-FBA1 ter |
| pMU3475 | TPI pro-GAP1-FBA1 ter |
| pMU3597 | ADH1 pro-N. crassa GDH2-PDC1 ter |
| pMU3605 | ADH1 pro-MEP3-PDC1 ter |
| pMU3606 | TEF2 pro-MEP3-ADH3ter |
| pMU3607 | TPI1 pro-MEP3-FBA1 ter |

TABLE 3

Primers used to create MAs.

| SEQ ID | Primer | Sequence | Description |
| --- | --- | --- | --- |
| 66 | X14961 | gcagttaccttttagcacccaac | 5' GDH1 5' flank |
| 67 | X14966 | ggtgtaggtaagcagaatgaggag | 3' GDH1 3' flank |

TABLE 3-continued

Primers used to create MAs.

| SEQ ID | Primer | Sequence | Description |
|---|---|---|---|
| 68 | X15464 | GTCCATGTAAAATGATTGCTCCAATGATTG AAAGAGGTTTAGACATTGGCTCTTCATTG | ENOt + PDC1t |
| 69 | X15465 | ctaagctcaatgaagagccaatgtctaaac ctctttcaatcattggagcaatcatttta | PDC1t + ENOt |
| 70 | X18846 | gtccatgtaaaatgattgctccaatgattg aaaagcacgcagcacgctgtatttacgtat | FCY3' + PDC1t |
| 71 | X18847 | AATTAAATACGTAAATACAGCGTGCTGCGT GCTTTTCAATCATTGGAGCAATCATTTTA | PDC1t + FCY3' |
| 72 | X18858 | agccagcttaaagagttaaaaatttcatag ctactacttattcccttcgagattatact | pTPI + FCY5' |
| 73 | X18859 | GTTCCTAGATATAATCTCGAAGGGAATAAG GTATAGCTATGAAATTTTTAACTCTTTAA | FCY5' + pTPI |
| 74 | X18860 | acatcatcttttaacttgaatttattctct agcagcacgcagcacgctgtatttacgtat | FCY3' + FBA1t |
| 75 | X18861 | AATTAAATACGTAAATACAGCGTGCTGCGT GCTGCTAGAGAATAAATTCAAGTTAAAAG | FBA1t + FCY3' |
| 76 | X18869 | AGATCCTGTGGTAGTGCTGTCTGAACAGAA | FCY3' + 2kb |
| 77 | X18955 | ataaaattaaatacgtaaatacagcgtgct gcgtgctcgattttttctaaaccgtgga | pADH1 + FCY3'rev |
| 78 | X19513 | acttggtgcggtccatgtaaaatgattgct ccaatgattgaaaatgaggaagaaatccaa | ADH3t + PDC1t |
| 79 | X19514 | TGAAGGTCATTAGGATTTGGATTTCTTCCT CATTTTCAATCATTGGAGCAATCATTTTAC | PDC1t + ADH3t |
| 80 | X19551 | agccagcttaaagagttaaaaatttcatag ctagggcgccataaccaaggtatctatag | pTEF2 + FCY5' |
| 81 | X19552 | TGGCGGTCTATAGATACCTTGGTTATGGCG CCCTAGCTATGAAATTTTTAACTCTTTAAG | FCY5' + pTEF2 |
| 82 | X19721 | aaagaaatgtcagagccagaatttcaacaa gctaagctttctaactgatctatccaaaa | pPGK + GDH15' |
| 83 | X19722 | TTTTCAGTTTTGGATAGATCAGTTAGAAAG CTTAGCTTGTTGAAATTCTGGCTCTGACAT | GDH15' + pPGK |
| 84 | X19726 | atccgaaatattccacggtttagaaaaaaa tcggatgctatgtttgaccaaggtgatgta | GDH13' + pADH1 |
| 85 | X19727 | TTAAAATACATCACCTTGGTCAAACATAGC ATCCGATTTTTTCTAAACCGTGGAATATT | pADH1 + GDH13' |
| 86 | X19948 | aaagaaatgtcagagccagaatttcaacaa gctgatgctatgtttgaccaaggtgatgta | GDH13' + GDH15' for deletion |
| 87 | X19949 | TTAAAATACATCACCTTGGTCAAACATAGCAT CAGCTTGTTGAAATTCTGGCTCTGACAT | GDH15' + GDH13' for deletion |
| 88 | X19950 | atccgaaatattccacggtttagaaaaaaat cgagcacgcagcacgctgtatttacgtat | FCY3' + pADH1 |
| 89 | X19967 | tgaaggtcattaggatttggatttcttcctca taaattagtgtgtgtgcattatatatat | PMA1t + ADH3t |
| 90 | X19968 | TTTTTAATATATATAATGCACACACACTAATT TATGAGGAAGAAATCCAAATCCTAATGA | ADH3t + PMA1t |
| 91 | X19969 | AATTAAATACGTAAATACAGCGTGCTGCGTGC TCCAGAAAGGCAACGCAAAATTTTTTT | pHXT7 + FCY3' |
| 92 | X19970 | ccctggaaaaaaaatttgcgttgcctttctg gagcacgcagcacgctgtatttacgtat | FCY3' + pHXT7 |
| 93 | X20022 | aggtagacgctacagtcacaggtgtcacaact | URE2 5' flank |

TABLE 3-continued

Primers used to create MAs.

| SEQ ID | Primer | Sequence | Description |
|---|---|---|---|
| 94 | X20023 | GGACGAGGCAAGCTAAACAGATCTCTAGACCT ATTGGTGTACAACTTAATTTGCAGCTTA | URE2 5' flank |
| 95 | X20024 | ccgtttcttttctttggactatcatgtagtc tcaggctgcttaaaaacaagaaagaaag | URE2 3' flank |
| 96 | X20025 | GAGTGGGATGCGCATATAGTGCATGAACCTAT | URE2 3' flank |
| 97 | X20026 | ttgttttaagctgcaaattaagttgtacacc aaaggctgcttaaaaacaagaaagaaag | URE2 3' + 5' for deletion |
| 98 | X20027 | CTTCTTCTTTCTTTCTTGTTTTTAAAGCAGCC TTTGGTGTACAACTTAATTTGCAGCTTA | URE2 5' + 3' for deletion |
| 99 | X20028 | ttgttttaagctgcaaattaagttgtacacca ataggtctagagatctgtttagcttgcc | pAGTEF + URE2 5' |
| 100 | X20029 | CTTCTTCTTTCTTTCTTGTTTTTAAAGCAGCC TGAGACTACATGATAGTCCAAAGAAAAG | pHXT2rc + URE2 3' |
| 101 | X20043 | ATAAAATTAAATACGTAAATACAGCGTGCTGC GTGCTATGAGGAAGAAATCCAAATCCT | ADH3 t tails for FCY1 3' flank |
| 102 | X20044 | tgaaggtcattaggatttggatttcttcctca tagcacgcagcacgctgtatttacgta | FCY 3' flank tails for ADH3t |
| 103 | X20282 | agccagcttaaagagttaaaaatttcatagc taccagaaaggcaacgcaaaatttttttt | pHXT7 + FCY5' |
| 104 | X20283 | CCCTGGAAAAAAAATTTTGCGTTGCCTTTCT GGTAGCTATGAAATTTTAACTCTTTAAG | FCY5' + pHXT7 |
| 105 | X20284 | ttttaatatatataatgcacacacactaat ttagcacgcagcacgctgtatttacgtat | FCY3' + PMA1t |
| 106 | X20285 | AATTAAATACGTAAATACAGCGTGCTGCGTG CTAAATTAGTGTGTGTGCATTATATATAT | PMA1t + FCY3' |
| 107 | X20286 | agccagcttaaagagttaaaaatttcatagc tatgtggtagaattcaaaagactatgtga | pGPM1 + FCY5' |
| 108 | X20287 | ATGGCATCACATAGTCTTTTGAATTCTACCA CATAGCTATGAAATTTTAACTCTTTAAG | FCY5' + pGPM1 |
| 109 | X20288 | ttttaatattgcttttcaattactgttattaa aagcacgcacacgctgtatttacgtat | FCY3' + TPIt |
| 110 | X20289 | AATTAAATACGTAAATACAGCGTGCTGCGTG CTTTTAATAACAGTAATTGAAAAGCAATA | TPIt + FCY3' |
| 111 | X20620 | ggtgattggaatggttatggttccggaatcgc | AUA1 5' Flank |
| 112 | X20621 | GGACGAGGCAAGCTAAACAGATCTCTAGACC TATATACTACATAGAAAGCAATTAAAAGA | AUA15' + pAGTEF |
| 113 | X20622 | ccgtttcttttctttggactatcatgtagtc tcctccacctaacaaacccgcaccaacac | AUA13' + pHXT2rc |
| 114 | X20623 | GTCATATGGCCTCTTAACGTGGTCCTTTGTGG | AUA1 3' Flank |
| 115 | X20630 | ttttatcttttaattgctttctatgtagtc tcctccacctaacaaacccgcaccaacac | pAGTEF + AUA1 5' |
| 116 | X20631 | TACTTGGTGTTGGTGCGGGTTTGTTAGGTGGA GGAGACTACATGATAGTCCAAAGAAAAG | pHXT2rc + AUA13' |
| 117 | X20632 | ttttatcttttaattgctttctatgtagta tactccacctaacaaacccgcaccaacac | AUA13' + AUA15' |
| 118 | X20633 | TACTTGGTGTTGGTGCGGGTTTGTTAGGTGGA GTATACTACATAGAAAGCAATTAAAAGA | AUA15' + AUA13' |
| 119 | X21123 | gcgacatgtgatgagattgcatgcacctcca cagaa | GDH2 5' Flank |

TABLE 3-continued

Primers used to create MAs.

| SEQ ID | Primer | Sequence | Description |
|---|---|---|---|
| 120 | X21124 | GGACGAGGCAAGCTAAACAGATCTCTAGACC TATCTTTATTCTTTTTATTGTTGTGAATT | GDH2 5' Flank + pAGTEF |
| 121 | X21125 | ccgtttcttttctttggactatcatgtagtc tcgcttcaataaaattgttttgtataaat | GDH2 3' Flank + pHXT2rc |
| 122 | X21126 | GGCAGCTATCTCTACTATCCCGTTTAGTACT ATCC | GDH2 3' Flank |
| 123 | X21127 | atattaaattcacaacaataaaaagaataaa gataggtctagagatctgtttagcttgcc | pAGTEF + GDH2 5' |
| 124 | X21128 | GAACTAATTTATACAAAACAATTTTATTGAA GCGAGACTACATGATAGTCCAAAGAAAAG | pHXT2rc + GDH2 5' |
| 125 | X21133 | atattaaattcacaacaataaaaagaataaa gagcttcaataaaattgttttgtataaa | GDH2 3' + GDH2 5' for deletion |
| 126 | X21135 | gcattgattgtctatcagagcatatcaaggt ggt | GDH3 5' Flank |
| 127 | X21136 | GGACGAGGCAAGCTAAACAGATCTCTAGACC TACGGTGACTGTTGCTACTTCCCTATATA | GDH3 5' Flank + pAGTEF |
| 128 | X21137 | ccgtttcttttctttggactatcatgtagt ctcccgtaagcgctattttcttttgttcg | GDH3 3' Flank + pHXT2rc |
| 129 | X21138 | GGCTAGGACCCCGTAAGGAGGAAAGAATAGG CAAG | GDH3 3' Flank |
| 130 | X21139 | tatatatatatagggaagtagcaacagtcacc gtaggtctagagatctgtttagcttgcc | pAGTEF + GDH3 5' |
| 131 | X21140 | TAGTTACGAACAAAAAGAAAATAGCGCTTAC GGGAGACTACATGATAGTCCAAAGAAAAG | pHXT2rc + GDH3 3' |
| 132 | X21147 | tatatatatatagggaagtagcaacagtcac cgccgtaagcgctattttcttttgttcg | GDH3 3' + GDH3 5' |
| 133 | X21148 | TAGTTACGAACAAAAAGAAAATAGCGCTTA CGGCGGTGACTGTTGCTACTTCCCTATATA | GDH3 5' + GDH3 3' |
| 134 | X21179 | ttgttttaagctgcaaattaagttgtacacc aagggcgccataaccaaggtatctataga | pTEF2 + URE2 5' |
| 135 | X21180 | TGGCGGTCTATAGATACCTTGGTTATGGCGC CCTTGGTGTACAACTTAATTTGCAGCTTA | URE2 5' + pTEF2 |
| 136 | X21181 | CTTCTTCTTTCTTTCTTGTTTTTAAAGCAGC CTCGATTTTTTTCTAAACCGTGGAATATT | pADH1rc + URE2 3' |
| 137 | X21182 | atccgaaatattcfcacggtttagaaaaaaa tcgaggctgctttaaaaacaagaaagaaag | URE2 3' + pADH1rc |
| 138 | X21289 | aaagaaatgtcagagccagaatttcaacaag ctaggtctagagatctgtttagcttgcct | pAGTEF + GDH1 5' |
| 139 | X21290 | TTAAAATACATCACCTTGGTCAAACATAGCAT CGAGACTACATGATAGTCCAAAGAAAAG | pHXT2rc + GDH1 3' |
| 140 | X21291 | GGGACGAGGCAAGCTAAACAGATCTCTAGAC CTAGCTTGTTGAAATTCTGGCTCTGACAT | GDH1 5' + pAGTEF |
| 141 | X21292 | ccgtttcttttctttggactatcatgtagtc tcgatgctatgtttgaccaaggtgatgt | GDH1 3' + pHXT2rc |
| 142 | X21319 | ttgttttaagctgcaaattaagttgtacacc aacgatttttttctaaaccgtggaatatt | pADH1 + URE2 5' |
| 143 | X21320 | ATCCGAAATATTCCACGGTTTAGAAAAAAAT CGTTGGTGTACAACTTAATTTGCAGCTTA | URE2 5' + pADH1 |
| 144 | X21321 | ttttcagttttggatagatcagttagaaag cttaggctgctttaaaaacaagaaagaaag | URE2 3' + PGKprc |

TABLE 3-continued

Primers used to create MAs.

| SEQ ID | Primer | Sequence | Description |
|---|---|---|---|
| 145 | X21322 | CTTCTTCTTTCTTTCTTGTTTTTAAAGCAGC CTAAGCTTTCTAACTGATCTATCCAAAAC | PGKprc + URE2 3' |
| 146 | X21507 | GAACTAATTTATACAAAACAATTTTATTGAA GCTCTTTATTCTTTTTATTGTTGTGAATT | GDH25' + GDH23' for deletion |
| 147 | X21735 | agccagcttaaagagttaaaaatttcatag ctacgatttttttctaaaccgtggaatatt | pADH1 + FCY5' |
| 148 | X21736 | ATCCGAAATATTCCACGGTTTAGAAAAAAAT CGTAGCTATGAAATTTTTAACTCTTTAAG | FCY5' + PADH1 |
| 149 | X21754 | gccaaagtggatttctcctactcaagctttgc | FCY5' Flank |
| 150 | X23319 | aaagaaatgtcagagccagaatttcaacaag ctcgatttttttctaaaccgtggaatatt | pADH1 + GDH15' |
| 151 | X23320 | ATCCGAAATATTCCACGGTTTAGAAAAAAAT CGAGCTTGTGAAATTCTGGCTCTGACAT | GDH1 5' + pADH1 |
| 152 | X23321 | gtccatgtaaaatgattgctccaatgattg aaagatgctatgtttgaccaaggtgatgta | GDH1 3' + PDC1t |
| 153 | X23322 | TTAAAATACATCACCTTGGTCAAACATAGCA TCTTTCAATCATTGGAGCAATCATTTTAC | PDC1t + GDH13' |
| 154 | X23408 | TTTTCAGTTTTGGATAGATCAGTTAGAAAGC TTTAGCTATGAAATTTTTAACTCTTTAAG | FCY5' + pPGK |
| 155 | X23409 | agccagcttaaagagttaaaaatttcatagc taaagctttctaactgatctatccaaaac | pPGK + FCY5' |

TABLE 4

Strain genotypes

| Strain | Description | Genotype | Associated MA Cassette(s) |
|---|---|---|---|
| M2390 | Type Strain | WT | |
| M3465 | Glycerol Reduction Strain | Δfdh1::MA0608Δfdh2::MA0280Δgpd2::MA0289 | MA0280, MA0289, MA0608 |
| M3467 | Glycerol Reduction Strain | Δfdh1::MA0608Δfdh2::MA0280Δgpd1::MA0290 | MA0280, MA0290, MA0608 |
| M3469 | Glycerol Reduction Strain | Δfdh1::MA0608Δfdh2::MA0280Δgpd1::MA0293 | MA0280, MA0608, MA0293 |
| M3624 | Glycerol Reduction Strain | Δfdh1::MA0608Δfdh2::MA0280Δgpd1::MA0290Δgpd2::MA0286 | MA0286, MA0280, MA0290, MA0608 |
| M4076 | GDH1 marked deletion | Δfdh1::MA0608Δfdh2::MA0280Δgpd1::MA0290Δgpd2::MA0286Δgdh1::MA0631 | MA0286, MA0280, MA0290, MA0608, MA0631 |
| M4117 | S. cerevisiae GHH2 over expression | Δfdh1::MA0608Δfdh2::MA0280Δgpd1::MA0290Δgpd2::MA0286Δgdh1::MA0425 | MA0286, MA0280, MA0290, MA0608, MA0425 |
| M4118 | S. cerevisiae GLN1/GLT1 over expression | Δfdh1::MA0608Δfdh2::MA0280Δgpd1::MA0290Δgpd2::MA0286Δgdh1::MA0426 | MA0286, MA0280, MA0290, MA0608, MA0426 |
| M4312 | URE2 marked deletion | Δfdh1::MA0608Δfdh2::MA0280Δgpd1::MA0290Δgpd2::MA0286Δure2::MA0622 | MA0286, MA0280, MA0290, MA0608, MA0622 |
| M4373 | GDH1 marked deletion | Δfdh1::MA0608Δfdh2::MA0280Δgpd2::MA0289Δgdh1::MA0631 | MA0280, MA0289, MA0608, MA0631 |
| M4375 | GDH1 marked deletion | Δfdh1::MA0608Δfdh2::MA0280Δgpd1::MA0290Δgdh1::MA0631 | MA0280, MA0290, MA0608, MA0631 |
| M4377 | GDH1 marked deletion | Δfdh1::MA0608Δfdh2::MA0280Δgpd1::MA0293Δgdh1::MA0631 | MA0280, MA0608, MA0293, MA0631 |
| M4400 | GDH1 clean deletion | Δfdh1::MA0608Δfdh2::MA0280Δgpd2::MA0289Δgdh1::MA0888 | MA0280, MA0289, MA0608, MA0888 |
| M4401 | GDH1 clean deletion | Δfdh1::MA0608Δfdh2::MA0280Δgpd1::MA0290Δgdh1::MA0888 | MA0280, MA0290, MA0608, MA0888 |
| M4402 | GDH1 clean deletion | Δfdh1::MA0608Δfdh2::MA0280Δgpd1::MA0293Δgdh1::MA0888 | MA0280, MA0608, MA0293, MA0888 |
| M4406 | URE2 clean deletion | Δfdh1::MA0608Δfdh2::MA0280Δgpd1::MA0290Δgpd2::MA0286Δure2::MA0622.1 | MA0286, MA0280, MA0290, MA0608, MA0622.1 |
| M4427 | DUR 1,2 over expression | Δfdh1::MA0608Δfdh2::MA0280Δgpd1::MA0290Δfcy1::MA0464.1 | MA0280, MA0290, MA0608, MA0464.1 |
| M4428 | DUR 1,2 over expression | Δfdh1::MA0608Δfdh2::MA0280Δgpd1::MA0290Δfcy1::MA0465.1 | MA0280, MA0290, MA0608, MA0465.1 |
| M4429 | DUR1,2 over expression | Δfdh1::MA0608Δfdh2::MA0280Δgpd1::MA0290Δfcy1::MA0467.1 | MA0280, MA0290, MA0608, MA0467.1 |
| M4430 | DUR1,2 over expression | Δfdh1::MA0608Δfdh2::MA0280Δgpd1::MA0290Δfcy1::MA0454.14 | MA0280, MA0290, MA0608, MA0454.14 |
| M4431 | DUR1,2 over expression | Δfdh1::MA0608Δfdh2::MA0280Δgpd1::MA0293Δfcy1::MA0464.1 | MA0280, MA0293, MA0608, MA0464.1 |
| M4432 | DUR1,2 over expression | Δfdh1::MA0608Δfdh2::MA0280Δgpd1::MA0293Δfcy1::MA0465.1 | MA0280, MA0293, MA0608, MA0465.1 |

TABLE 4-continued

Strain genotypes

| Strain | Description | Genotype | Associated MA Cassette(s) |
|---|---|---|---|
| M4433 | DUR1,2 over expression | Δfdh1::MA0608Δfdh2::MA0280Δgpd1::MA0293Δfcy1::MA0467.1 | MA0280, MA0290, MA0608, MA0467.1 |
| M4434 | DUR1,2 over expression | Δfdh1::MA0608Δfdh2::MA0280Δgpd1::MA0293Δfcy1::MA0454.14 | MA0280, MA0290, MA0608, MA0454.14 |
| M4469 | *S. cerevisiae* GDH2 over expression | Δfdh1::MA0608Δfdh2::MA0280Δgpd2::MA0289Δgdh1::MA0425 | MA02S0, MA0289, MA0608, MA0425 |
| M4471 | *S. cerevisiae* GDH2 over expression | Δfdh1::MA0608Δfdh2::MA0280Δgpd1::MA0293Δgdh1::MA0425 | MA0280, MA0608, MA0293, MA0425 |
| M4507 | AUA1 marked deletion | Δfdh1::MA0608Δfdh2::MA0280Δgpd1::MA0290Δgdh2::MA0486Δaua1::MA0617 | MA0286, MA0280, MA0290, MA0608, MA0617 |
| M4538 | GDH1 marked deletion | Δgdh1::MA0631 | MA0631 |
| M4540 | AUA1 marked deletion | Δaual::MA0617 | MA0617 |
| M4542 | URE2 marked deletion | Δfdh1::MA0608Δfdh2::MA0280Δgpd1::MA0293Δure2::MA0622 | MA0280, MA0608, MA0293, MA0622 |
| M4571 | AUA1 clean deletion | Δfdh1::MA0608Δfdh2::MA0280Δgpd1::MA0290Δgpd2::MA0286Δaua1::MA0617.1 | MA0286, MA0280, MA0290; MA0608, MA0617.1 |
| M4573 | GDH1 clean deletion | Δfdh1::MA0608Δfdh2::MA0280Δgpd1::MA0290Δgpd2::MA0286Δgdh1::MA0888 | MA0286, MA0280, MA0290, MA0608, MA0888 |
| M4590 | GDH1 clean deletion | Δgdh1::MA0888 | MA0888 |
| M4591 | AUA1 clean deletion | Δaual::MA0617.1 | MA0617.1 |
| M4592 | URE2 clean deletion | Δfdh1::MA0608Δfdh2::MA0280Δgpd1::MA0293Δure2::MA0622.1 | MA0280, MA0608, MA0293, MA0622.1 |
| M4614 | URE2 marked deletion | Δfdh1::MA0608Δfdh2::MA0280Δgpd1::MA0293Δgpd2::MA0286Δgdh1::MA0425Δure2::MA0622 | MA0286, MA0280, MA0290, MA0608, MA0425, MA0622 |
| M4615 | URE2 marked deletion | Δfdh1::MA0608Δfdh2::MA0280Δgpd1::MA0293Δgpd2::MA0286Δgdh1::MA0426Δure2::MA0622 | MA0286, MA0280, MA0290, MA0608, MA0426, MA0622 |
| M4616 | URE2 marked deletion | Δure2::MA0622 | MA0622 |
| M4622 | *S. cerevisiae* GDH2 over expression | Δgdh1::MA0425 | MA0425 |
| M4623 | *S. cerevisiae* GLN1/GLT1 over expression | Δgdh1::MA0426 | MA0426 |
| M4624 | *S. cerevisiae* GLN1/GLT1 over expression | Δgdh1::MA0426 | MA0426 |
| M4625 | *S. cerevisiae* GLN1/GLT1 over expression | Δfdh1::MA0608Δfdh2::MA0280Δgpd2::MA0289Δgdh1::MA0426 | MA0280, MA0289, MA0608, MA0426 |
| M4625 | *S. cerevisiae* GLN1/GLT1 over expression | Δfdh1::MA0608Δfdh2::MA0280Δgpd1::MA0293Δgdh1::MA0426 | MA0280, MA0608, MA0293, MA0426 |
| M4626 | *S. cerevisiae* GLN1/GLT1 over expression | Δfdh1::MA0608Δfdh2::MA0280Δgpd1::MA0293Δgdh1::MA0426 | MA0280, MA0608, MA0293, MA0426 |
| M4654 | GDH3 marked deletion | Δgdh3::MA0615 | MA0615 |
| M4655 | GDH2 marked deletion | Δfdh1::MA0608Δfdh2::MA0280Δgpd1::MA0290Δgpd2::MA0286Δgdh1::MA0426Δgdh2::MA0616 | MA0286, MA0280, MA0290, MA0608, MA0426, MA0616 |
| M4656 | GDH3 marked deletion | Δfdh1::MA0608Δfdh2::MA0280Δgpd1::MA0290Δgpd2::MA0286Δgdh1::MA0426Δgdh3::MA0615 | MA0286, MA0280, MA0290, MA0608, MA0426, MA0615 |
| M4657 | GDH3 marked deletion | Δfdh1::MA0608Δfdh2::MA0280Δgpd1::MA0290Δgpd2::MA0286Δgdh1::MA0425Δgdh3::MA0615 | MA0286, MA0280, MA0290, MA0608, MA0425, MA0615 |
| M4674 | URE2 clean deletion | Δfdh1::MA0608Δfdh2::MA0280Δgpd1::MA0290Δgpd2::MA0286Δgdh1::MA0425Δure2::MA0622.1 | MA0286, MA0280, MA0290, MA0608, MA0425, MA0622.1 |
| M4675 | URE2 clean deletion | Δfdh1::MA0608Δfdh2::MA0280Δgpd1::MA0290Δgpd2::MA.0286Δgdh1::MA0426Δure2::MA0622.1 | MA0286, MA0280, MA0290, MA0608, MA0426, MA0622.1 |
| M4676 | URE2 clean deletion | Δure2::MA0622.1 | MA0622.1 |
| M4677 | GDH2 marked deletion | Δgdh2::MA0616 | MA0616 |
| M4690 | GDH3 clean deletion | Δgdh3::MA0615.1 | MA0615.1 |
| M4691 | GDH2 clean deletion | Δfdh1::MA0608Δfdh2::MA0280Δgpd1::MA0290Δgpd2::MA0286Δgdh1::MA0426Δgdh2::MA0616.1 | MA0286, MA0280, MA0290, MA0608, MA0426, MA0616.1 |
| M4692 | GDH3 clean deletion | Δfdh1::MA0608Δfdh2::MA0280Δgpd1:MA0290Δgpd2::MA0286Δgdh1::MA0426Δgdh3::MA0615.1 | MA0286, MA0280, MA0290, MA0608, MA0426, MA0615.1 |
| M4693 | GDH3 clean deletion | Δfdh1::MA0608Δfdh2::MA0280Δgpd1::MA0290Δgpd2::MA0286Δgdh1::MA0425Δgdh3::MA0615.1 | MA0286, MA0280, MA0290, MA0608, MA0425, MA0615.1 |
| M4694 | GDH2 clean deletion | Δgdh2::MA0616.1 | MA0616.1 |
| M4748 | DUR3 over expression | Δfcy1::MA0464 | MA0464 |
| M4749 | GAP1 over expression | Δfcy1::MA0464.4 | MA0464.4 |
| M4750 | MEP1 over expression | Δfcyl::MA0464.2 | MA0464.2 |
| M4751 | DUR1,2 over expression | Δfcy1::MA0465.1 | MA0465.1 |
| M4752 | MEP1 over expression | Δfcyl::MA0434.2 | MA0434.2 |
| M4753 | MEP2 over expression | Δfcy1::MA0434.3 | MA0434.3 |
| M4754 | DUR3 over expression | Δfcy1::MA0434 | MA0434 |
| M4755 | GAP1 over expression | Δfcy1::MA0434.4 | MA0434.4 |
| M4756 | MEP2 over expression | Δfcy1.MA0464.2 | MA0464.2 |
| M4810 | DUR3 over expression | Δfcy1::MA0467 | MA0467 |
| M4811 | DUR3 over expression | Δfcy1::MA0467 | MA0467 |

TABLE 4-continued

Strain genotypes

| Strain | Description | Genotype | Associated MA Cassette(s) |
|---|---|---|---|
| M4812 | VIEP1 over expression | Δfcyl::MA0467.2 | MA0467.2 |
| M4813 | MEP1 over expression | Δfcyl::MA0467.2 | MA0467.2 |
| M4814 | GAP1 over expression | Δfcyl::MA0467.4 | MA0467.4 |
| M4815 | GAP1 over expression | Δfcyl::MA0467.4 | MA0467.4 |
| M5841 | *N. crassa* GDH2 over expression | Δfdh1::MA0608Δfdh2::MA0280Δgpd1::MA0290Δgpd2::MA0286Δgdh1::MA0837 | MA0280, MA0608, MA0286, MA0290, MA0837 |
| M5842 | *N. crassa* GDH2 over expression | Δfdh1::MA0608Δfdh2::MA0280Δgpd1::MA0290Δgpd2::MA0286Δgdh1::MA0837 | MA0280, MA0608, MA0286, MA0290, MA0837 |
| M5843 | *N. crassa* GDH2 over expression | Δfdh1::MA0608Δfdh2::MA0280Δgpd1::MA0290Δgpd2::MA0286Δgdh1::MA0837 | MA0280, MA0608, MA0286, MA0290, MA0837 |
| M5844 | *N. crassa* GDH2 over expression | Δfdh1::MA0608Δfdh2::MA0280Δgpd1::MA0290Δgpd2::MA0286Δgdh1::MA0837 | MA0280, MA0608, MA0286, MA0290, MA0837 |

Example 1

Deletion of GDH1 and Overexpression of GDH2 or GLT1/GLN1

M3624 (Δgpd1::GPD2-*B.adolescentis*pflA/pFlB/adhEΔgpd2::GPD1-*B. adolecentis*pflA/pflB/adhEΔfdh1Δfdh2::*B.adolescentis*pflA/pflB/adhE) has an approximately 85% reduction in glycerol formation when grown on >30% solids corn mash. However, the strain is unable to complete the fermentation even after extended incubation periods. Two modifications of the ammonium assimilation pathway were constructed in M3624 and evaluated for fermentation performance. The modifications were a deletion of GDH1 and over-expression of Gdh2, resulting in strain M4117 (M3634 Gdh2; Δgdh1). The second modification was a deletion of GDH1 and overexpression of GLT and GLN1, resulting in strain M4118 (M3634 Glt1; Gln1; Δgdh1). These strains were compared to M3624 and the conventional yeast control (M2390 (a wild type unmodified strain isolated from industrial sources)) following fermentation of 31% solids corn mash.

An industrial corn mash was prepared to a final solids concentration of 31% supplemented with penicillin (0.006 mg/mL) and urea (0.5 g/l). Glucoamylase was added at a concentration of 0.6 AGU/gTS. Fermentation was stopped by addition of each strain to an final starting concentration of 0.1 g/l. Vials were capped with a rubber stopper and sealed. A 23-gauge needle was inserted through the stopper to vent and for the safety of the experiment. Vials were incubated at 35° C. with shaking at 125 rpm. At the termination of the experiment samples were prepared for HPLC analysis of ethanol and residual sugars.

The results in FIG. 69 illustrate that both M4117 and M4118 reach a much higher final ethanol titer than M3624, which was unable to complete the fermentation. Relative to M2390 both M4117 and M4118 had ethanol titers that were 4.2% and 5.2% higher respectively.

Example 2

Deletion of GDH1

Figure 1:
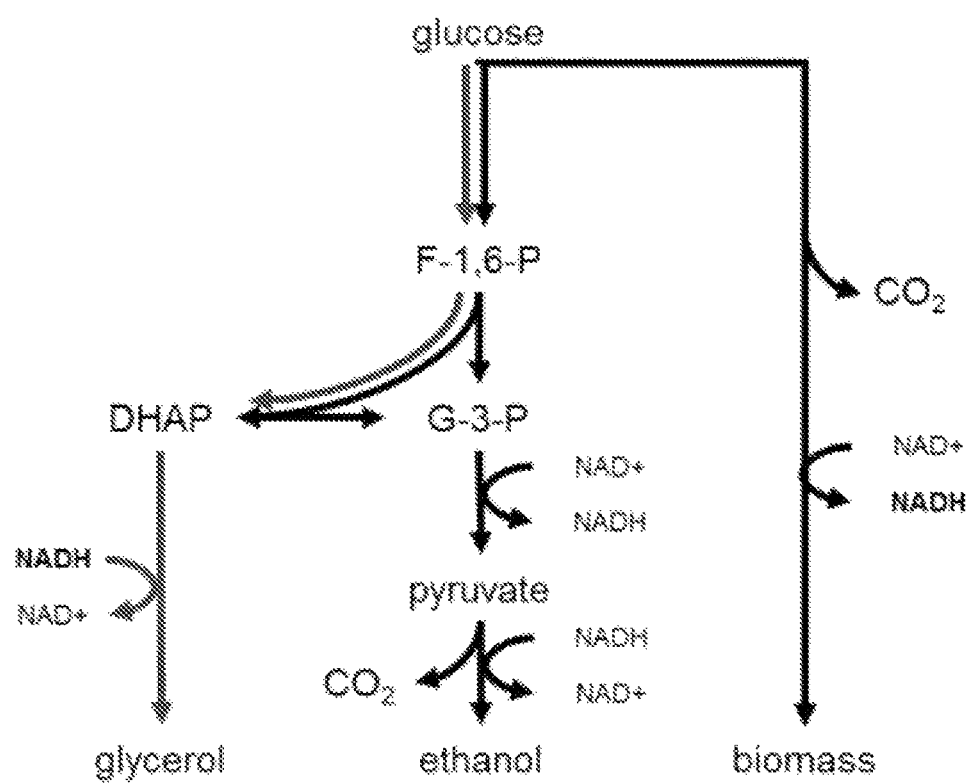
Figure 2:
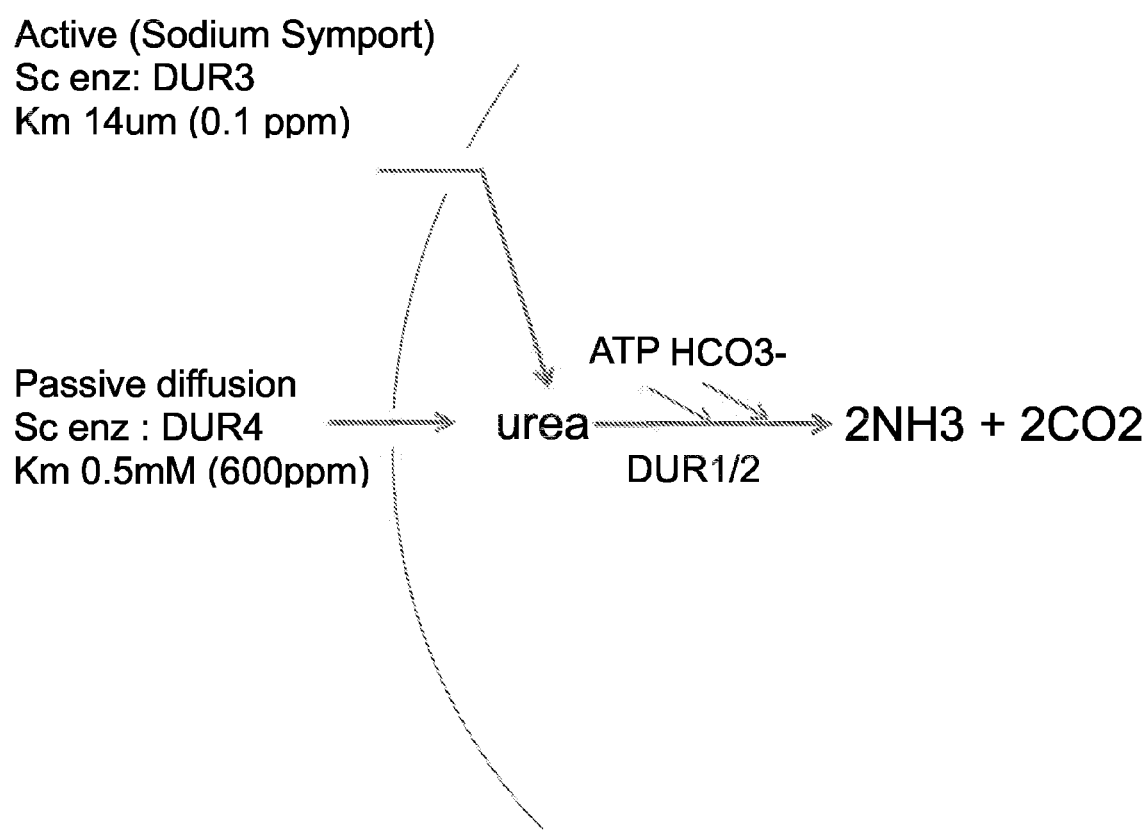
Figure 3:
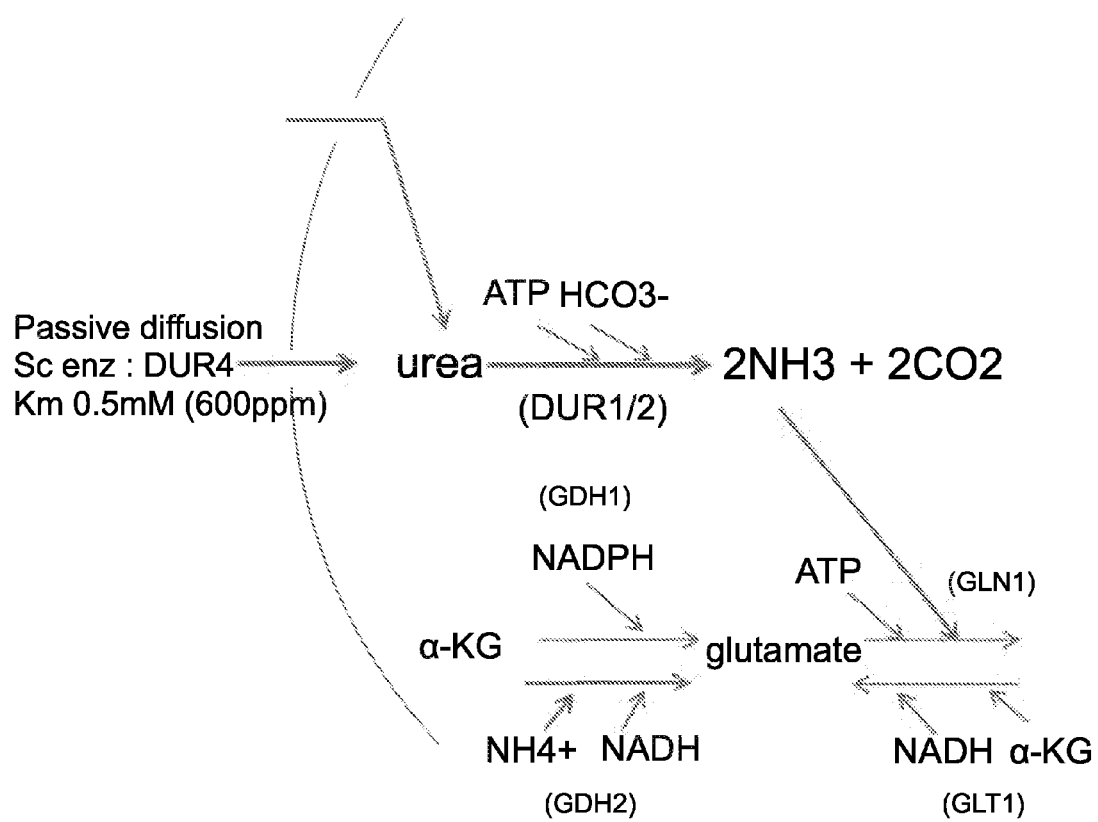
FIG. 3 depicts the process by which an unmodified *S. cerevisiae* assimilates urea.
Figure 4:
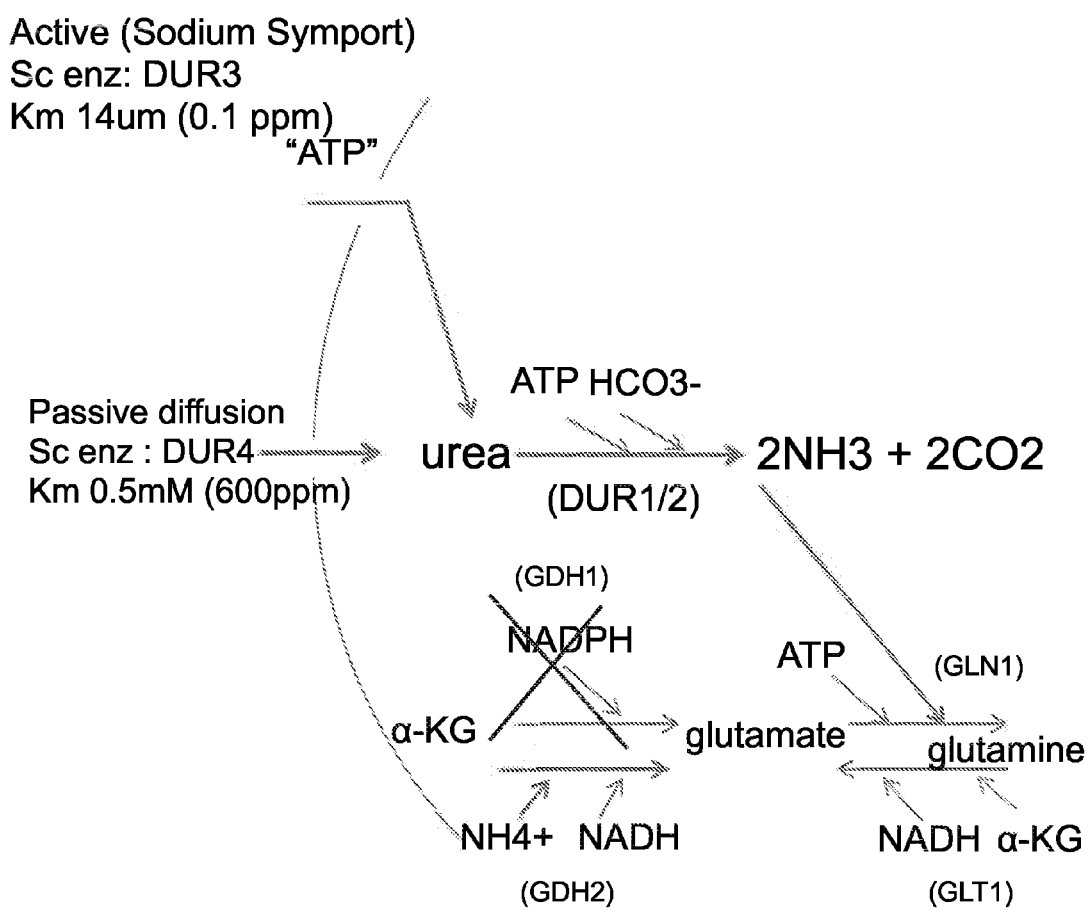
FIG. 4 depicts process by which a genetically modified glycerol reduction strain which contains a deletion of Gdh1 assimilates urea.
Figure 5:
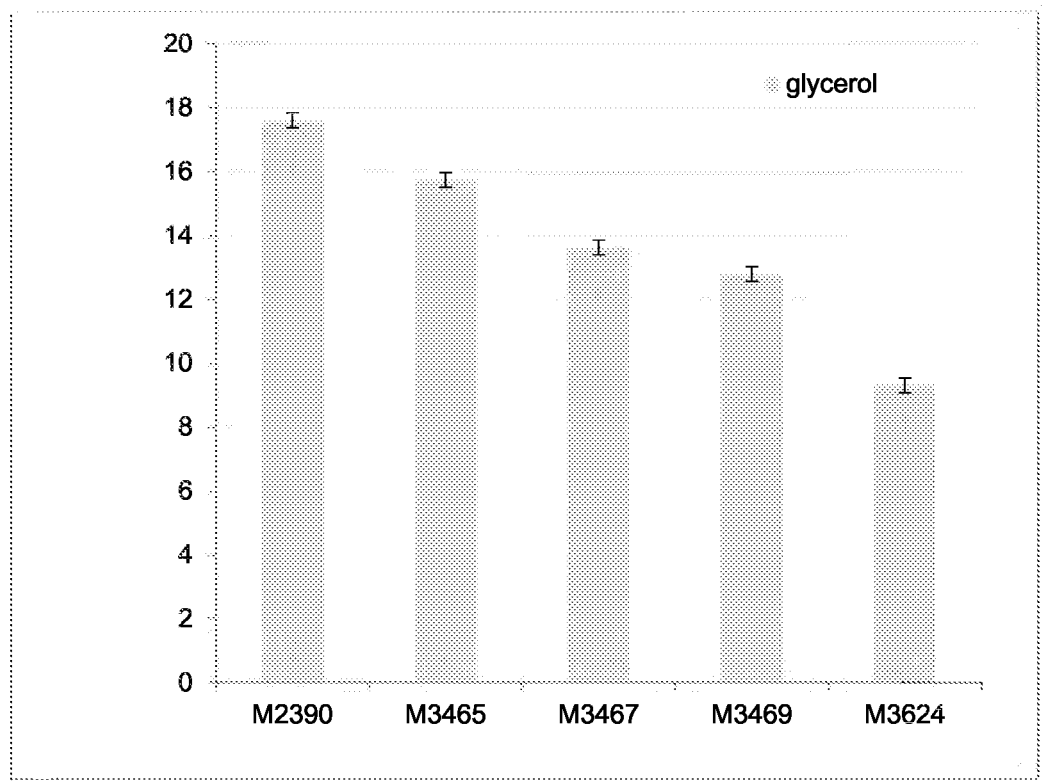
FIG. 5 depicts the glycerol titers of the wild type and glycerol reduction strains containing the formate pathway (M2390 (wildtype), M3465, M3467, M3469, and M3624 are depicted). This data shows total glycerol present in corn mash which contained 7 g/l glycerol prior to fermentation.
Figure 6:
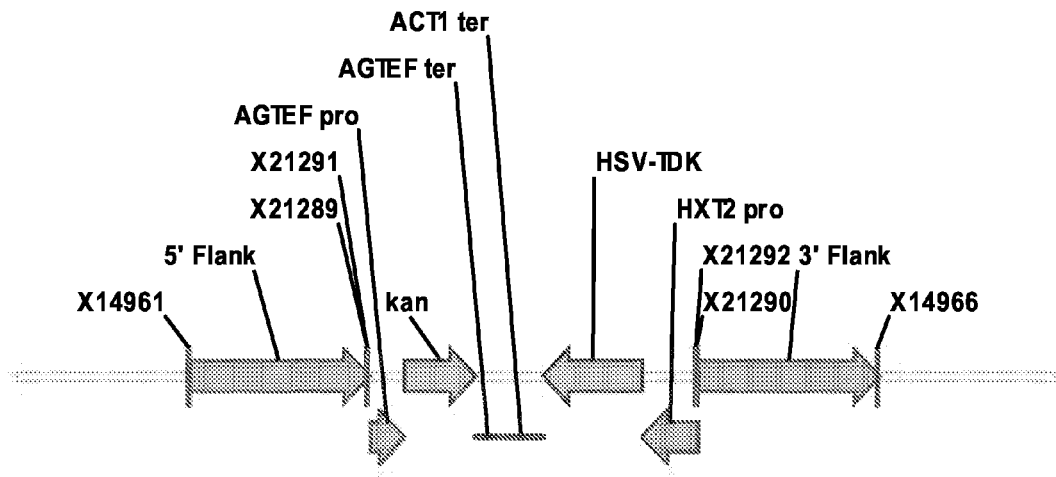
FIG. 6 depicts a schematic diagram of the MA0631 insertion cassette.
Figure 7:
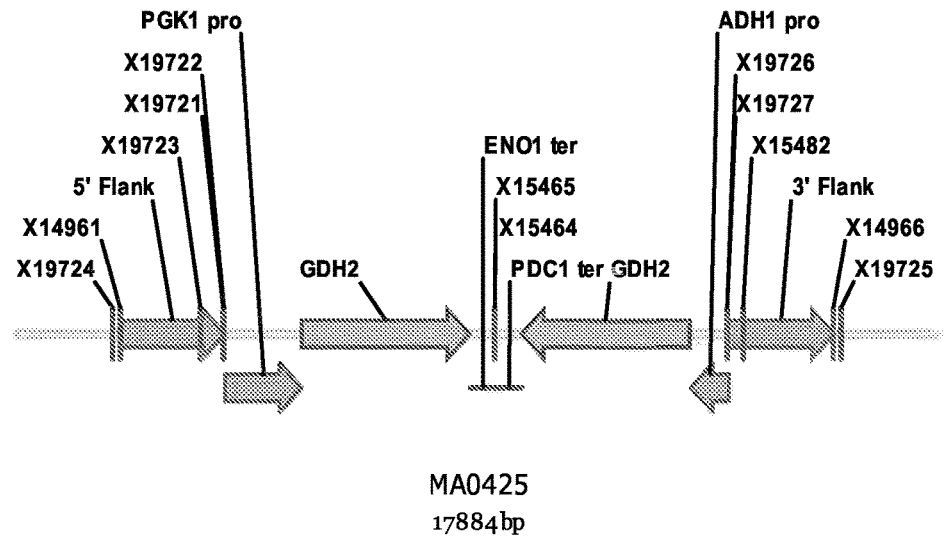
FIG. 7 depicts a schematic diagram of the MA0425 insertion cassette.
Figure 8:
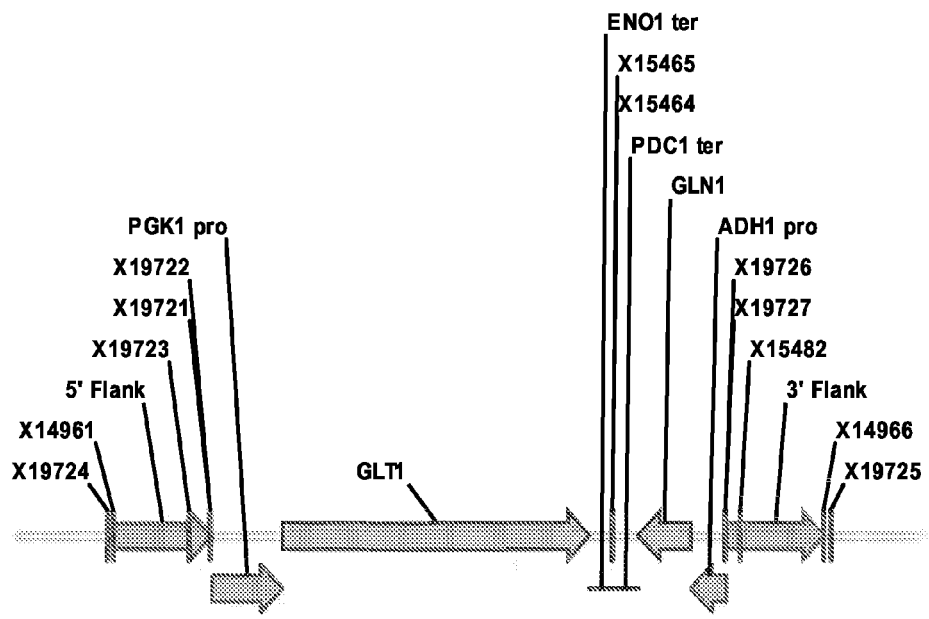
FIG. 8 depicts a schematic diagram of the MA0426 insertion cassette.
Figure 9:
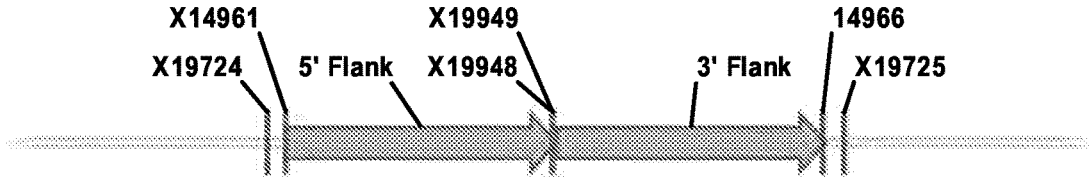
FIG. 9 depicts a schematic diagram of the MA0888 insertion cassette.

As shown in FIG. 5, M3465 (Δgpd2::*B.adolescentis*pflA/pflB/adhEΔfdh1Δfdh2::*B.adolescentis*pflA/pflB/adhE), M3467 (Δfdh1Δfdh2::PFK-pro-adhE-HXT-ter ENO1-pro-pflB-ENO1-ter ADH1-pro-adhE-PDC10-ter TPI-pro-pflA-FBA-ter Δgpd1::GPD2::PFK-pro-adhE-HXT-ter ENO1-pro-pflB-ENO1-ter ADH1-pro-adhE-PDC10-ter TPI-pro-pflA-FBA-ter) and M3469 (Δgd1::*B.adolescentis* pflA/pflB/adhE fdh1Δfdh2Δ::*B.adolescentis*pflA/pflB/adhE) have degrees of glycerol reduction ranging from 20% to ~45% relative to the control strain M2390. A clean deletion of GDH1 was constructed in each of these backgrounds resulting in M4400 (M3465 Δgdh1), M4401(M3467 Δgdh1) and M4402 (M3469 Δgdh1) and compared to the conventional yeast control (M2390) following fermentation of 31% solids corn mash (The fermentation was performed as described in Example 1). As shown in FIG. 70, all three glycerol reduction strains engineered with a deletion of GDH1 reached a higher ethanol titer than their respective parent strain.

Example 3

Overexpression of DUR1/2

Four different DUR1/2 expression cassettes were constructed in both M3467 Δfdh1Δfdh2::PFK-pro-adhE-HXT-ter ENO1-pro-pflB-ENO1-ter ADH1-pro-adhE-PDC10-ter TPI-pro-pflA-FBA-ter Δgpd1::GPD2::PFK-pro-adhE-HXT7-ter ENO1-pro-pflB-ENO1-ter ADH1-pro-adhE-PDC10-ter TPI-pro-pflA-FBA-ter) and M3469 (Δgpd1:: *B. adolescentis* pflA/pflB/adhE fdh1Δfdh2Δ::*B.adolescentis*-pflA/pflB/adhE) resulting in strains M4427-M3343 (Table 5). These strains were compared to their parent strain and the conventional yeast control (M2390) following fermentation of 31% solids corn mash (The fermentation was performed as described in Example 1). As shown in FIG. 71, all strains containing an overexpression of DUR1/2 reached the same or higher ethanol titers than their respective parent strain but the TEF2 and ADH1 promoter appeared particularly affective. Promoters and terminators used and that could be used include: *S. cerevisiae* TEF 2 promoter: SEQ ID NO: 58, *S. cerevisiae* HXT7 promoter: SEQ ID NO: 59, *S. cerevisiae*, *S. cerevisiae* ADH1 promoter: SEQ ID NO: 60, *S. cerevisiae* TPI promoter: SEQ ID NO: 61, *S. cerevisiae* FBA1 terminator: SEQ ID NO: 62. *S. cerevisiae* PDC1 terminator: SEQ ID NO: 63. *S. cerevisiae* PMA1 terminator: SEQ IS NO: 64, and *S. cerevisiae* ADH3 terminator: SEQ ID NO: 65.

TABLE 5

Description of constructions and strain designations containing over-expression of DUR1/2

| Parent strain | Strain designation | Genetic modification |
|---|---|---|
| M3467 | M4427 | MA0464.1: expression of DUR1,2 from the TEF2 promoter |

TABLE 5-continued

Description of constructions and strain designations
containing over-expression of DUR1/2

| Parent strain | Strain designation | Genetic modification |
|---|---|---|
| M3467 | M4428 | MA0465.1: expression of DUR1,2 from the HXT7 promoter |
| M3467 | M4429 | MA467.1: expression of DUR1,2 from the ADH1 promoter |
| M3467 | M4430 | MA454.14: expression of DUR1,2 from the HXT7/TEF2 promoters |
| M3469 | M4431 | MA0464.1: expression of DUR1,2 from the TEF2 promoter |
| M3469 | M4432 | MA0465.1: expression of DUR1,2 from the HXT7 promoter |
| M3469 | M4433 | MA467.1: expression of DUR1,2 from the ADH1 promoter |
| M3469 | M4434 | MA454.14: expression of DUR1,2 from the HXT7/TEF2 promoters |

Example 4

Deletion of URE2

To evaluate an alteration in the *S. cerevisiae* nitrogen catabolite repression system in glycerol reduction backgrounds, a deletion of URE2 was constructed in M3624 (Example 1), creating strain M4406 (M3624 Δure2). This strain was compared to M3624 and the conventional yeast control (M2390) following fermentation of 31% solids corn mash (The fermentation was performed as described in Example 1). As shown in FIG. 72, M4406 reached a higher titer than M3624 however a yield increase over the conventional strain was not observed and there was ~15 g/l residual glucose. This is an indication that additional modifications to the NCR system may give improved performance or that an adaptation of M4406 may be required to obtain the potential yield increase.

Example 5

Regulation of Nitrogen Utilization

Preferred nitrogen sources generally repress transcription of genes required to utilize non-preferred nitrogen sources. Urea is added as a supplemental nitrogen source in corn mash fermentation; however, there are significant quantities of amino acids and ammonia, both of which are preferred nitrogen sources over urea. Expression of the urea transporter (Dur3) and the urea:amido lyase responsible for intracellular degradation (Dur1/2) may be repressed in the presence amino acids and ammonia as part of a phenomenon referred to as Nitrogen Catabolite Repression (NCR). This repression could slow the rate of urea uptake or require larger quantities to be added. It would be an economic benefit to a corn ethanol producer if constitutive expression of Dur3 and Dur1,2 allowed them to either reduce the amount of urea needed or accelerate fermentation rate.

The NCR is controlled by Ure2 and four transcription factors known as Gln3, Gat1, Dal80, and Gzf3. Ure2 participates in repressing gene expression in the presence of non-preferred nitrogen source. It has been observed that deletion of URE2 activates the expression of genes involved in the uptake of non-preferred nitrogen sources. Inactivation of Ure2 results in dephosphorylation and nuclear localization of the transcription factor Gln3.

Example 5A

Deletion of URE2 Deletion of URE2 Results in Nuclear Localization of GLN3 and Activation of NCR Sensitive Genes To evaluate an alteration in the *S. cerevisiae* nitrogen catabolite repression system in glycerol reduction backgrounds, a deletion of Ure2 is constructed as in Example 4. A deletion of URE2 will be constructed in M3624 (Example 1). Strains in which URE2 is deleted show a nuclear localization of Gln3, and an activation of NCR sensitive genes, including Dur3 and Dur1/2.

Example 5B

Overexpression GLN3 Results in Activation of NCR Sensitive Genes

To evaluate an alteration in the *S. cerevisiae* nitrogen catabolite repression system in glycerol reduction backgrounds, Gln3 (SEQ ID NOs: 156 and 157) is overexpressed. Strains in which Gln3 is overexpressed show an activation of NCR sensitive genes, including Dur3 and Dur1/2.

Example 6

Deletion of GDH1 and Expression of *S. cerevisiae* GDH2

The results show that strain M3624 (Example 1) was able to reach a slightly higher titer than strain M2390 (WT), producing 1.5 g/l more ethanol (FIG. 73). To create strain M4117 (M3634 Gdh2; Δgdh1), the GDH1 gene was deleted and replaced with 4 copies of the *S. cerevisiae* GDH2 gene expression cassette. The results in FIG. 73 below demonstrate that when compared to M3624, M4117 had a clear improvement of 3.7 g/l more ethanol. The data shown in FIG. 74 shows that M3624 makes 1.3 g/l glycerol which is 87% less than the wild type strain M2390, which made 10 g/l. The deletion of GDH1 and addition of the *S. cerevisiae* GDH2 expression cassette decreased the glycerol titers to around 1 g/l. These results illustrate that the combination of glycerol reduction through formate production is synergistic with modifications to the ammonium assimilation pathway.

Example 7

Deletion of GDH1 and Expression of *N. crassa* GDH2

Figure 10:
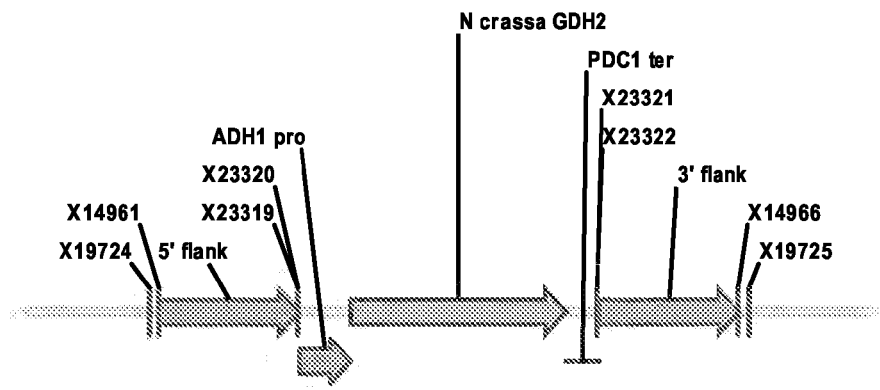
FIG. 10 depicts a schematic diagram of the MA0837 insertion cassette.
Figure 11:
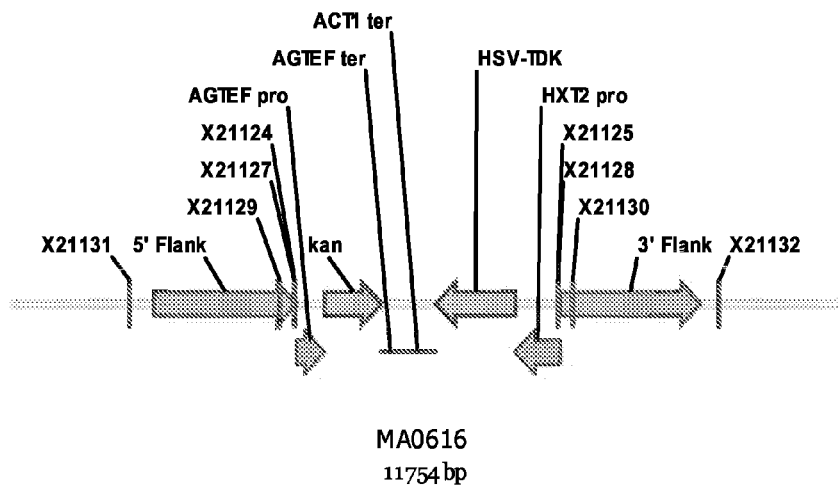
FIG. 11 depicts a schematic diagram of the MA0616 insertion cassette.
Figure 12:
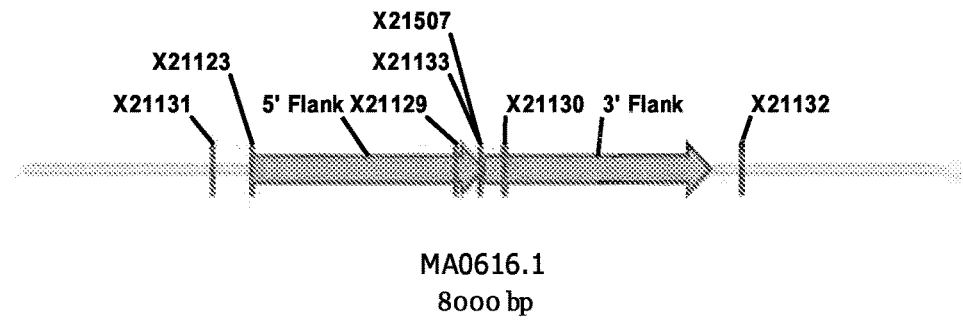
FIG. 12 depicts a schematic diagram of the MA0616.1 insertion cassette.
Figure 13:
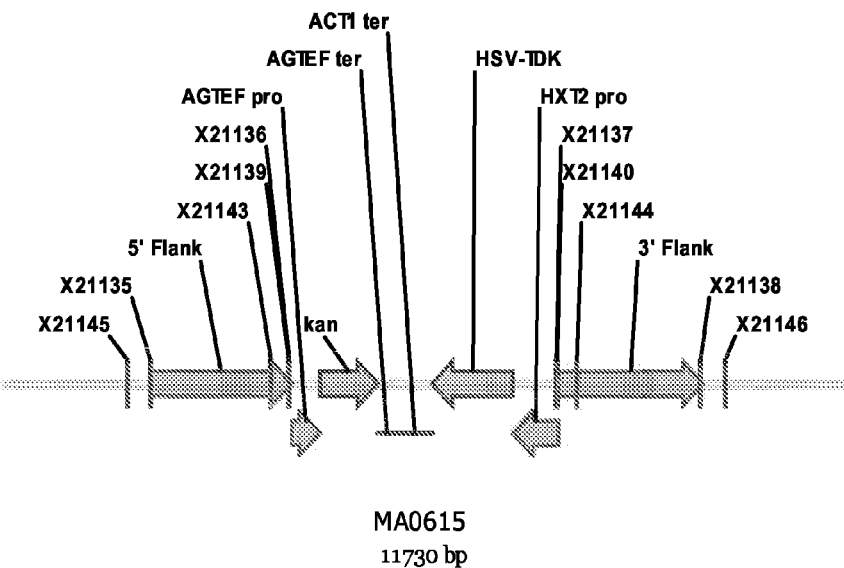
FIG. 13 depicts a schematic diagram of the MA0615 insertion cassette.
Figure 14:
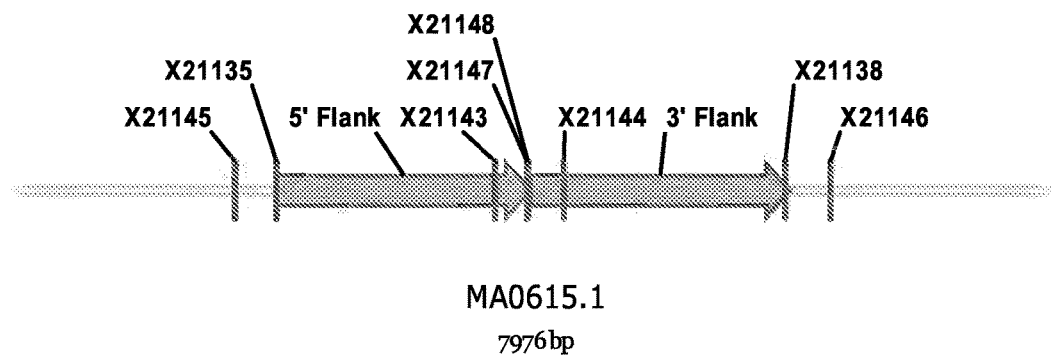
FIG. 14 depicts a schematic diagram of the MA0615.1 insertion cassette.
Figure 15:
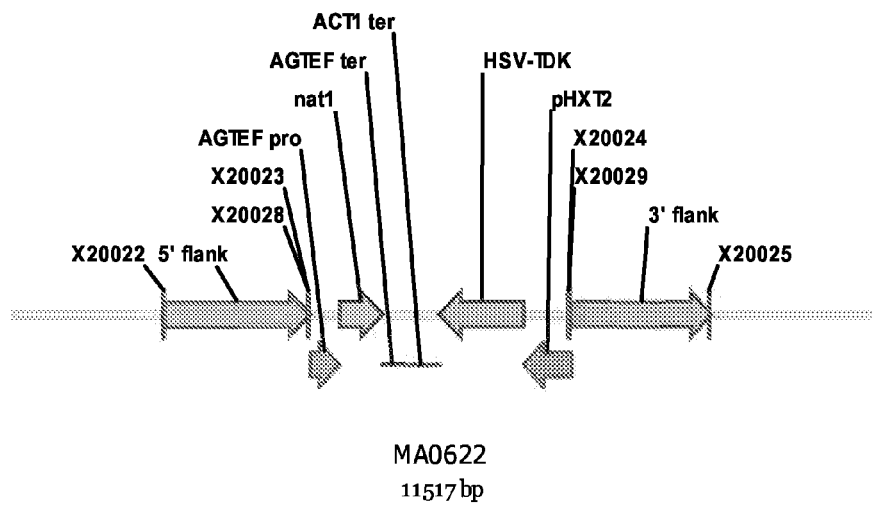
FIG. 15 depicts a schematic diagram of the MA0622 insertion cassette.
Figure 16:
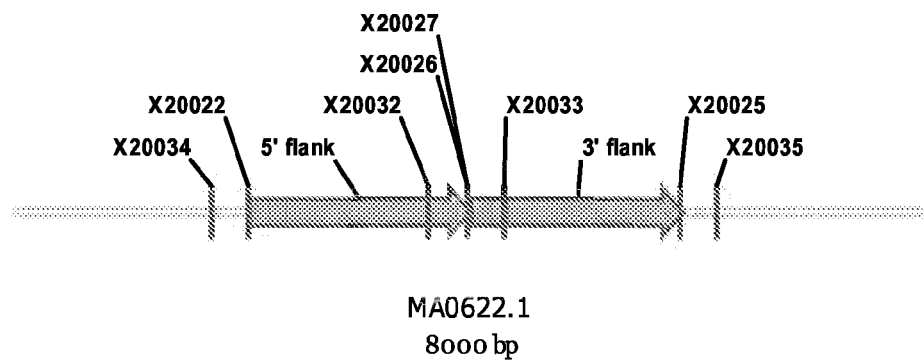
FIG. 16 depicts a schematic diagram of the MA0622.1 insertion cassette.
Figure 17:
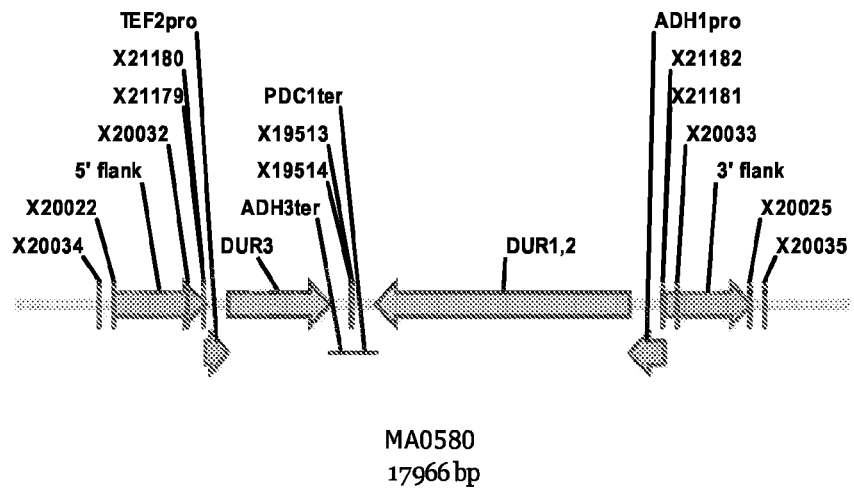
FIG. 17 depicts a schematic diagram of the MA0580 insertion cassette.
Figure 18:
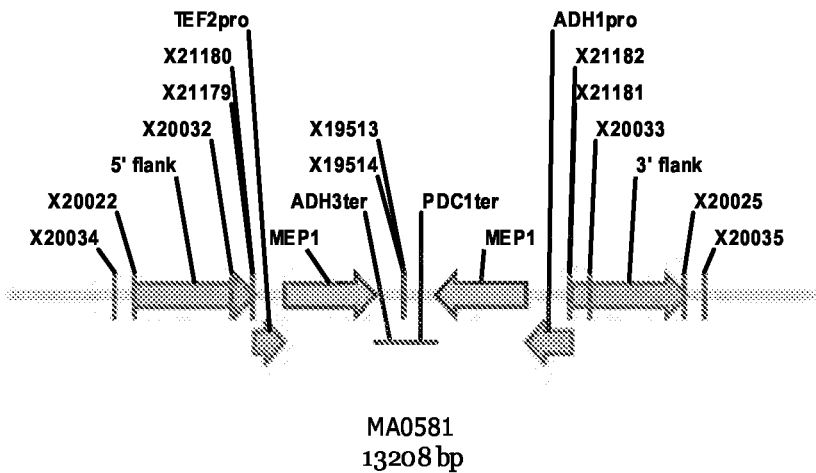
FIG. 18 depicts a schematic diagram of the MA0581 insertion cassette.
Figure 19:
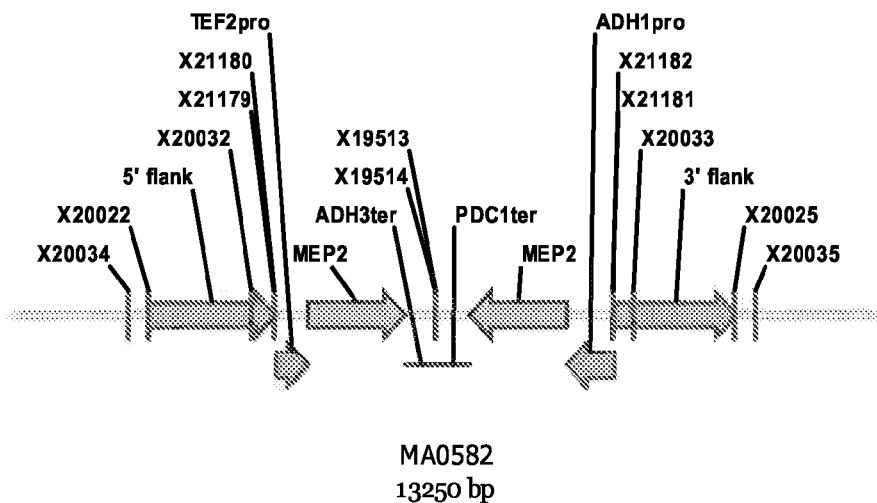
FIG. 19 depicts a schematic diagram of the MA0582 insertion cassette.
Figure 20:
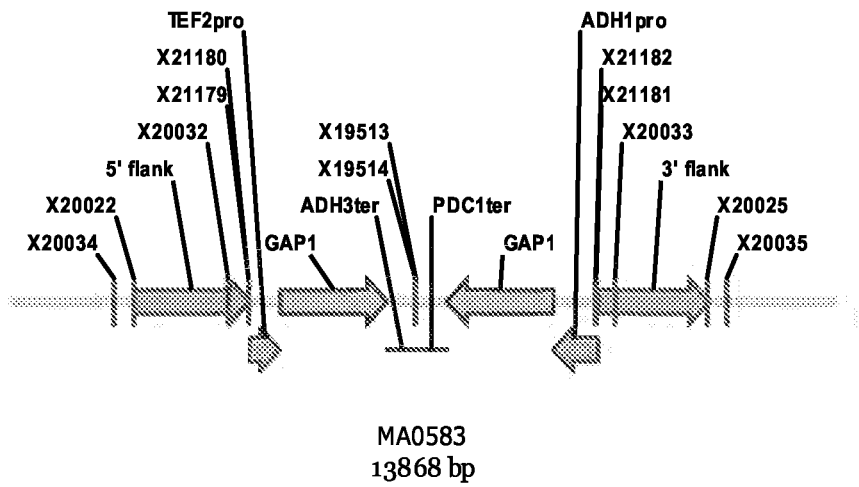
FIG. 20 depicts a schematic diagram of the MA0583 insertion cassette.
Figure 21:
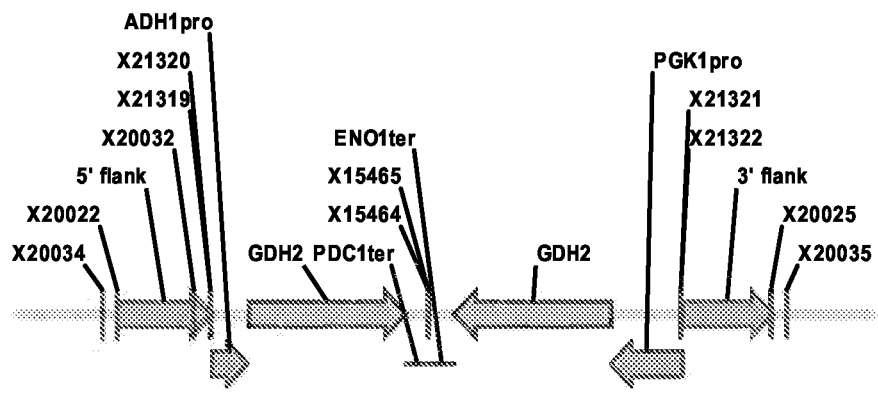
FIG. 21 depicts a schematic diagram of the MA0584 insertion cassette.
Figure 22:
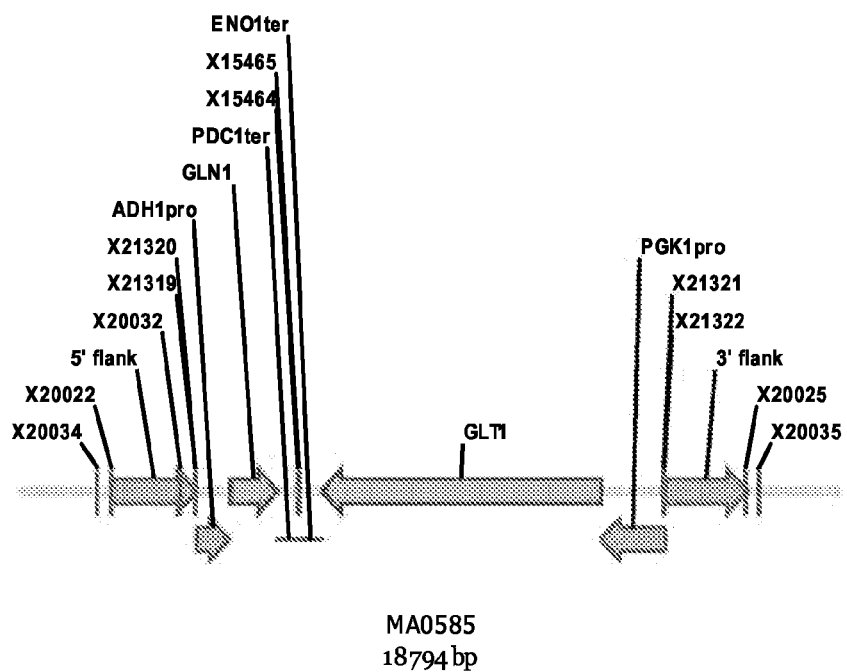
FIG. 22 depicts a schematic diagram of the MA0585 insertion cassette.
Figure 23:
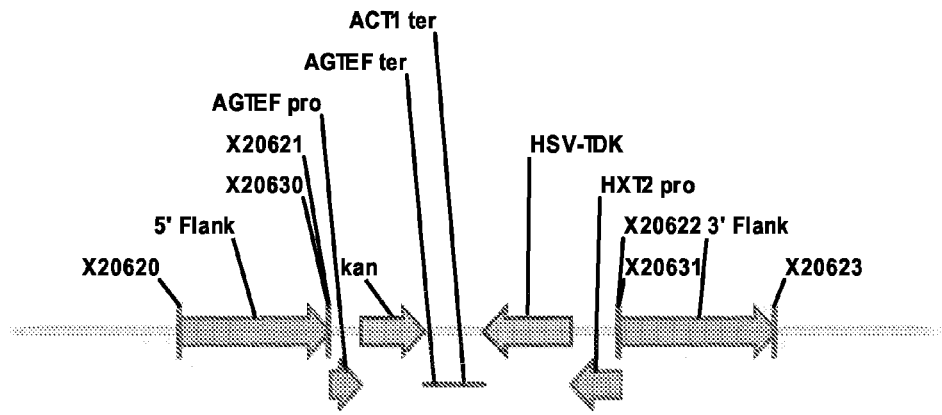
FIG. 23 depicts a schematic diagram of the MA0617 insertion cassette.
Figure 24:
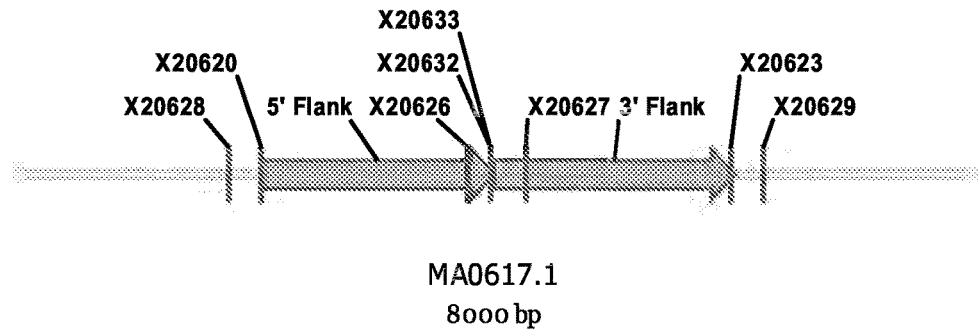
FIG. 24 depicts a schematic diagram of the MA0617.1 insertion cassette.
Figure 25:
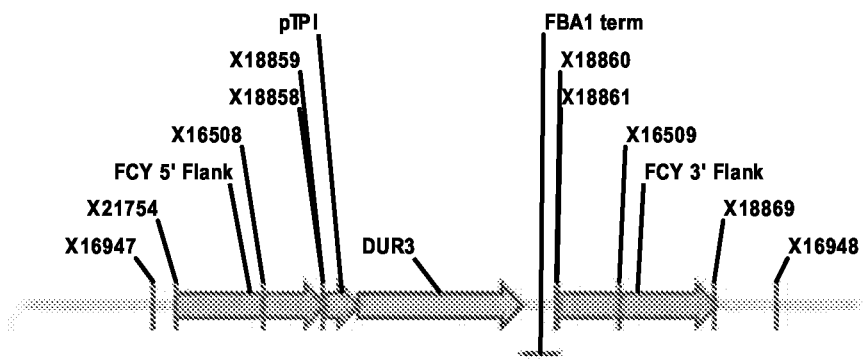
FIG. 25 depicts a schematic diagram of the MA0434 insertion cassette.
Figure 26:
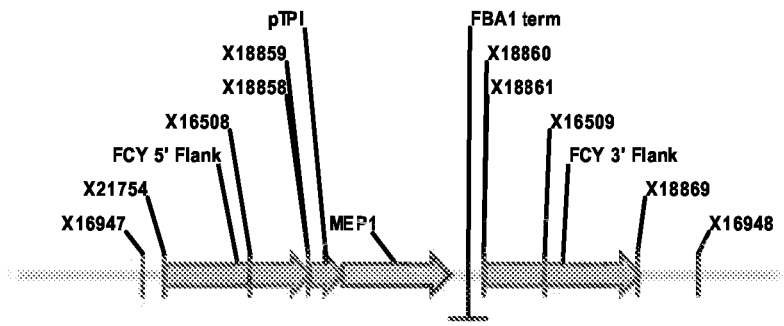
FIG. 26 depicts a schematic diagram of the MA0434.2 insertion cassette.
Figure 27:
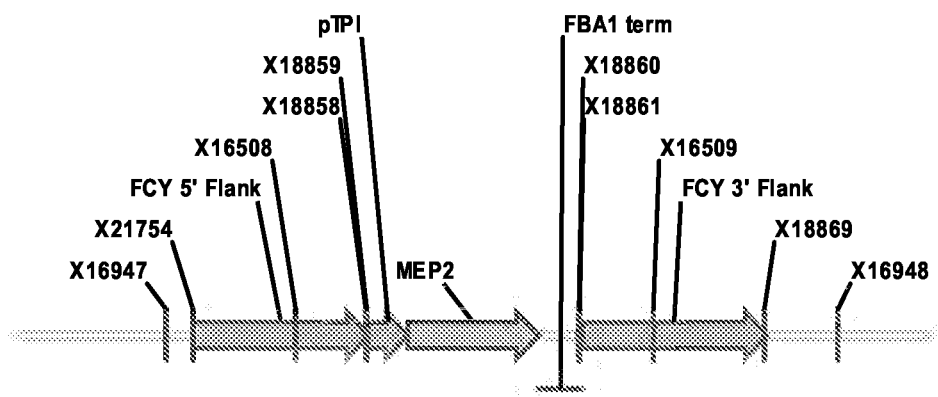
FIG. 27 depicts a schematic diagram of the MA0434.3 insertion cassette.
Figure 28:
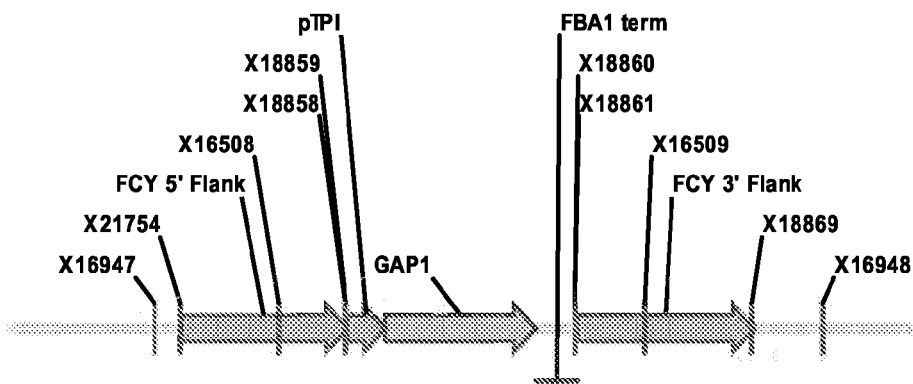
FIG. 28 depicts a schematic diagram of the MA0434.4 insertion cassette.
Figure 29:
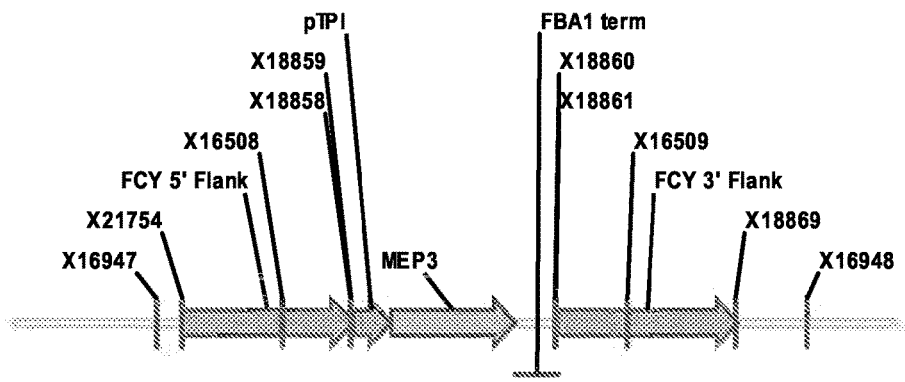
FIG. 29 depicts a schematic diagram of the MA0434.5 insertion cassette.
Figure 30:
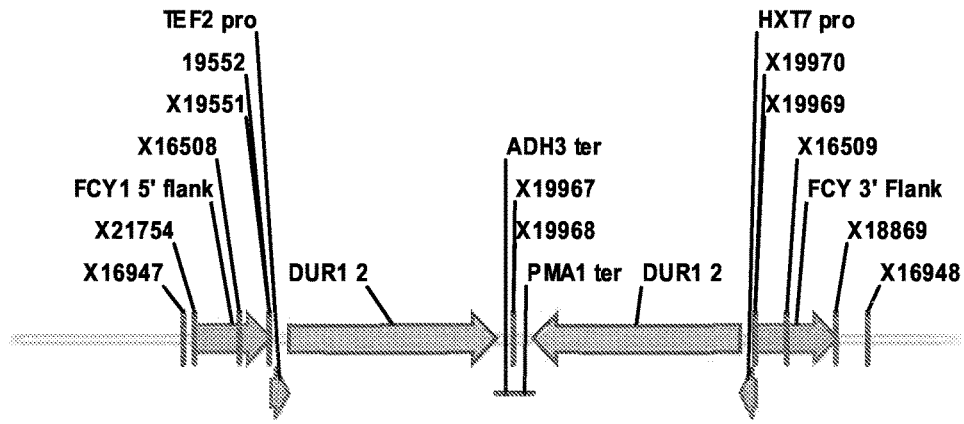
FIG. 30 depicts a schematic diagram of the MA0454.14 insertion cassette.
Figure 31:
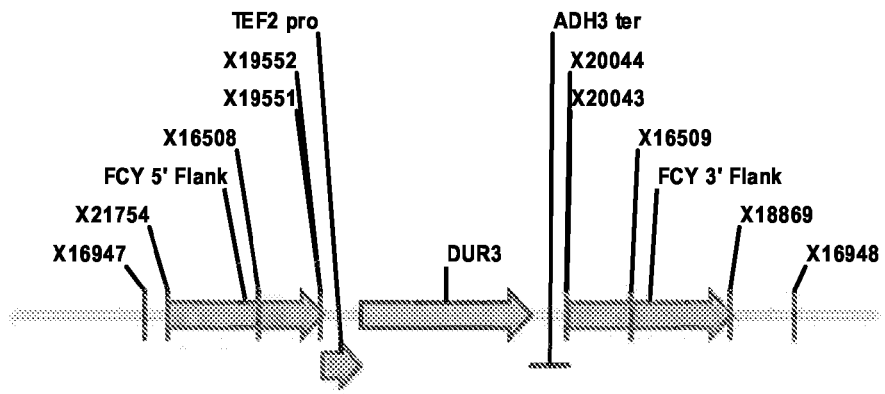
FIG. 31 depicts a schematic diagram of the MA0464 insertion cassette.
Figure 32:
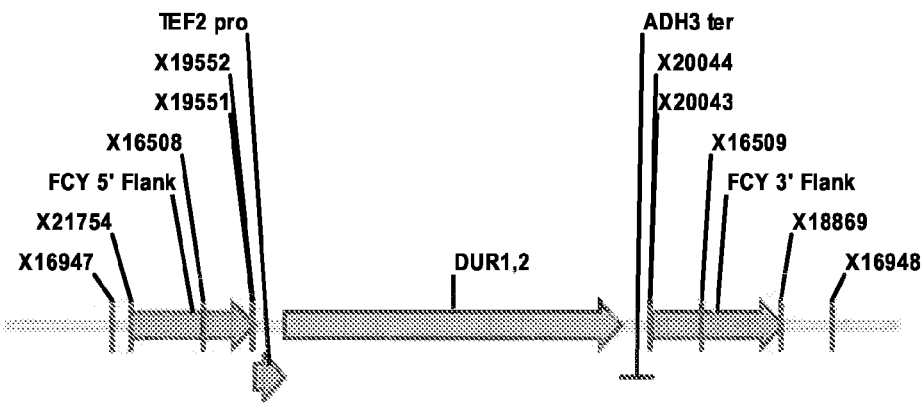
FIG. 32 depicts a schematic diagram of the MA0464.1 insertion cassette.
Figure 33:
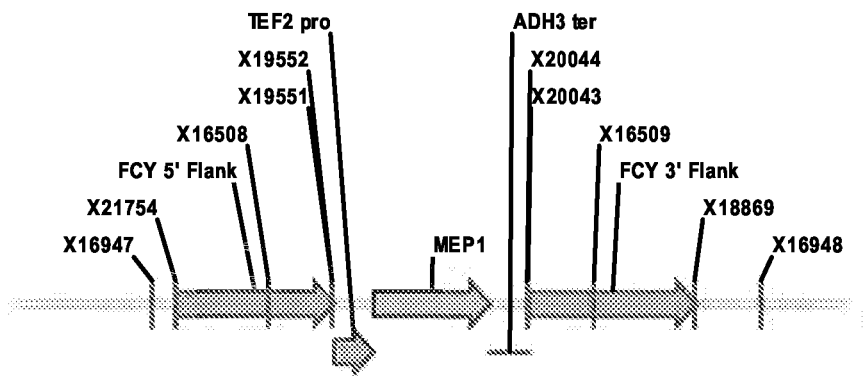
FIG. 33 depicts a schematic diagram of the MA0464.2 insertion cassette.
Figure 34:
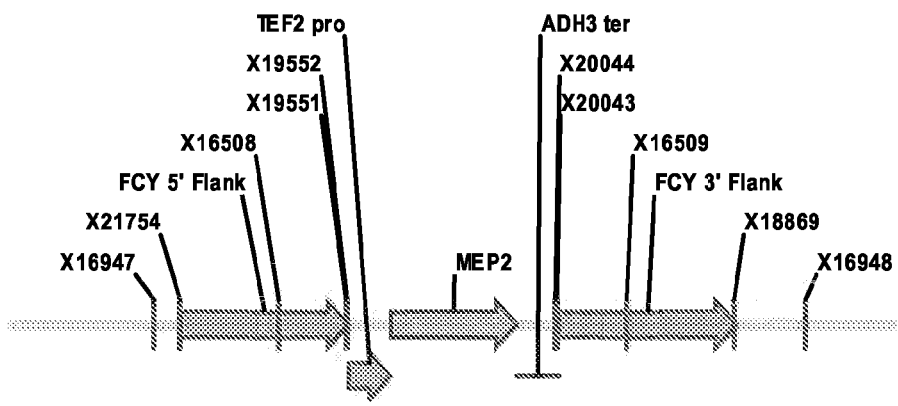
FIG. 34 depicts a schematic diagram of the MA0464.3 insertion cassette.
Figure 35:
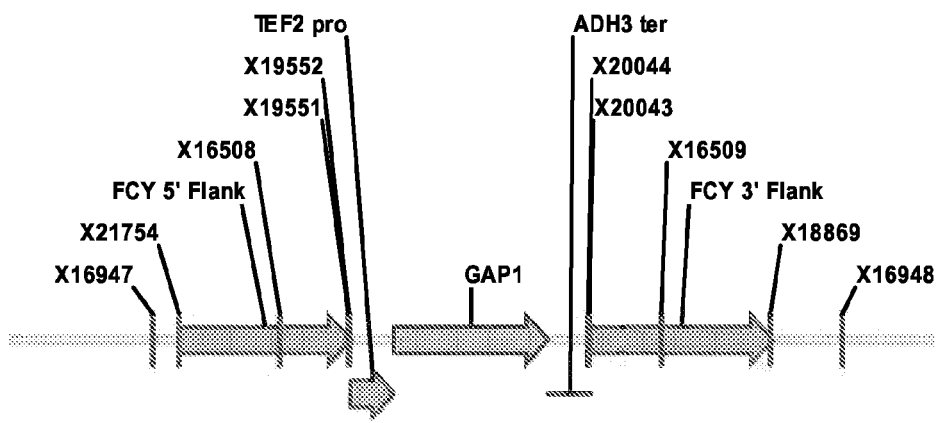
FIG. 35 depicts a schematic diagram of the MA0464.4 insertion cassette.
Figure 36:
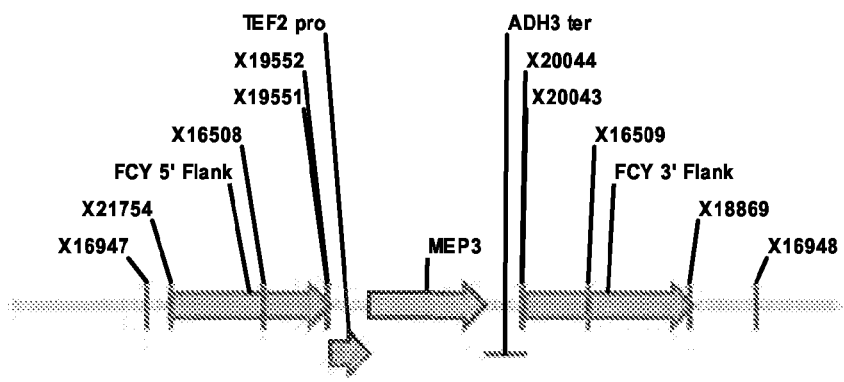
FIG. 36 depicts a schematic diagram of the MA0464.5 insertion cassette.
Figure 37:
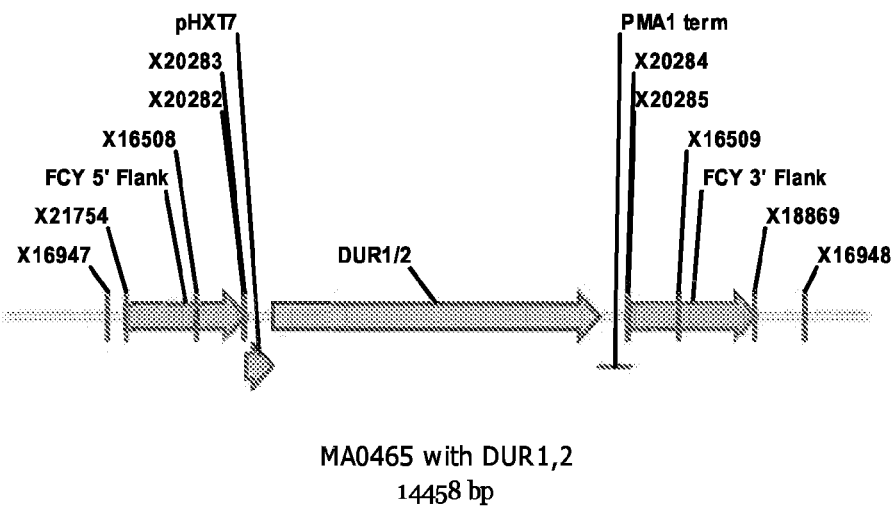
FIG. 37 depicts a schematic diagram of the MA0465.1 insertion cassette.
Figure 38:
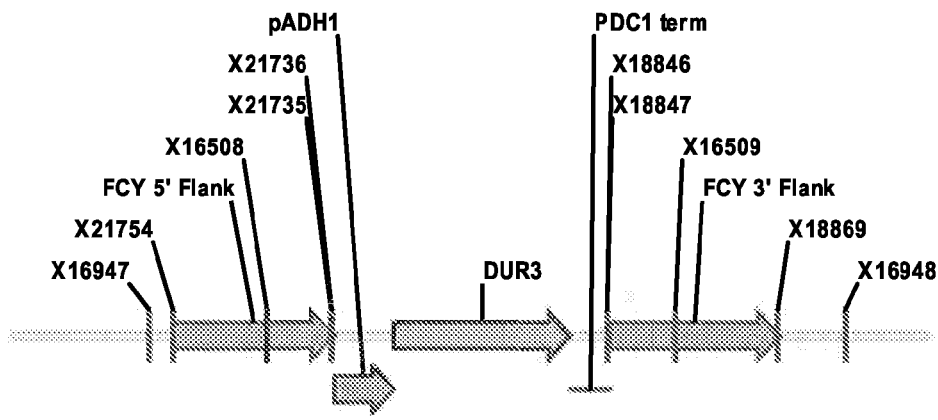
FIG. 38 depicts a schematic diagram of the MA0467 insertion cassette.
Figure 39:
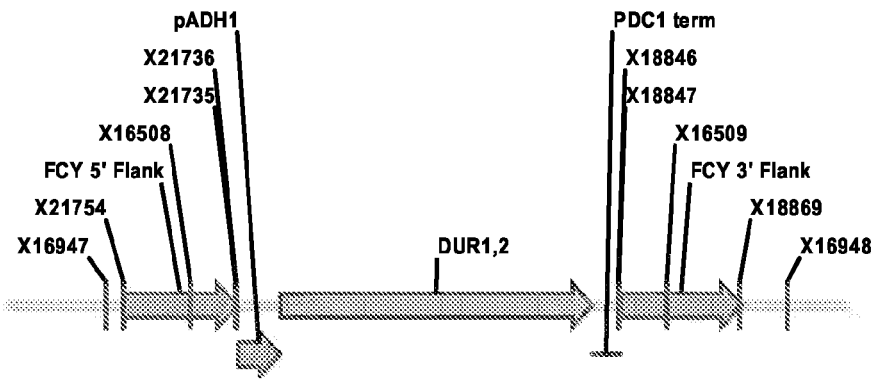
FIG. 39 depicts a schematic diagram of the MA0467.1 insertion cassette.
Figure 40:
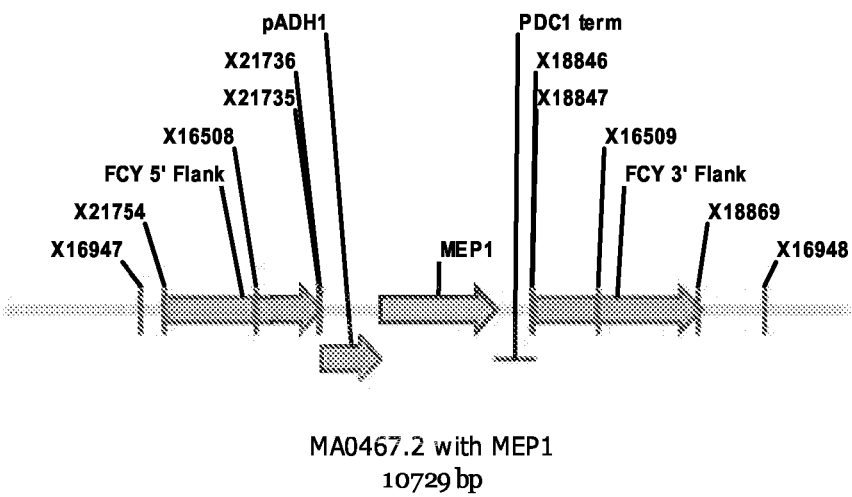
FIG. 40 depicts a schematic diagram of the MA0467.2 insertion cassette.
Figure 41:
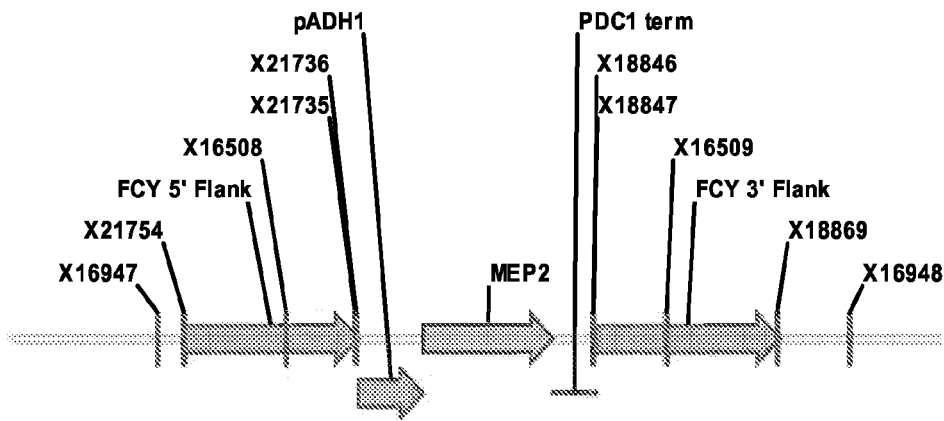
FIG. 41 depicts a schematic diagram of the MA0467.3 insertion cassette.
Figure 42:
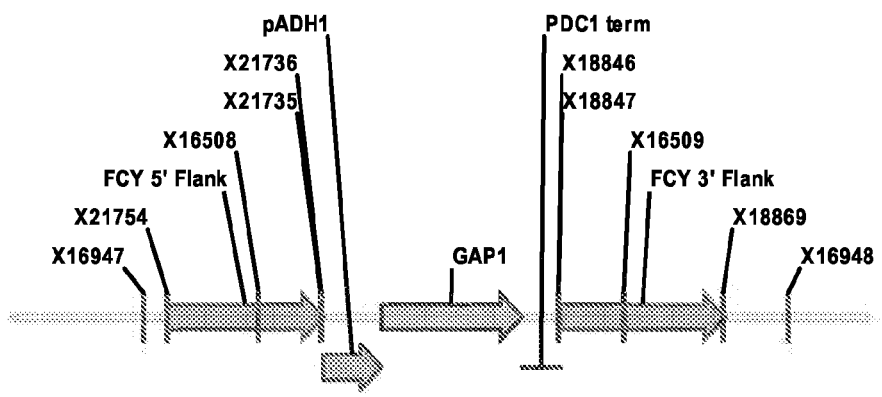
FIG. 42 depicts a schematic diagram of the MA0467.4 insertion cassette.
Figure 43:
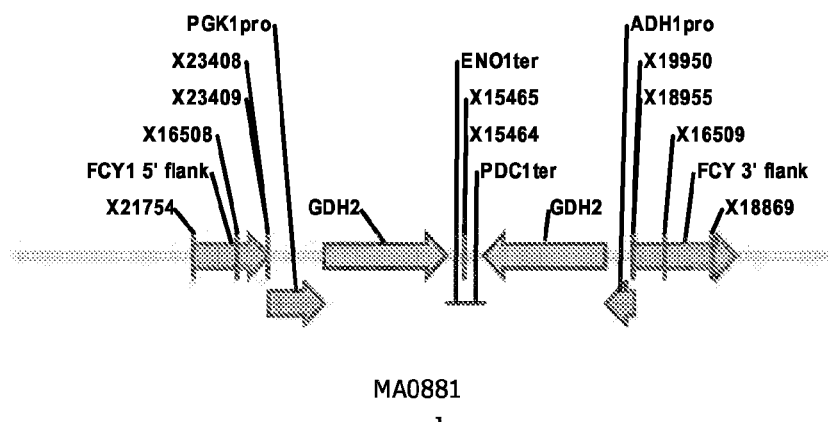
FIG. 43 depicts a schematic diagram of the MA0881 insertion cassette.
Figure 44:
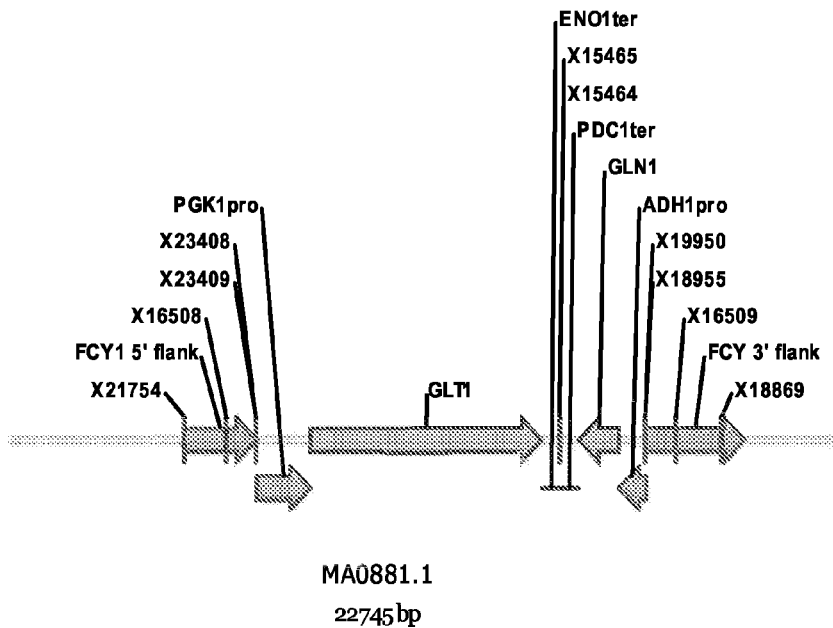
FIG. 44 depicts a schematic diagram of the MA0881.1 insertion cassette.

To create strains M5841-M5844, the GDH1 gene was deleted and replaced with 4 copies of the *N. crassa* GDH2 gene expression cassette in FIG. 10. Each strain resulted from independent colonies and have the same genotype (Table 6). The results shown in FIG. 73 demonstrate that the addition of the *N. crassa* GDH2 to M3624 resulted in titers that were between 3.6 g/l and 4.3 g/l higher than M3624. The data shown in FIG. 74 shows that M3624 makes 1.3 g/l glycerol which is 87% less than the wild type strain M2390, which made 10 g/l. The deletion of GDH1 and addition of the *N. crassa* GDH2 expression cassette decreased the glycerol titers to around 1 g/l. These results support the conclusion that a combination of glycerol reduction through formate production is synergistic with modifications to the ammonium assimilation pathway, even when using a heterologous expression of GDH2.

TABLE 6

Glycerol deletion strains which thriller comprise a deletion of gdh1 and an expression of Gdh2.

| Strain | Genotype |
| --- | --- |
| M2390 | WT |
| M3624 | Δfdh1Δfdh2::4a2pΔgpd1::gpd24a2pΔgpd2::gpd14a2p |
| M4117 | Δfdh1Δfdh2::4a2pΔgpd1::gpd24a2pΔgpd2::gpd14a2pΔScgdh1::4gdh2 |
| M5841 | Δfdh1Δfdh2::4a2pΔgpd1::gpd24a2pΔgpd2::gpd14a2pΔNcrassagdh1::4gdh2 |
| M5842 | Δfdh1Δfdh2::4a2pΔgpd1::gpd24a2pΔgpd2::gpd14a2pΔNcrassagdh1::4gdh2 |
| M5843 | Δfdh1Δfdh2::4a2pΔgpd1::gpd24a2pΔgpd2::gpd14a2pΔNcrassagdh1::4gdh2 |
| M5844 | Δfdh1Δfdh2::4a2pΔgpd1::gpd24a2pΔgpd2::gpd14a2pΔNcrassagdh1::4gdh2 |

The strains in Table 6 were inoculated in vials containing 4 ml industrial corn mash (mini-vials). The fermentation was allowed to proceed for 68 hrs and samples were run on an HPLC to obtain ethanol and glycerol values.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

Those skilled in the art will recognize. or be able to ascertain using no more than routine experimentation, many equivalents to the specific embodiments of the invention described herein. Such equivalents are intended to be encompassed by the following claims.

The strains shown in examples are M2390, M3465, M3467, M3469, M3624, M4117, M4118, M4400, M4401, M4402, M4406, M4427, M4428, M4429, M4430, M4431, M4432, M4433 and M4434. The details of the aforesaid strains such as description, genotype and associated MA cassettes are listed in Table 4.

What is claimed is:

1. A recombinant yeast comprising:
   a) at least one engineered genetic modification that leads to the up-regulation of one or more native and/or heterologous enzymes that function in one or more ethanol production pathways;
   b) at least one engineered genetic modification that leads to the down-regulation of an enzyme in a glycerol-production pathway; and,
   c) at least one engineered genetic modification that leads to the up-regulation or down-regulation of an enzyme in a nitrogen-assimilation pathway;
   wherein the upregulated enzyme that acts in the ethanol production pathway is selected from the group consisting of pyruvate formate lyase (EC 2.3.1.54), pyruvate formate lyase activating enzyme (EC 1.91.1.4), bifunctional acetaldehyde-alcohol dehydrogenase selected from a group of enzymes having both of the following Enzyme Commission Numbers: EC 1.2.1.10 and 1.111; and an NADPH-dependent bifunctional acetaldehyde-alcohol dehydrogenase selected from a group of enzymes having both of the following Enzyme Commission Numbers: EC 1.2.1.10 and 1.1.1.2;
   wherein the down-regulated enzyme in the glycerol-production pathway is selected from the group consisting of glycerol-3-phosphate dehydrogenase 1 polynucleotide (GPD1) (EC 1.1.1.8), glycerol-3-phosphate dehydrogenase 1 polypeptide (Gpd1) (EC 1.1.1.8), glycerol-3-phosphate dehydrogenase 2 polynucleotide (GPD2) (EC 1.1.1.8), glycerol-3-phosphate dehydrogenase 2 polypeptide (Gpd2) (EC 1.1.1.8), glycerol-3-phosphate phosphatase 1 polynucleotide (GPP1) (EC 3.1.3.21), a glycerol-3-phosphate phosphatase polypeptide 1 (Gpp1) (EC 3.1.3.21), a glycerol-3-phosphate phosphatase 2 polynucleotide (GPP2) (EC 3.1.3.21), and glycerol-3-phosphate phosphatase polypeptide 2 (Gpp2) (EC 3.1.3.21); and
   wherein the down-regulated enzyme in the nitrogen-assimilation pathway is glutamate dehydrogenase (Gdh) (EC 1.4.1.4); or
   wherein the up-regulated enzyme in the nitrogen-assimilation pathway is at least one enzyme selected from the group consisting of glutamate dehydrogenase (Gdh) (EC 1.4.1.2), glutamate synthase (Glt) (EC 1.4.1.14), and glutamine synthase (Gln) (EC 6.3.1.2); an ammonium transporter; a urea-amido lyase (EC 6.3.4.6); and a urea transporter.

2. The recombinant yeast of claim 1, wherein the up-regulated enzyme in the nitrogen-assimilation pathway is a Gdh7 isolated from an organism from a genus selected from the group consisting of *Saccharomyces* and *Neurospora* (Gdh2); a Glt1 isolated from an organism from the genus *Saccharomyces* (Glt1); a Gln1 isolated from an organism from the genus *Saccharomyces* (Gln1'); a MEP protein selected from the group consisting of; Mep1, Mep2, and Mep3 and isolated from an organism from a genus selected from the genus *Saccharomyces*; a urea-amido lyase isolated from an organism from the germs *Saccharomyces*; a Dur3 or a Dur4 isolated from an organism from the genus *Saccharomyces*; or a Gln 3 isolated from the genus *Saccharomyces*.

3. The recombinant yeast of claim 1, wherein the down-regulated enzyme in the nitrogen-assimilation pathway is encoded by a polypeptide sequence at least 80%, 90%, 95%, or 100% identical to a polypeptide sequence selected from the group consisting of: SEQ ID NOs: 25 and 31 (*S. cerevisiae* Gdh1 and Gdh3).

4. The recombinant yeast of claim 1, wherein the up-regulated enzyme in the nitrogen-assimilation pathway is encoded by a polypeptide sequence at least 80%, 90%, 95% or 100% identical to a polypeptide sequence selected from the group consisting of: SEQ ID NOs: 27 and 29 (Gdh2); a polypeptide sequence at least 80%, 90%, 95% or 100% identical to a polypeptide sequence encoded by SEQ ID NO: 33 (Glt1); a polypeptide sequence at least 80%, 90%, 95% or 100% identical to a polypeptide sequence encoded by SEQ ID NO: 35 (Gln1); a polypeptide sequence at least 80%, 90%, 95% or 100% identical to a polypeptide sequence encoded by SEQ ID NO: 19 (Mep1); a polypeptide sequence at least 80%, 90%, 95% or 100% A identical to a polypeptide sequence encoded by SEQ ID NO: 21 (Mep2); a polypeptide sequence at least 80%, 90%, 95% or 100% identical to a polypeptide sequence encoded by SEQ ID NO: 23 (Mep3); a polypeptide sequence at least 80%, 90%, 95% or 100% identical to a polypeptide sequence encoded by SEQ ID NO: 37 (Dur1/2); a polypeptide sequence at least 80%, 90%, 95% or 100% identical to a polypeptide sequence encoded by: SEQ ID NO: 39 (Dur3); or a polypeptide sequence at least 80%, 90%, 95% or 100% identical to a polypeptide sequence encoded by SEQ ID NO: 156 (Gln3).

5. The recombinant yeast of claim 1, wherein the enzyme in the glycerol production pathway is encoded by a polypeptide sequence at least 80%, 90%, 95% or 100% identical to the polypeptide sequence encoded by: SEQ ID NO: 5 (Gpd1); a polypeptide sequence at least 80%, 90%, 95% or 100% identical to the polypeptide sequence encoded by: SEQ ID NO: 7 (Gpd2); a polypeptide sequence at least 80%, 90%, 95% or 100% identical to the polypeptide sequence encoded by: SEQ ID NO: 159 (Gpp1); or a polypeptide sequence at least 80%, 90%, 95% or 100% identical to the polypeptide sequence encoded by: SEQ ID NO: 161 (Gpp2).

6. The recombinant yeast of claim 1, wherein the enzyme that acts in the ethanol production pathway is encoded by a polypeptide sequence at least 80%, 90%, 95% or 100% identical to the polypeptide sequence encoded by SEQ ID NO: 9 (*B. adolescentis* Pfl); encoded by a polypeptide sequence at least 80%, 90%, 95% or 100% identical, to the polypeptide sequence encoded by SEQ ID NO: 11 (*B. adolescentis* Pfl-activating enzyme); encoded by a polypeptide sequence at least 80%, 90%, 95% or 100% identical to the polypeptide sequence encoded by SEQ ID NO: 13 (*B. adolescentis* AdhE); or encoded by a polypeptide sequence at least 80%, 90%, 95% or 100% identical to a polypeptide sequence selected from a group consisting of SEQ ID NOs: 15 and 17.

7. The recombinant yeast of claim 1, wherein the microorganism further comprises a down-regulation in one or more native enzymes encoded by a formate dehydrogenase enzyme selected from the group consisting of: EC 1.2.1.43 and EC 1.2.1.2;
and/or a heterologous GPD1 polynucleotide operably linked to a native GPD2 promoter;
and/or a heterologous GPD2 polynucleotide operably linked to a native GPD1 promoter;
and/or an up-regulation or down-regulation of a regulatory element.

8. The recombinant yeast of claim 7 wherein the down-regulated enzyme is encoded by a polypeptide sequence at least 80%, 90%, 95% or 100% identical to a polypeptide sequence encoded by SEQ ID NO: 2 (Fdh1); or a polypeptide sequence at least 80%, 90%, 95% or 100% identical to a polypeptide sequence encoded by the polynucleotide sequence of SEQ ID NO: 3 (Fdh2).

9. The recombinant yeast of claim 7, wherein the regulatory element is selected from the group consisting of Ure2 and Aual.

10. The recombinant yeast of claim 1, wherein the microorganism further comprises at least one additional up-regulated enzyme, wherein the at least one additional up-regulated enzyme is a glucoamylase enzyme with an EC number 3.2.1.3; a permease; or a protease with EC number: 3.4.23.41.

11. The recombinant yeast of claim 10, wherein the up-regulated enzyme is encoded by a polypeptide sequence at least 80%, 90%, 95% or 100% identical to a polypeptide sequence encoded by SEQ ID NO: 163 (glucoamylase); a polypeptide sequence at least 80%, 90%, 95% or 100% identical to a polypeptide sequence encoded by SEQ ID NO: 53 (Gap); or a polypeptide sequence at least 80%, 90%, 95% or 100% identical to a polypeptide sequence selected from a group consisting of SEQ ID NOs: 41, 43, 45, 47, 49, and 51 (protease).

12. The recombinant yeast of claim 1, wherein the up-regulated enzymes are under the control of a heterologous promoter.

13. The recombinant yeast of claim 1, wherein the microorganism produces ethanol at a higher yield than an otherwise identical microorganism lacking the genetic modifications, or the recombinant microorganism produces an ethanol titer from about 1% to about 10% more than an otherwise identical microorganism lacking the genetic modifications, or the recombinant microorganism produces an ethanol titer of at least 125 g/L, or the microorganism produces glycerol at a lower yield than an otherwise identical microorganism lacking the genetic modifications, optionally the microorganism produces a glycerol titer of from about 10 to about 100% less than an otherwise identical microorganism lacking the genetic modifications.

14. A recombinant yeast comprising: down-regulated Gpd1, down-regulated Gpd2, down-regulated Fdh1, down-regulated Fdh2, down-regulated Gdh1, up-regulated AdhE, up-regulated pyruvate formate lyase, an up-regulated pyruvate formate lyase-activating enzyme, GPD1 under the control of the GPD2 promoter, GPD2 under the control of the GPD1 promoter, and up-regulated Gdh2; or a recombinant yeast comprising: down-regulated Gpd1, down-regulated Gpd2, down-regulated Fdh1, down-regulated Fdh2, down-regulated Gdh1, up-regulated AdhE, up-regulated pyruvate formate lyase, an up-regulated pyruvate formate lyase-activating enzyme, GPD1 under the control of the GPD2 promoter, GPD2 under the control of the GPD1 promoter, up-regulated Glt1 and up-regulated Gln1; or a recombinant yeast comprising: down-regulated Gpd1, down-regulated Fdh1, down-regulated Fdh2, down-regulated Gdh1, up-regulated AdhE, up-regulated pyruvate formate lyase, an up-regulated pyruvate formate lyase-activating enzyme, GPD1 under the control of the GPD2 promoter, GPD2 under the control of the GPD1 promoter, up-regulated Glt1 and up-regulated Gln; or a recombinant yeast comprising: down-regulated Gpd2, down-regulated Fdh1, down-regulated Fdh2, down-regulated Gdh1, up-regulated AdhE, up-regulated pyruvate formate lyase, and an up-regulated pyruvate formate lyase-activating enzyme; or a recombinant yeast comprising: down-regulated Gpd1, down-regulated Fdh1, down-regulated Fdh2, down-regulated Gdh1, up-regulated AdhE, up-regulated pyruvate formate lyase, an unregulated pyruvate formate lyase-activating enzyme, and GPD2 under the control of the GPD1 promoter; a recombinant yeast comprising: down-regulated Gpd1, down-regulated Fdh1, down-regulated Fdh2, down-regulated Gdh1, up-regulated AdhE, up-regulated pyruvate formate lyase, and an up-regulated pyruvate formate lyase-activating enzyme; or a recombinant yeast comprising: down-regulated Gpd1, down-regulated Fdh1, down-regulated Fdh2, up-regulated AdhE, up-regulated pyruvate formate lyase, an up-regulated pyruvate formate lyase-activating enzyme, upregulated-DUR1/2 , and GPD2 under the control of the GPD1 promoter; or a recombinant yeast comprising: down-regulated Gpd1, down-regulated Fdh1, down-regulated Fdh2, up-regulated AdhE, up-regulated pyruvate formate lyase, an up-regulated pyruvate formate lyase-activating enzyme, and up-regulated DUR1/2 ; or a recombinant yeast comprising: down-regulated Gpd1, down-regulated Gpd2, down-regulated Fdh1, down-regulated Fdh2, down-regulated Ure2, up-regulated AdhE, up-regulated pyruvate formate lyase, an up-regulated pyruvate formate lyase-activating enzyme, GPD1 under the control of the GPD2 promoter, and GPD2 under the control of the GPD1 promoter; or a recombinant yeast comprising: down-regulated Gpd1, down-regulated Gpd2, down-regulated Fdh1, down-regulated Fdh2, up-regulated AdhE, up-regulated pyruvate formate lyase, an up-regulated pyruvate formate lyase-activating enzyme, up-regulated GDH2, GPD1 under the control of the GPD2 promoter, and GPD2 under the control of the GPD1 promoter.

15. A composition comprising a recombinant yeast from claim 1 and a carbon-containing feedstock; wherein the feedstock is selected from the group, consisting of woody biomass, grasses, sugar-processing residues, municipal waste, agricultural wastes or any combination thereof.

16. A co-culture comprising at least two host cells wherein
a) one of the host cells comprises a recombinant yeast from claim 1; and,
b) another host cell that is genetically distinct from (a).

17. The recombinant yeast of claim 9, wherein the regulatory element is encoded by polypeptide sequence at least 80%, 90%, 95% or 100% identical to a polypeptide sequence encoded by a polynucleotide, sequence of SEQ ID NO: 55 (Ure2) or a polypeptide sequence at least 80%, 90%, 95% or 100% identical to a polypeptide sequence encoded by a polynucleotide sequence of SEQ ID NO: 57 (Aua1).

18. The recombinant yeast of claim 10, wherein the at least one additional up-regulated enzyme is a glucoamylase enzyme with an EC number 3.2.1.3 isolated from the genus *Saccharomycopsis*; a permease isolated from the genus *Saccharomyces* (permease); or a protease with. EC number: 3.4.23.41 isolated from a genus selected from the group consisting of: *Zea, Neurospora, Podospora*[*] and *Magnaporthe*.

19. The recombinant yeast of claim 12, wherein the heterologous promoter is selected from a group consisting of: TEF2 (SEQ ID NO: 58), HXT7 (SEQ ID NO: 59), ADH1 (SEQ ID NO: 60), and TP1 (SEQ ID NO: 61).

20. The recombinant yeast of claim 14, wherein the recombinant yeast comprises an up-regulated DUR1/2 driven by a TEF2 promoter, an HXT7 promoter, a ADH1 promoter or an HXT7/TEF2 promoter.

21. The recombinant yeast of claim 14, wherein the recombinant yeast further comprises an up-regulated DUR3 and/or DUR1/2 and/or Gln3.

* * * * *

UNITED STATES PATENT AND TRADEMARK OFFICE
CERTIFICATE OF CORRECTION

PATENT NO. : 10,604,772 B2
APPLICATION NO. : 14/771831
DATED : March 31, 2020
INVENTOR(S) : Aaron Argyros et al.

Page 1 of 1

It is certified that error appears in the above-identified patent and that said Letters Patent is hereby corrected as shown below:

In the Claims

At Column 241, Claim number 1, Line number 28, please replace "1.111" with --1.1.1.1--

At Column 241, Claim number 2, Line number 64, please replace ";" with --;--

At Column 241, Claim number 2, Line number 65, please remove "a genus selected from"

At Column 241, Claim number 2, Line number 67, please replace "germs" with --genus--

At Column 243, Claim number 13, Line number 51, please remove "of" after "titer"

Signed and Sealed this
Second Day of August, 2022

Katherine Kelly Vidal
*Director of the United States Patent and Trademark Office*